US012806069B2

(12) United States Patent
Andino et al.

(10) Patent No.: US 12,806,069 B2
(45) Date of Patent: Nov. 24, 2026

(54) APPARATUS AND METHODS OF RETINAL INJECTION

(71) Applicant: Clearside Biomedical, Inc., Alpharetta, GA (US)

(72) Inventors: Rafael Victor Andino, Grayson, GA (US); Chen-rei Wan, Smyrna, GA (US); Clay G. Prickett, Atlanta, GA (US); Jay Hope, Nashville, TN (US); Jordan Mykleby, Nashville, TN (US); Nicolo Garbin, Houston, TX (US); Bradford A. Range, Dacula, GA (US); Justin D. Henry, Atlanta, GA (US)

( * ) Notice: Subject to any disclaimer, the term of this patent is extended or adjusted under 35 U.S.C. 154(b) by 423 days.

(21) Appl. No.: 18/298,332

(22) Filed: Apr. 10, 2023

(65) Prior Publication Data

US 2023/0363941 A1 Nov. 16, 2023

Related U.S. Application Data

(63) Continuation-in-part of application No. PCT/US2021/054395, filed on Oct. 11, 2021.

(Continued)

(51) Int. Cl.
*A61F 9/00* (2006.01)
*A61F 9/007* (2006.01)

(52) U.S. Cl.
CPC ........ *A61F 9/0017* (2013.01); *A61F 9/00736* (2013.01)

(58) Field of Classification Search
CPC .. A61F 9/0017; A61F 9/00736; A61F 9/0026; A61F 9/0079
See application file for complete search history.

(56) References Cited

U.S. PATENT DOCUMENTS 1,527,291 A 2/1925 Guillermo et al.
2,187,259 A 1/1940 Barnhart (Continued)

FOREIGN PATENT DOCUMENTS

CA 2639322 A1 3/2009
CN 1604799 A 4/2005

(Continued)

OTHER PUBLICATIONS

Abbott Laboratories Inc., Abbott Park, Illinois, USA, Abbott Medical Optics, “HEALON5 OVD,” 2004, [online]. Retrieved from the Internet: URL: http://abbottmedicaloptics.com/products/cataract/ovds/healon5-viscoelastic. Retrieved from the Internet on: Aug. 16, 2016, 5 pages.

(Continued)

*Primary Examiner* — Jacqueline F Stephens
(74) *Attorney, Agent, or Firm* — Sheppard, Mullin, Richter & Hampton LLP

(57) ABSTRACT

Embodiments described herein relate to systems and methods of retinal injection. In some aspects, a method includes inserting a distal end portion of a hollow conduit of a medical injector into an eye of a patient until the distal end portion reaches a reference location, the medical injector having a housing from which the hollow conduit distally extends and confirming disposal of the distal end portion of the hollow conduit in the reference location. After the confirming, the method further includes extending the distal end portion of the hollow conduit distally relative to the housing and from the reference location such that the distal end portion enters an injection region of the eye. With the distal end portion of the hollow conduit disposed in the injection region of the eye, medicament is conveyed into the injection region via the hollow conduit.

7 Claims, 75 Drawing Sheets

Related U.S. Application Data

(60) Provisional application No. 63/330,613, filed on Apr. 13, 2022, provisional application No. 63/115,654, filed on Nov. 19, 2020, provisional application No. 63/089,829, filed on Oct. 9, 2020.

(56) References Cited

U.S. PATENT DOCUMENTS

| | | | |
|---|---|---|---|
| 2,623,521 | A | 12/1952 | Shaw |
| 2,841,145 | A | 7/1958 | Epps |
| 2,939,459 | A | 6/1960 | Lazarte et al. |
| 3,376,999 | A | 4/1968 | De Hart et al. |
| 3,477,432 | A | 11/1969 | Shaw |
| 3,739,947 | A | 6/1973 | Baumann et al. |
| 3,762,540 | A | 10/1973 | Baumann et al. |
| 3,788,320 | A | 1/1974 | Dye |
| 3,838,690 | A | 10/1974 | Friedman |
| 3,962,430 | A | 6/1976 | O'Neill |
| 3,964,482 | A | 6/1976 | Gerstel et al. |
| 4,230,112 | A | 10/1980 | Smith |
| 4,303,071 | A | 12/1981 | Smith |
| 4,317,448 | A | 3/1982 | Smith |
| 4,377,897 | A | 3/1983 | Eichenbaum et al. |
| 4,383,530 | A | 5/1983 | Bruno |
| 4,417,887 | A | 11/1983 | Koshi |
| 4,432,964 | A | 2/1984 | Shell et al. |
| 4,564,016 | A | 1/1986 | Maurice et al. |
| 4,573,993 | A | 3/1986 | Hoag et al. |
| 4,601,708 | A | 7/1986 | Jordan |
| 4,615,331 | A | 10/1986 | Kramann |
| 4,627,841 | A | 12/1986 | Dorr |
| 4,662,870 | A | 5/1987 | Augustine et al. |
| 4,662,878 | A | 5/1987 | Lindmayer |
| 4,689,040 | A | 8/1987 | Thompson |
| 4,708,147 | A | 11/1987 | Haaga |
| 4,717,383 | A | 1/1988 | Phillips et al. |
| 4,755,169 | A | 7/1988 | Sarnoff et al. |
| 4,795,432 | A | 1/1989 | Karczmer |
| 4,804,371 | A | 2/1989 | Vaillancourt |
| 4,826,490 | A | 5/1989 | Byrne et al. |
| 4,826,871 | A | 5/1989 | Gressel et al. |
| 4,883,483 | A | 11/1989 | Lindmayer |
| 4,889,529 | A | 12/1989 | Haindl |
| 4,941,874 | A | 7/1990 | Sandow et al. |
| 4,966,773 | A | 10/1990 | Gressel et al. |
| 5,015,240 | A | 5/1991 | Soproni et al. |
| 5,024,662 | A | 6/1991 | Menes et al. |
| 5,025,811 | A | 6/1991 | Dobrogowski et al. |
| 5,057,072 | A | 10/1991 | Phipps |
| 5,066,276 | A | 11/1991 | Wang |
| 5,098,389 | A | 3/1992 | Cappucci |
| 5,100,394 | A | 3/1992 | Dudar et al. |
| 5,104,381 | A | 4/1992 | Gresl et al. |
| 5,137,447 | A | 8/1992 | Hunter |
| 5,137,509 | A | 8/1992 | Freitas |
| 5,164,188 | A | 11/1992 | Wong |
| 5,172,807 | A | 12/1992 | Dragan et al. |
| 5,181,909 | A | 1/1993 | McFarlane |
| 5,211,638 | A | 5/1993 | Dudar et al. |
| 5,273,530 | A | 12/1993 | Del Cerro et al. |
| 5,279,564 | A | 1/1994 | Taylor |
| 5,284,474 | A | 2/1994 | Adair |
| 5,292,310 | A | 3/1994 | Yoon |
| 5,295,972 | A | 3/1994 | Mischenko |
| 5,295,974 | A | 3/1994 | O'Laughlin |
| 5,300,084 | A | 4/1994 | Johnson |
| 5,312,361 | A | 5/1994 | Zadini et al. |
| 5,320,609 | A | 6/1994 | Haber et al. |
| 5,354,286 | A | 10/1994 | Mesa et al. |
| 5,358,489 | A | 10/1994 | Wyrick |
| 5,364,374 | A | 11/1994 | Morrison et al. |
| 5,364,734 | A | 11/1994 | Pawlowski et al. |
| 5,395,310 | A | 3/1995 | Untereker et al. |
| 5,397,313 | A | 3/1995 | Gross |
| 5,399,159 | A | 3/1995 | Chin et al. |
| 5,401,247 | A | 3/1995 | Yoon |
| 5,409,457 | A | 4/1995 | Del Cerro et al. |
| 5,443,505 | A | 8/1995 | Wong et al. |
| 5,454,409 | A | 10/1995 | McAffer et al. |
| 5,527,306 | A | 6/1996 | Haining |
| 5,538,503 | A | 7/1996 | Henley |
| 5,547,467 | A | 8/1996 | Pliquett et al. |
| 5,575,780 | A | 11/1996 | Saito |
| 5,632,740 | A | 5/1997 | Koch et al. |
| 5,658,256 | A | 8/1997 | Shields |
| D383,049 | S | 9/1997 | Concari et al. |
| 5,667,491 | A | 9/1997 | Pliquett et al. |
| 5,681,825 | A | 10/1997 | Lindqvist et al. |
| 5,752,942 | A | 5/1998 | Doyle et al. |
| 5,766,198 | A | 6/1998 | Li |
| 5,766,242 | A | 6/1998 | Wong et al. |
| 5,767,079 | A | 6/1998 | Glaser et al. |
| 5,779,668 | A | 7/1998 | Grabenkort |
| 5,788,679 | A | 8/1998 | Gravlee, Jr. |
| 5,792,099 | A | 8/1998 | DeCamp et al. |
| 5,817,075 | A | 10/1998 | Giungo |
| 5,824,072 | A | 10/1998 | Wong |
| 5,839,715 | A | 11/1998 | Leinsing |
| 5,893,397 | A | 4/1999 | Peterson et al. |
| 5,911,223 | A | 6/1999 | Weaver et al. |
| 5,919,158 | A | 7/1999 | Saperstein et al. |
| 5,951,520 | A | 9/1999 | Burzynski et al. |
| 5,952,378 | A | 9/1999 | Stjernschantz et al. |
| 5,968,022 | A | 10/1999 | Saito |
| 6,003,566 | A | 12/1999 | Thibault et al. |
| 6,039,093 | A | 3/2000 | Mrotzek et al. |
| 6,083,199 | A | 7/2000 | Thorley et al. |
| 6,139,534 | A | 10/2000 | Niedospial, Jr. et al. |
| 6,149,623 | A | 11/2000 | Reynolds |
| 6,154,671 | A | 11/2000 | Parel et al. |
| 6,159,218 | A | 12/2000 | Aramant et al. |
| 6,189,580 | B1 | 2/2001 | Thibault et al. |
| 6,209,738 | B1 | 4/2001 | Jansen et al. |
| 6,258,078 | B1 | 7/2001 | Thilly |
| 6,280,470 | B1 | 8/2001 | Peyman |
| 6,299,603 | B1 | 10/2001 | Hecker et al. |
| 6,309,347 | B1 | 10/2001 | Takahashi et al. |
| 6,309,374 | B1 | 10/2001 | Hecker et al. |
| 6,319,225 | B1 | 11/2001 | Sugita et al. |
| 6,319,240 | B1 | 11/2001 | Beck |
| 6,334,856 | B1 | 1/2002 | Allen et al. |
| 6,378,526 | B1 | 4/2002 | Bowman et al. |
| 6,378,714 | B1 | 4/2002 | Jansen et al. |
| 6,379,340 | B1 | 4/2002 | Zinger et al. |
| 6,387,078 | B1 | 5/2002 | Gillespie, III |
| 6,397,849 | B1 | 6/2002 | Bowman et al. |
| 6,413,245 | B1 | 7/2002 | Yaacobi et al. |
| 6,432,090 | B1 | 8/2002 | Brunel |
| 6,491,670 | B1 | 12/2002 | Toth et al. |
| 6,494,865 | B1 | 12/2002 | Alchas |
| 6,503,231 | B1 | 1/2003 | Prausnitz et al. |
| 6,503,240 | B1 | 1/2003 | Niedospial, Jr. et al. |
| 6,517,523 | B1 | 2/2003 | Kaneko et al. |
| 6,524,581 | B1 | 2/2003 | Adamis |
| 6,540,725 | B1 | 4/2003 | Ponzi |
| 6,544,246 | B1 | 4/2003 | Niedospial, Jr. |
| 6,546,283 | B1 | 4/2003 | Beck et al. |
| 6,551,299 | B2 | 4/2003 | Miyoshi et al. |
| 6,558,361 | B1 | 5/2003 | Yeshurun |
| 6,564,630 | B1 | 5/2003 | Klemp |
| 6,568,439 | B1 | 5/2003 | Se et al. |
| 6,569,123 | B2 | 5/2003 | Alchas et al. |
| 6,571,837 | B2 | 6/2003 | Jansen et al. |
| 6,589,202 | B1 | 7/2003 | Powell |
| 6,601,721 | B2 | 8/2003 | Jansen et al. |
| 6,611,707 | B1 | 8/2003 | Prausnitz et al. |
| 6,626,309 | B1 | 9/2003 | Jansen et al. |
| 6,638,244 | B1 | 10/2003 | Reynolds |
| 6,656,433 | B2 | 12/2003 | Sasso |
| 6,715,520 | B2 | 4/2004 | Andreasson et al. |
| 6,729,370 | B2 | 5/2004 | Norton et al. |
| 6,738,526 | B1 | 5/2004 | Betrisey et al. |
| 6,743,211 | B1 | 6/2004 | Prausnitz et al. |
| 6,773,916 | B1 | 8/2004 | Thiel et al. |

(56) References Cited

U.S. PATENT DOCUMENTS

| | | | |
|---|---|---|---|
| D499,153 | S | 11/2004 | Kuo |
| 6,832,994 | B2 | 12/2004 | Niedospial, Jr. et al. |
| 6,875,205 | B2 | 4/2005 | Leinsing |
| 6,883,222 | B2 | 4/2005 | Landau |
| 6,918,889 | B1 | 7/2005 | Brunel |
| 6,936,053 | B1 | 8/2005 | Weiss |
| 6,957,745 | B2 | 10/2005 | Thibault et al. |
| 6,997,917 | B2 | 2/2006 | Niedospial, Jr. et al. |
| 7,025,389 | B2 | 4/2006 | Cuschieri et al. |
| 7,025,774 | B2 | 4/2006 | Freeman et al. |
| 7,150,735 | B2 | 12/2006 | Hickle |
| 7,207,965 | B2 | 4/2007 | Simon |
| 7,207,980 | B2 | 4/2007 | Christian et al. |
| 7,211,062 | B2 | 5/2007 | Kwon |
| 7,214,212 | B2 | 5/2007 | Pommereau et al. |
| 7,226,439 | B2 | 6/2007 | Prausnitz et al. |
| 7,316,676 | B2 | 1/2008 | Peyman et al. |
| 7,326,194 | B2 | 2/2008 | Zinger et al. |
| 7,425,207 | B2 | 9/2008 | Miller et al. |
| 7,435,237 | B2 | 10/2008 | Tan |
| 7,468,057 | B2 | 12/2008 | Ponzi |
| 7,470,257 | B2 | 12/2008 | Norton et al. |
| 7,488,308 | B2 | 2/2009 | Lesch, Jr. |
| 7,510,547 | B2 | 3/2009 | Fangrow |
| 7,510,548 | B2 | 3/2009 | Fangrow |
| D590,690 | S | 4/2009 | Bertini |
| D598,543 | S | 8/2009 | Vogel et al. |
| 7,569,035 | B1 | 8/2009 | Wilmot et al. |
| 7,615,041 | B2 | 11/2009 | Sullivan et al. |
| 7,632,261 | B2 | 12/2009 | Zinger et al. |
| 7,648,491 | B2 | 1/2010 | Rogers |
| 7,678,077 | B2 | 3/2010 | Harris et al. |
| 7,678,078 | B1 | 3/2010 | Peyman et al. |
| 7,722,581 | B2 | 5/2010 | Peyman |
| 7,799,009 | B2 | 9/2010 | Niedospial, Jr. et al. |
| 7,879,018 | B2 | 2/2011 | Zinger et al. |
| 7,914,803 | B2 | 3/2011 | Chowhan et al. |
| 7,918,814 | B2 | 4/2011 | Prausnitz et al. |
| 7,918,874 | B2 | 4/2011 | Siegal |
| 7,947,660 | B2 | 5/2011 | Clark et al. |
| 7,967,772 | B2 | 6/2011 | McKenzie et al. |
| 7,975,733 | B2 | 7/2011 | Horppu et al. |
| 7,981,101 | B2 | 7/2011 | Walsh |
| 8,003,124 | B2 | 8/2011 | Varner et al. |
| 8,009,162 | B2 | 8/2011 | Takatori |
| 8,016,809 | B2 | 9/2011 | Zinger et al. |
| 8,025,653 | B2 | 9/2011 | Capitaine et al. |
| 8,034,105 | B2 | 10/2011 | Stegmann et al. |
| 8,070,739 | B2 | 12/2011 | Zinger et al. |
| 8,099,162 | B2 | 1/2012 | Roy |
| 8,114,110 | B2 | 2/2012 | Bednarek et al. |
| 8,123,729 | B2 | 2/2012 | Yamamoto et al. |
| 8,123,736 | B2 | 2/2012 | Kraushaar et al. |
| 8,137,312 | B2 | 3/2012 | Sundar et al. |
| 8,157,784 | B2 | 4/2012 | Rogers |
| 8,162,914 | B2 | 4/2012 | Kraushaar et al. |
| 8,167,863 | B2 | 5/2012 | Yow |
| 8,172,830 | B2 | 5/2012 | Christian et al. |
| 8,173,617 | B2 | 5/2012 | Clark et al. |
| 8,177,768 | B2 | 5/2012 | Leinsing |
| 8,187,248 | B2 | 5/2012 | Zihlmann |
| 8,192,408 | B2 | 6/2012 | Nazzaro et al. |
| 8,197,435 | B2 | 6/2012 | Prausnitz et al. |
| 8,197,443 | B2 | 6/2012 | Sundar et al. |
| 8,197,459 | B2 | 6/2012 | Jansen et al. |
| 8,221,353 | B2 | 7/2012 | Cormier et al. |
| 8,225,826 | B2 | 7/2012 | Horppu et al. |
| 8,235,967 | B2 | 8/2012 | Chevallier et al. |
| D667,111 | S | 9/2012 | Robinson |
| 8,257,336 | B2 | 9/2012 | Zihlmann |
| 8,262,641 | B2 | 9/2012 | Vedrine et al. |
| 8,287,494 | B2 | 10/2012 | Ma |
| D672,506 | S | 12/2012 | Szymanski |
| 8,323,227 | B2 | 12/2012 | Hamatake et al. |
| 8,328,772 | B2 | 12/2012 | Kinast et al. |
| 8,337,421 | B2 | 12/2012 | Freeman et al. |
| 8,337,509 | B2 | 12/2012 | Schieber et al. |
| 8,348,924 | B2 | 1/2013 | Christian et al. |
| 8,409,165 | B2 | 4/2013 | Niedospial, Jr. et al. |
| 8,425,473 | B2 | 4/2013 | Ho et al. |
| 8,430,862 | B2 | 4/2013 | Peyman et al. |
| 8,460,242 | B2 | 6/2013 | Paques et al. |
| 8,469,939 | B2 | 6/2013 | Fangrow, Jr. |
| 8,475,404 | B2 | 7/2013 | Foshee et al. |
| 8,480,646 | B2 | 7/2013 | Nord et al. |
| 8,506,515 | B2 | 8/2013 | Burns et al. |
| 8,512,309 | B2 | 8/2013 | Shemesh et al. |
| 8,529,492 | B2 | 9/2013 | Clauson et al. |
| 8,535,333 | B2 | 9/2013 | De Juan, Jr. et al. |
| 8,540,692 | B2 | 9/2013 | Fangrow |
| 8,545,430 | B2 | 10/2013 | Silvestrini |
| 8,545,554 | B2 | 10/2013 | Novakovic et al. |
| 8,562,545 | B2 | 10/2013 | Freeman et al. |
| 8,574,214 | B2 | 11/2013 | Kuhn et al. |
| 8,574,217 | B2 | 11/2013 | Peyman |
| 8,602,959 | B1 | 12/2013 | Park et al. |
| 8,608,723 | B2 | 12/2013 | Lev et al. |
| 8,617,121 | B2 | 12/2013 | Lanin et al. |
| 8,628,508 | B2 | 1/2014 | Weitzel et al. |
| 8,632,589 | B2 | 1/2014 | Helmy |
| 8,636,713 | B2 | 1/2014 | Prausnitz et al. |
| 8,652,118 | B2 | 2/2014 | Peyman |
| 8,663,167 | B2 | 3/2014 | Bartha |
| 8,663,303 | B2 | 3/2014 | Horvath et al. |
| 8,668,676 | B2 | 3/2014 | Chang |
| 8,702,659 | B2 | 4/2014 | Lanin et al. |
| 8,747,365 | B2 | 6/2014 | De Sausmarez Lintell |
| 8,752,598 | B2 | 6/2014 | Denenburg et al. |
| 8,758,306 | B2 | 6/2014 | Lopez et al. |
| 8,795,226 | B2 | 8/2014 | Kuhn et al. |
| 8,808,225 | B2 | 8/2014 | Prausnitz et al. |
| 8,808,242 | B2 | 8/2014 | Paques et al. |
| D713,958 | S | 9/2014 | Srinivasan et al. |
| 8,821,870 | B2 | 9/2014 | Robinson et al. |
| D715,125 | S | 10/2014 | Hung |
| 8,852,137 | B2 | 10/2014 | Horvath et al. |
| 8,864,740 | B2 | 10/2014 | Schabbach et al. |
| D718,602 | S | 12/2014 | Musser |
| D719,256 | S | 12/2014 | Ohashi |
| 8,920,375 | B2 | 12/2014 | Gonnelli |
| D726,908 | S | 4/2015 | Yu et al. |
| D733,289 | S | 6/2015 | Blanchard et al. |
| D740,098 | S | 10/2015 | Kuo et al. |
| 9,180,044 | B2 | 11/2015 | Touchard et al. |
| 9,180,047 | B2 | 11/2015 | Andino et al. |
| 9,539,139 | B2 | 1/2017 | Andino et al. |
| 9,636,253 | B1 | 5/2017 | Andino et al. |
| 9,664,926 | B2 | 5/2017 | Mitsui |
| 9,770,361 | B2 | 9/2017 | Andino et al. |
| 9,788,995 | B2 | 10/2017 | Prausnitz et al. |
| 9,937,075 | B2 | 4/2018 | Andino et al. |
| 10,188,550 | B2 | 1/2019 | Andino et al. |
| 10,517,756 | B2 | 12/2019 | Andino et al. |
| 10,555,833 | B2 | 2/2020 | Andino et al. |
| 10,632,013 | B2 | 4/2020 | Prausnitz et al. |
| 10,722,396 | B2 | 7/2020 | Andino et al. |
| 10,905,586 | B2 | 2/2021 | Prausnitz et al. |
| 10,952,894 | B2 | 3/2021 | Hammack et al. |
| 10,973,681 | B2 | 4/2021 | Andino et al. |
| 11,559,428 | B2 | 1/2023 | Andino et al. |
| 11,596,545 | B2 | 3/2023 | Andino et al. |
| 11,752,101 | B2 | 9/2023 | Yamamoto et al. |
| 11,944,703 | B2 | 4/2024 | Yamamoto et al. |
| 12,090,088 | B2 | 9/2024 | Hammack et al. |
| 12,201,558 | B2 | 1/2025 | Andino et al. |
| 2001/0008961 | A1 | 7/2001 | Hecker et al. |
| 2001/0051798 | A1 | 12/2001 | Hochman |
| 2002/0042594 | A1 | 4/2002 | Lum et al. |
| 2002/0082527 | A1 | 6/2002 | Liu et al. |
| 2002/0082543 | A1 | 6/2002 | Park et al. |
| 2002/0142459 | A1 | 10/2002 | Williams et al. |
| 2003/0009113 | A1 | 1/2003 | Olson |
| 2003/0050602 | A1 | 3/2003 | Pettis et al. |
| 2003/0083645 | A1 | 5/2003 | Angel et al. |

(56) References Cited

U.S. PATENT DOCUMENTS

2003/0088204 A1 5/2003 Joshi
2003/0171722 A1 9/2003 Paques et al.
2004/0019331 A1 1/2004 Yeshurun
2004/0039253 A1 2/2004 Peyman et al.
2004/0049150 A1 3/2004 Dalton et al.
2004/0059256 A1 3/2004 Perez
2004/0072105 A1 4/2004 Yeshurun et al.
2004/0106904 A1 6/2004 Gonnelli et al.
2004/0122359 A1 6/2004 Wenz et al.
2004/0164454 A1 8/2004 Gartstein et al.
2004/0186084 A1 9/2004 Alam et al.
2004/0199130 A1 10/2004 Chornenky et al.
2004/0249404 A1 12/2004 Haefliger
2004/0265365 A1 12/2004 Daddona et al.
2005/0009910 A1 1/2005 Hughes et al.
2005/0033230 A1 2/2005 Alchas et al.
2005/0070819 A1 3/2005 Poux et al.
2005/0089545 A1 4/2005 Kuwano et al.
2005/0096282 A1 5/2005 Lewin et al.
2005/0101582 A1 5/2005 Lyons et al.
2005/0101882 A1 5/2005 Leira et al.
2005/0101967 A1 5/2005 Weber et al.
2005/0137525 A1 6/2005 Wang et al.
2005/0148034 A1 7/2005 Hariri et al.
2005/0171507 A1 8/2005 Christian et al.
2005/0181017 A1 8/2005 Hughes et al.
2005/0203575 A1 9/2005 Carson et al.
2005/0209565 A1 9/2005 Yuzhakov et al.
2005/0244462 A1 11/2005 Farooq
2005/0244463 A1 11/2005 Huang et al.
2005/0256499 A1 11/2005 Pettis et al.
2005/0281862 A1 12/2005 Karakelle et al.
2006/0013859 A1 1/2006 Yamada et al.
2006/0036318 A1 2/2006 Foulkes
2006/0055090 A1 3/2006 Lee et al.
2006/0084942 A1 4/2006 Kim et al.
2006/0086689 A1 4/2006 Raju
2006/0089607 A1 4/2006 Chen
2006/0173418 A1 8/2006 Rinaudo et al.
2006/0178614 A1 8/2006 Nemati
2006/0189608 A1 8/2006 Bingaman
2006/0195187 A1 8/2006 Stegmann et al.
2006/0202385 A1 9/2006 Xu et al.
2006/0229562 A1 10/2006 Marsh et al.
2006/0233858 A1 10/2006 Tzekov et al.
2006/0259008 A1 11/2006 Orilla
2006/0271025 A1 11/2006 Jones et al.
2007/0016103 A1 1/2007 Calasso et al.
2007/0060927 A1 3/2007 Longson et al.
2007/0073197 A1 3/2007 Prausnitz et al.
2007/0082841 A1 4/2007 Higuchi et al.
2007/0093742 A1 4/2007 Higuchi et al.
2007/0093877 A1 4/2007 Beecham et al.
2007/0149944 A1 6/2007 Tashiro et al.
2007/0191863 A1 8/2007 De Juan et al.
2007/0202186 A1 8/2007 Yamamoto et al.
2007/0233037 A1 10/2007 Gifford, et al.
2007/0260201 A1 11/2007 Prausnitz et al.
2007/0268340 A1 11/2007 Dacquay et al.
2007/0270745 A1 11/2007 Nezhat et al.
2007/0270768 A1 11/2007 Dacquay et al.
2007/0282405 A1 12/2007 Wong et al.
2007/0287985 A1 12/2007 Estes et al.
2008/0008762 A1 1/2008 Robinson et al.
2008/0015539 A1 1/2008 Pieroni et al.
2008/0027371 A1 1/2008 Higuchi et al.
2008/0033351 A1 2/2008 Trogden et al.
2008/0058704 A1 3/2008 Hee et al.
2008/0058717 A1 3/2008 Spector
2008/0065002 A1 3/2008 Lobl et al.
2008/0082841 A1 4/2008 Juenemann et al.
2008/0097335 A1 4/2008 Trogden et al.
2008/0097346 A1 4/2008 Charles
2008/0097390 A1 4/2008 Dacquay et al.
2008/0131484 A1 6/2008 Robinson et al.
2008/0152694 A1 6/2008 Lobl et al.
2008/0177239 A1 7/2008 Li et al.
2008/0183123 A1 7/2008 Behar-Cohen et al.
2008/0200883 A1 8/2008 Tomono
2008/0208255 A1 8/2008 Siegal
2008/0228127 A1 9/2008 Burns et al.
2008/0234625 A1 9/2008 Dacquay et al.
2008/0300634 A1 12/2008 Gray
2009/0030381 A1 1/2009 Lind et al.
2009/0076463 A1 3/2009 Attinger
2009/0081277 A1 3/2009 Robinson et al.
2009/0082321 A1 3/2009 Edelman et al.
2009/0082713 A1 3/2009 Friden
2009/0088721 A1 4/2009 De Bizemont et al.
2009/0105749 A1 4/2009 De Juan et al.
2009/0148527 A1 6/2009 Robinson et al.
2009/0187167 A1 7/2009 Sexton et al.
2009/0259180 A1 10/2009 Choi
2009/0287161 A1 11/2009 Traub et al.
2009/0312782 A1 12/2009 Park
2010/0010452 A1 1/2010 Paques et al.
2010/0015158 A1 1/2010 Robinson et al.
2010/0030150 A1 2/2010 Paques et al.
2010/0057011 A1 3/2010 Charles
2010/0074925 A1 3/2010 Carmon
2010/0074957 A1 3/2010 Robinson et al.
2010/0081707 A1 4/2010 Ali et al.
2010/0100054 A1 4/2010 Cormier et al.
2010/0152646 A1 6/2010 Girijavallabhan et al.
2010/0152667 A1 6/2010 Kietzmann
2010/0152676 A1 6/2010 Clements et al.
2010/0160889 A1 6/2010 Smith et al.
2010/0173866 A1 7/2010 Hee et al.
2010/0191176 A1 7/2010 Ho et al.
2010/0191177 A1 7/2010 Chang et al.
2010/0211079 A1 8/2010 Aramant
2010/0241102 A1 9/2010 Ma
2010/0312120 A1 12/2010 Meier
2010/0318034 A1 12/2010 Goncalves
2011/0022023 A1 1/2011 Weitzel et al.
2011/0060310 A1 3/2011 Prestrelski et al.
2011/0112546 A1 5/2011 Juan, Jr. et al.
2011/0152775 A1 6/2011 Lopez et al.
2011/0202012 A1 8/2011 Bartlett
2011/0213317 A1 9/2011 Chen et al.
2011/0238075 A1 9/2011 Clauson et al.
2011/0251561 A1 10/2011 Inou et al.
2011/0264028 A1 10/2011 Ramdas et al.
2011/0282298 A1 11/2011 Agian et al.
2011/0288492 A1 11/2011 Holmqvist
2011/0295152 A1 12/2011 Sasaki et al.
2011/0306923 A1 12/2011 Roy
2012/0004245 A1 1/2012 May et al.
2012/0008327 A1 1/2012 Brennan et al.
2012/0024987 A1 2/2012 Nagele
2012/0029360 A1 2/2012 Hendriks et al.
2012/0035524 A1 2/2012 Silvestrini
2012/0059346 A1 3/2012 Sheppard et al.
2012/0078224 A1 3/2012 Lerner et al.
2012/0083727 A1 4/2012 Barnett
2012/0095414 A1 4/2012 Lanin et al.
2012/0095438 A1 4/2012 Lanin et al.
2012/0101475 A1 4/2012 Wilmot et al.
2012/0116306 A1 5/2012 Heald et al.
2012/0123351 A1 5/2012 Lanin et al.
2012/0123386 A1 5/2012 Tsals
2012/0123437 A1 5/2012 Horvath et al.
2012/0123440 A1 5/2012 Horvath et al.
2012/0123473 A1 5/2012 Hernandez
2012/0130207 A1 5/2012 O'Dea et al.
2012/0136318 A1 5/2012 Lanin et al.
2012/0157880 A1 6/2012 Haselby et al.
2012/0165723 A1 6/2012 Horvath et al.
2012/0191064 A1 7/2012 Conston et al.
2012/0197208 A1 8/2012 Bruggemann et al.
2012/0203193 A1 8/2012 Rogers
2012/0220917 A1 8/2012 Silvestrini et al.
2012/0220978 A1 8/2012 Lev et al.
2012/0226260 A1 9/2012 Prausnitz et al.

(56) References Cited

U.S. PATENT DOCUMENTS

| | | | |
|---|---|---|---|
| 2012/0232522 | A1 | 9/2012 | Prausnitz et al. |
| 2012/0259288 | A1 | 10/2012 | Wagner et al. |
| 2012/0271272 | A1 | 10/2012 | Hammack et al. |
| 2012/0296307 | A1 | 11/2012 | Holt et al. |
| 2013/0035662 | A1 | 2/2013 | Decker et al. |
| 2013/0041265 | A1 | 2/2013 | Sostek et al. |
| 2013/0060202 | A1 | 3/2013 | Thorley et al. |
| 2013/0072900 | A1 | 3/2013 | Colantonio |
| 2013/0079716 | A1 | 3/2013 | Thorley et al. |
| 2013/0096533 | A1 | 4/2013 | Freeman et al. |
| 2013/0102973 | A1 | 4/2013 | Thorley et al. |
| 2013/0116523 | A1 | 5/2013 | Jung et al. |
| 2013/0138049 | A1 | 5/2013 | Kemp et al. |
| 2013/0140208 | A1 | 6/2013 | Hemmann |
| 2013/0150803 | A1 | 6/2013 | Shetty et al. |
| 2013/0190694 | A1 | 7/2013 | Barrow-Williams et al. |
| 2013/0211335 | A1 | 8/2013 | Paques et al. |
| 2013/0216623 | A1 | 8/2013 | Yamamoto et al. |
| 2013/0218102 | A1 | 8/2013 | Iwase et al. |
| 2013/0226103 | A1 | 8/2013 | Papiorek |
| 2013/0237910 | A1 | 9/2013 | Shetty et al. |
| 2013/0237916 | A1 | 9/2013 | Hanson et al. |
| 2013/0245600 | A1 | 9/2013 | Yamamoto et al. |
| 2013/0253416 | A1 | 9/2013 | Rotenstreich |
| 2013/0331786 | A1 | 12/2013 | Hofmann |
| 2013/0338612 | A1 | 12/2013 | Smith et al. |
| 2014/0012226 | A1 | 1/2014 | Hochman |
| 2014/0018771 | A1 | 1/2014 | Shekalim |
| 2014/0031833 | A1 | 1/2014 | Novakovic et al. |
| 2014/0039391 | A1 | 2/2014 | Clarke et al. |
| 2014/0039413 | A1 | 2/2014 | Jugl et al. |
| 2014/0094752 | A1 | 4/2014 | Hiles |
| 2014/0107566 | A1 | 4/2014 | Prausnitz et al. |
| 2014/0114243 | A1 | 4/2014 | Smith et al. |
| 2014/0124528 | A1 | 5/2014 | Fangrow |
| 2014/0135716 | A1 | 5/2014 | Clarke et al. |
| 2014/0200518 | A1 | 7/2014 | Ekman et al. |
| 2014/0224688 | A1 | 8/2014 | Slemmen et al. |
| 2014/0236098 | A1 | 8/2014 | Mica et al. |
| 2014/0243754 | A1 | 8/2014 | Clarke et al. |
| 2014/0249539 | A1 | 9/2014 | Mica et al. |
| 2014/0257207 | A1 | 9/2014 | Clarke et al. |
| 2014/0261727 | A1 | 9/2014 | Mansour et al. |
| 2014/0261877 | A1 | 9/2014 | Ivosevic et al. |
| 2014/0276649 | A1 | 9/2014 | Ivosevic et al. |
| 2014/0296802 | A1 | 10/2014 | Geiger et al. |
| 2014/0309599 | A1 | 10/2014 | Schaller |
| 2014/0323979 | A1 | 10/2014 | Henley et al. |
| 2014/0323985 | A1 | 10/2014 | Hourmand et al. |
| 2014/0330213 | A1 | 11/2014 | Hourmand et al. |
| 2014/0350479 | A1 | 11/2014 | Hourmand et al. |
| 2015/0013827 | A1 | 1/2015 | Kuhn |
| 2015/0013835 | A1 | 1/2015 | Cordes |
| 2015/0025474 | A1 | 1/2015 | Riedel et al. |
| 2015/0038905 | A1 | 2/2015 | Andino et al. |
| 2015/0045731 | A1 | 2/2015 | Gupta et al. |
| 2015/0045744 | A1 | 2/2015 | Gupta et al. |
| 2015/0051545 | A1 | 2/2015 | Henderson et al. |
| 2015/0051581 | A1 | 2/2015 | Andino et al. |
| 2015/0110717 | A1 | 4/2015 | Distel et al. |
| 2015/0133415 | A1 | 5/2015 | Whitcup |
| 2015/0148615 | A1* | 5/2015 | Brennan .................. A61B 3/16 128/853 |
| 2015/0157359 | A1 | 6/2015 | Shinzato et al. |
| 2015/0209180 | A1 | 7/2015 | Prausnitz et al. |
| 2015/0223977 | A1 | 8/2015 | Oberkircher et al. |
| 2015/0320596 | A1 | 11/2015 | Gifford, III et al. |
| 2016/0015895 | A1 | 1/2016 | Blondino et al. |
| 2016/0015908 | A1 | 1/2016 | Uemura et al. |
| 2016/0106584 | A1 | 4/2016 | Andino et al. |
| 2016/0106587 | A1 | 4/2016 | Jarrett et al. |
| 2016/0166819 | A1 | 6/2016 | Simmers |
| 2016/0193080 | A1 | 7/2016 | Hammack et al. |
| 2016/0199581 | A1 | 7/2016 | Cachemaille et al. |
| 2016/0250417 | A1 | 9/2016 | Olson |
| 2016/0354239 | A1 | 12/2016 | Roy |
| 2016/0354244 | A1 | 12/2016 | Horvath et al. |
| 2017/0086725 | A1 | 3/2017 | Woo et al. |
| 2017/0224534 | A1 | 8/2017 | Andino et al. |
| 2017/0273827 | A1 | 9/2017 | Prausnitz et al. |
| 2017/0290702 | A1 | 10/2017 | Yamamoto et al. |
| 2017/0340560 | A1 | 11/2017 | Yamamoto et al. |
| 2018/0028358 | A1 | 2/2018 | Andino et al. |
| 2018/0042767 | A1 | 2/2018 | Andino et al. |
| 2018/0333297 | A1* | 11/2018 | Andino .................. A61J 1/201 |
| 2019/0000669 | A1 | 1/2019 | Hammack et al. |
| 2019/0231592 | A1 | 8/2019 | Andino et al. |
| 2019/0290485 | A1 | 9/2019 | Andino et al. |
| 2019/0307606 | A1 | 10/2019 | Andino et al. |
| 2019/0350755 | A1 | 11/2019 | Andino et al. |
| 2020/0030143 | A1 | 1/2020 | Andino et al. |
| 2020/0237556 | A1 | 7/2020 | Prausnitz et al. |
| 2020/0330269 | A1 | 10/2020 | Bley et al. |
| 2020/0390692 | A1 | 12/2020 | Yamamoto et al. |
| 2021/0022918 | A1 | 1/2021 | Prausnitz et al. |
| 2021/0169689 | A1 | 6/2021 | Bley et al. |
| 2021/0212940 | A1 | 7/2021 | Yamamoto et al. |
| 2021/0220173 | A1 | 7/2021 | Andino et al. |
| 2021/0366311 | A1 | 11/2021 | Fisher et al. |
| 2021/0393436 | A1 | 12/2021 | Prausnitz et al. |
| 2022/0062040 | A1 | 3/2022 | Hammack et al. |
| 2022/0062041 | A1 | 3/2022 | Hammack et al. |
| 2022/0280386 | A1 | 9/2022 | Andino et al. |
| 2022/0347014 | A1 | 11/2022 | Yamamoto et al. |
| 2023/0157869 | A1 | 5/2023 | Andino et al. |
| 2023/0372235 | A1 | 11/2023 | Yamamoto et al. |
| 2025/0025452 | A1 | 1/2025 | Kansara et al. |
| 2025/0152413 | A1 | 5/2025 | Andino et al. |
| 2025/0177201 | A1 | 6/2025 | Hammack |
| 2025/0186253 | A1 | 6/2025 | Andino |
| 2025/0345206 | A1 | 11/2025 | Andino |

FOREIGN PATENT DOCUMENTS

| | | | |
|---|---|---|---|
| CN | 1608587 | A | 4/2005 |
| CN | 1674954 | A | 9/2005 |
| CN | 1681547 | A | 10/2005 |
| CN | 1706365 | A | 12/2005 |
| CN | 1736474 | A | 2/2006 |
| CN | 1946445 | A | 4/2007 |
| CN | 101031256 | A | 9/2007 |
| CN | 101052434 | A | 10/2007 |
| CN | 101351239 | A | 1/2009 |
| CN | 201192452 | Y | 2/2009 |
| CN | 101559249 | A | 10/2009 |
| CN | 201356711 | Y | 12/2009 |
| CN | 201591741 | U | 9/2010 |
| CN | 103037802 | A | 4/2013 |
| CN | 103857431 | A | 6/2014 |
| CN | 204364577 | U | 6/2015 |
| EA | 006961 | B1 | 6/2006 |
| EP | 1568359 | A1 | 8/2005 |
| EP | 2193821 | A1 | 6/2010 |
| EP | 2307055 | A2 | 4/2011 |
| EP | 3446679 | A1 | 2/2019 |
| JP | 2001525826 | A | 12/2001 |
| JP | 2009183441 | A | 8/2009 |
| JP | 2009531298 | A | 9/2009 |
| JP | 5828535 | B1 | 12/2015 |
| KR | 20040096561 | A | 11/2004 |
| RU | 2344767 | C2 | 1/2009 |
| RU | 2353393 | C2 | 4/2009 |
| RU | 2428956 | C2 | 9/2011 |
| WO | WO-9208406 | A1 | 5/1992 |
| WO | WO-9401124 | A1 | 1/1994 |
| WO | WO-9412217 | A1 | 6/1994 |
| WO | WO-9609838 | A1 | 4/1996 |
| WO | WO-9851348 | A2 | 11/1998 |
| WO | WO-0007530 | A2 | 2/2000 |
| WO | WO-0007565 | A2 | 2/2000 |
| WO | WO-0117589 | A1 | 3/2001 |
| WO | WO-0141685 | A2 | 6/2001 |
| WO | WO-03002094 | A2 | 1/2003 |
| WO | WO-03024507 | A2 | 3/2003 |

(56) References Cited

FOREIGN PATENT DOCUMENTS

| | | | |
|---|---|---|---|
| WO | WO-2004000389 | A2 | 12/2003 |
| WO | WO-2004105864 | A1 | 12/2004 |
| WO | WO-2005011741 | A2 | 2/2005 |
| WO | WO-2005032510 | A1 | 4/2005 |
| WO | WO-2005046641 | A2 | 5/2005 |
| WO | WO-2005069831 | A2 | 8/2005 |
| WO | WO-2005074942 | A1 | 8/2005 |
| WO | WO-2005107845 | A1 | 11/2005 |
| WO | WO-2006004595 | A2 | 1/2006 |
| WO | WO-2006020714 | A2 | 2/2006 |
| WO | WO-2006042252 | A2 | 4/2006 |
| WO | WO-2006058189 | A2 | 6/2006 |
| WO | WO-2006128034 | A1 | 11/2006 |
| WO | WO-2006138719 | A2 | 12/2006 |
| WO | WO-2007069697 | A1 | 6/2007 |
| WO | WO-2007099406 | A2 | 9/2007 |
| WO | WO-2007100745 | A2 | 9/2007 |
| WO | WO-2007130105 | A1 | 11/2007 |
| WO | WO-2007131050 | A2 | 11/2007 |
| WO | WO-2010009034 | A2 | 1/2010 |
| WO | WO-2010054660 | A1 | 5/2010 |
| WO | WO-2010132751 | A1 | 11/2010 |
| WO | WO-2011057065 | A1 | 5/2011 |
| WO | WO-2011123722 | A1 | 10/2011 |
| WO | WO-2011139713 | A2 | 11/2011 |
| WO | WO-2012051575 | A2 | 4/2012 |
| WO | WO-2012162459 | A1 | 11/2012 |
| WO | WO-2013098166 | A1 | 7/2013 |
| WO | WO-2013151904 | A1 | 10/2013 |
| WO | WO-2014028285 | A1 | 2/2014 |
| WO | WO-2014036009 | A1 | 3/2014 |
| WO | WO-2014074823 | A1 | 5/2014 |
| WO | WO-2014179698 | A2 | 11/2014 |
| WO | WO-2014197317 | A1 | 12/2014 |
| WO | WO-2015015467 | A1 | 2/2015 |
| WO | WO-2015110660 | A1 | 7/2015 |
| WO | WO-2015175954 | A1 | 11/2015 |
| WO | WO-2015196085 | A2 | 12/2015 |
| WO | WO-2016042162 | A1 | 3/2016 |
| WO | WO-2016042163 | A2 | 3/2016 |
| WO | WO-2017192565 | A1 | 11/2017 |
| WO | WO-2022076938 | A1 | 4/2022 |
| WO | WO-2024015652 | A1 | 1/2024 |

OTHER PUBLICATIONS

Al-Shaikh, B. et al., 2007, "Essentials of Anaesthetic Equipment," Edinburgh: Churchill Livingstone, 3rd Edition, 7 pages.

Amaratunga, A. et al., "Inhibition of Kinesin Synthesis and Rapid Anterograde Axonal Transport in Vivo by an Antisense Oligonucleotide," The Journal of Biological Chemistry, Aug. 1993, vol. 268, No. 23, pp. 17427-17430.

Anthem, USA, "Medical Policy. Suprachoroidal Injection of a Pharmacologic Agent," Last Review Date: Nov. 14, 2013, [online]. Retrieved from the Internet: URL: http://www.anthem.com/medicalpolicies/policies/mp_pw_b076412.htm. Retrieved from the Internet on: Oct. 24, 2014, American Medical Association, 3 pages.

Beer, P. J. et al., "Photographic Evidence of Vitreous Wicks After Intravitreal Injections," Retina Today, 2(2):24-39 (Mar. 2007).

Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lympholization Techniques," Invest Ophthalmol Vis Sci., 51:E-Abstract 5330 (2010), 2 pages.

Bunnelle, E., "Syringe Diameters," [online] 2005. Cchem.berkeley.edu. Available at: http://www.cchem.berkeley.edu/rsgrp/Syringediameters.pdf [Accessed Mar. 11, 2022], 3 pages.

Careforde Healthcare, B Braun Glass Loss-Of-Resistance Syringes # 332158—10cc Glass Loss-Of-Resistance Syringe, Luer Slip Metal Tip, 10/cs, (2014), 2 pages.

Careforde Inc., Careforde Healthcare, Chicago, IL, "B Braun Glass Loss-Of-Resistance Syringes # 332155—5cc Glass Loss-Of-Resistance Syringe, Luer Lock Metal Tip, 10/cs," [online]. Retrieved from the Internet: http://careforde.com/b-braun-glass-loss-of-resistance-syringes-332155-5cc-glass-loss-of-resistance-syringe-luer-lock-metal-tip-10-cs/. Retrieved from the Internet on: Oct. 16, 2014, (2014), 2 pages.

Careforde Inc., Careforde Healthcare, Chicago, IL, "B Braun Perifix Plastic Loss-Of-Resistance Syringes # 332152—8cc Plastic Luer Lock Loss-of-Resistance Syringe, 50/cs," [online]. Retrieved from the Internet: http://careforde.com/b-braun-perifix-plastic-loss-of-resistance-syringes-332152-8cc-plastic-luer-lock-loss-of-resistance-syringe-50-cs/. Retrieved from the Internet on: Oct. 16, 2014, (2014), 2 pages.

Choy, Y. B. et al., "Mucoadhesive microdiscs engineered for ophthalmic drug delivery: effect of particle geometry and formulation on preocular residence time," Investigative Ophthalmology & Visual Science, 49:4808-4815 (2008).

Dinning, W. J., "Steroids and the eye-indications and complications," Postgraduate Medical Journal, vol. 52, 1976, pp. 634-638.

Dogliotti, A. M., "Research and Clinical Observations on Spinal Anesthesia: With Special Reference to the Peridural Technique," Current Researches in Anesthesia & Analgesia, Mar.-Apr. 1933, vol. 12, Issue 2, pp. 59-65.

Edwards, A. et al., "Fiber matrix model of sclera and corneal stroma for drug delivery to the eye," AIChE Journal, 44(1):214-225 (1998).

Einmahl, et al., "Evaluation of a novel biomaterial in the suprachoroidal space of the rabbit eye" Investigative Ophthalmology & Visual Science, vol. 43, Issue 5, 2002, pp. 1533-1539.

Einmahl, S et al., "Ocular biocompatibility of a poly(ortho ester) characterized by autocatalyzed degradation," J. Biomed. Mater. Res., 67(1):44-53 (2003).

"Epidural," Wikipedia [online], retrieved from the internet on Sep. 3, 2014, URL: http:/en.wikipedia.org/wiki/Epidural, 21 pages.

Examination Report for Indian Application No. 201917009102, mailed Jul. 16, 2021, 6 pages.

Examination Report for Singapore Application No. 11201509051V, dated Feb. 1, 2017, 4 pages.

Examination Report No. 1 for Australian Application No. 2014259694, dated May 24, 2018, 2 pages.

Examination Report No. 1 for Australian Application No. 2015230874, dated Jul. 28, 2017, 11 pages.

Extended European Search Report for European Application No. 07751620.1, mailed Jan. 15, 2013, 10 pages.

Extended European Search Report for European Application No. 11777924.9, mailed Feb. 4, 2015, 7 pages.

Extended European Search Report for European Application No. 13833318.2, dated Apr. 1, 2016, 7 pages.

Extended European Search Report for European Application No. 14791646.4, dated Nov. 21, 2016, 6 pages.

Extended European Search Report for European Application No. 17880800.2, mailed Jun. 2, 2020, 13 pages.

Extended European Search Report for European Application No. 18176149.5, mailed Jan. 22, 2019, 10 pages.

Extended European Search Report for European Application No. 18176172.7, mailed Feb. 6, 2019, 11 pages.

Extended European Search Report for European Application No. 18199418.7, mailed Jul. 5, 2019, 9 pages.

Feldkamp, L. A. et al., "Practical cone-beam algorithm," J. Opt. Soc. Am. A, 1(6):612-619 (1984).

Final Office Action for U.S. Appl. No. 17/711,495 dated Jan. 17, 2023, 36 pages.

Final Rejection Office Action for U.S. Appl. No. 16/178,162 mailed on May 16, 2022, 55 pages.

Final Rejection Office Action for U.S. Appl. No. 17/523,168 mailed on Aug. 30, 2022, 20 pages.

First Examination Report for Indian Application No. 10270/DELNP/2015, mailed Apr. 5, 2021, 7 pages.

First Examination Report for Indian Application No. 3345/KOLNP/2008, dated May 21, 2015, 3 pages.

First Office Action for Chinese Application No. 200780014501.3, dated Mar. 11, 2010, 6 pages.

First Office Action for Chinese Application No. 201110093644.6, dated Mar. 26, 2012, 11 pages.

(56) References Cited

OTHER PUBLICATIONS

First Office Action for Chinese Application No. 201180060268.9, issued Oct. 10, 2014, 9 pages.
First Office Action for Chinese Application No. 201480025034.4, dated Apr. 24, 2018, 10 pages.
First Office Action for Chinese Application No. 201510144330.2, issued Apr. 5, 2016, 17 pages.
First Office Action for Chinese Application No. 201610805842.3, issued Jul. 21, 2017, 4 pages.
First Office Action for Chinese Application No. 201780062253.3, mailed Dec. 25, 2020, 22 pages.
First Office Action for Chinese Application No. 201910430078.X, issued Feb. 1, 2021, 8 pages.
Furrer, P. et al., "Ocular tolerance of preservatives and alternatives," European Journal of Pharmaceutics and Biopharmaceutics, 53(3):263-280 (2002).
Geroski, D. H. et al., "Drug delivery for posterior segment eye disease," Invest. Ophthalmol. Vis. Sci., 41(5):961-964 (2000).
Gilger, et al., "A Novel Bioerodible Deep Scleral Lamellar Cyclosporine Implant for Uveitis," Invest Ophthalmol Vis Sci, vol. 47, Issue 6, 2006, pp. 2596-2605.
Habib, A. S. et al., "The AutoDetect Syringe Versus the Glass Syringe for the Loss of Resistance Technique in Parturients," Duke University Medical Center, Durham, North Carolina, Oct. 2007, 2 pages.
Haller, J. A., "Intraocular Steroids in the Office. New formulations offer preservative-free triamcinolone without relying on compounding pharmacies," Retinal Physician [online]. Retrieved from the Internet: URL: https://www.retinalphysician.com/supplements/2009/february-2009/special-edition/intraocular-steroids-in-the-office, Feb. 1, 2009, 4 pages.
Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E-Abstract 3710, ARVO (2002), 2 pages.
Harvardapparatus.com. 2011. Syringe Selection Guide. [online] Available at: https://www.harvardapparatus.com/media/harvard/pdf/Syringe%20Selection%20Guide.pdf , [Accessed Mar. 11, 2022], 4 pages.
Heller, J., Ocular delivery using poly(ortho esters), Adv. Drug. Deliv. Rev., 57(14):2053-2062 (2005).
Hogan et al., Chapter Eight, Choroid, In Histology of the Human Eye, 9 pages (1971).
HomeCEU, "How Does Iontophoresis Work?", [Online], Retrieved from the Internet: https://www.homeceuconnection.com/blog/how-does-iontophoresis-work/, 2018, 5 pages.
International Preliminary Report on Patentability for International Application No. PCT/US2021/054395 dated Apr. 20, 2023, 11 pages.
International Search Report and Written Opinion for International Application No. PCT/US2007/004874, mailed Jun. 4, 2008, 6 pages.
International Search Report and Written Opinion for International Application No. PCT/US2007/068055, mailed Nov. 7, 2007, 13 pages.
International Search Report and Written Opinion for International Application No. PCT/US2011/033987, mailed Feb. 14, 2012, 7 pages.
International Search Report and Written Opinion for International Application No. PCT/US2011/056433, mailed Apr. 25, 2012, 17 pages.
International Search Report and Written Opinion for International Application No. PCT/US2013/056863, mailed Nov. 26, 2013, 8 pages.
International Search Report and Written Opinion for International Application No. PCT/US2014/036590, mailed Dec. 10, 2014, 10 pages.
International Search Report and Written Opinion for International Application No. PCT/US2015/036715, mailed Jan. 19, 2016, 9 pages.
International Search Report and Written Opinion for International Application No. PCT/US2017/030609, mailed Oct. 6, 2017, 12 pages.
International Search Report and Written Opinion for International Application No. PCT/US2017/046553, mailed Dec. 13, 2017, 14 pages.
International Search Report and Written Opinion for International Application No. PCT/US2017/065796, mailed Apr. 12, 2018, 9 pages.
International Search Report and Written Opinion for International Application No. PCT/US2021/054395, mailed Mar. 14, 2022, 16 pages.
Invitation pursuant to Article 94(3) and Rule 71(1) for European Application No. 07751620.1, mailed Feb. 29, 2016, 3 pages.
Invitation to Pay Additional Fees for International Application No. PCT/US2021/054395, mailed Dec. 8, 2021, 4 pages.
Invitation to Respond to Written Opinion for Singapore Application No. 200805936-2, dated Oct. 15, 2012, 7 pages.
Jain, A., "Pseudo loss of resistance in epidural space localization: A complication of subcutaneous emphysema or simply a faulty technique," Saudi J. Anaseth, 5(1):108-109 (2011) (Abstract).
Jiang, J. et al., "Coated Microneedles for Drug Delivery to the Eye," Investigative Ophthalmology & Visual Science, 48(9):4038-4043 (2007).
Jiang, J et al., "Intrascleral drug delivery to the eye using hollow microneedles," Pharmaceutical Research, 26(2):395-403 (2009).
Jiang, J. et al., "Measurement and Prediction of Lateral Diffusion within Human Sclera," Investigative Ophthalmology & Visual Science, 47(7):3011-3016 (2006).
Karim, R. et al., "Interventions for the treatment of uveitic macular edema: a systematic review and meta-analysis," Clinical Ophthalmology, 7:1109-1144 (2013).
Kim, S. H. et al., "Assessment of Subconjunctival and Intrascleral Drug Delivery to the Posterior Segment Using Dynamic Contrast-Enhanced Magnetic Resonance Imaging," Invest Ophthalmol Vis Sci, vol. 48, No. 2, Feb. 2007, pp. 808-814.
Lee, C. H. et al., "Thixotropic property in pharmaceutical formulations," Journal of Controlled Release (2009) 136:88-98.
Lee, S-B et al., "Drug delivery through the sclera: effects of thickness, hydration and sustained release systems," Experimental Eye Research, 78:599-607 (2004).
Lindfield, D. et al., "Suprachoroidal Devices in Glaucoma. The Past, Present, and Future of Surgery for Suprachoroidal Drainage," Cataract & Refractive Surgery Today Europe, [online], Oct. 2013, Retrieved from the Internet: URL: http://bmctoday.net/crstodayeurope/2013/10/article.asp?f=suprachoroidal-devices-in-glaucoma. Retrieved from the Internet on: Oct. 24, 2014, Bryn Mawr Communications LLC, Wayne, PA, USA, 3 pages.
Loewen, N., "The suprachoroidal space in glaucoma surgery," Jul. 2012, 4 pages.
Mansoor, S. et al., "Pharmacokinetics and Biodistribution of Triamcinolone Acetonide Following Suprachoroidal Injection into the Rabbit Eye In Vivo Using a Microneedle," Investigative Ophthalmology & Visual Science, ARVO Annual Meeting Abstract, Apr. 2011, vol. 52, 6585, 2 pages.
Maurice, D., "Review: Practical Issues in Intravitreal Drug Delivery," J. Ocul. Pharmacol. Ther., 17(4):393-401 (2001).
McAllister, D. V. et al., "Microfabricated needles for transdermal delivery of macromolecules and nanoparticles: Fabrication methods and transport studies," Proceedings of the Natural Academy of Science, vol. 100, No. 24, 2003, pp. 13755-13760.
Non-Final Office Action for U.S. Appl. No. 17/208,235 dated Aug. 21, 2023, 20 pages.
Non-Final Office Action for U.S. Appl. No. 17/711,495 mailed on Sep. 7, 2022, 26 pages.
Non-Final Office Action for U.S. Appl. No. 17/711,495, filed Aug. 2, 2022, 15 pages.
Norman, D., Epidural analgesia using loss of resistance with air versus saline: Does it make a difference? Should we reevaluate our practice?, AANA Journal, 71(6):449-453 (Dec. 2003).
Notice of Opposition for European Application No. 14791646.4, dated Mar. 29, 2022, 38 pages.

(56) References Cited

OTHER PUBLICATIONS

Notice of Reasons for Rejection for Japanese Application No. 2016-068174, mailed Mar. 1, 2017, 8 pages.
Notice of Reasons for Rejection for Japanese Application No. 2016-512068, mailed Mar. 26, 2018, 4 pages.
Notice of Reasons for Rejection for Japanese Application No. 2018-142345, mailed Jun. 6, 2019, 6 pages.
Notice of Reasons for Rejection for Japanese Application No. 2018-557826, mailed Mar. 29, 2021, 13 pages.
Notification of Reason for Rejection for Japanese Application No. 2008-556462, dated Jul. 24, 2012, 15 pages.
Notification of Reason(s) for Rejection for Japanese Application No. 2013-534049, mailed Sep. 1, 2015, 11 pages.
Office Action for Brazilian Application No. 112012027416-3, mailed Nov. 14, 2021, 4 pages.
Office Action for Brazilian Application No. 112015027762-4, dated Jan. 28, 2022, 19 pages.
Office Action for Brazilian Application No. PI 0708133-2, dated Feb. 26, 2019, 11 pages.
Office Action for Canadian Application No. 2797258, dated Nov. 21, 2016, 3 pages.
Office Action for Canadian Application No. 2,882,184, dated Aug. 18, 2020, 3 pages.
Office Action for Canadian Application No. 2,882,184, dated Jan. 24, 2020, 6 pages.
Office Action for Canadian Application No. 2,882,184, dated May 1, 2019, 3 pages.
Office Action for Canadian Application No. 2,911,290, dated Jun. 18, 2020, 5 pages.
Office Action for Canadian Application No. CA20173062845 mailed Jul. 21, 2023, 4 pages.
Office Action for Chinese application No. CN201910430078, mailed on Jul. 7, 2022, 7 pages.
Office Action for Eurasian Application No. 201592109, mailed Apr. 1, 2016, 4 pages.
Office Action for Eurasian Application No. 201592109, mailed Jan. 31, 2018, 2 pages.
Office Action for European Application No. 07751620.1, dated Dec. 11, 2014, 5 pages.
Office Action for European Application No. 07751620.1, dated Sep. 13, 2013, 7 pages.
Office Action for European Application No. 11776049.6, mailed Oct. 25, 2016, 4 pages.
Office Action for European Application No. 11777924.9, mailed Oct. 1, 2019, 5 pages.
Office Action for European Application No. 13833318.2, dated Apr. 20, 2021, 4 pages.
Office Action for European Application No. 13833318.2, dated Aug. 26, 2020, 5 pages.
Office Action for European Application No. 14791646.4, dated Dec. 4, 2017, 5 pages.
Office Action for European Application No. 14791646.4, dated Feb. 11, 2020, 5 pages.
Office Action for European Application No. 14791646.4, dated Sep. 17, 2018, 5 pages.
Office Action for European Application No. 17755007.6, mailed Jun. 25, 2021, 6 pages.
Office Action for European Application No. 17880800.2, mailed Apr. 14, 2022, 10 pages.
Office Action for European Application No. 18176172.7, mailed Feb. 7, 2020, 4 pages.
Office Action for European Application No. 18199418.7, mailed May 18, 2022, 5 pages.
Office Action for European Application No. 18199418.7, mailed Nov. 10, 2020, 5 pages.
Office Action for European Application No. EP20180199418 dated Apr. 13, 2023, 04 pages.
Office Action for Indian Application No. 10099/DELNP/2012, mailed Jul. 2, 2019, 5 pages.
Office Action for Israel application No. I286808, mailed on Oct. 20, 2022, 7 pages.
Office Action for Israeli Application No. 242395, dated Aug. 10, 2020, 12 pages.
Office Action for Israeli Application No. 242395, dated May 7, 2019, 7 pages.
Office Action for Israeli Application No. 264764, dated Feb. 28, 2022, 7 pages.
Office Action for Korean Application No. 10-2015-7034411, dated Nov. 16, 2020, 8 pages.
Office Action for Mexican Application No. MX20180013502 mailed Aug. 4, 2023, 3 pages.
Office Action for Mexican Application No. MX/a/2015/015282, dated May 15, 2019, 8 pages.
Office Action for New Zealand Application No. 714172, dated Dec. 12, 2018, 3 pages.
Office Action for New Zealand Application No. 714172, dated Feb. 1, 2018, 4 pages.
Office Action for New Zealand Application No. 714172, dated Jul. 24, 2018, 4 pages.
Office Action for U.S. Appl. No. 11/709,941, mailed Apr. 12, 2016, 25 pages.
Office Action for U.S. Appl. No. 11/709,941, mailed Dec. 14, 2018, 17 pages.
Office Action for U.S. Appl. No. 11/709,941, mailed Dec. 27, 2016, 28 pages.
Office Action for U.S. Appl. No. 11/709,941, mailed Feb. 11, 2015, 14 pages.
Office Action for U.S. Appl. No. 11/709,941, mailed Jan. 16, 2018, 32 pages.
Office Action for U.S. Appl. No. 11/709,941, mailed Jun. 24, 2014, 11 pages.
Office Action for U.S. Appl. No. 11/709,941, mailed Mar. 23, 2011, 9 pages.
Office Action for U.S. Appl. No. 11/709,941, mailed Oct. 27, 2011, 8 pages.
Office Action for U.S. Appl. No. 11/743,535, mailed Aug. 19, 2010, 7 pages.
Office Action for U.S. Appl. No. 11/743,535, mailed Dec. 29, 2009, 6 pages.
Office Action for U.S. Appl. No. 12/767,768, mailed Jun. 10, 2011, 5 pages.
Office Action for U.S. Appl. No. 13/273,775, mailed Feb. 12, 2015, 13 pages.
Office Action for U.S. Appl. No. 13/273,775, mailed Jul. 3, 2014, 12 pages.
Office Action for U.S. Appl. No. 13/447,246, mailed Oct. 28, 2013, 5 pages.
Office Action for U.S. Appl. No. 13/453,407, mailed Mar. 20, 2013, 5 pages.
Office Action for U.S. Appl. No. 13/842,218, mailed Jul. 5, 2016, 11 pages.
Office Action for U.S. Appl. No. 13/842,288, mailed Oct. 6, 2015, 10 pages.
Office Action for U.S. Appl. No. 14/136,657, mailed Dec. 16, 2016, 7 pages.
Office Action for U.S. Appl. No. 14/268,687, mailed May 19, 2016, 6 pages.
Office Action for U.S. Appl. No. 14/424,685, mailed Dec. 12, 2016, 15 pages.
Office Action for U.S. Appl. No. 14/424,685, mailed Jun. 10, 2016, 10 pages.
Office Action for U.S. Appl. No. 14/523,243, mailed Feb. 27, 2015, 14 pages.
Office Action for U.S. Appl. No. 14/821,310, mailed Jul. 14, 2017, 11 pages.
Office Action for U.S. Appl. No. 15/398,538, mailed Apr. 16, 2019, 8 pages.
Office Action for U.S. Appl. No. 15/398,538, mailed Jul. 20, 2018, 12 pages.
Office Action for U.S. Appl. No. 15/619,065, mailed Jan. 28, 2020, 24 pages.

(56) References Cited

OTHER PUBLICATIONS

Office Action for U.S. Appl. No. 15/619,065, mailed Jun. 11, 2021, 18 pages.
Office Action for U.S. Appl. No. 15/619,065, mailed Jun. 13, 2019, 30 pages.
Office Action for U.S. Appl. No. 15/619,065, mailed Nov. 27, 2020, 23 pages.
Office Action for U.S. Appl. No. 15/675,035, mailed Jun. 11, 2020, 14 pages.
Office Action for U.S. Appl. No. 15/708,779, mailed Jul. 15, 2019, 8 pages.
Office Action for U.S. Appl. No. 15/872,206, mailed May 1, 2020, 8 pages.
Office Action for U.S. Appl. No. 15/872,206, mailed Oct. 19, 2020, 9 pages.
Office Action for U.S. Appl. No. 15/946,838, mailed Jun. 27, 2019, 7 pages.
Office Action for U.S. Appl. No. 16/178,162, mailed Jun. 10, 2020, 18 pages.
Office Action for U.S. Appl. No. 16/178,162, mailed May 11, 2021, 48 pages.
Office Action for U.S. Appl. No. 16/381,213, mailed May 31, 2019, 7 pages.
Office Action for U.S. Appl. No. 16/591,067, mailed Nov. 18, 2019, 7 pages.
Office Action for U.S. Appl. No. 16/826,443, mailed Jun. 1, 2020, 6 pages.
Office Action for U.S. Appl. No. 17/217,455, mailed Jun. 23, 2021, 13 pages.
Office Action for U.S. Appl. No. 17/217,455, mailed Oct. 21, 2021, 15 pages.
Office Action for U.S. Appl. No. 17/523,168, mailedMar. 7, 2022, 11 pages.
Olsen, T., "Drug Delivery to the Suprachoroidal Space Shows Promise," Retina Today, pp. 36-39 (Mar/Apr. 2007).
Olsen, T. W. et al., "Cannulation of the Suprachoroidal Space: A Novel Drug Delivery Methodology to the Posterior Segment," American J. Opthamology, 142(5):777-787 (2006).
Partial European Search Report for European Application No. 18176172.7, mailed Oct. 30, 2018, 13 pages.
Patel, S. et al., "Drug Binding to Sclera," Invest Ophthalmol Vis Sci., 50:E-Abstract 5968 (2009), 2 pages.
Patel, S. et al., "Suprachoroidal Drug Delivery Using Microneedles," Invest. Ophthalmol. Vis. Sci., 49:E-Abstract 5006 (2008), 2 pages.
Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.
Patel, S. R. et al., "Targeted administration into the suprachoroidal space using a microneedle for drug delivery to the posterior segment of the eye," Investigative Ophthalmology & Visual Science, 53(8):4433-4441 (Jul. 2012).
Patel, S. R., "Suprachoroidal drug delivery to the eye using hollow microneedles," Dissertation, Georgia Institute of Technology, May 2011, 177 pages.
Penkov, M. A. et al., "A ten-year experience with usage of the method of supra-choroidal administration of medicinal substances," Oftalmol. Zh., 35(5):281-285 (1980) (Translated from Russian).
Prausnitz, et al., "Permeability of Cornea, Sclera, and Conjunctiva: A Literature Analysis for Drug Delivery to the Eye", Journal of Pharmaceutical Sciences, vol. 87, Issue 12, 1998, pp. 1479-1488.
Prausnitz, M. R. et al., "Measurement and prediction of transient transport across sclera for drug delivery to the eye," Industrial and Engineering Chemistry Research, 37(8):2903-2907 (1998).
Prausnitz, M. R., "Microneedles for Ocular Drug Delivery," Review of Olsen, T., Drug Delivery to the Suprachoroidal Space Shows Promise, Retina Today, Mar./Apr. 2007, p. 39.
Preliminary Office Action for Brazilian Application No. 112012027416-3, mailed Jul. 11, 2021, 2 pages.
Preliminary Office Action for Brazilian Application No. 112015027762-4, dated Jan. 17, 2020, 6 pages.
Preliminary Rejection for Korean Application No. 10-2021-7023167, dated Aug. 17, 2021, 7 pages.
Rowe-Rendleman, C. L. et al., "Prophylactic Intra-Scleral Injection of Steroid Compounds in Rabbit Model of Retinal Neovascularization," Invest Ophthalmol Vis. Sci.,43:E-Abstract 3872, ARVO (2002), 2 pages.
Saberski, L. R. et al., "Identification of the epidural space: Is loss of resistance to air a safe technique? A review of the complications related to the use of air," Regional Anesthesia, 22(1):3-15 (1997).
Search Report and Written Opinion for Singapore Application No. 11201509051V, dated Nov. 2, 2016, 6 pages.
Search Report and Written Opinion for Singapore Application No. 200805936-2, dated Jun. 8, 2010, 13 pages.
Second Office Action for Chinese Application No. 200780014501.3, dated Aug. 26, 2010, 10 pages.
Second Office Action for Chinese Application No. 201110093644.6, dated Sep. 7, 2012, 8 pages.
Second Office Action for Chinese Application No. 201180060268.9, issued Jun. 18, 2015, 4 pages.
Second Office Action for Chinese Application No. 201510144330.2, issued Dec. 20, 2016, 13 pages.
Second Office Action for Chinese Application No. 201910430078.X, issued Aug. 18, 2021, 5 pages.
Shuler, R. K. et al., "Scleral Permeability of a Small, Single-Stranded Oligonucleotide," Journal of Ocular Pharmacology and Therapeutics, 20(2): 159-168 (2004) (Abstract).
Stein, L. et al., "Clinical gene therapy for the treatment of RPE65-associated Leber congenital amaurosis," Expert Opin. Biol. Ther., Mar. 2011, vol. 11, No. 3, pp. 429-439.
Summons to Attend Oral Proceedings Pursuant to Rule 115(1) EPC for European Application No. 07751620.1, mailed Jun. 13, 2017, 8 pages.
Supplementary Search Report for Singapore Application No. 200805936-2, dated May 26, 2011, 8 pages.
Supplementary Search Report for Singapore Application No. 200805936-2, dated May 6, 2011, 8 pages.
Syringepump.com. 2012. NE-300 Just Infusion™ Syringe Pump. [online] Available at: https://www.syringepump.com/download/NE-300Brochure.pdf [Accessed Mar. 11, 2022], 5 pages.
Third Office Action for Chinese Application No. 201110093644.6, dated Dec. 14, 2012, 3 pages.
Third Office Action for Chinese Application No. 201180060268.9, issued Feb. 5, 2016, 6 pages.
Third Office Action for Chinese Application No. 201510144330.2, issued Jun. 28, 2017, 3 pages.
Third Office Action for Chinese Application No. 201910430078.X, issued Mar. 29, 2022, 12 pages.
Wang, P. M. et al., "Minimally Invasive Extraction of Dermal Interstitial Fluid for Glucose Monitoring Using Microneedles," Diabetes Technology & Therapeutics, 7(1):131-141 (2005).
You, X. D. et al., "Chitosan drug delivery system implanting into suprachoroidal space for perforating ocular injury in rabbits," International Journal of Ophthalmology, 5(1):74-76 (2005) [English Abstract].
Anonymous, "Pocket Guide: The Beauty of Diversity in Science and Nature," Arvo 2023, New Orleans, LA, Apr. 23-27, 2023, 84 pages.
EP Application No. 14808034.4, Extended European Search Report mailed Jan. 23, 2017; Applicant Clearside Biomedical, Inc.; 7 pages.
EP Application No. 21878692.9, Extended European Search Report mailed Jul. 12, 2024; Applicant Clearside Biomedical, Inc.; 8 pages.
EP Application No. EP24151456.1, Extended European Search Report mailed Jun. 3, 2024; Applicant Clearside Biomedical, Inc.; 7 pages.
Habot-Wilner et al., "Suprachoroidally Injected Pharmacological Agents for the Treatment of Chorio-retinal Diseases: a Targeted Approach," Acta Ophthalmologica, Aug. 2019, vol. 97, No. 5, pp. 460-472.
Kansara et al., "Suprachoroidal Delivery of Cls-301, a Potent Small Molecule Integrin Antagonist, Offers Multimonth Durability and High Bioavailability in the Chorioretina," IOVS ARVO Journals Investigative Ophthalmology & Visual, Jun. 2023, vol. 64, No. 8, pp. 1-2.

(56) References Cited

OTHER PUBLICATIONS

PCT Application No. PCT/US2024/025876, International Search Report and Written Opinion mailed Jul. 19, 2024; Applicant Clearside Biomedical, Inc.; 11 pages.
Vanhove, et al., "Systemic Exposure Following Intravitreal Administration of Therapeutic Agents: an Integrated Pharmacokinetic Approach. 1. Thr-149," Journal of Pharmacokinetics and Pharmacodynamics, Dec. 2021, vol. 48, No. 6, pp. 825836.

* cited by examiner

2600

2600

APPARATUS AND METHODS OF RETINAL INJECTION

CROSS-REFERENCE TO RELATED APPLICATIONS

This application is a continuation-in-part of International Patent Application No. PCT/US2021/054395, filed Oct. 11, 2021, entitled "Apparatus and Methods of Retinal Injection," which claims priority to and the benefit of U.S. Provisional Application No. 63/115,654, filed Nov. 19, 2020, entitled "Apparatus and Methods of Retinal Injection," and U.S. Provisional Application No. 63/089,829, filed Oct. 9, 2020, entitled "Apparatus and Methods of Retinal Injection," the disclosures of which are hereby incorporated by reference in their entireties.

This application also claims priority to and the benefit of U.S. Provisional Application No. 63/330,613 filed Apr. 13, 2022, entitled "Apparatus and Methods of Retinal Injection," the disclosure of which is hereby incorporated by reference in its entirety.

BACKGROUND

Embodiments described herein relate to systems and methods of retinal injection. Systems and methods described herein can be employed in non-surgical and/or minimally invasive procedures (e.g., in an office setting, without surgical imaging, etc.). Retinal injection has several uses in the medical industry, including injection of pharmaceutical agents. In terms of size and dimensions, each eye is different. The total size of an eye may differ from patient to patient. Additionally, the thicknesses, density, and other characteristics of various tissue layers (e.g., choroid, retina) in the eye may vary from one patient to another. This variability in tissue layer size, for example, can make it difficult to standardize tooling or methods when precisely injecting into a region of the eye. If using the outermost surface of the eye or a region external to the eye as a reference point, it can be difficult to efficiently and accurately locate a specific tissue or tissue interface in the eye. Therefore, an important industrial advancement to be made is a system and/or a method of effectively targeting a retinal region of an eye.

SUMMARY

Embodiments described herein relate to systems and methods of retinal injection. In some aspects, a method includes inserting a distal end portion of a hollow conduit of a medical injector into an eye of a patient until the distal end portion reaches a reference location, the medical injector having a housing from which the hollow conduit distally extends and confirming positioning of the distal end portion of the hollow conduit in the reference location. After the confirming, the method further includes extending the distal end portion of the hollow conduit distally relative to the housing and from the reference location such that the distal end portion enters an injection region of the eye. With the distal end portion of the hollow conduit disposed in the injection region of the eye, medicament is conveyed into the injection region via the hollow conduit.

In some embodiments, the reference location can be a suprachoroidal space (SCS) of the eye.

In some embodiments, the injection region can be between the SCS and a boundary layer between a retinal layer and vitreous space of the eye.

In some embodiments, extending the distal end portion of the hollow conduit includes extending the distal end portion of the hollow conduit between about 50 micrometers and about 5 mm.

In some embodiments, confirming positioning of the distal end portion of the hollow conduit in the reference location can include sensing a pressure differential within the reference location.

In some embodiments, confirming positioning of the distal end portion of the hollow conduit in the reference location can include measuring a pressure within the reference location, the pressure meeting a predetermined threshold pressure.

In some embodiments, confirming positioning of the distal end portion of the hollow conduit in the reference location can include measuring a light emissivity gradient between a sclera of the eye and a retinal pigment epithelium or choroid of the eye.

In some embodiments, the inserting is performed such that a centerline of the hollow conduit and a surface line tangential to a target surface of the eye can define an angle of entry of between about 0 degrees and about 180 degrees.

In some embodiments, the medicament can be at least one of a gene therapy, a VEGF, a VEGF inhibitor, a PDGFR inhibitor, a tyrosine kinase inhibitor, a complement inhibitor, an integrin inhibitor, a plasma kallikrein inhibitor, an angiopoietin-2 inhibitor, a Tie-2 agonist, or a combination thereof.

In some embodiments, the medicament can comprise an integrin inhibitor, axitinib, MK-409, or aflibercept.

In some embodiments, the gene therapy can comprise a nucleic acid.

In some embodiments, the nucleic acid can be DNA or RNA.

In some embodiments, the nucleic acid can be transcribed to form an anti-sense transcript, wherein the anti-sense transcript inhibits synthesis of an endogenous protein.

In some embodiments, the nucleic acid can comprise a gene sequence and a promoter sequence.

In some embodiments, the nucleic acid can be translated to express a protein.

In some embodiments, the protein can be selected from a VEGF, a VEGF inhibitor, a PDGFR inhibitor, a tyrosine kinase inhibitor, a complement inhibitor, an integrin inhibitor, a plasma kallikrein inhibitor, an angiopoietin-2 inhibitor, a Tie-2 agonist, or a combination thereof.

In some embodiments, the gene therapy comprises a nucleic acid and a non-viral nanoparticle or a viral vector.

In some aspects, a method comprises inserting a distal end portion of a hollow conduit of a medical injector a first distance into an eye of a patient, the hollow conduit being in fluidic communication with a medicament container, the medicament container including a medicament, monitoring pressure in at least one of the hollow conduit or the medicament container to detect a change in pressure, and confirming positioning of the distal end portion of the hollow conduit in a first region of the eye, the first region being proximal to the retina of the eye, based on the detection of the change in pressure. After confirming positioning of the distal end portion of the hollow conduit in the first region of the eye, the method can include inserting the distal end portion of the hollow conduit a second distance into a region between the SCS and a boundary layer between a retinal layer and vitreous space of the eye, and with the distal end portion of the hollow conduit into the retina of the eye, injecting at least a portion of the medicament into the region between the SCS and the boundary layer between the retinal layer and vitreous space via the hollow conduit.

In some embodiments, the second distance can be between about 50 micrometers and about 5 mm.

In some embodiments, the change in pressure can be a drop in pressure. In some embodiments, the change in pressure meets a predefined threshold pressure drop of at least about 5 mmHg.

In some embodiments, the first region of the eye is in the SCS, between the sclera and the choroid of the eye.

In some aspects, a method comprises inserting a distal end portion of a hollow conduit of a medical injector a first distance into an eye of a patient, the hollow conduit being in fluidic communication with a medicament container, the medicament container including a medicament, monitoring light emissivity in the anatomical location at the distal end portion of the hollow conduit, and confirming positioning of the distal end portion of the hollow conduit in a first region of the eye, the first region being proximal to the retina of the eye, based on a light emissivity gradient between a sclera of the eye and a retinal pigment epithelium of the eye. After confirming positioning of the distal end portion of the hollow conduit in the first region of the eye, the method can include inserting the distal end portion of the hollow conduit a second distance into a region between the SCS and a boundary layer between a retinal layer and vitreous space of the eye, and with the distal end portion of the hollow conduit into the retina of the eye, injecting at least a portion of the medicament into the region between the SCS and the boundary layer between the retinal layer and vitreous space via the hollow conduit.

In some embodiments, the second distance can be between about 50 micrometers and about 5 mm.

In some embodiments, the method can include monitoring pressure in at least one of the hollow conduit or the medicament container to detect a change in pressure.

In some embodiments, inserting the distal end portion of the hollow conduit the second distance into the region between the SCS and the boundary layer between the retinal layer and vitreous space of the eye can be manual.

In some embodiments, inserting the distal end portion of the hollow conduit the second distance into the region between the SCS and the boundary layer between the retinal layer and vitreous space of the eye can be automatic.

In some embodiments, inserting the distal end portion of the hollow conduit the second distance into the region between the SCS and the boundary layer between the retinal layer and vitreous space of the eye is via a motor or mechanical assistance.

In some aspects, an apparatus can include a housing, the housing including an actuator and a hollow conduit, the hollow conduit having a distal end, the actuator configured to advance the hollow conduit from a first position to a second position relative to the housing, a measurement device configured to measure a physical property at the distal end of the hollow conduit, and an injection controller including an inner volume fluidically coupled to the hollow conduit, the injection controller configured to deliver a medicament from the inner volume to the distal end of the hollow conduit.

In some embodiments, the measurement device can include a pressure measurement device configured to measure a pressure at the distal end of the hollow conduit.

In some embodiments, the pressure measurement device can be a manometer in fluidic communication with the hollow conduit.

In some embodiments, the measurement device includes a light emissivity measurement device.

In some embodiments, the light emissivity measurement device can include an emitter, a receiver, and a fiber optic cable, the fiber optic cable running from the distal end of the hollow conduit to the receiver.

In some embodiments, the pressure device is a manometer, and the apparatus can further include a puncture cap coupled to the housing, the puncture cap configured to be punctured by a spike to create a fluidic coupling between the manometer and the inner volume of the injection controller.

In some embodiments, the manometer can be fluidically coupled to the inner volume of the injection controller via one or more pressure tubes.

In some embodiments, the distal end of the hollow conduit can be beveled, such that the hollow conduit includes a beveled surface.

In some embodiments, a centerline of the hollow conduit and a line extending distally from the beveled surface can be between about 30 degrees and about 60 degrees.

In some aspects, an apparatus includes a housing, the housing including a vacuum space and hollow conduit, the hollow conduit having a distal end. The apparatus includes a vacuum handle, the vacuum handle configured to reduce pressure in the vacuum space and pull layers of an eye toward the distal end of the hollow conduit and secure the layers of the eye to prevent lateral movements of a retina and/or a choroid relative to a sclera. The apparatus includes a measurement device configured to measure a physical property at the distal end of the hollow conduit and an injection controller including an inner volume fluidically coupled to the hollow conduit, the injection controller configured to deliver a medicament from the inner volume to the distal end of the hollow conduit.

In some aspects, an apparatus includes a housing with a pressurized space and hollow conduit, the hollow conduit having a distal end. The apparatus includes a measurement device configured to measure a physical property at the distal end of the hollow conduit. The apparatus further includes an injection controller including an inner volume fluidically coupled to the hollow conduit, the injection controller configured to deliver a medicament from the inner volume to the distal end of the hollow conduit. The pressurized space is in physical contact with the injection controller and is configured to maintain a constant pressure while advancing the injection controller.

In some aspects, an apparatus includes a housing, the housing including an actuator and a hollow conduit, the hollow conduit having a distal end, the actuator configured to advance the hollow conduit from a first position to a second position relative to the housing. The apparatus includes a measurement device configured to measure a physical property at the distal end of the hollow conduit. The apparatus includes an injection controller with an inner volume, the inner volume configured to be fluidically coupled to the hollow conduit upon advancement of the hollow conduit via the actuator, the injection controller configured to deliver a medicament from the inner volume to the distal end of the hollow conduit.

In some aspects, a method includes inserting a distal end portion of a hollow conduit of a medical injector a first distance into an eye of a patient, the hollow conduit being in fluidic communication with a medicament container, the medicament container including a medicament. The method includes monitoring impedance in an anatomical location within the eye at the distal end portion of the hollow conduit. The method includes confirming positioning of the distal end portion of the hollow conduit in a first region of the eye, the first region being proximal to the retina of the eye, based on an electrical impedance gradient between a sclera of the eye and a retinal pigment epithelium of the eye. After confirming disposal of the distal end portion of the hollow conduit in the first region of the eye, the method includes inserting the distal end portion of the hollow conduit a second distance into a region between an SCS and a boundary layer between a retinal layer and vitreous space of the eye. With the distal end portion of the hollow conduit into the retina of the eye, the method includes injecting at least a portion of the medicament into the region between the SCS and the boundary layer between the retinal layer and vitreous space via the hollow conduit.

In some aspects, a method includes inserting a distal end portion of a hollow conduit of a medical injector a first distance into an eye of a patient, the hollow conduit being in fluidic communication with a medicament container, the medicament container including a medicament. The method includes monitoring acoustic wave measurements in an anatomical location within the eye at the distal end portion of the hollow conduit and confirming positioning of the distal end portion of the hollow conduit in a first region of the eye, the first region being proximal to the retina of the eye, based on an acoustic wave gradient between a sclera of the eye and a retinal pigment epithelium of the eye. After confirming disposal of the the distal end portion of the hollow conduit in the first region of the eye, the method includes inserting the distal end portion of the hollow conduit a second distance into a region between an SCS and a boundary layer between a retinal layer and vitreous space of the eye. With the distal end portion of the hollow conduit in the retina of the eye, the method includes injecting at least a portion of the medicament into the region between the SCS and the boundary layer between the retinal layer and vitreous space via the hollow conduit.

In some aspects, a method includes applying a sealing surface on a distal end of an injection apparatus to at least one of a surface of a sclera of an eye or a conjunctiva of the eye, and pushing a first container into a second container to pressurize a liquid within the second container, the second container in fluidic communication with a catheter. The method further includes advancing the catheter through the sealing surface, such that a distal end of the catheter at least partially penetrates an SCS of the eye, the pressurizing of the liquid within the second container causing at least a portion of the liquid to flow from the second container and into the SCS via the catheter due to a reduced backpressure upon entry of the distal end of the catheter into the SCS. The method further includes advancing a hollow conduit, such that a distal end portion of the hollow conduit is distal to a distal end of the catheter, and the distal end of the hollow conduit enters a retina of the eye, the hollow conduit in fluidic communication with a medicament container, the medicament container including a medicament disposed therein. With the distal end portion of the hollow conduit disposed within the retina, the method includes injecting at least a portion of the medicament into the retina via the hollow conduit.

In some aspects, an apparatus can include a housing, a fluid container at least partially disposed in the housing, the fluid container configured to contain a liquid and configured to move independently of the housing, and a medicament container at least partially disposed in the fluid container, the medicament container configured to contain a medicament, the medicament container configured to increase a pressure in the fluid container upon an application of force on the medicament container when the medicament container contains the medicament. The apparatus further includes an outer hollow conduit fixedly coupled to a distal end of the fluid container, the outer hollow conduit fluidically coupled to the fluid container and an inner hollow conduit fixedly coupled to a distal end of the medicament container, the inner hollow conduit fluidically coupled to a volume defined by the medicament container, the inner hollow conduit having a distal end configured to move distally through a lumen defined by the outer hollow conduit upon distal movement by the medicament container. The apparatus further includes an injection controller at least partially disposed in the medicament container, the injection controller configured to push medicament through the inner hollow conduit and move independent of the medicament container.

In some aspects, an apparatus can include a sheath having an edge capable of piercing a sclera of an eye, a catheter slidably disposed within a lumen of the sheath and configured to extend beyond a distal end of the sheath, a balloon fixed to a distal end of the catheter, the balloon configured to inflate when a distal end of the catheter extends into at least two adjacent ocular tissue layers, a medicament container configured to contain a medicament, and a hollow conduit slidably coupled to the catheter, the hollow conduit configured to move independently of the catheter. The hollow conduit has a distal end portion, the distal end portion configured to extend beyond the balloon the hollow conduit is fluidically coupled to the medicament container and configured to deliver the medicament to a target region of the eye via the distal end portion of the hollow conduit, the target region distal to the balloon.

In some aspects, a method includes at least partially penetrating a sclera of an eye with a distal end of a sheath and advancing a catheter such that a distal end of the catheter enters an SCS of an eye, the catheter disposed in the sheath and moving independently of the sheath. The method further includes inflating a balloon disposed at a distal end of the catheter so as to create a force against a choroid, advancing a hollow conduit such that a distal end of the hollow conduit extends into a retina, the hollow conduit disposed in the catheter and moving independently of the catheter, and injecting a medicament into the retina via the hollow conduit.

In some aspects, a method includes inserting an outer sleeve into an eye, the outer sleeve having an inner lumen, inserting a cannula into the eye through the inner lumen of the outer sleeve, the cannula having a distal end with a balloon disposed thereon, inflating the balloon to create tension between two adjacent layers of the eye to secure the balloon therebetween, advancing distally a hollow conduit through the cannula, such that a distal end of the hollow conduit enters a target region of the eye distal to the balloon, the hollow conduit being in fluidic communication with a medicament container, the medicament container including a medicament. With the inflated balloon secured between the two adjacent layers of the eye, the method includes injecting medicament from the medicament container into the target region via the hollow conduit.

In some aspects, an apparatus includes a housing, a catheter at least partially disposed in the housing and configured to slidably move within the housing, a hollow conduit fixedly coupled to the catheter and at least partially disposed in the catheter, a medicament container fluidically coupled to the hollow conduit and configured to dispense a medicament to a target region in an eye, and a balloon coupled to a distal end of the catheter. The hollow conduit extends beyond the distal end of the catheter and the balloon, and wherein the balloon is configured to expand in a region proximal to a distal end of the hollow conduit, creating a tension between adjacent layers of the eye.

In some aspects, a method includes inserting a distal end portion of a hollow conduit of a medical injector a first distance into a first location within an eye, inserting a distal end portion of a catheter of the medical injector a second distance into the eye, such that a balloon coupled to the distal end portion of the catheter is disposed within a region defined between a sclera of the eye and a retina of the eye, the second distance being less than the first distance, and inflating the balloon to at least one of create or expand a space within the region, such that the distal end portion of the hollow conduit changes from the first location to a second location within the eye. With the hollow conduit in the second position within the eye, the method includes injecting via the hollow conduit a medicament ento the region.

DETAILED DESCRIPTION

Figure 1:
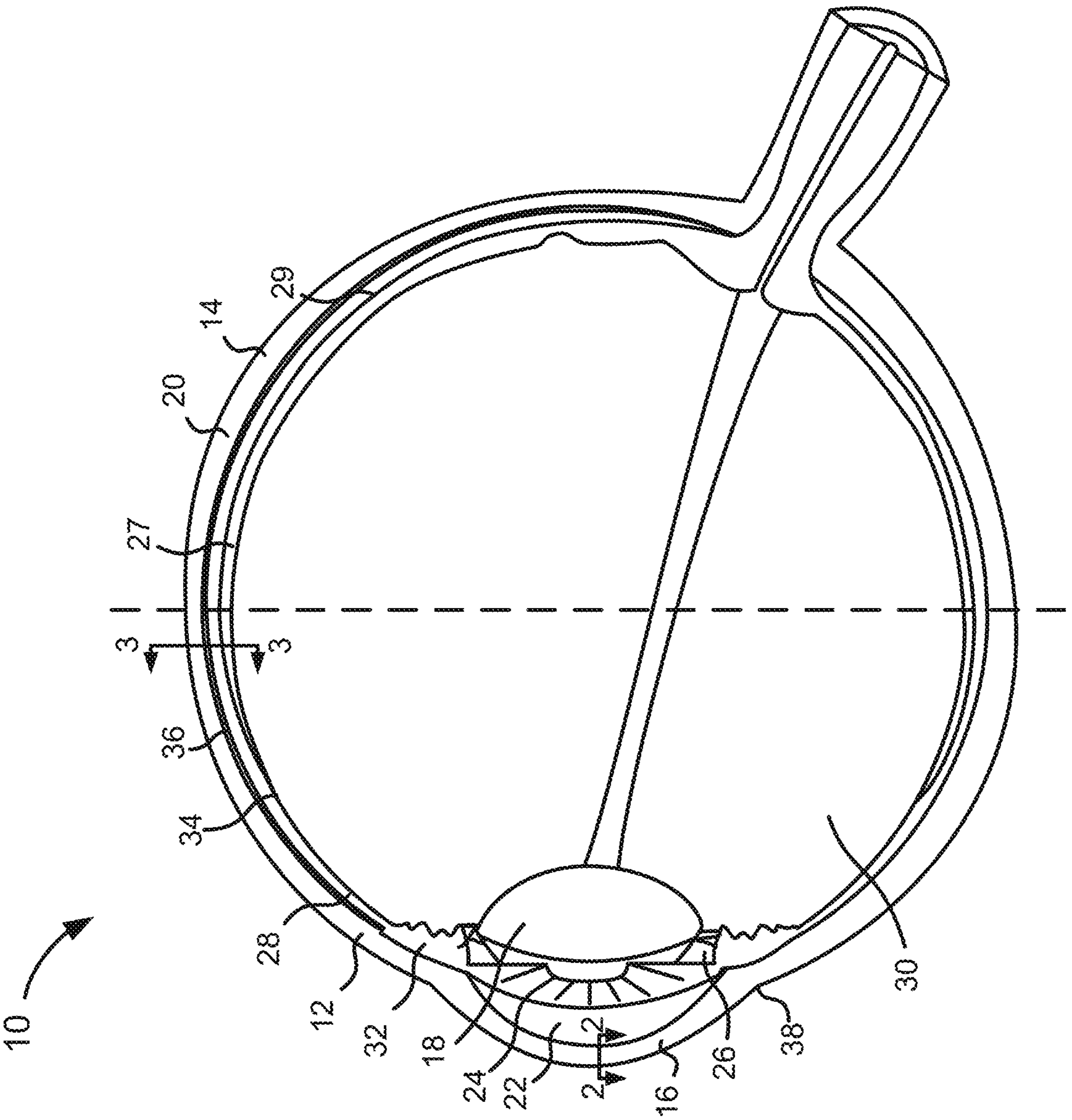
FIG. 1 is a cross-sectional view of an illustration of a human eye.

Embodiments described herein relate to systems and methods of retinal injection. These can include systems, devices, and methods to assist in the insertion of a delivery member (e.g., a needle, microneedle, a solid microneedle, a trocar, a catheter, a hollow trephine, cannula, microneedle patch, hollow microneedle, or hollow conduit) into the eye, or more specifically, a retinal space of the eye or a retinal tissue. In some embodiments, systems, devices, and methods described herein are for insertion of a delivery member into a region proximal to the retinal space of the eye or retinal tissue (e.g., between the choroid and the retina, or within the choroid adjacent its distal edge such that injectate injected therein could travel towards and into the retina). Human eyes can vary widely in overall size, as well as thickness of various tissue layers. Whether injecting an injectate (e.g., a medicament) into a tissue layer proximal to the vitreous body (i.e., pushing the delivery member through a few layers of tissue) or distal to the vitreous body (i.e., pushing the delivery member through the layers of tissue proximal to the vitreous body, the vitreous body, and a few layers of tissue distal to the vitreous body), a large amount of variability exists from patient to patient. For example, sclera thickness in the human eye can range anywhere from about 350 μm to about 700 μm. Using landmarks in the anatomy of the eye can aid in locating a reference location. Use of a reference location within the eye can significantly reduce variability in eye injections, as it reduces the number of tissue layers and physical space between a known location in the eye and an injection point. Said another way, use of the reference location reduces challenges associated with or otherwise addresses the portion of the eye with relatively great variability across patients. Based on accurate location of the reference location, the choroid, the retinal pigment epithelium (RPE) layer, the rods and cones, the bipolar cells, and/or any regions therebetween can be found.

Embodiments described herein can include methods and apparatus for detecting a reference location in an eye and injecting an injectate into a retinal tissue. In some embodiments, the reference location can be in the SCS. In some embodiments, the reference location can be the RPE. In some embodiments, the reference location can be in a region between a suprachoroidal space (SCS) and a retinal pigment epithelium (RPE) layer. In some embodiments, the reference location can be between the sclera and the choroid. In some embodiments, the detection of the reference location can be via a pressure change. In some embodiments, the detection of the reference location can be via an emissivity measurement. For example, light can be shined through a pupil and emissivity can be measured, based on how much of the incident light is detected at a distal end of the delivery member. In some embodiments, acoustic measurements can be made to measure tissue water contents. Each tissue in the human eye has a different water content, so water content measurements would change at each interface between layers. In some embodiments, impedance can be measured at various locations to locate the reference location, as electrical resistivity changes from layer to layer.

Embodiments described herein can also include devices for measuring the aforementioned properties and delivering injectate. The use of the aforementioned properties to locate the reference location and the different tissues of the eye can substantially reduce costs and patient discomfort in the medicament delivery process. Examples of ocular delivery devices are described in U.S. Pat. No. 9,539,139 entitled, "Apparatus and Methods for Ocular Injection," filed May 2, 2014 ("the '139 patent"), the disclosure of which is incorporated herein by reference in its entirety.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of a delivery member or hollow conduit described herein first inserted inside the patient's body would be the distal end, while the opposite end of the microneedle (e.g., the end of the medical device being manipulated by the operator) would be the proximal end of the microneedle.

As used herein, a "set" can refer to multiple features or a singular feature with multiple parts. For example, when referring to set of walls, the set of walls can be considered as one wall with distinct portions, or the set of walls can be considered as multiple walls.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the terms "delivery member", "puncture member", and "puncturing member" are used interchangeably to refer to an article configured to pierce tissue layers and deliver a substance to a target tissue layer, for example, a needle, a microneedle, a solid microneedle, a trocar, a catheter, a hollow trephine, or any other suitable delivery device.

As used herein, the terms "medicament container", and "medicament containment chamber" are used interchangeably to refer to an article configured to contain a volume of a substance, for example, a medicament.

The term "fluid-tight" is understood to encompass both a hermetic seal (i.e., a seal that is gas-impervious) as well as a seal that is liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at a constant position and at fluid pressures of less than about 5 psig, less than about 10 psig, less than about 20 psig, less than about 30 psig, less than about 50 psig, less than about 75 psig, less than about 100 psig and all values in between. Similarly, a "substantially liquid-tight" seal includes a seal that prevents the passage of a liquid (e.g., a liquid medicament) therethrough when the seal is maintained at a constant position and is exposed to liquid pressures of less than about 5 psig, less than about 10 psig, less than about 20 psig, less than about 30 psig, less than about 50 psig, less than about 75 psig, less than about 100 psig and all values in between.

The embodiments and methods described herein can be used to deliver substances to various target tissues in the eye. For reference, FIGS. 1-4B are include various views of a human eye 10 (with FIGS. 2-4B being cross-sectional views). While specific regions are identified, those skilled in the art will recognize that the proceeding identified regions do not constitute the entirety of the eye 10, rather the identified regions are presented as a simplified example suitable for the discussion of the embodiments herein. The eye 10 includes both an anterior segment 12 (the portion of the eye in front of and including the lens) and a posterior segment 14 (the portion of the eye behind the lens). The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The cornea 16 and the sclera 20 collectively form a limbus 38 at the point at which they meet. The exposed portion of the sclera 20 on the anterior segment 12 of the eye is protected by a clear membrane referred to as the conjunctiva 45 (see e.g., FIG. 3). Underlying the sclera 20 is the choroid 28 and the retina 27, collectively referred to as retinachoroidal tissue. The retinal pigment epithelium (RPE) 29 is the most outer layer of the retina 27, depicted adjacent to the choroid 28. A vitreous humour 30 (also referred to as the "vitreous" or "vitreous space") is disposed between a ciliary body 32 (including a ciliary muscle and a ciliary process) and the retina 27. The anterior portion of the retina 27 forms an *ora serrata* 34. The loose connective tissue, or potential space, between the choroid 28 and the sclera 20 is referred to as the suprachoroid or suprachoroidal space (SCS). FIG. 2 illustrates the cornea 16, which is composed of the epithelium 40, the Bowman's layer 41, the stroma 42, the Descemet's membrane 43, and the endothelium 44.

Figure 3:
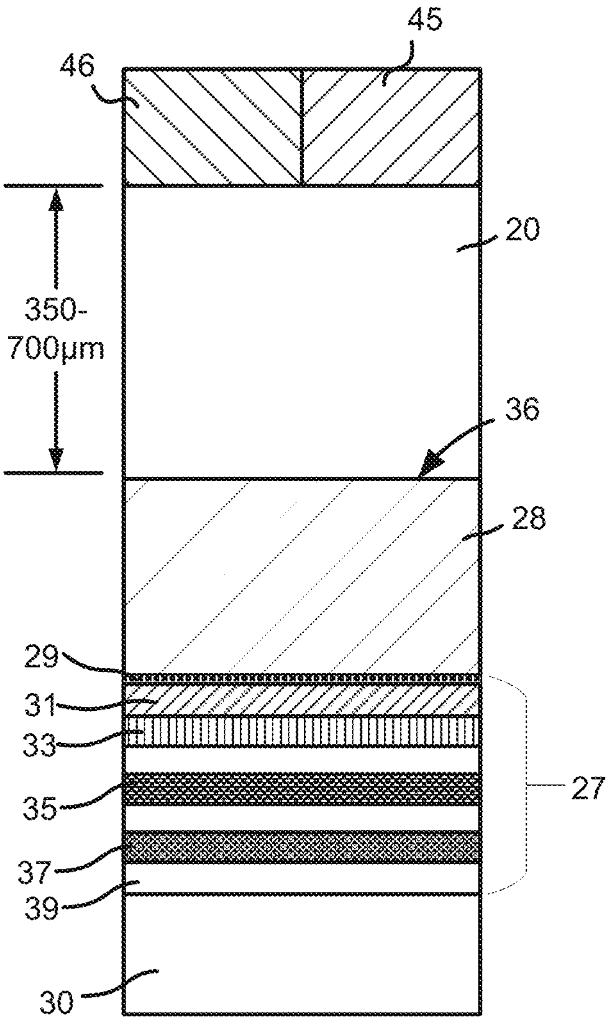
FIGS. 3, 4A, and 4B are cross-sectional views of a portion of the human eye of FIG. 1 taken along the line 3-3, illustrating the suprachoroidal space without the presence of a fluid, the suprachoroidal space with the presence of a fluid, and the retina with the presence of fluid, respectively.

FIG. 3 illustrates the sclera 20 with surrounding Tenon's Capsule 46 or conjunctiva 45, suprachoroidal space 36, choroid 28, and retina 27, substantially without fluid and/or tissue separation in the suprachoroidal space 36 (i.e., the in this configuration, the space is "potential" suprachoroidal space). As shown in FIG. 3, the sclera 20 has a thickness between about 350 μm and 700 μm. FIG. 3 illustrates sections of the retina 27 including RPE 29, rod and cone outer segments 31, rod and cone nuclei 33, bipolar cells 35, ganglion cells 37, and nerve fibers to the optic nerve 39. FIG. 3 also includes the vitreous humour 30.

Figure 4A:
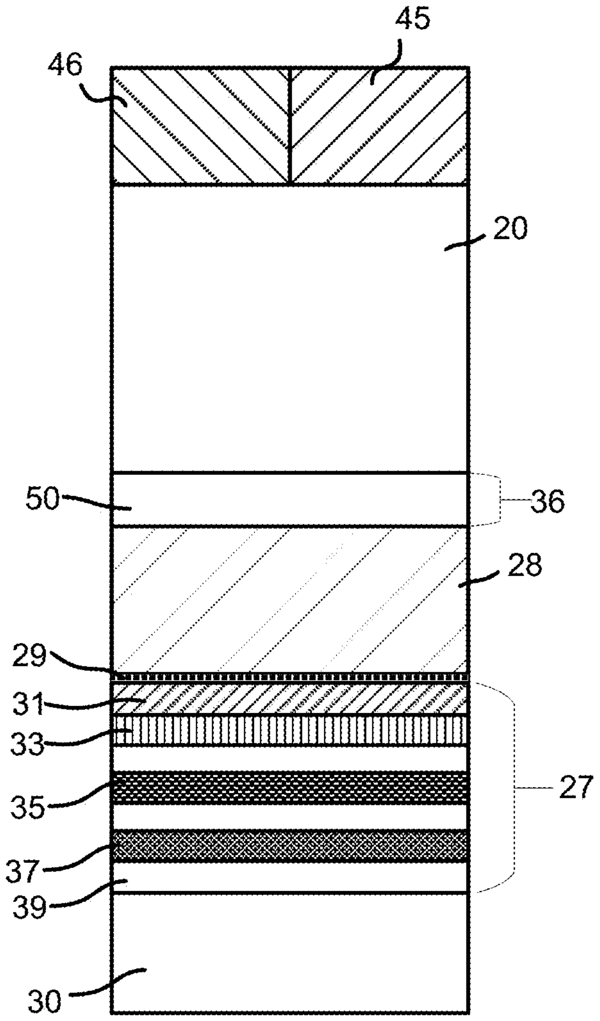
Figure 4B:
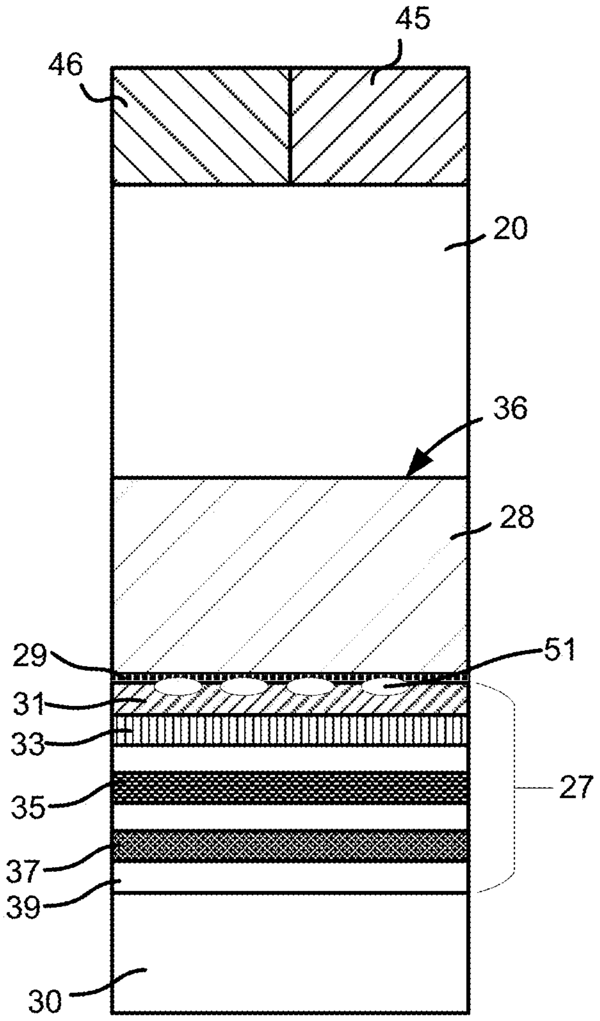

FIG. 4A illustrates the sclera 20 with the surrounding Tenon's Capsule 46 or the conjunctiva 45, suprachoroidal space 36, choroid 28, RPE 29, retina 27, with fluid 50 in the SCS 36. FIG. 4B illustrates the sclera 20 with the surrounding Tenon's Capsule 46 or the conjunctiva 45, suprachoroidal space 36, choroid 28, RPE 29, retina 27, with fluid 51 in the retina 27 (between the RPE 29 and the rod and cone outer segments 31).

As used herein, the term "suprachoroidal space," or SCS which is synonymous with suprachoroid, or suprachoroidia, describes the space (or volume) and/or potential space (or potential volume) in the region of the eye 10 disposed between the sclera 20 and choroid 28. This region primarily is composed of closely packed layers of long pigmented processes derived from each of the two adjacent tissues; however, a space can develop in this region because of fluid or other material buildup in the suprachoroidal space and the adjacent tissues. The suprachoroidal space can be expanded by fluid buildup because of some disease state in the eye or because of some trauma or surgical intervention. In some embodiments, the fluid buildup is intentionally created by the delivery, injection and/or infusion of a drug formulation into the suprachoroid to create and/or expand further the suprachoroidal space 36 (i.e., by disposing a drug formulation therein). This volume may serve as a pathway for uveoscleral outflow (i.e., a natural process of the eye moving fluid from one region of the eye to the other through) and may become a space in instances of choroidal detachment from the sclera.

As used herein, the term "retina" or "retinal space" can include the space (or volume) and/or potential space (or potential volume) between the RPE 29, and (1) the interface between the nerve fibers to the optic nerve 39 and the vitreous body 30, or (2) the photo receptor layer 31.

As used herein, the space between the choroid 28 and the retina 27 can include the space (or volume) and/or potential space (or potential volume) on either side adjacent to the RPE 29 or space within the RPE 29 itself.

Figure 2:
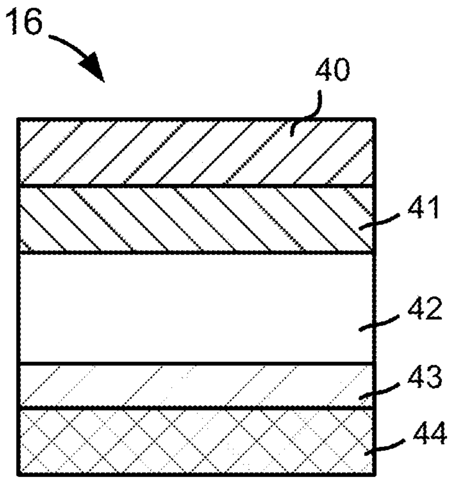
FIG. 2 is a cross-sectional view of portion of the human eye of FIG. 1, taken along the line 2-2.

The dashed line in FIG. 1 represents the equator of the eye 10. In some embodiments, the insertion site of any of the microneedles and/or methods described herein is between the equator and the limbus 38 (i.e., in the anterior portion 12 of the eye 10). For example, in some embodiments, the insertion site is between about two millimeters and 10 millimeters (mm) posterior to the limbus 38. In other embodiments, the insertion site of the microneedle is at about the equator of the eye 10. In still other embodiments, the insertion site is posterior the equator of the eye 10.

Figure 5:
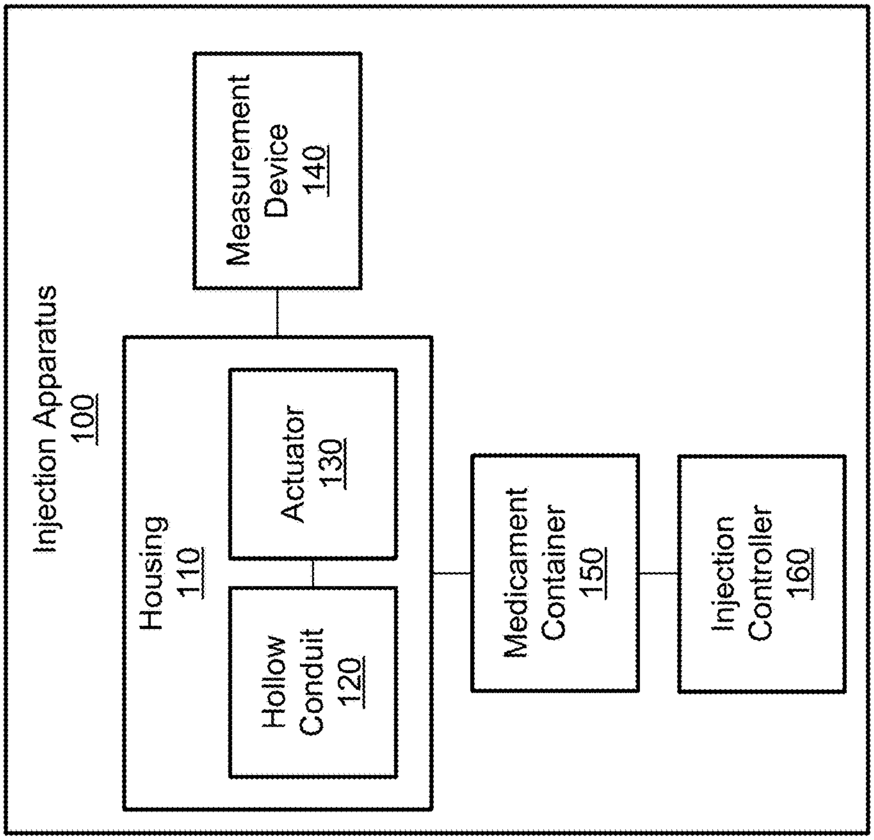
FIG. 5 is a schematic illustration of an injection apparatus, according to an embodiment.

FIG. 5 is a schematic illustration of an injection apparatus 100, according to an embodiment. As shown, the injection apparatus 100 includes an injection housing 110. The injection housing 110 contains a hollow conduit 120 and an actuator 130 coupled to the hollow conduit 120. The injection apparatus 100 further includes a measurement device 140, a medicament container 150, and an injection controller 160. The measurement device 140 is coupled to the injection housing 110 and measures a parameter at a distal end of the hollow conduit 120. The injection controller 160 controls delivery of injectate (e.g., medicament) from the medicament container 150 to the hollow conduit 120 and out of the distal end of the hollow conduit 120.

In some embodiments, the injection housing 110 can be composed of a rigid material. In some embodiments, the injection housing 110 can be composed of a flexible material. In some embodiments, the injection housing 110 can be composed of a polymer, glass, a metal, a tubing material (e.g., Tygon®), or any combination thereof. In some embodiments, the injection housing 110 can have a volume of at least about 1 ml, at least about 2 ml, at least about 3 ml, at least about 4 ml, at least about 5 ml, at least about 6 ml, at least about 7 ml, at least about 8 ml, at least about 9 ml, at least about 10 ml, at least about 20 ml, at least about 30 ml, at least about 40 ml, at least about 50 ml, at least about 60 ml, at least about 70 ml, at least about 80 ml, at least about 90 ml, at least about 100 ml, at least about 200 ml, at least about 300 ml, or at least about 400 ml. In some embodiments, the injection housing 110 can have a volume of no more than about 500 ml, no more than about 400 ml, no more than about 300 ml, no more than about 200 ml, no more than about 100 ml, no more than about 90 ml, no more than about 80 ml, no more than about 70 ml, no more than about 60 ml, no more than about 50 ml, no more than about 40 ml, no more than about 30 ml, no more than about 20 ml, no more than about 10 ml, no more than about 9 ml, no more than about 8 ml, no more than about 7 ml, no more than about 6 ml, no more than about 5 ml, no more than about 4 ml, no more than about 3 ml, or no more than about 2 ml.

Combinations of the above-referenced volumes of the injection housing 110 are also possible (e.g., at least about 1 ml and no more than about 500 ml or at least about 20 ml and no more than about 100 ml), inclusive of all values and ranges therebetween. In some embodiments, the injection housing 110 can have a volume of about 1 ml, about 2 ml, about 3 ml, about 4 ml, about 5 ml, about 6 ml, about 7 ml, about 8 ml, about 9 ml, about 10 ml, about 20 ml, about 30 ml, about 40 ml, about 50 ml, about 60 ml, about 70 ml, about 80 ml, about 90 ml, about 100 ml, about 200 ml, about 300 ml, about 400 ml, or about 500 ml.

In some embodiments, the hollow conduit 120 can be adjustable to move such that the distal end of the hollow conduit 120 moves or extends from a first position relative to the housing 110 to a second position (different from the first position) relative to the housing 110. In some embodiments, the distal end of the hollow conduit 120 can protrude from the housing 110 a first distance while in the first position and a second distance while in the second position. In some embodiments, the distal end of the hollow conduit 120 can be flush with the housing 110. In some embodiments, the first distance and/or the second distance can be at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, at least about 9.5 mm, at least about 10 mm, at least about 11 mm, at least about 12 mm, at least about 13 mm, at least about 14 mm, at least about 15 mm, at least about 16 mm, at least about 17 mm, at least about 18 mm, or at least about 19 mm. In some embodiments, the first distance and/or the second distance can be no more than about 20 mm, no more than about 19 mm, no more than about 18 mm, no more than about 17 mm, no more than about 16 mm, no more than about 15 mm, no more than about 14 mm, no more than about 13 mm, no more than about 12 mm, no more than about 11 mm, no more than about 10 mm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, no more than about 1.5 mm, or no more than about 1 mm.

Combinations of the above-referenced values for the first distance and/or the second distance are also possible (e.g., at least about 0.5 mm and no more than about 20 mm or at least about 2 mm and no more than about 10 mm), inclusive of all values and ranges therebetween. In some embodiments, the first distance and/or the second distance can be about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 11 mm, about 12 mm, about 13 mm, about 14 mm, about 15 mm, about 16 mm, about 17 mm, about 18 mm, about 19 mm, or about 20 mm.

In some embodiments, the hollow conduit 120 can be fluidically coupled to the medicament container 150. In some embodiments, the injection apparatus 100 can be operable in a first configuration, wherein the hollow conduit 120 is fluidically isolated from the medicament container 150 and a second configuration, wherein the hollow conduit 120 is fluidically coupled to the medicament container 150. For example, a seal can be broken by the user, bringing the hollow conduit 120 and the medicament container 150 into fluidic communication with one another. In some embodiments, the hollow conduit 120 can be a needle, a microneedle (e.g., 25 gauge, 27 gauge, 30 gauge, or smaller), a solid microneedle, a trocar, a catheter, a hollow trephine, or any other suitable delivery device. In some embodiments, the hollow conduit 120 can be a solid microneedle that can be inserted into a portion of the eye and left in the eye. In some embodiments, the solid microneedle can include medicament that can be delivered into the eye over an extended period of time (e.g., about 1 day, about 5 days, about 10 days, about 15 days, about 20 days, about 25 days, about 30 days, about 60 days, about 90 days, about 120 days, about 150 days, about 180 days, about 6 months, or about 1 year, inclusive of all values and ranges therebetween). In some embodiments, the distal end of the hollow conduit 120 can be tapered, as described in the '139 patent. In some embodiments, the hollow conduit 120 can be a flexible conduit.

In addition to the distal end, the hollow conduit 120 also has a proximal end (i.e., an end closer to the user). In some embodiments, the proximal end of the hollow conduit 120 can be disposed in the housing 110. In some embodiments, the proximal end of the hollow conduit 120 can be disposed in the medicament container 150. In some embodiments, the hollow conduit 120 can move independently of the actuator 130. In other words, the hollow conduit 120 can move from a first position to a second position relative to the housing 110 while the actuator 130 stays in place relative to the housing 110. In some embodiments, the hollow conduit 120 and the actuator 130 can move together, relative to the housing 110. In some embodiments, the hollow conduit 120 and the actuator 130 can move the same distance or substantially the same distance relative to the housing 110. In some embodiments, the hollow conduit 120 can move a first distance relative to the housing 110 while the actuator 130 moves a second distance relative to the housing 110. In some embodiments, the first distance can be larger than the second distance. In some embodiments, the first distance can be smaller than the second distance.

In some embodiments, the hollow conduit 120 can have a beveled end. In some embodiments, the opening at the distal end of the hollow conduit 120 can have a first side adjacent to the tip of the bevel and a second side adjacent to the heel of the bevel. In some embodiments, the first side can be distal to the second side by a bevel distance. Tuning the bevel distance can aid in proper disposal of medicament. If the bevel distance is too small, this can cause the effective opening at the distal end of the hollow conduit 120 to be small enough, such that application of a small pressure is not sufficient to dispense medicament. Conversely, if the bevel distance is too large, the opening at the distal end of the hollow conduit 120 can extend into multiple regions of the eye, reducing the precision of the injection. In some embodiments, the bevel distance can be at least about 1 μm, at least about 2 μm, at least about 3 μm, at least about 4 μm, at least about 5 μm, at least about 6 μm, at least about 7 μm, at least about 8 μm, at least about 9 μm, at least about 10 μm, at least about 20 μm, at least about 30 μm, at least about 40 μm, at least about 50 μm, at least about 60 μm, at least about 70 μm, at least about 80 μm, at least about 90 μm, at least about 100 μm, at least about 200 μm, at least about 300 μm, at least about 400 μm, at least about 500 μm, at least about 600 μm, at least about 700 μm, at least about 800 μm, or at least about 900 μm. In some embodiments, the bevel distance can be no more than about 1 mm, no more than about 900 μm, no more than about 800 μm, no more than about 700 μm, no more than about 600 μm, no more than about 500 μm, no more than about 400 μm, no more than about 300 μm, no more than about 200 μm, no more than about 100 μm, no more than about 90 μm, no more than about 80 μm, no more than about 70 μm, no more than about 60 μm, no more than about 50 μm, no more than about 40 μm, no more than about 30 μm, no more than about 20 μm, no more than about 10 μm, no more than about 9 μm, no more than about 8 μm, no more than about 7 μm, no more than about 6 μm, no more than about 5 μm, no more than about 4 μm, no more than about 3 μm, or no more than about 2 μm.

Combinations of the above-referenced bevel distances are also possible (e.g., at least about 1 μm and no more than about 1 mm or at least about 50 μm and no more than about 150 μm), inclusive of all values and ranges therebetween. In some embodiments, the bevel distance can be about 1 μm, about 2 μm, about 3 μm, about 4 μm, about 5 μm, about 6 μm, about 7 μm, about 8 μm, about 9 μm, about 10 μm, about 20 μm, about 30 μm, about 40 μm, about 50 μm, about 60 μm, about 70 μm, about 80 μm, about 90 μm, about 100 μm, about 200 μm, about 300 μm, about 400 μm, about 500 μm, about 600 μm, about 700 μm, about 800 μm, about 900 μm, or about 1 mm.

In some embodiments, the hollow conduit 120 can have a beveled end with a bevel angle (i.e., an angle created between a centerline of the hollow conduit 120 and a line extending distally from the beveled surface at the distal end of the hollow conduit 120) of at least about 5 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, or at least about 85 degrees. In some embodiments, the bevel angle can be no more than about 90 degrees, no more than about 85 degrees, no more than about 80 degrees, no more than about 75 degrees, no more than about 70 degrees, no more than about 65 degrees, no more than about 60 degrees, no more than about 55 degrees, no more than about 50 degrees, no more than about 45 degrees, no more than about 40 degrees, no more than about 35 degrees, no more than about 30 degrees, no more than about 25 degrees, no more than about 20 degrees, no more than about 15 degrees, or no more than about 10 degrees. Combinations of the above-referenced bevel angles are also possible (e.g., at least about 5 degrees and no more than about 90 degrees or at least about 45 degrees and no more than about 75 degrees), inclusive of all values and ranges therebetween. In some embodiments, the bevel angle can be about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, or about 85 degrees. A bevel at the distal end of the hollow conduit 120 can make the hollow conduit 120 sharper, such that it can more easily penetrate the sclera without causing additional deformation to the sclera. In some embodiments, the distal end of the hollow conduit 120 can be unbeveled.

In some embodiments, the actuator 130 can be coupled to an inner wall of the housing 110. In some embodiments, the actuator 130 can be coupled to an inner wall of the medicament container 150. In some embodiments, the actuator 130 can move within the housing 110 and/or the medicament container 150 from a first position to a second position. In other words, the actuator 130 can move a distance relative to the housing 110 and/or the medicament container 150. In some embodiments, the actuator 130 can move a distance relative to the housing 110 and/or the medicament container 150 of at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, at least about 9.5 mm, at least about 10 mm, at least about 11 mm, at least about 12 mm, at least about 13 mm, at least about 14 mm, at least about 15 mm, at least about 16 mm, at least about 17 mm, at least about 18 mm, or at least about 19 mm. In some embodiments, the actuator 130 can move a distance relative to the housing 110 and/or the medicament container 150 of no more than about 20 mm, no more than about 19 mm, no more than about 18 mm, no more than about 17 mm, no more than about 16 mm, no more than about 15 mm, no more than about 14 mm, no more than about 13 mm, no more than about 12 mm, no more than about 11 mm, no more than about 10 mm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, no more than about 1.5 mm, or no more than about 1 mm.

Combinations of the above-referenced values for the distance moved by the actuator 130 relative to the housing 110 and/or the medicament container 150 are also possible (e.g., at least about 0.5 mm and no more than about 20 mm or at least about 2 mm and no more than about 10 mm), inclusive of all values and ranges therebetween. In some embodiments, the actuator 130 can move a distance relative to the housing 110 and/or the medicament container 150 of about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 11 mm, about 12 mm, about 13 mm, about 14 mm, about 15 mm, about 16 mm, about 17 mm, about 18 mm, about 19 mm, or about 20 mm.

In some embodiments, the actuator 130 can be operated automatically. In some embodiments, the actuator 130 can be activated manually. In some embodiments, the actuator 130 can be connected to a micrometer. In some embodiments, the actuator 130 can be activated by the manual adjustment of a micrometer. In some embodiments, the actuator 130 can be operated by mechanical assistance. In some embodiments, the actuator 130 can be operated manually with mechanical assistance. In some embodiments, the actuator 130 can be operated automatically with mechanical assistance. In some embodiments, the actuator 130 can be operated by a motor. In some embodiments, the actuator 130 can be operated by a piezomotor. In some embodiments, the apparatus 100 can include an adapter (not shown) to act as an interface between the hollow conduit 120 and the actuator 130. In some embodiments, the adapter can be a press fit adapter to ensure a tight fit between the hollow conduit 120 and the actuator 130. The press fit adapter can aid in preventing proximal and distal movements of the hollow conduit 120. The press fit adapter can also aid in preventing wobbling (i.e., side-to-side movements) of the hollow conduit 120.

The measurement device 140 measures a parameter at the distal end and/or near the distal end of the hollow conduit 120 to detect the SCS, or any other desired reference location. In some embodiments, the parameter can be a physical parameter. In some embodiments, the parameter can include pressure, emissivity, acoustic vibrations, and/or impedance. In some embodiments, the measurement device 140 can measure the parameter at a measurement point, the measurement point proximal to the distal end of the hollow conduit 120. In some embodiments, the measurement point can be proximal to the distal end of the hollow conduit 120 by at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, or at least about 9.5 mm. In some embodiments, the measurement point can be proximal to the distal end of the hollow conduit 120 by no more than about 10 mm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, no more than about 1.5 mm, or no more than about 1 mm.

Combinations of the above-referenced distances between the distal end of the hollow conduit 120 and the measurement point's location, proximal to the distal end of the hollow conduit 120 are also possible (e.g., at least about 0.5 mm and no more than about 10 mm), inclusive of all values and ranges therebetween. In some embodiments, the measurement point can be proximal to the distal end of the hollow conduit 120 by about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 10 mm.

In some embodiments, the measurement device 140 can include a manometer, a barometer, a pressure tube, a piezometer, a bourdon gauge, a diaphragm pressure gauge, a micro manometer, or any combination thereof. In some embodiments, the measurement device 140 can be fluidically coupled to the distal end of the hollow conduit 120. In some embodiments, the measurement device 140 can include a digital pressure transducer. In some embodiments, when measuring pressure, the measurement device 140 can be rated for accuracy to within about 0.1 mmHg, about 0.2 mmHg, about 0.3 mmHg, about 0.4 mmHg, about 0.5 mmHg, about 0.6 mmHg, about 0.7 mmHg, about 0.8 mmHg, about 0.9 mmHg, about 1 mmHg, about 2 mmHg, about 3 mmHg, about 4 mmHg, about 5 mmHg, about 6 mmHg, about 7 mmHg, about 8 mmHg, about 9 mmHg, or about 10 mmHg, inclusive of all values and ranges therebetween.

In some embodiments, the measurement device 140 can measure light emissivity at and/or near the distal end of the hollow conduit 120. In some embodiments, the measurement device 140 can include a fiber optic cable with an emitter and receiver. In some embodiments, the emitter can emit light through the pupil and the fiber optic cable can absorb an amount of light at the distal end of the hollow conduit 120, transferring the light to the receiver. The emissivity can then be calculated as a fraction of the light intensity at the receiver to the intensity of the light emitted from the emitter. Each layer of the eye absorbs and reflects light differently In some embodiments, the measurement device 140 can measure light scattered from the eye at or near the distal end of the hollow conduit 120. In some embodiments, the measurement device 140 can include an Optical Coherence Tomography (OCT) device. The OCT device can include an interferometer comprising a housing, a light source, a beam splitter, a detector, and one or more auxiliary optical components including, for example, lenses, objectives, prisms, collimators, and the like. The light source can be configured to generate broad-bandwidth light which is directed to the beam splitter and divided into a reference light beam and a probing and/or sampling light beam. The reference light beam can be directed towards a mirror to be reflected, while the probing and/or sampling light beam can be directed to an eye of a subject and/or patient through the pupil of the eye. Light from the probing and/or sampling light beam scattered and reflected back by the eye can be collected at or near the distal end of the hollow conduit 120. The reference light beam and the light backscattered and reflected by the eye can be re-combined to give rise to an interference pattern. The interference pattern can be processed and/or analyzed to determine spacial dimensions and/or produce cross-sectional images of the various layers of the eye. In some embodiments, the OCT probe can be configured to direct the probing and/or sampling light beam along a predetermined direction, giving rise to an interference pattern (e.g., an A-scan) from which spacial dimensions (e.g., depth) of tissue layers of the eye and/or other microstructures present along the predetermined direction can be obtained and/or be determined. In some embodiments, the OCT probe can be configured to direct the probing and/or sampling light beam along multiple predetermined directions, such that the OCT probe can generate a plurality of A-scans. A cross-sectional tomogram (e.g., a B-scan) can be generated by combining the plurality of A-scans. In such implementations, the OCT probe can include a motor and/or an actuator configured to move the light source, an optical fiber, and/or any suitable component of the OCT probe in order to direct the probing and/or sampling light beam along the multiple predetermined directions.

In some embodiments, the OCT device can include any suitable light source(s). For example, in some embodiments the light source(s) can include a broad band superluminescent diode (SLD), an ultrashort pulsed laser, and/or a supercontinuum laser. The light source(s) can be configured to produce and/or emit light of one or more wavelengths. For example, in some embodiments the light source(s) can produce the light of about 750 nm, about 760 nm, about 780 nm, about 800 nm, about 820 nm, about 840 nm, about 860 nm, about 880 nm, about 900 nm, about 920 nm, about 940 nm, about 960 nm, about 980 nm, about 1000 nm, about 1020 nm, about 1040 nm, about 1060 nm, about 1080 nm, about 1100 nm, about 1120 nm, about 1140 nm, about 1160 nm, about 1180 nm, or about 1200 nm, inclusive of all values and ranges therebetween.

In some embodiments, the OCT device can include any suitable detector(s). For example, in some embodiments, the OCT device can include one or more balanced photodetectors, including, but not limited to, polarization-insensitive photodetectors, polarization-dependent photodetectors, free-space-compatible photodetectors, fiber-coupled photodetectors or the like. In some embodiments, the OCT device can include different combinations of light sources and detector (s). For example, in some embodiments, the OCT device can include a broadband wavelength light source and a linear image sensor detector (e.g., a diffraction grating component coupled to a detector). The broadband wavelength light source can generate light and direct it through the pupil. The linear image sensor detector can detect interference light spectrally dispersed obtained from light scattered, which can be processed by Fourier-Transforming to produce images in the depth direction of the eye (e.g., Spectral Domain—Optical Coherence Tomography, SD—OCT). In some embodiments, the OCT device can include a wavelength-swept light source and a differential detector. The wavelength-swept light source can be configured to sweep the wavelength temporarily and then direct its output light through the pupil to generate interference light. The generated interference light can then be detected with the differential detector and then processed by Fourier-Transforming to produce images in the depth direction of the eye (e.g., Swept Source—Optical Coherence Tomography, SS—OCT).

In some embodiments, the measurement device 140 can include a fiber optic Optical Coherence Tomography probe device (e.g., OCT probe). In such embodiments, the OCT probe can include a shell and/or housing, a light source, one or more optical fibers, a detector, and one or more auxiliary components which can include, among others, objectives, lenses, filters, prisms collimators, and the like. The housing can be any suitable structure that houses and/or accommodates one or more components of the OCT probe, including for example, the light source, the optical fiber, the detector and/or the auxiliary components. In some embodiments, the housing of the OCT probe can be configured to house the optical fiber and the one or more auxiliary components. The housing of the OCT probe can also provide one or more ports and/or interfaces from which other components of the OCT probe can be coupled, including for example, one or more light source(s), and one or more photodetector(s). The shell and/or housing of the OCT probe can be a hollow structure that defines an interior volume in which an optical fiber and other components of the OCT probe can be accommodated. In some embodiments, the shell and/or housing of the OCT probe can be cylindrical. In other embodiments, the shell and/or housing of the OCT probe can be a shape characterized by a length and any suitable cross-sectional area such as, for example, triangular, square, hexagonal, trapezoidal, octagonal, or the like. In some embodiments, shell and/or housing of the OCT probe can have a closed end. In some embodiments, the closed end of the shell and/or housing of the OCT probe can be a bevelled edge shape. In other embodiments, the closed end of the shell and/or housing of the OCT probe can be any suitable shape including, for example, conical, franseen, and/or diamond shape. The shell and/or housing of the OCT probe can accommodate one or more optical fibers.

The optical fiber can be any suitable fiber capable of transporting light. The optical fiber can be configured to receive a light beam from the light source. For example, in some embodiments a light source can generate a light beam. The generated light beam can be directed to the optical fiber via a fiber optic circulator. The fiber optic circulator can be a passive, polarization-independent device that acts as a signal router. In some embodiments, the optical fiber can be a single-mode fiber. In some embodiments, the optical fiber have a solid core (e.g., the entire cross-sectional area of the fiber is solid). In some embodiments the optical fiber can have a first portion with a solid core structure and a second portion with a no-core structure (e.g., the interior region of the fiber is hollow, surrounded by an annular region of solid fiber). In some embodiments, the portion of the optical fiber having a no-core structure can be disposed on one end of the optical fiber. The no-core structure portion can be configured to expand the light beam transported by the optical fiber. In some embodiments, the optical fiber can also include one or more portions made of a graded-Index (GRIN) multimode fibers. In such embodiments, the GRIN fiber can be configured to focus the light transported by the optical fiber. In some embodiments, the OCT probe can also include a prism disposed within the shell and/or housing of the OCT probe. In some embodiments, the prism can be configured to re-direct the light from the optical fiber to a predetermined angle. For example, in some embodiments, the OCT probe can include a prism configured to re-direct the light from the optical fiber at an angle of about 30 deg, about 32 deg, about 34 deg, about 36 deg, about 38 deg, about 40 deg, about 42 deg, about 44 deg, about 46 deg, about 48 deg, about 50 deg, about 52 deg, about 54 deg, about 56 deg, about 58 deg, or about 60 deg, inclusive of all values and ranges therebetween.

The detectors of the OCT probe can be similar to and/or the same as the detectors described above with reference to the OCT measurement device. In some embodiments the OCT probe can be an SS—OCT that uses a wavelength-swept light source. In other embodiments, the OCT probe can be an SD—OCT that uses a broadband wavelength light source. In some embodiments, the OCT probe can be an SS-OCT probe in which the light emitted by the swept source is split by a fiber coupler into a probing and/or sampling light beam and reference light beam. The probing and/or sampling light beam can be transmitted and/or directed by a fiber optic circulator to the optical fiber, and more especially to one end portion of the optical fiber, as further described herein. The reference signal beam can be reflected by a mirror. The probing and/or sampling light beam from the probe signal can be scattered and reflected back by the eye, and then recombined with the reference light and detected by a balanced photodetector. Interference patterns and/or data obtained from the interaction of the reference and probing and/or sampling light and detected by the detector can be processed by a processor and/or a computer unit to produce tomographic images of the eye. In some embodiments, tomographic images of the eye can be produced with the OCT probe in real time or near real time. The tomographic images can be used to determine an injection region of the eye in which a medicament and/or an injectate needs to be delivered, as further described herein.

Figure 32:
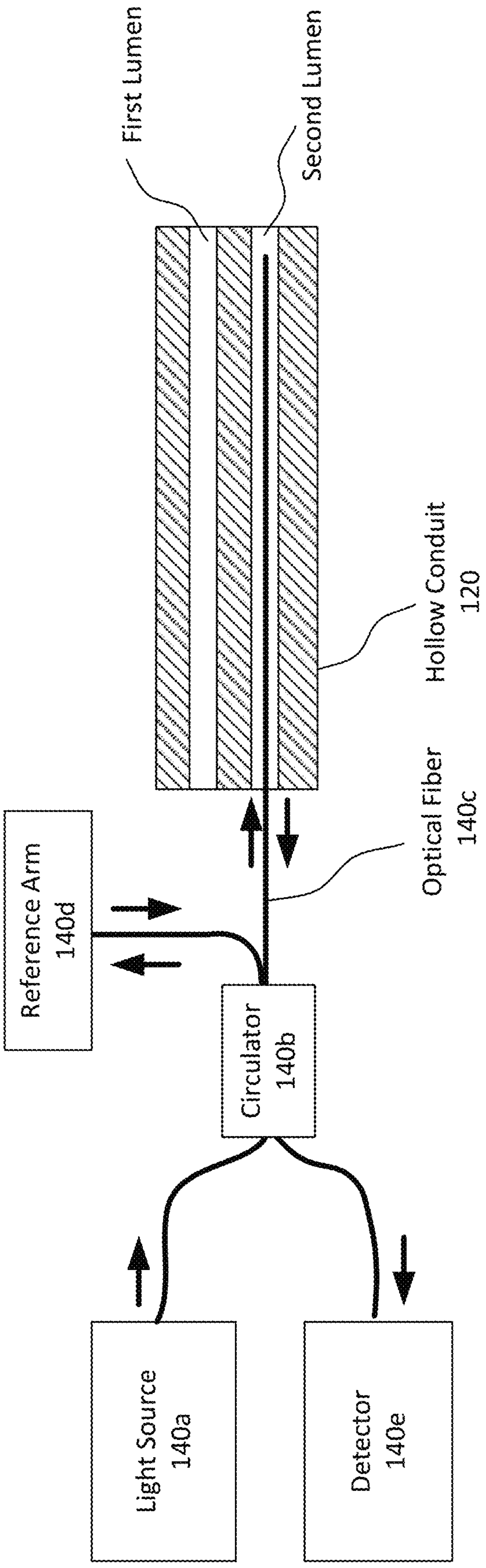
FIG. 32 shows a schematic representation of an OCT probe configured to identify an injection region of the eye of a subject and/or patient, according to an embodiment.

In some embodiments, the OCT probe, or at least a portion therefor, can be disposed within the hollow conduit 120, as schematically shown in FIG. 32. The OCT probe can include a light source 140*a*, a fiber optic circulator 140*b*, an optical fiber 140*c*, a reference arm 140*d*, and a detector 140*e*. The light source 140*a* can be used to generate and/or emit light, similar to, and or the same as the light sources previously described. Light generated and/or emitted by the light source 140*a* can be split into a reference light beam and a sampling and/or probing light beam with the aid of a fiber coupler (not shown in FIG. 32). The fiber optic circulator 140*b* can direct the reference light beam to the reference arm 140*d*, where it can be reflected. The fiber optic circulator 140*b* can also direct the sampling and/or probing light beam via the optical fiber 140*c* to an eye of a subject and/or patient. As shown in FIG. 32, the optical fiber 140*c*, or a portion thereof, can be disposed within the hollow conduit 120. The hollow conduit 120 can be multi-lumen conduit having at least a first lumen and a second lumen. The first lumen can be used to transport an injectate from the housing 110 to an injection region. The second lumen can be used to accommodate the optical fiber 140*c*, as well as any other suitable components including, for example, lenses, objectives, collimators, prisms, and the like. The second lumen can include a distal end portion configured to transmit the sampling and/or probing light beam to the pupil of the eye of the subject and/or patient. Light scattered and/or reflected back by the eye of the subject and/or patient can be collected at or near the distal end of the hollow conduit 120 by the optical fiber 140*c* and be directed back to the circulator 140*b* for re-combining with the reference light beam. The re-combined light can be rise to an interference pattern that can be detected and/or measured by the detector 140*e*. The detector 140 can be coupled to a processor (not shown in FIG. 32) configured to analyze the interference patterns to determine spacial dimensions and/or produce images of the various regions and/or layers of the eye. In this manner, real-time imaging can be provided while the hollow conduit 120 is advanced into an eye, thereby providing the operator with an indication of when a distal end of the hollow conduit 120 has reached a target injection region (e.g., the SCS, SRS, retina, or any other suitable space within the eye). With the distal end disposed at, in, or adjacent to the target injection region, a medicament can be delivered via the first lumen of the hollow conduit (in instances in which the optical fiber is disposed within the second lumen).

In use, a distal end portion of the hollow conduit 120 can be advanced to a first distance into the eye of a subject and/or patient. The light source 140*a* can generate a light beam which can be split into a reference light beam and a sampling and/or probing light beam. The reference light beam can be directed to the reference arm 140*d*, where it can be reflected with the aid of a mirror and/or a beam splitter. The sampling and/or probing light beam can be directed via the optical fiber 140*c* to the distal end of the hollow conduit 120 where it can be transmitted into the eye of the patient. The optical fiber 140*c* can also collect at or near the distal end of the hollow conduit 120 light scattered and/or reflected back by the eye of the subject and/or patient. The detector 140*e* can detect and/or measure the light scattered and/or reflected back by the eye of the subject and/or patient. A processor operably coupled to the detector 140*e* can receive signals associated with the light detected by the detector 140*e* and generate one or more spacial dimension(s) and/or images of the eye of the patient and/or subject. The generated one or more spacial dimension(s) and/or images of the eye of the patient can be used to identify an injection region of the eye of the subject and/or patient. The hollow conduit 120 can be advanced into the eye of the patient such that the distal end portion of the the hollow conduit 120 enters the injection region. A medicament and/or an injectate can then be conveyed via the first lumen of the hollow conduit.

In some embodiments, the measurement device 140 can measure an acoustic wave gradient at and/or near the distal end of the hollow conduit 120. The measurement device 140 can include an acoustic wave emitter and acoustic wave receiver. The tissue layers in the eye have differing water contents. Acoustic waves can be emitted from the sound emitter near the distal end of the hollow conduit 120 and interfaces between tissue layers can be detected based on how quickly the acoustic waves return to the acoustic wave receiver.

In some embodiments, the measurement device 140 can measure an electrical impedance gradient at and/or near the distal end of the hollow conduit 120. In some embodiments, the measurement device 140 can include an ohmmeter. In some embodiments, the measurement device 140 can measure an ionic current impedance gradient at and/or near the distal end of the hollow conduit 120. In some embodiments, the measurement device 140 can measure a resistivity gradient at and/or near the distal end of the hollow conduit 120. Tissue layers in the eye can have slightly different impedance or resistivity values, and detection of these gradients can aid in determining reference location in the eye.

In some embodiments, the medicament container 150 can include a reservoir that can contain an injectate or a medicament. As shown, the medicament container 150 is external to the injection housing 110. In some embodiments, the housing 110 can act as the medicament container 150. In some embodiments, the medicament container 150 can be an additional vessel inside the housing 110. In some embodiments, the injection apparatus 100 can include multiple medicament containers 150. For example, a first vial containing a medicament can be provided separately and attached externally to the housing 110 and medicament can transfer from the first vial to a second vial housed within the housing 110. In some embodiments, the medicament container 150 can include a syringe. In some embodiments, the medicament container 150 can have a volume of at least about 0.1 mL, at least about 0.2 mL, at least about 0.3 mL, at least about 0.4 mL, at least about 0.5 mL, at least about 0.6 mL, at least about 0.7 mL, at least about 0.8 mL, at least about 0.9 mL, at least about 1 mL, at least about 2 mL, at least about 3 mL, at least about 4 mL, at least about 5 mL, at least about 6 mL, at least about 7 mL, at least about 8 mL, at least about 9 mL, at least about 10 mL, at least about 20 mL, at least about 30 mL, at least about 40 mL, at least about 50 mL, at least about 60 mL, at least about 70 mL, at least about 80 mL, at least about 90 mL, at least about 100 mL, at least about 200 mL, at least about 300 mL, or at least about 400 mL. In some embodiments, the medicament container 150 can have a volume of no more than about 500 mL, no more than about 400 mL, no more than about 300 mL, no more than about 200 mL, no more than about 100 mL, no more than about 90 mL, no more than about 80 mL, no more than about 70 mL, no more than about 60 mL, no more than about 80 mL, no more than about 70 mL, no more than about 60 mL, no more than about 50 mL, no more than about 40 mL, no more than about 90 mL, no more than about 80 mL, no more than about 70 mL, no more than about 60 mL, no more than about 50 mL, no more than about 40 mL, no more than about 30 mL, no more than about 20 mL, no more than about 10 mL, no more than about 9 mL, no more than about 8 mL, no more than about 7 mL, no more than about 6 mL, no more than about 5 mL, no more than about 4 mL, no more than about 3 mL, no more than about 2 mL, no more than about 1 mL, no more than about 0.9 mL, no more than about 0.8 mL, no more than about 0.7 mL, no more than about 0.6 mL, no more than about 0.5 mL, no more than about 0.4 mL, no more than about 0.3 mL, or no more than about 0.2 mL.

Combinations of the above-referenced volumes of the medicament container are also possible (e.g., at least about 1 mL and no more than about 500 mL or at least about 50 mL and no more than about 100 mL), inclusive of all values and ranges therebetween. In some embodiments, the medicament container 150 can have a volume of about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 2 mL, about 3 mL, about 4 mL, about 5 mL, about 6 mL, about 7 mL, about 8 mL, about 9 mL, about 10 mL, about 20 mL, about 30 mL, about 40 mL, about 50 mL, about 60 mL, about 70 mL, about 80 mL, about 90 mL, about 100 mL, about 200 mL, about 300 mL, about 400 mL, or about 500 mL.

In some embodiments, the injection controller 160 can be automatic. In some embodiments, the injection controller 160 can be manual. In some embodiments, the injection controller 160 can include a syringe plunger. In some embodiments, the injection controller 160 can be disposed in the medicament container 150. As shown, the injection controller 160 is external to the housing 110. In some embodiments, the injection controller 160 can be disposed in the housing 110.

In use, the housing 110 can be brought to a location close to the eye, such that the distal end of the hollow conduit 120 is near the outer surface of the eye. The distal end of the hollow conduit 120 is then advanced a first distance relative to the outer surface of the eye into the reference location in the eye. In some embodiments, the actuator 130 can advance the distal end of the hollow conduit 120 to the reference location. The reference location is detected based on measurements done by the measurement device 140. In some embodiments, the reference location is detected based on a sudden change in pressure detected by the measurement device 140. In some embodiments, the reference location is detected based on a change in emissivity detected by the measurement device 140. Once the reference location is detected, the actuator 130 can advance the hollow conduit 120 a second distance into the eye, relative to the outer surface of the eye, such that the distal end of the hollow conduit 120 reaches the injection region. In some embodiments, the injection region can be between the SCS and a boundary layer between a retinal layer and vitreous space of the eye. In some embodiments, the injection region can be between two layers of retinal tissue (e.g., retinal pigment epithelium and photoreceptor). In some embodiments, the second distance can be between about 50 μm and about 1 cm from the reference location. In some embodiments, the second distance can be at least about 50 μm, at least about 100 μm, at least about 150 μm, at least about 200 μm, at least about 250 μm, at least about 300 μm, at least about 350 μm, at least about 400 μm, at least about 450 μm, at least about 500 μm, at least about 550 μm, at least about 600 μm, at least about 650 μm, at least about 700 μm, at least about 750 μm, at least about 800 μm, at least about 850 μm, at least about 900 μm, at least about 950 μm, at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, or at least about 9.5 mm from the reference location. In some embodiments, the second distance can be no more than about 1 cm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, no more than about 1.5 mm, no more than about 1 mm, no more than about 950 μm, no more than about 900 μm, no more than about 850 μm, no more than about 800 μm, no more than about 750 μm, no more than about 700 μm, no more than about 650 μm, no more than about 600 μm, no more than about 550 μm, no more than about 500 μm, no more than about 450 μm, no more than about 400 μm, no more than about 350 μm, no more than about 300 μm, no more than about 250 μm, no more than about 200 μm, no more than about 150 μm, or no more than about 100 μm from the reference location.

Combinations of the above-referenced values of the second distance from the reference location are also possible (e.g., at least about 50 μm and no more than about 1 cm or at least about 100 μm and no more than about 500 μm), inclusive of all values and ranges therebetween. In some embodiments, the second distance can be about 50 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 1 cm from the reference location.

Since the reference location has been identified, the placement of the distal end of the hollow conduit 120 into the injection region can be done with a high confidence level, due to the proximity of the injection region to the reference location. In some embodiments, the hollow conduit 120 can be manually advanced the second distance into the eye once the reference location is detected. Once the distal end of the hollow conduit 120 has reached the injection region, the injection controller 160 propels injectate from the medicament container 150 to the injection region via the hollow conduit 120. After the injection, the hollow conduit 120 can be removed from the eye.

In some embodiments, a kit that includes an injection apparatus for delivering a medicament to an injection region of a target tissue can include all or parts of the concepts described herein. For example, in some embodiments, a kit can include an injection apparatus (e.g., the injection apparatus 100, or any other injection apparatus described herein), a housing that can include, for example, a hollow conduit (e.g., the hollow conduit 120 or any other hollow conduit described herein) and an actuator (e.g., the actuator 130 or any other actuator described herein), a measurement device (e.g., the measurement device 140, or any other measurement device described herein), a medicament container (e.g., the medicament container 150 or any other medicament container described herein), an injection controller (e.g., the injection controller 160 or any other injection controller described herein), and/or any other device or apparatus configured to facilitate delivery of the medicament to the target tissue, for example, the eye.

Figure 6:
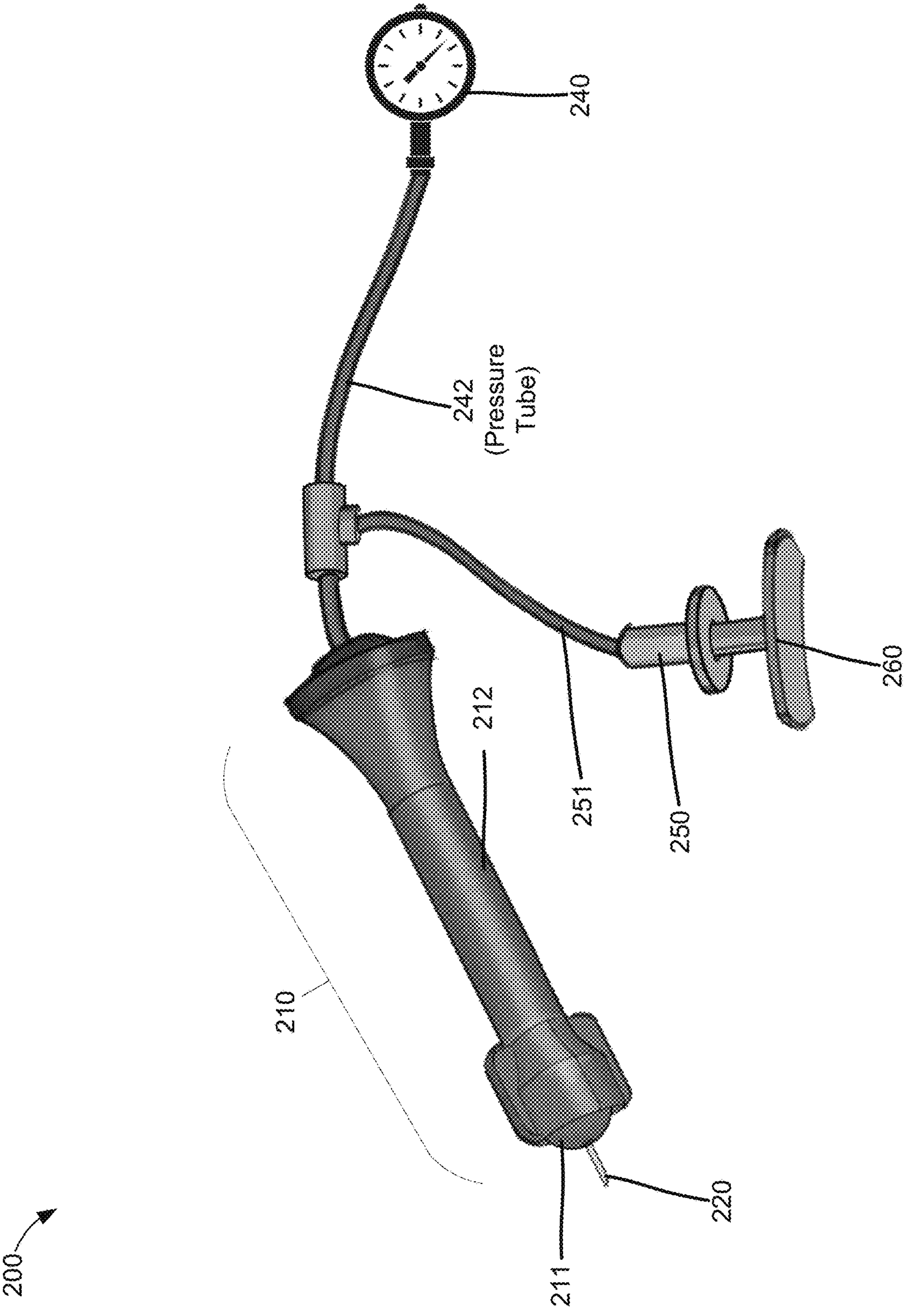
FIG. 6 is an illustration of an injection apparatus, according to an embodiment.

FIG. 6 is an illustration of an injection apparatus 200, according to an embodiment. The injection apparatus 200 includes a housing 210, a hollow conduit 220, a pressure measurement device 240, a medicament container 250, and an injection controller 260. The injection apparatus 200 also includes an actuator (not shown), contained within the housing 210. The pressure measurement device 240 is fluidically coupled to the housing 210 via a pressure tube 210.

In some embodiments, the housing 210, the hollow conduit 220, the actuator, the pressure measurement device 240, the medicament container 250, and the injection controller 260 can be the same or substantially similar to the housing 110, the hollow conduit 120, the actuator 130, the pressure measurement device 140, the medicament container 150, and the injection controller 160, respectively, as described above with reference to FIG. 5. Thus, certain aspects of the housing 210, the hollow conduit 220, the actuator, the pressure measurement device 240, the medicament container 250, and the injection controller 260 are not described in greater detail herein.

In some embodiments, the housing 210 can include a disposable cartridge 211 loaded into a reusable sheath 212. In some embodiments, the disposable cartridge 211 can act as an adapter between the hollow conduit 220 and the housing 210. In some embodiments, the disposable cartridge 211 can be loaded into the reusable sheath 212 via threading. In some embodiments, the disposable cartridge 211 can be loaded into the reusable sheath 212 via a latch coupling. In some embodiments, the disposable cartridge 211 can be loaded into the reusable sheath 212 via a coupling. In some embodiments, the coupling can be a latch coupling. In some embodiments, the disposable cartridge 211 can be removable by squeezing coupled ridges such that the disposable cartridge 211 can be removed from the reusable sheath 212 (i.e., a "childproof" lock).

In some embodiments, the hollow conduit 220 can be disposable. In some embodiments, the hollow conduit 220 and the disposable cartridge 211 can be permanently or irreversibly coupled together (e.g., via an adhesive). In some embodiments, the hollow conduit 220 can be independently removable from the disposable cartridge 211, such that the hollow conduit 220 can be removed and replaced more often than the disposable cartridge 211.

The pressure measurement device 240 is fluidically coupled to a distal end of the hollow conduit 220. This fluidic coupling is via the pressure tube 242. In some embodiments, the pressure tube 242 can be primed with fluid, such as the injectate. In some embodiments, the pressure tube 242 can be primed with fluid prior to the insertion of the distal end of the hollow conduit 220 into the human eye. In some embodiments, the injection controller 260 can push injectate through an injection tube 251 to prime the pressure tube 242. The injection tube 251 is fluidically coupled to the pressure tube 242. In some embodiments, the pressure measurement device 240 and the pressure tube 242 can act as a manometer after the pressure tube 242 is primed with fluid. Based on the fluid coupling between the distal end of the hollow conduit 220 and the pressure measurement device 240, the pressure at the distal end of the hollow conduit 220 can be determined via the reading of the pressure measurement device 240. In some embodiments, the pressure measurement device 240 can include a digital pressure transducer.

In some embodiments, the medicament container 250 and the injection controller 260 can be tethered or physically coupled to the housing 210. In some embodiments, the medicament container 250 and the injection controller 260 can be tethered or physically coupled to the pressure measurement device 240. In some embodiments, the injection controller 260 can be manually operated. Manual operation of the injection controller 260 can enable doctor- or operator-controlled injection and tactile feedback of speed and pressure. In some embodiments, the injection controller 260 can be automatically actuated.

In use, the housing 210 can be brought to a location close to the eye, such that the distal end of the hollow conduit 220 is near the outer surface of the eye. The distal end of the hollow conduit 220 is then advanced a first distance into the reference location in the eye. In some embodiments, the actuator can advance the distal end of the hollow conduit 220 to the reference location. The reference location is detected based on pressure measurements done by the pressure measurement device 240, which is fluidically coupled to the distal end of the hollow conduit 220 via the pressure tube 242. Once the reference location is detected, the actuator can advance the hollow conduit 220 a second distance into the eye, such that the distal end of the hollow conduit 220 reaches the injection region. Once the distal end of the hollow conduit 220 has reached the injection region, the injection controller 260 propels injectate from the medicament container 250 to the injection region via the injection tube 251 and the hollow conduit 220. After the injection, the hollow conduit 220 can be removed from the eye.

Figure 7A:
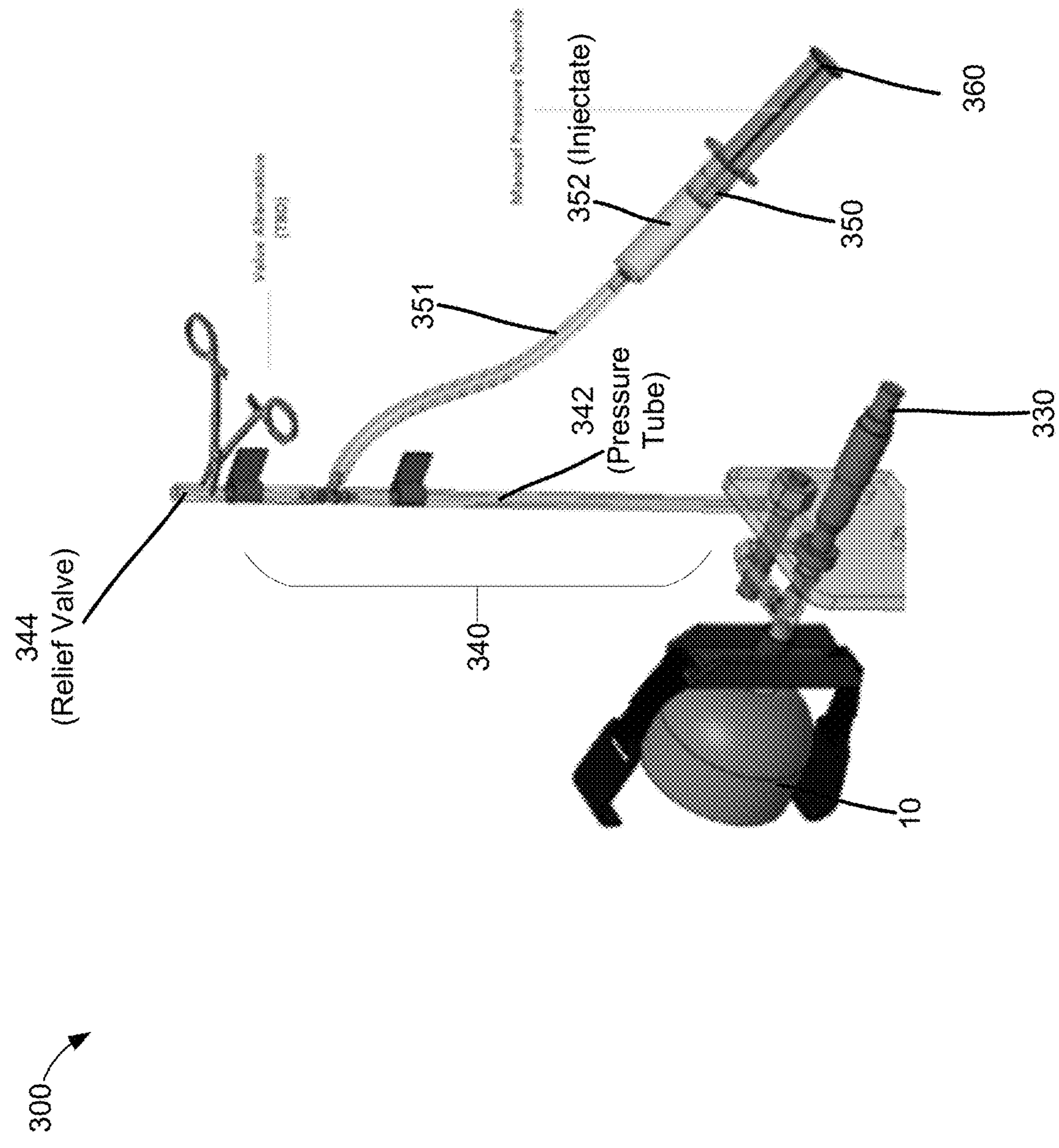
FIGS. 7A-7B are illustrations of an injection apparatus, according to an embodiment.
Figure 7B:
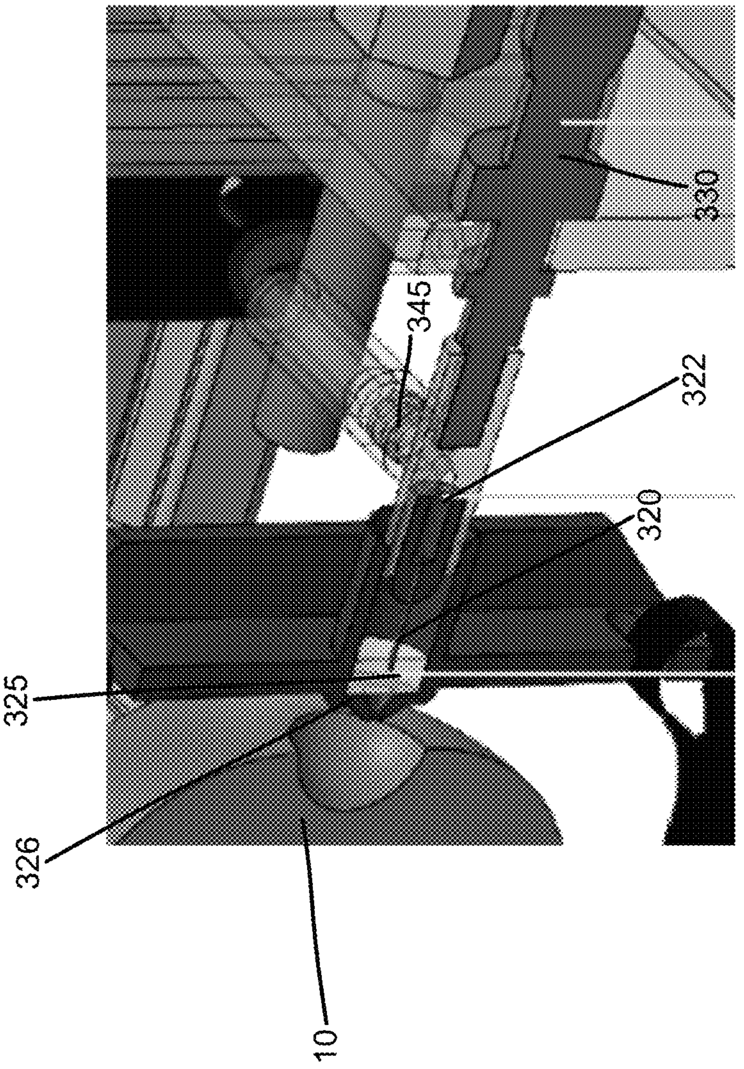

FIGS. 7A and 7B show an illustration of an injection apparatus 300, according to an embodiment. FIG. 7A shows a full view of the injection apparatus 300 in close proximity to a human eye 10, while FIG. 7B shows an interface between portions of the injection apparatus 300 and the human eye 10 in greater detail. The injection apparatus 300 includes a hollow conduit 320, an adapter 322, a puncture membrane 325, a conjunctiva depressor 326, an actuator 330, a pressure measurement device 340 with a pressure tube 342, a relief valve 344, and a T-adapter 345, a medicament container 350 with an injection tube 351, and an injection controller 360.

In some embodiments, the hollow conduit 320, the actuator 330, the pressure measurement device 340, the pressure tube 342, the medicament container 350, the injection tube 351, and the injection controller 360 can be the same or substantially similar to the hollow conduit 220, the actuator, the pressure measurement device 240, the pressure tube 242, the medicament container 250, the injection tube 251, and the injection controller 260, respectively, as described above with reference to FIG. 6. Thus, certain aspects of the hollow conduit 320, the actuator 330, the pressure measurement device 340, the pressure tube 342, the medicament container 350, the injection tube 351, and the injection controller 360 are not described in greater detail herein.

In some embodiments, the adapter 322 can act as a sheath to hold the hollow conduit 320. In some embodiments, the adapter 322 can be press fit to ensure a tight fit between the hollow conduit 320 and the T-adapter 345. In some embodiments, an outer surface of the adapter 322 can form a seal with an inner surface of the T-adapter 345. In some embodiments, the adapter 322 can be composed of a polymer. In some embodiments, the adapter 322 can be composed of a rigid material. In some embodiments, the hollow conduit 320 can be fixed in place in the adapter 322 and fluidically coupled to the pressure line 342.

The puncture membrane 325 can aid in sealing an interface between the hollow conduit 320 and the eye 10. This can aid in preventing leakage of fluid from the hollow conduit 320 or from the adapter 322. In some embodiments, the puncture membrane 325 can be composed of an elastomer material. In some embodiments, the puncture membrane 325 can have a thickness of at least about 100 μm, at least about 200 μm, at least about 300 μm, at least about 400 μm, at least about 500 μm, at least about 600 μm, at least about 700 μm, at least about 800 μm, at least about 900 μm, at least about 1 mm, at least about 2 mm, at least about 3 mm, or at least about 4 mm. In some embodiments, the puncture membrane 325 can have a thickness of no more than about 5 mm, no more than about 4 mm, no more than about 3 mm, no more than about 2 mm, no more than about 1 mm, no more than about 900 μm, no more than about 800 μm, no more than about 700 μm, no more than about 600 μm, no more than about 500 μm, no more than about 400 μm, no more than about 300 μm, or no more than about 200 μm. Combinations of the above-referenced thicknesses of the puncture membrane 325 are also possible (e.g., at least about 100 μm and no more than about 5 mm or at least about 1 mm and no more than about 3 mm), inclusive of all values and ranges therebetween. In some embodiments, the puncture membrane 325 can have a thickness of about 100 μm, about 200 μm, about 300 μm, about 400 μm, about 500 μm, about 600 μm, about 700 μm, about 800 μm, about 900 μm, about 1 mm, about 2 mm, about 3 mm, about 4 mm, or about 5 mm.

The conjunctiva depressor 326 can be opened to spread the patient's conjunctiva prior to insertion of the hollow conduit 320 into the eye. In some embodiments, the conjunctiva depressor 326 can include a top portion that moves upward and a bottom portion that moves downward. In some embodiments, the conjunctiva depressor 326 can open to create a gap of at least about 100 μm, at least about 200 μm, at least about 300 μm, at least about 400 μm, at least about 500 μm, at least about 600 μm, at least about 700 μm, at least about 800 μm, at least about 900 μm, at least about 1 mm, at least about 2 mm, at least about 3 mm, at least about 4 mm, at least about 5 mm, at least about 6 mm, at least about 7 mm, at least about 8 mm, at least about 9 mm, at least about 1 cm, or at least about 2 cm. In some embodiments, the conjunctiva depressor 326 can open to create a gap of no more than about 3 cm, no more than about 2 cm, no more than about 1 cm, no more than about 9 mm, no more than about 8 mm, no more than about 7 mm, no more than about 6 mm, no more than about 5 mm, no more than about 4 mm, no more than about 3 mm, no more than about 2 mm, no more than about 1 mm, no more than about 900 μm, no more than about 800 μm, no more than about 700 μm, no more than about 600 μm, no more than about 500 μm, no more than about 400 μm, no more than about 300 μm, or no more than about 200 μm. Combinations of the above-referenced gaps created by the conjunctiva depressor 326 are also possible (e.g., at least about 100 μm and no more than about 3 cm or at least about 1 mm and no more than about 5 mm), inclusive of all values and ranges therebetween. In some embodiments, the conjunctiva depressor 326 can open to create a gap of about 100 μm, about 200 μm, about 300 μm, about 400 μm, about 500 μm, about 600 μm, about 700 μm, about 800 μm, about 900 μm, about 1 mm, about 2 mm, about 3 mm, about 4 mm, about 5 mm, about 6 mm, about 7 mm, about 8 mm, about 9 mm, about 1 cm, about 2 cm, or about 3 cm.

As shown, the actuator 330 is coupled to the T-adapter 345. In some embodiments, a portion of the actuator 330 can be further advanced into the T-adapter 345 to make contact with the adapter 322. A portion of the actuator 330 can be yet further advanced to advance the hollow conduit 320. In some embodiments, the actuator 330 can be a micrometer. In some embodiments, the actuator 330 can be manually operated. In some embodiments, the actuator 330 can be operated by hand. In some embodiments, the actuator 330 can be automatically operated.

In some embodiments, the actuator 330 can have a lateral range of motion (i.e., right-to-left motion in FIG. 7B) of at least about 5 mm, at least about 6 mm, at least about 7 mm, at least about 8 mm, at least about 9 mm, at least about 1 cm, at least about 2 cm, at least about 3 cm, or at least about 4 cm. In some embodiments, the actuator 330 can have a lateral range of motion of no more than about 5 cm, no more than about 4 cm, no more than about 3 cm, no more than about 2 cm, no more than about 1 cm, no more than about 9 mm, no more than about 8 mm, no more than about 7 mm, or no more than about 6 mm. Combinations of the above-referenced ranges for the lateral range of motion of the actuator 330 are also possible (e.g., at least about 5 mm and no more than about 5 cm or at least about 8 mm and no more than about 2 cm), inclusive of all values and ranges therebetween. In some embodiments, the actuator 330 can have a lateral range of motion of about 5 mm, about 6 mm, about 7 mm, about 8 mm, about 9 mm, at least about 1 cm, about 2 cm, about 3 cm, about 4 cm, or about 5 cm.

As shown, the pressure measurement device 340 acts as a manometer. The T-adapter 345 couples the pressure tube 342, the adapter 322, and the actuator 330. Also included in the pressure measurement device 340 is a relief valve 344 for venting or sealing the pressure tube 342.

As shown, the medicament container 350 is a syringe that includes injectate 352. In some embodiments, the injectate 352 can be medicament. In some embodiments, the injectate 352 can include triamcinolone acetonide, a vascular endothelial growth factor (VEGF), a VEGF inhibitor, or a combination thereof.

In some embodiments, the injectate 352 can include any of the medicaments disclosed in the '139 patent. As shown, the injection controller 360 is a syringe plunger. In some embodiments, the injection controller 360 can include a sealing device (e.g., an O-ring and/or a gasket) disposed around a perimeter of the injection controller 360 to create a seal with an inner wall of the medicament container 350. In embodiments, the medicament comprises an anti-inflammatory compound, a tyrosine kinase inhibitor, an integrin inhibitor, a complement inhibitor, a VEGF inhibitor, and/or a gene therapy. In embodiments, the medicament comprises an αvβ3 inhibitor, an αvβ5 inhibitor, an αvβ1 inhibitor, an α4β1 inhibitor, or an α4β7 inhibitor. In embodiments, the medicament comprises axitinib, MK-409, or aflibercept.

In embodiments, the medicament comprises a gene therapy. In embodiments, the gene therapy comprises a nucleic acid. In embodiments, the nucleic acid is DNA. In embodiments, the nucleic acid is RNA. In embodiments, the nucleic acid is transcribed to form transcripts. In further embodiments, at least one transcript is an anti-sense transcript. In embodiments, the anti-sense transcript inhibits the synthesis of an endogenous protein. In embodiments, the anti-sense transcript inhibits an endogenous protein with a dominant-negative mutation. In embodiments, the nucleic acid molecule comprises a gene sequence and a promoter sequence. In embodiments, the nucleic acid is less than 10 kb, less than 20 kb, or less than 30 kb.

In embodiments, the nucleic acid is translated to a protein. In embodiments, the nucleic acid encodes a protein selected from the group consisting of a cytokine, chemokine, a growth factor, an anti-angiogenesis factor, and an antibody or antibody fragment or construct. In embodiments, the nucleic acid encodes a wild-type form of a protein, where a mutant form of the protein causes an ocular disease.

In embodiments, the nucleic acid encodes a protein selected from the group consisting of ABCA4, GUCY2D, RPE65, ELOVL4, CHM, CRB1, MYO7A, CDH23, CLRN1, ADGRV1, CIB2, HARS, PCDH15, USH2A, USH1C, USH1G, GPR98, WHRN, CEP290, MERTK, RPGR, Rodospin, PDE6B, VEGF-A, an anti-complement protein, an anti-VEGF protein, an anti-TNFα protein, and rod-derived cone viability factor.

In embodiments, the gene therapy is delivered in a non-viral nanoparticle or a viral vector. In embodiments, non-viral nanoparticle is a lipid-based nanoparticle. In embodiments, the nanoparticle is a polymer-based nanoparticle. In embodiments, the nanoparticle is a peptide or protein-based nanoparticle. In embodiments, the nanoparticle is an inorganic nanoparticle. In embodiments, the nanoparticle is a carbon-based nanoparticle. In embodiments, the nanoparticle size ranges from about 5 nm to about 500 nm.

In embodiments, the viral vector is an adenovirus, (Ad), adenoassociated virus (AAV), or lentivirus. In embodiments, the viral vector is a self-complementary AAV (scAAV) or helper-dependent adenovirus (HD-Ad). AAV vectors suitable for use in the methods and compositions herein include, but are not limited to, AAV1, AAV2, AAV3, AAV4, AAV5, AAV6, AAV7, AAV8, and AAV9.

In embodiments, the VEGF antagonist is selected from the group consisting of aflibercept, ziv-aflibercept, bevacizumab, sonepcizumab, VEGF sticky trap, an anti-VEGF Fab, RGX-314, cabozantinib, foretinib, vandetanib, nintedanib, regorafenib, cediranib, ranibizumab, lapatinib, sunitinib, sorafenib, plitidepsin, verteporfin, bucillamine, axitinib, pazopanib, fluocinolone acetonide, AL8326, 2C3 antibody, AT001 antibody, XtendVEGF antibody, HuMax-VEGF antibody, R3 antibody, AT001/r84 antibody, HyBEV, ANG3070, APX003 antibody, APX004 antibody, ponatinib, BDM-E, VGX100 antibody, VGX200, VGX300, COSMIX, DLX903/1008 antibody, ENMD2076, INDUS815C, R84 antibody, KD019, NM3, MGCD265, MG516, MP0260, NT503, anti-DLL4/VEGF bispecific antibody, PAN90806, Palomid 529, BD0801 antibody, XV615, lucitanib, motesanib diphosphate, AAV2-sFLT01, soluble Flt1 receptor, AV-951, Volasertib, CEP11981, KH903, lenvatinib, lenvatinib mesylate, terameprocol, PF00337210, PRS050, carboxyamidotriazole orotate, hydroxychloroquine, linifanib, AGN150998, MP0112, AMG386, PD173074, AVA101, BMS690514, KH902, golvatinib (E7050), dovitinib, dovitinib lactate (TKI258, CHIR258), ORA101, ORA102, PTC299, pegaptanib sodium, troponin, EG3306, vatalanib, Bmab100, GSK2136773, Anti-VEGFR Alterase, Avila, CEP7055, CLT009, ESBA903, GW654652, HMPL010, GEM220, HYB676, JNJ17029259, TAK593, Nova21012, Nova21013, CP564959, smart Anti-VEGF antibody, AG028262, AG13958, CVX241, SU14813, PRS055, PG501, PG545, PTI101, TG100948, ICS283, XL647, enzastaurin hydrochloride, BC194, COT601M06.1, COT604M06.2, MabionVEGF, Apatinib, RAF265 (CHIR-265), TSU-68 (SU6668, Orantinib), Brivanib (BMS-540215), AEE788 (NVP-AEE788), OSI-930, CYC116, Ki8751, Telatinib, KRN 633, SAR131675, Dilactic Acid, BMS-794833, Brivanib Alaninate (BMS-582664), Semaxanib (SU5416), ZM 323881 HCl, Cabozantinib malate (XL184), ZM 306416, AL3818, allogenic mesenchymal precursor cells combined with an anti-VEGF antagonist (e.g., anti-VEGF antibody), tivozanib (KRN-951), SP01 (curcumin), ALG1001, and everolimus (Afinitor®).

In some embodiments, the patient can be positioned such that the eye 10 is mounted in position adjacent to the injection apparatus 300. The conjunctiva depressor 326 can separate conjunctiva for proper sealing when inserting the hollow conduit 320. The injection controller 360 then pumps injectate 352 through the injection tube 351 to prime the pressure tube 342. The relief valve 344 can then be opened to vent the pressure line 342, thereby applying back pressure to the distal end of the hollow conduit 320. The actuator 330 then pushes the adapter 322 and the hollow conduit 320 forward until a pressure change is observed in the pressure measurement device 340, indicating that the reference location has been located. Once the reference location has been located, the relief valve 344 can be closed, stopping injection of injectate 352 into the SCS. The actuator 330 can then advance the adapter 322 and the hollow conduit 320 an additional distance (e.g., between about 50 μm and about 2 mm or between about 100 μm and about 150 μm) to advance into the retinal tissue. Once advanced into the retinal tissue, injectate can be injected into the retinal layer via the injection controller 360.

Figure 8:
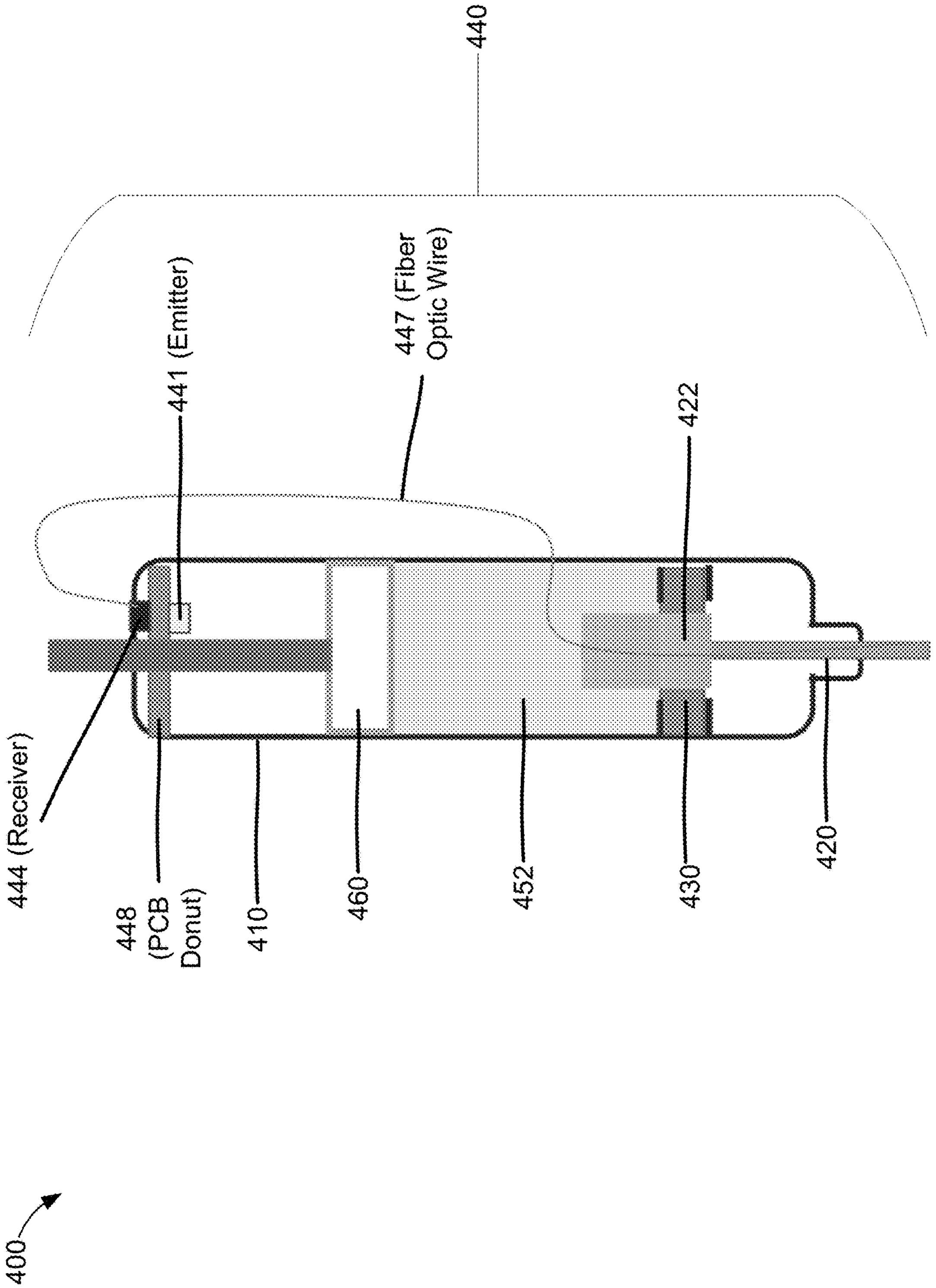
FIG. 8 is an illustration of an injection apparatus, according to an embodiment.

Either of the aforementioned embodiments can be used to locate a reference location, extend a hollow conduit into a target region, and inject an injectate into a target region. There are several ways the reference location can be located, some of which have been described above. Embodiments described in FIGS. 6, 7A, and 7B detail embodiments that employ pressure measurements to locate the reference location. FIG. 8 is an illustration of an injection apparatus 400 that uses light emissivity measurements to locate a reference location, according to an embodiment. FIG. 8 is a cross-sectional view of the apparatus 400. In some embodiments, the apparatus 400 can have a cylindrical shape or a substantially cylindrical shape. As shown, the injection apparatus 400 includes a housing 410, a hollow conduit 420, an adapter 422, an actuator 430, a light emissivity measurement device 440, injectate 452, and an injection controller 460. In some embodiments, the housing 410, the hollow conduit 420, the adapter 422, the actuator 430, the injectate 452, and the injection controller 460 can be the same or substantially similar to the housing 310, the hollow conduit 320, the adapter 322, the actuator 330, the injectate 352, and the injection controller 360, respectively, as described above with reference to FIGS. 7A and 7B. Thus, certain aspects of the housing 410, the hollow conduit 420, the adapter 422, the actuator 430, the injectate 452, and the injection controller 460 are not described in greater detail herein.

As shown, the injectate 452 is disposed directly in the housing 410. In other words, the injection apparatus 400 does not include a second vessel to contain the injectate 452. In some embodiments, the injectate 452 can be disposed in a second structure external to the housing 410. As shown, the housing 410 contains the hollow conduit 420, the adapter 422, the actuator 430, the injectate 452, and the injection controller 460. In some embodiments, the adapter 422 can form a fluid-tight seal with the actuator 430. In some embodiments, the adapter 422 can have a sufficient length in the longitudinal direction (i.e., the vertical direction in FIG. 8), such that the adapter 422 can move in the vertical direction while still maintaining a seal with the actuator 430. In some embodiments, the adapter 422 can have a longitudinal length longer than the longitudinal length of the actuator 430.

In some embodiments, the adapter 422 can have a longitudinal length of at least about 1 mm, at least about 2 mm, at least about 3 mm, at least about 4 mm, at least about 5 mm, at least about 6 mm, at least about 7 mm, at least about 8 mm, at least about 9 mm, at least about 1 cm, at least about 2 cm, at least about 3 cm, or at least about 4 cm. In some embodiments, the adapter can have a longitudinal length of no more than about 5 cm, no more than about 4 cm, no more than about 3 cm, no more than about 2 cm, no more than about 1 cm, no more than about 9 mm, no more than about 8 mm, no more than about 7 mm, no more than about 6 mm, no more than about 5 mm, no more than about 4 mm, no more than about 3 mm, or no more than about 2 mm. Combinations of the above-referenced longitudinal length values for the adapter 422 are also possible (e.g., at least about 1 mm and no more than about 5 cm or at least about 5 mm and no more than about 1 cm), inclusive of all values and ranges therebetween. In some embodiments, the adapter 422 can have a longitudinal length of about 1 mm, about 2 mm, about 3 mm, about 4 mm, about 5 mm, about 6 mm, about 7 mm, about 8 mm, about 9 mm, about 1 cm, about 2 cm, about 3 cm, about 4 cm, or about 5 cm.

In some embodiments, the actuator 430 can have a longitudinal length of at least about 500 μm, at least about 600 μm, at least about 700 μm, at least about 800 μm, at least about 900 μm, at least about 1 mm, at least about 2 mm, at least about 3 mm, at least about 4 mm, at least about 5 mm, at least about 6 mm, at least about 7 mm, at least about 8 mm, at least about 9 mm, or at least about 1 cm. In some embodiments, the adapter can have a longitudinal length of no more than about 2 cm, no more than about 1 cm, no more than about 9 mm, no more than about 8 mm, no more than about 7 mm, no more than about 6 mm, no more than about 5 mm, no more than about 4 mm, no more than about 3 mm, or no more than about 2 mm. Combinations of the above-referenced longitudinal length values for the adapter 422 are also possible (e.g., at least about 500 μm and no more than about 2 cm or at least about 5 mm and no more than about 1 cm), inclusive of all values and ranges therebetween. In some embodiments, the adapter 422 can have a longitudinal length of about 500 μm, about 600 μm, about 700 μm, about 800 μm, about 900 μm about 1 mm, about 2 mm, about 3 mm, about 4 mm, about 5 mm, about 6 mm, about 7 mm, about 8 mm, about 9 mm, about 1 cm, or about 2 cm.

In some embodiments, the actuator 430 can include a piezo motor. In some embodiments, the actuator 430 can be operable to move the hollow conduit 420 and the adapter 422 relative to the housing 410 while the actuator 430 remains stationary relative to the housing 410. In some embodiments, the actuator 430 can move relative to the housing 410 along an inner wall of the housing 410. In some embodiments, the actuator 430 can have a longitudinal range of motion of at least about 1 mm, at least about 2 mm, at least about 3 mm, at least about 4 mm, at least about 5 mm, at least about 6 mm, at least about 7 mm, at least about 8 mm, at least about 9 mm, at least about 1 cm, at least about 2 cm, at least about 3 cm, or at least about 4 cm. In some embodiments, the actuator 430 can have a longitudinal range of motion of no more than about 5 cm, no more than about 4 cm, no more than about 3 cm, no more than about 2 cm, no more than about 1 cm, no more than about 9 mm, no more than about 8 mm, no more than about 7 mm, no more than about 6 mm, no more than about 5 mm, no more than about 4 mm, no more than about 3 mm, or no more than about 2 mm.

Combinations of the above-referenced range of motion values for the longitudinal range of motion of the actuator 430 are also possible (e.g., at least about 1 mm and no more than about 5 cm or at least about 5 mm and no more than about 1 cm), inclusive of all values and ranges therebetween. In some embodiments, the actuator 430 can have a longitudinal range of motion of about 1 mm, about 2 mm, about 3 mm, about 4 mm, about 5 mm, about 6 mm, about 7 mm, about 8 mm, about 9 mm, about 1 cm, about 2 cm, about 3 cm, about 4 cm, or about 5 cm.

As shown, the emissivity measurement device 440 includes an emitter 441 that shines light through the pupil via a fiber optic wire 447. The fiber optic wire 447 is physically coupled the distal end of the hollow conduit 420 and to a receiver 444. The emissivity measurement device 440 further includes a printed circuit board 448 to control the operation of the emissivity measurement device 440. In some embodiments, the printed circuit board 448 can include drivers and/or firmware to control the emissivity measurement device 440. Based on the intensity of light emitted from the emitter 441 and the intensity of light detected in the receiver 444, emissivity can be calculated. In some embodiments, the fiber optic wire 447 can run through the hollow conduit 420. In some embodiments, the fiber optic wire 447 can be affixed to the outside of the hollow conduit 420.

In some embodiments, the emitter 441 can emit light at an intensity of at least about 5 lumens, at least about 10 lumens, at least about 15 lumens, at least about 20 lumens, at least about 25 lumens, at least about 30 lumens, at least about 35 lumens, at least about 40 lumens, or at least about 45 lumens. In some embodiments, the emitter 441 can emit light at intensity of no more than about 50 lumens, no more than about 45 lumens, no more than about 40 lumens, no more than about 35 lumens, no more than about 30 lumens, no more than about 25 lumens, no more than about 20 lumens, no more than about 15 lumens, or no more than about 10 lumens. Combinations of the above-referenced intensities of light emitted from the emitter 441 are also possible (e.g., at least about 5 lumens and no more than about 50 lumens or at least about 10 lumens and no more than about 20 lumens), inclusive of all values and ranges therebetween. In some embodiments, the emitter 441 can emit light at an intensity of about 5 lumens, about 10 lumens, about 15 lumens, about 20 lumens, about 25 lumens, about 30 lumens, about 35 lumens, about 40 lumens, about 45 lumens, or about 50 lumens.

Alternatively, and/or additionally to the light emissivity device 440, in some embodiments the injection apparatus 400 can include an OCT probe (not shown in FIG. 8). The OCT probe can have a shell and/or housing which accommodates an optical fiber as well as other components such as lenses, prisms and other auxiliary components. The OCT probe can also include and/or be coupled to one or more light source(s) and a photodetector(s) such as those described above with reference to the OCT probe measurement device 140. The shell and/or housing of the OCT probe can be a hollow structure that defines an interior volume in which the optical fiber and other components of the OCT probe can be accommodated. The shell and/or housing of the OCT probe can be a cylindrical shape which includes a closed end having a suitable shape such as bevelled, conical, franseen, and/or diamond shape. The optical fiber can be any suitable fiber capable of transporting light. In some embodiments, the OCT probe can be an SS-OCT that uses a wavelength-swept light source. In other embodiments, the OCT probe can be an SD-OCT that uses a broadband wavelength light source. In some embodiments, the OCT probe can be configured to direct a probing and/or sampling light beam along a predetermined direction, giving rise to an interference pattern (e.g., an A-scan) from which spacial dimensions (e.g., depth) of tissue layers of the eye and/or other microstructures present along the predetermined direction can be obtained and/or be determined. In some embodiments, the OCT probe can be configured to direct a probing and/or sampling light beam along multiple predetermined directions, such that the OCT probe can generate a plurality of A-scans. A cross-sectional tomogram (e.g., a B-scan) can be generated by combining the plurality of A-scans. In such implementations, the OCT probe can include a motor and/or an actuator configured to move the light source, an optical fiber, and/or any suitable component of the OCT probe in order to direct the probing and/or sampling light beam along the multiple predetermined directions. In some embodiments, the OCT probe can be run through the hollow conduit 420. That is, in some embodiments, the OCT probe and/or a portion thereof, can be disposed within the hollow conduit 420. In some embodiments, the hollow conduit 420 can include and/or define a lumen. The lumen can be sized and configured such that the OCT probe (or at least a portion thereof) can be disposed and/or housed within the lumen of the hollow conducit 420. The lumen of the hollow conduit 420 can also be sized and configured to transport a medicament and/or an injectate disposed in the medical injector to an injection region in the eye. Alternatively, in some embodiments the hollow conduit 420 can be a multi-lumen conduit having at least a first lumen and a second lumen, the second lumen being different from the first lumen. The first lumen can be used to transport the injectate 452 from the housing 410 to the injection region. The second lumen can be used to accommodate the OCT probe such that the OCT probe can generate interference patterns that can be processed and/or analyzed to determine spacial dimensions and/or produce images of the various regions and/or layers of the eye. The reference location can then be detected based on the images produced by the OCT probe.

As shown, the injection controller 460 is disposed directly in the housing 410. In some embodiments, the injection controller 460 can move longitudinally within the housing 410 to push the injectate 452 through the hollow conduit 420. In some embodiments, a sealing member can be disposed around the perimeter of the injection controller 460 to create a seal between the inner surface of the housing 410 and the perimeter of the injection controller 460. In some embodiments, the injection controller 460 can be a plunger.

In use, the housing 410 can be brought to a location close to the eye, such that the distal end of the hollow conduit 420 is near the outer surface of the eye. The distal end of the hollow conduit 420 is then advanced a first distance into the reference location in the eye. In some embodiments, the actuator 430 can advance the distal end of the hollow conduit 420 to the reference location. The reference location is detected based on emissivity measurements done by the emissivity measurement device 440, which operates as described above. In some embodiments, the reference location is detected based on OCT data and/or images produced with an OCT probe included in the hollow conduit 420, as described above. Once the reference location is detected, the actuator 430 can advance the hollow conduit 420 and/or the adapter 422 a second distance into the eye, such that the distal end of the hollow conduit 420 reaches the injection region. Once the distal end of the hollow conduit 420 has reached the injection region, the injection controller 460 propels injectate 452 from the housing 410 to the injection region via the hollow conduit 420. After the injection, the hollow conduit 420 can be removed from the eye.

Figure 9:
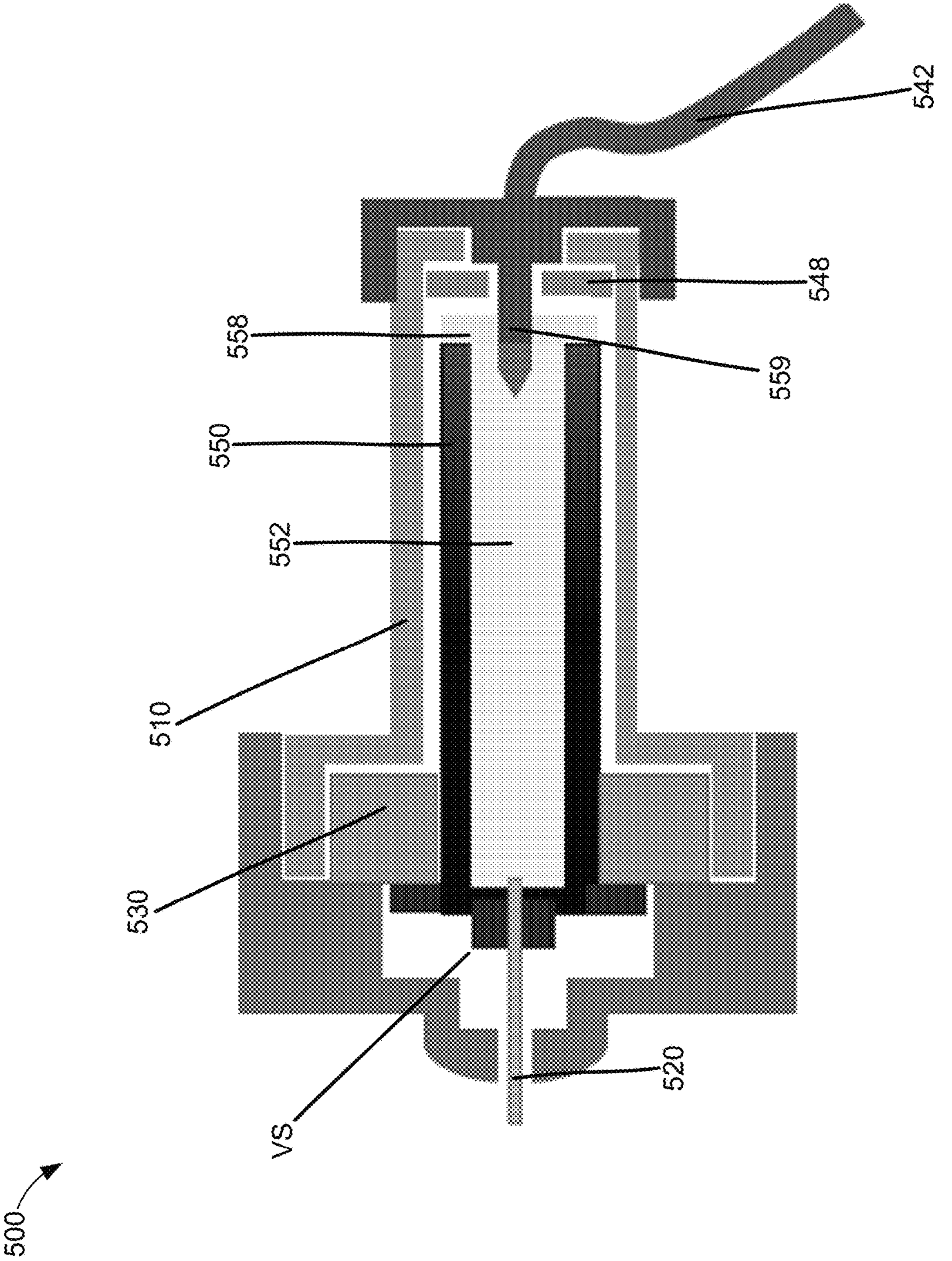
FIG. 9 is an illustration of an injection apparatus, according to an embodiment.

FIG. 9 is an illustration of an injection apparatus 500, according to an embodiment. As shown, the injection apparatus 500 includes a housing 510, a hollow conduit 520, an actuator 530, a pressure line 542, a printed circuit board 548, a medicament container 550, and an injectate 552.

In some embodiments, the housing 510, hollow conduit 520, the actuator 530, the pressure line 542, and the medicament container 550 can be the same or substantially similar to the housing 210, the hollow conduit 220, the actuator, the pressure line 242, and the medicament container 250, respectively, as described above with reference to FIG. 6. Thus, certain aspects of the housing 510, hollow conduit 520, the actuator 530, the pressure line 542, and the medicament container 550 are not described in greater detail herein.

As shown, the actuator 530 is operable to advance the medicament container 550 and the hollow conduit 520 through the housing 510. Upon actuation, the actuator 530 can propel the medicament container 550 into the void space VS, thereby advancing the hollow conduit 520 and the distal end of the hollow conduit 520. In some embodiments, the actuator 530 can include a piezo motor. In some embodiments, the actuator 530 can propel the medicament container 550 relative to the housing 510, while the actuator 530 remains stationary with reference to the housing 510.

As shown, the medicament container 550 is a separate vessel from the housing 510 disposed in the housing 510. In some embodiments, the medicament container 550 can be external to the housing 510. The medicament container 550 includes a puncture cap 558. The puncture cap 558 can be punctured by a puncture spike 559. After the puncture cap 558 is punctured, fluidic communication is established between the distal end of the hollow conduit 520 and the pressure line 542. In some embodiments, injectate 552 can be released into the pressure line 542 to prime the pressure line 542, such that a manometer can be formed. The puncture cap 558 can ensure that the injectate 552 is sealed and undisturbed until the medicament container 550 is loaded into the housing 510. In some embodiments, the printed circuit board 548 can control pressure transduction within the pressure line 542 and/or the medicament container 550. In some embodiments, the injection apparatus 500 can include an emissivity measurement device (not shown). In some embodiments, the emissivity measurement device can be the same or substantially similar to the emissivity measurement device 440 described above, with reference to FIG. 8. In some embodiments, the printed circuit board 548 can control the emissivity measurement device. In some embodiments, the injection apparatus 500 can include OCT probe (not shown in FIG. 9). In some embodiments, the OCT probe can be the same or substantially similar to the OCT probe described above, with reference to the injection apparatus 400, and the measurement device 140. In some embodiments, the printed circuit board 548 can control the OCT probe.

In use, the housing 510 can be brought to a location close to the eye, such that the distal end of the hollow conduit 520 is near the outer surface of the eye. The distal end of the hollow conduit 520 is then advanced a first distance into the reference location in the eye. In some embodiments, the actuator 530 can advance the distal end of the hollow conduit 520 to the reference location. The puncture spike 559 can pierce the puncture cap 558 to create a fluidic coupling between the pressure line 542 and the distal end of the hollow conduit 520. The reference location is detected based on pressure measurements in the pressure line 542. Once the reference location is detected, the actuator 530 can advance the hollow conduit 520 a second distance into the eye, such that the distal end of the hollow conduit 520 reaches the injection region. Once the distal end of the hollow conduit 520 has reached the injection region, an injection controller (not shown) propels injectate 552 from the housing 510 to the injection region via the hollow conduit 520. After the injection, the hollow conduit 520 can be removed from the eye.

Figure 10:
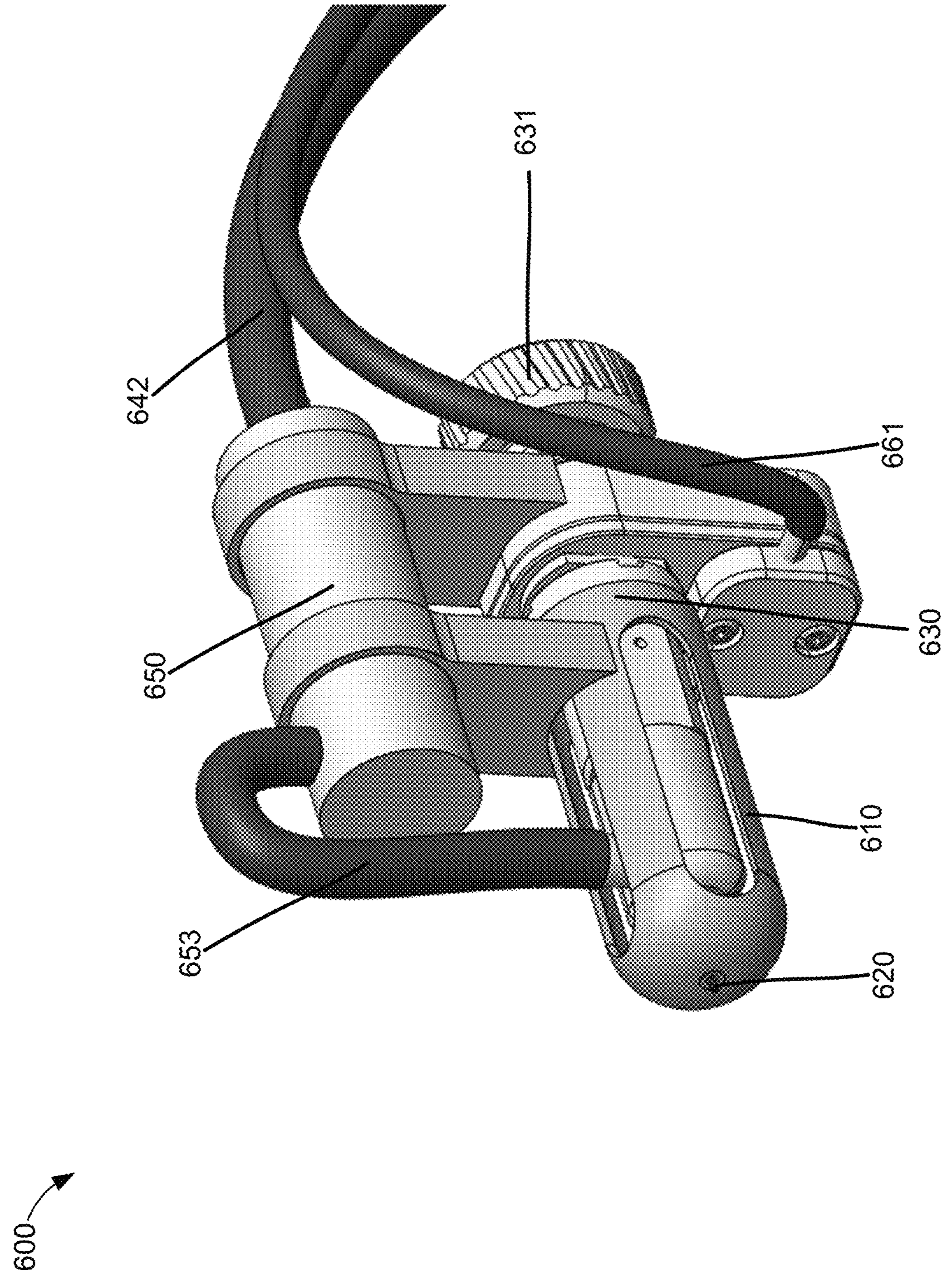
FIG. 10 is an illustration of an injection apparatus, according to an embodiment.

FIG. 10 is an illustration of an injection apparatus 600, according to an embodiment. As shown, the injection apparatus 600 includes a housing 610, a hollow conduit 620, an actuator 630, a manual actuator dial 631, a pressure line 642, a medicament container 650, and a control line 661. In some embodiments, the housing 610, the hollow conduit 620, the actuator 630, the pressure line 642, and the medicament container 650 can be the same or substantially similar to the housing 210, the hollow conduit 220, the actuator, the pressure line 242, and the medicament container 250, respectively, as described above with reference to FIG. 6. Thus, certain aspects of the housing 610, the hollow conduit 620, the actuator 630, the pressure line 642, and the medicament container 650 are not described in further detail herein.

In some embodiments, the injection apparatus 600 can include both an automatic actuator and a manual actuator. In some embodiments, the actuator 630 can include a piezo motor. In some embodiments, the manual actuator dial 631 can control a micrometer based actuator. In some embodiments, the micrometer-based actuator can be a second actuator. The use of two different types of actuators can allow for both automatic and manual advancement of the hollow conduit 620, depending on the preference of the person administering the injection.

As shown, the medicament container 650 is a separate vessel from the housing 610. Injectate can flow from the medicament container 650 to the hollow conduit 620 via a medicament line 653. In some embodiments, the pressure line 642 can act as a portion of a manometer, the same or substantially similar to the pressure line 542 described above, with reference to FIG. 9. In some embodiments, the control line 661 can control operation of the actuator 630. In some embodiments, the control line 661 can control inputs into a motor in the actuator 630

In some embodiments the injection apparatus 600 can include an OCT probe (not shown in FIG. 10). The OCT probe can have a shell and/or housing which accommodates an optical fiber as well as other components such as lenses, prisms and other auxiliary components. The OCT probe can also include and/or be coupled to one or more light source(s)

and a photodetector(s) such as those described above with reference to the OCT probe measurement device 140. The shell and/or housing of the OCT probe can be a hollow structure that defines an interior volume in which the optical fiber and other components of the OCT probe can be accommodated. The shell and/or housing of the OCT probe can be cylindrical shape which includes a closed end having a suitable shape such as bevelled, conical, franseen, and/or diamond shape. The optical fiber can be any suitable fiber capable of transporting light. In some embodiments, the OCT probe can be an SS—OCT that uses a wavelength-swept light source. In other embodiments, the OCT probe can be an SD—OCT that uses a broadband wavelength light source. In some embodiments, the OCT probe can be run through the hollow conduit 620. Furthermore, in some embodiments, the hollow conduit 620 can be a multi-lumen conduit having at least a first lumen and a second lumen, the second lumen being different from the first lumen. The first lumen can be used to transport the injectate to the injection region. The second lumen can be used to accommodate the OCT probe such that the OCT probe can generate interference patterns that can be processed and/or analyzed to determine spacial dimensions and/or produce images of the various regions and/or layers of the eye. The images can be used to deliver the injected to a desired region of the eye.

In use, the housing 610 can be brought to a location close to the eye, such that the distal end of the hollow conduit 620 is near the outer surface of the eye. The distal end of the hollow conduit 620 is then advanced a first distance into the reference location in the eye. In some embodiments, the actuator 630 can advance the distal end of the hollow conduit 620 to the reference location. The reference location is detected based on pressure measurements in the pressure line 642. In some embodiments, the reference location is detected based on tomographic images produced with an OCT probe included in the hollow conduit 620. Once the reference location is detected, the actuator 630 can advance the hollow conduit 620 a second distance into the eye, such that the distal end of the hollow conduit 620 reaches the injection region. Once the distal end of the hollow conduit 620 has reached the injection region, an injection controller (not shown) propels injectate from the medicament container 650 to the injection region via the medicament line 653 and the hollow conduit 520. After the injection, the hollow conduit 620 can be removed from the eye.

Figure 11:
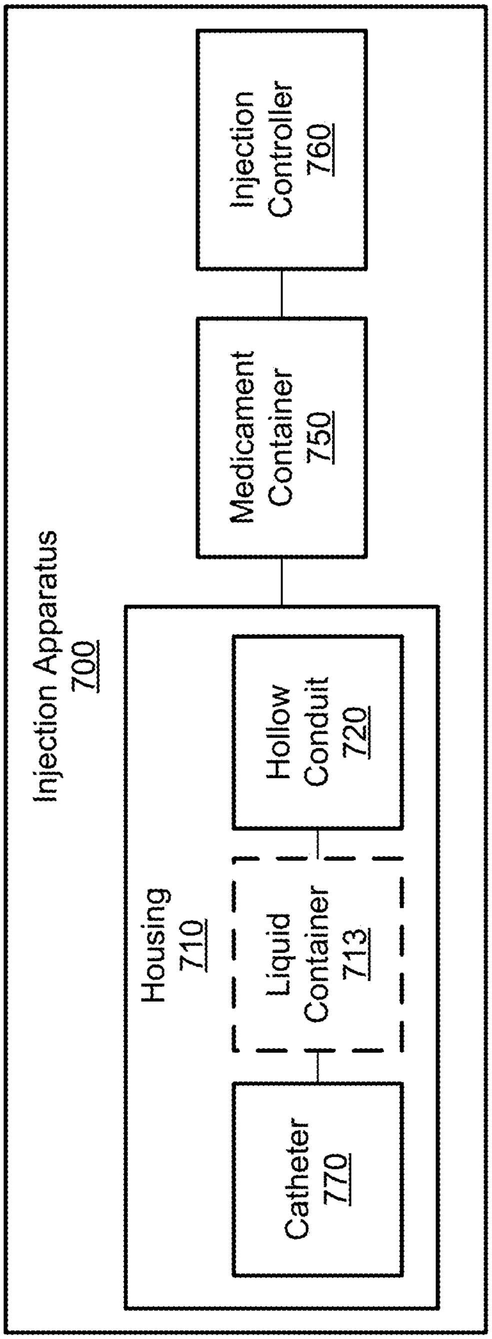
FIG. 11 is a schematic illustration of an injection apparatus, according to an embodiment.

FIG. 11 is a schematic illustration of an injection apparatus 700, according to an embodiment. In some implementations, the injection apparatus 700 can be configured to locate a first region (e.g., an SCS) of a target tissue (e.g., an eye), and use the location of that first region to deliver a medicament to a second region (e.g., a retina or subretinal space (SRS)) of the target tissue.

As shown, the injection apparatus 700 includes a housing 710 configured to be engaged with a hollow conduit 720 and a catheter 770. The housing 710 includes a fluid container 713 disposed therein. The injection apparatus 700 further includes a medicament container 750 contacting and slidably movable within the housing 710. An injection controller 760 is slidably engaged with the medicament container 750 and controls injection of medicament via the hollow conduit 720. In other words, medicament in the medicament container 750 can be pushed out of the injection apparatus 700 via the movement of the injection controller 760 from a first position to a second position relative to the housing 710. In some implementations, the housing 710, the hollow conduit 720, the medicament container 750, and the injection controller 760 can be the same or substantially similar to the housing 110, the hollow conduit 120, the medicament container 150, and the injection controller 160, as described above with reference to FIG. 5. Thus, certain aspects of the housing 710, the hollow conduit 720, the medicament container 750, and the injection controller 760 are not described in greater detail herein.

The fluid container 713 is contained in the housing 710 and can contain a liquid. The fluid container 713 is fluidically coupled to the catheter 770 such that the liquid can exit the fluid container 713 via the catheter 770. The fluid container 713 is slidably coupled to the housing 710 such that the fluid container 713 can be moved into and out of the housing 710. The medicament container 750 is slidably coupled to the fluid container 713, such that the medicament container 750 can be moved into and out of the fluid container 713. Movement of the medicament container 750 into the fluid container 713 applies a pressure to the liquid in the fluid container 713, causing the liquid to be pushed through the catheter 770 and out of the injection apparatus 700.

The hollow conduit 720 has a smaller diameter than the catheter 770 such that the hollow conduit 720 can slidably move into and out of the catheter 770. The hollow conduit 720 has a length such that a distal end of the hollow conduit 720 extends beyond a distal end of the catheter 770 when the medicament container 750 is advanced toward a distal end of the fluid container 713.

The medicament container 750 is fluidically coupled to the hollow conduit 720 such that medicament can flow from the medicament container 750 to outside the injection apparatus 700 via the hollow conduit 720. The injection controller 760 is slidably coupled to the medicament container 750, such that advancement of the injection controller 760 applies a pressure to the medicament in the medicament container 750, causing the medicament to flow out of the injection apparatus 700 via the hollow conduit 720.

In use, to initiate an injection, the injection apparatus 700 is moved distally toward a target surface (i.e. a conjunctiva and/or sclera of an eye) when the fluid container 713 is in a first configuration (or position) within the housing 710. In the first configuration, the fluid container 713 is a first distance from a distal end of the housing 710. In some implementations, the distal end of the housing 710 can contact the target surface to form a seal with the target surface. A distal tip of the catheter 770 is inserted into the sclera via movement of the fluid container 713 from the first configuration to a second configuration. In the second configuration, the fluid container 713 is a second distance from the distal end of the housing 710, the second distance less than the first distance. In some embodiments, movement of the fluid container 713 from the first configuration to the second configuration can be manual (e.g., via use of hands/fingers). In other words, a user can manually push the fluid container 713 (e.g., via a flange or plunger) in a distal direction relative to the housing 710. In some embodiments, movement of the fluid container 713 from the first configuration to the second configuration can be automated. In some implementations, initial insertion of the catheter 770 into the target surface can include inserting the catheter 770 into the target surface until an outer surface (e.g., distal-most end) of the housing 710 contacts the target surface. In some implementations, the contact between the outer surface of the housing 710 and the target surface can deform the target surface. In some implementations, the contact between the outer surface of the housing 710 and the target surface can form a substantially fluid-tight seal with the conjunctiva around the insertion site of the catheter 770. In some implementations, insertion of the distal end of the catheter 770 into the target surface can be at an angle relative to a line tangent to the target surface (i.e., an angle of entry). In some implementations, the angle of entry can be at least about 0 degrees, at least about 1 degree, at least about 2 degrees, at least about 3 degrees, at least about 4 degrees, at least about 5 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 85 degrees, at least about 90 degrees, at least about 95 degrees, at least about 100 degrees, at least about 105 degrees, at least about 110 degrees, at least about 115 degrees, at least about 120 degrees, at least about 125 degrees, at least about 130 degrees, at least about 135 degrees, at least about 140 degrees, at least about 145 degrees, at least about 150 degrees, at least about 155 degrees, at least about 160 degrees, at least about 165 degrees, at least about 170 degrees, at least about 175 degrees, at least about 176 degrees, at least about 177 degrees, at least about 178 degrees, or at least about 179 degrees. In some embodiments, the angle of entry can be no more than about 180 degrees, no more than about 179 degrees, no more than about 178 degrees, no more than about 177 degrees, no more than about 176 degrees, no more than about 175 degrees, no more than about 170 degrees, no more than about 165 degrees, no more than about 160 degrees, no more than about 155 degrees, no more than about 150 degrees, no more than about 145 degrees, no more than about 140 degrees, no more than about 135 degrees, no more than about 130 degrees, no more than about 125 degrees, no more than about 120 degrees, no more than about 115 degrees, no more than about 110 degrees, no more than about 105 degrees, no more than about 100 degrees, no more than about 95 degrees, no more than about 90 degrees, no more than about 85 degrees, no more than about 80 degrees, no more than about 75 degrees, no more than about 70 degrees, no more than about 65 degrees, no more than about 60 degrees, no more than about 55 degrees, no more than about 50 degrees, no more than about 45 degrees, no more than about 40 degrees, no more than about 35 degrees, no more than about 30 degrees, no more than about 25 degrees, no more than about 20 degrees, no more than about 15 degrees, no more than about 10 degrees, no more than about 5 degrees, no more than about 4 degrees, no more than about 3 degrees, no more than about 2 degrees, or no more than about 1 degree. In some implementations, the distal end of the catheter 770 can be inserted into the target surface substantially tangent to the target surface. In some implementations, the distal end of the catheter 770 can be inserted into the target surface completely tangent to the target surface.

Combinations of the above-referenced angles of entries are also possible (e.g., at least about 0 degrees and no more than about 180 degrees), inclusive of all values and ranges therebetween. In some embodiments, the angle of entry can be about 0 degrees, about 1 degree, about 2 degrees, about 3 degrees, about 4 degrees, about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 95 degrees, about 100 degrees, about 105 degrees, about 110 degrees, about 115 degrees, about 120 degrees, about 125 degrees, about 130 degrees, about 135 degrees, about 140 degrees, about 145 degrees, about 150 degrees, about 155 degrees, about 160 degrees, about 165 degrees, about 170 degrees, about 175 degrees, about 176 degrees, about 177 degrees, about 178 degrees, about 179 degrees, or about 180 degrees. In some embodiments, an angle control device can be placed on the outer surface of the eye to guide the movement of the hollow conduit and guide the angle of entry.

In some implementations, the housing 710 can include a mechanism to limit and/or prevent proximal movement of the distal tip of the catheter 770 relative to the housing 710. For example, in some implementations, the housing 710 can include a shoulder (not shown) that engages a corresponding shoulder (not shown) of the catheter 770 to prevent proximal movement of the catheter 770 relative to the housing 710.

In some instances, the injection apparatus 700 can be moved distally to complete the initial insertion of the catheter 770 into the target surface. For example, the user can manually apply a force to a portion of the medicament container 750 and/or the housing 710. Said another way, the initial insertion operation can be a manual operation that does not rely on any stored energy device (e.g., springs, compressed gas containers, or the like) to produce the force to move the medicament container 750 and/or the housing 710. During the initial insertion, the injection apparatus 700 is advanced distally such that the distal end of the catheter 770 is in contact with the sclera and/or the choroid. The high densities of the sclera or choroid relative to the retina can provide a resistance to movement of the catheter 770 relative to the target surface and a resistance to flow of the liquid from inside the fluid container 713. After the initial insertion, at least a portion of the liquid from inside the fluid container 713 can be conveyed through the catheter 770 via movement of the medicament container 750 from a first position relative to the fluid container 713 and/or the housing 710 to a second position relative to the fluid container 713 and/or the housing 710, the second position distal to the first position. Said another way, advancement of the medicament container 750 can simultaneously convey the liquid from the fluid container 713 to a target region via the catheter 770, as a distal end of the medicament container 750 can press on the liquid to push the liquid through the catheter 770. In the second configuration, the medicament container 750 is a second distance from the distal end of the housing 710, the second distance less than the first distance. In some implementations, the liquid within the fluid container 713 can be pressurized (e.g., via a spring springing mechanism). By pressurizing the fluid container 713, the forces acting on the liquid in the fluid container 713 can become unbalanced when the distal end of the catheter 770 reaches a region of lower resistance (e.g., the SCS), causing the medicament container 750 to move in a distal direction relative to the housing 710. The medicament container 750 then moves to a second configuration (or position) relative to the housing 710. In other words, the medicament container 750 can move in a distal direction (thereby injecting the liquid into a target region) via a loss-of-resistance mechanism. More specifically, the medicament container 750 can be subject to an outside force (e.g., a spring or a springing mechanism), but the high density of the sclera and/or choroid relative to the SCS can create a backpressure and prevent movement of the medicament container 750 relative to the housing 710. Once the distal end of the injection apparatus 700 advances to a less dense region (e.g., the SCS), the medicament container 750 can advance distally relative to the fluid container 713 and the housing 710, thereby releasing liquid from the fluid container 713. In some embodiments, the distal movement of the medicament container 750 relative to the housing 710 and the fluid container 713 can be manually actuated (e.g., via use of hands/fingers). In other words, a user can manually push the medicament container 750 (e.g., via a flange) in a distal direction relative to the housing 710 and the fluid container 713.

In use, the medicament container 750 can move relative to the housing 710 in response to the entry of the distal end of the injection apparatus 700 into the less dense region (e.g., the SCS). In other words, the medicament container 750 can move relative to the housing 710 in response to the aforementioned loss-of-resistance mechanism. The movement of the medicament container 750 relative to the housing 710 can cause the liquid to be deployed from the fluid container 713 via the catheter 770. This deployment of the liquid can thereby inform the user that the distal end of the catheter 770 has entered the SCS. After the SCS has been located via the loss-of-resistance mechanism, the hollow conduit 720 can be advanced, such that a distal end of the hollow conduit 720 reaches a desired injection region. Alternatively, and/or additionally, in some embodiments the injection apparatus 700 can include an OCT probe (not shown in FIG. 11). The OCT probe can also include and/or be coupled to one or more light source(s) and a photodetector(s) such as those described above with reference to the OCT probe measurement device 140. The shell and/or housing of the OCT probe can be a hollow structure that defines an interior volume in which the optical fiber and other components of the OCT probe can be accommodated. The shell and/or housing of the OCT probe can be a cylindrical shape which includes a closed end having a suitable shape such as bevelled, conical, franseen, and/or diamond shape. The optical fiber can be any suitable fiber capable of transporting light. In some embodiments, the OCT probe can be an SS—OCT that uses a wavelength-swept light source. In other embodiments, the OCT probe can be an SD—OCT that uses a broadband wavelength light source. In some embodiments, the OCT probe can be run through the hollow conduit 720. Furthermore, in some embodiments, the hollow conduit 720 can be a multi-lumen conduit having at least a first lumen and a second lumen, the second lumen being different from the first lumen. The first lumen can be used to transport an injectate to the injection region. The second lumen can be used to accommodate the OCT probe such that the OCT probe can generate interference patterns that can be processed and/or analyzed to determine spacial dimensions and/or produce images of the various regions and/or layers of the eye. The tomography images generated with the OCT probe can be used to determine and/or identify a desired injection region The hollow conduit 720 is coupled to the medicament container 750 and the distal movement of the medicament container 750 causes the hollow conduit 720 to advance in a distal direction, such that a distal end of the hollow conduit 720 extends beyond the distal end of the catheter 770. In other words, the distal end of the hollow conduit 720 can enter a target tissue for medicament injection at a location distal to the catheter 770 (e.g., the SRS). Upon entry of the hollow conduit 720 into the target tissue, the injection controller 760 can be actuated to inject medicament into the target tissue. In some embodiments, the user can manually apply a force (e.g., via use of hands/fingers) to a portion of the medicament container 760 to induce injection of the medicament into the target tissue. In some embodiments, the SCS can be used as a reference location to find the target tissue (e.g., the SRS) for medicament injection. For example, upon finding the SCS, the medicament container 750 and the hollow conduit 720 can be advanced, such that the distal end of the hollow conduit 720 is advanced beyond the distal end of the catheter by about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm, inclusive of all values and ranges therebetween. In other words, the distal end of the hollow conduit 720 reaches the target tissue, and injection of the medicament from the medicament container 750 occurs.

FIGS. 12A-12F illustrate an injection apparatus 800 and a method of using the injection apparatus 800, according to an embodiment. As shown, the injection apparatus 800 includes a housing 810, a fluid container 813, a fluid container hub 814, a handle 815, a sealing surface 816, a seal 817, a fluid container flange 819, a hollow conduit 820, a medicament container 850, a medicament container hub 851, a medicament container flag 853, adapters 855, 856, an injection controller 860, and an outer conduit 870. As shown, the outer conduit 870 is a catheter. In some embodiments, the outer conduit 870 can can be an outer conduit, such that the hollow conduit 820 is an inner conduit that moves within the outer conduit. In some embodiments, the outer conduit 870 can be a multi-lumen conduit. In other words, the outer conduit 870 can have multiple lumens, through which inner conduits (e.g., the inner conduit 820) can move. This can allow for delivery of a first liquid and/or medicament to a first location in the eye and a delivery of a second liquid and/or medicament to a second location in the eye. The second location can be deeper in the eye than the first location (e.g., the second location can be in the SRS and the first location can be in the SCS).

Figure 12A:
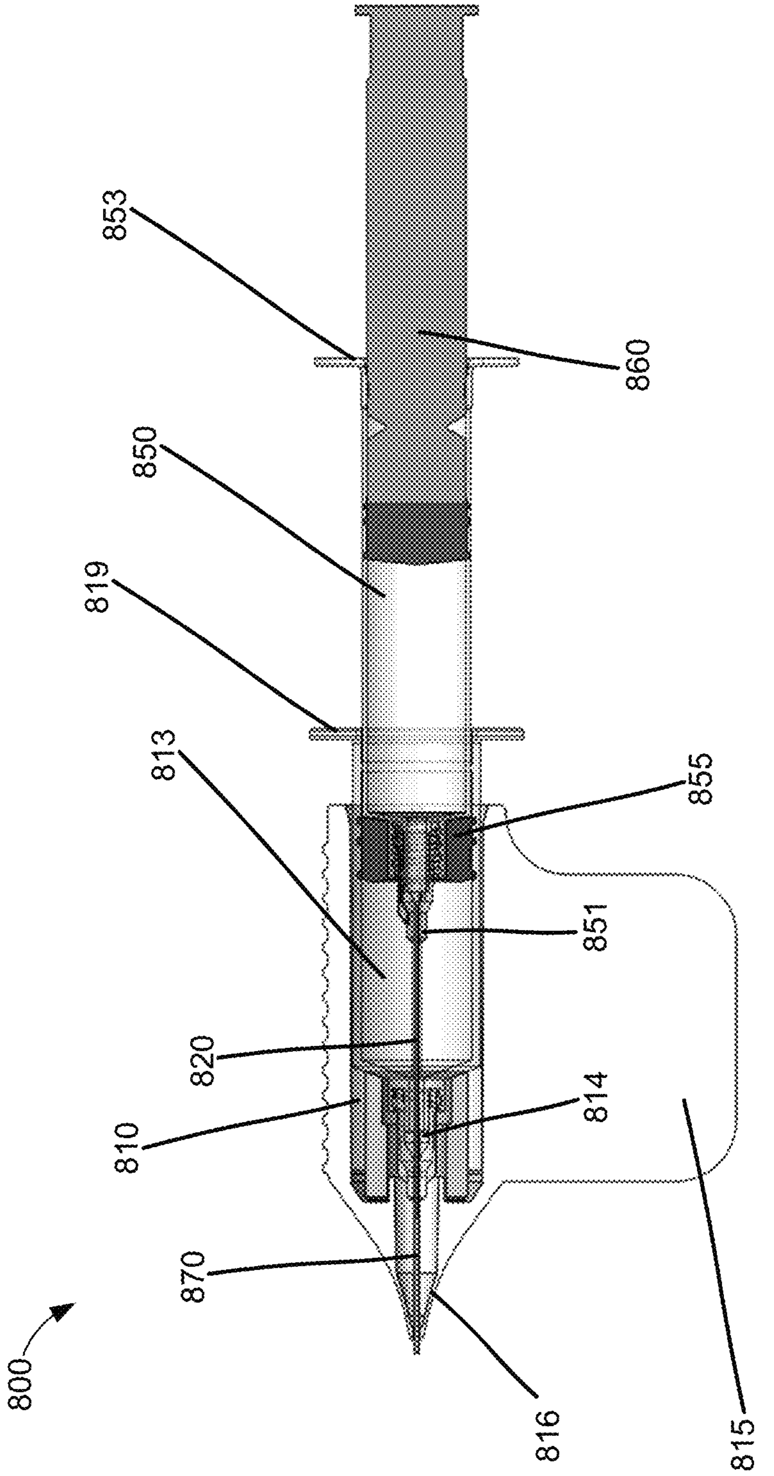
FIGS. 12A-12F illustrate a method and apparatus for performing an injection into the retinal tissue, according to an embodiment.
Figure 12B:
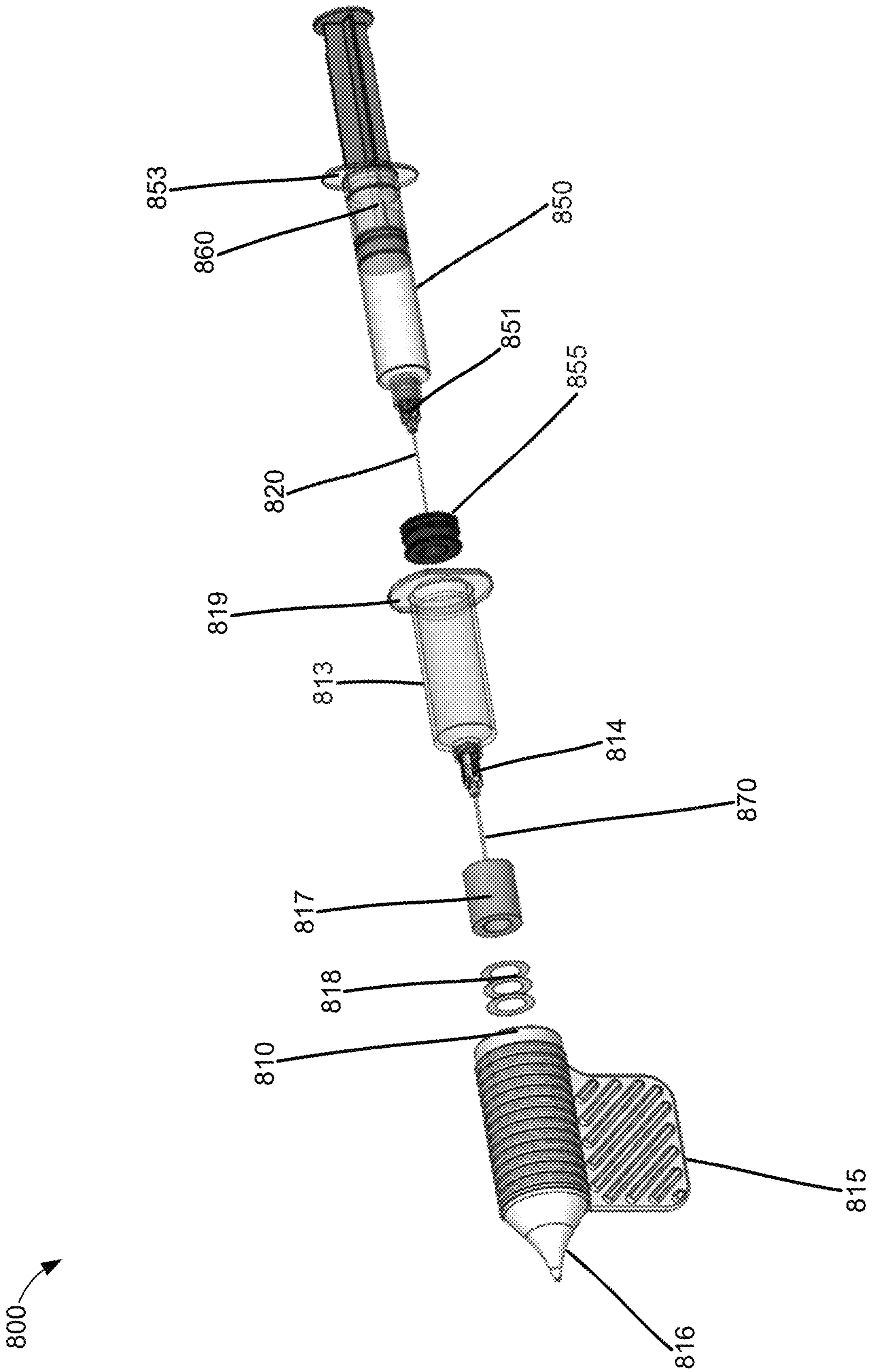

FIG. 12A shows a cross-sectional view of the injection apparatus 800 while FIG. 12B shows an exploded view of the injection apparatus 800. In some implementations, the housing 810, the fluid container 813, the hollow conduit 820, the medicament container 850, and the injection controller 860 can be the same or substantially similar to the housing 710, the fluid container 713, the hollow conduit 720, the medicament container 750, and the injection controller 760, as described above with reference to FIG. 11. Thus, certain aspects of the housing 810, the fluid container 813, the hollow conduit 820, the medicament container 850, and the injection controller 860 are not described in greater detail herein.

As shown, the handle 815 can include a flat planar shape extending outwardly from a central axis of the housing 810. In some instances, the handle 815 can provide a grip for the user to hold while operating the injection apparatus 800. In some instances, the handle 815 can provide a means for stopping the injection apparatus 800 from rolling (e.g., when placed on a table or platform). The sealing surface 816 provides a surface against which a seal can be formed when the injection apparatus 800 contacts a surface (e.g., conjunctiva or sclera) of the eye. In some instances, the medicament container flange 853 can provide a grip for the user or a platform for the user to manually move the fluid container 813 relative to the housing 810. Similarly, the injection controller 860 can provide a grip for the user or a platform for the user to manually move the medicament container 850 relative to the housing 810 and/or the medicament container 850. The adapters 855, 856 provide a key-lock pair to secure the medicament container 850 and the fluid container 813 together.

The fluid container 813 is at least partially housed in the housing 810 and can move from a first position (i.e., a proximal position) relative to the housing 810 to a second position (i.e., a distal position) relative to the housing 810. The catheter 870 is fixedly coupled to the fluid container 813. In moving from the first position to the second position, the fluid container 813 can correspondingly cause the catheter 870 to move distally such that a distal end of the catheter 870 extends beyond the sealing surface 816.

The medicament container 850 is at least partially housed in the fluid container 813 and can move from a first position (i.e., a proximal position) relative to the fluid container 813 to a second position (i.e., a distal position) relative to the fluid container 813. The hollow conduit 820 is fixedly and fluidically coupled to the medicament container 850. In moving from the first position to the second position, the medicament container 850 can cause the hollow conduit 820 to move distally through a lumen of the catheter 870 such that a distal end of the hollow conduit extends beyond the distal end of the catheter 870. The seal 817 can slide along the interior of the fluid container 813 with the medicament container 850. The seal 817 can prevent fluid from exiting the fluid container 813 through the proximal end of the fluid container 813.

Rotation of the different components of the injection apparatus 800 afford versatility of motion of the components of the injection apparatus 800. In some embodiments, the medicament container 850 is not fixedly coupled to the housing 810, allowing the medicament container 850 to rotate relative to the housing 810. In some embodiments, the medicament container 850 is coupled to the fluid container 813 via the adapters 855, 856. The adapter 855 can be coupled to the fluid container flange 819 and the adapter 856 can be coupled to the outside surface of the medicament container 850. In some embodiments, the medicament container 850 is not fixedly coupled to the fluid container 813, allowing the medicament container 850 to rotate relative to the housing 810.

In some embodiments, rotation of the hollow conduit 820 can aid in advancement of the hollow conduit 820 through target tissue, particularly if the hollow conduit 820 has a beveled (i.e., angled) distal tip. The angle of the distal tip of the hollow conduit 820 can allow the beveled distal tip to act like a blunt tip trocar that pushes tissue away to make room for passage of the hollow conduit 820 through the target tissue easier (as compared to an unbeveled distal tip). Said another way, the operator can rotate the medicament container 850 (and the hollow conduit 820 fixedly coupled to the medicament container 850), relative to the housing 810 and the fluid container 813, by gripping the medicament container 850 (e.g., by the medicament container flange 853). This rotation of the medicament container 850 and the hollow conduit 820 can be done while the housing 810 and the fluid container 813 are relatively stationary and not rotating (as the medicament containter 850 and the hollow conduit 820 are rotatable relative to the housing 810 and the fluid container 813). Keeping the housing 810 and the fluid container 813 stationary can prevent scoring on the surface of the eye (e.g., by the sealing surface 816). While the distal tip of the hollow conduit 820 is extended beyond the sealing surface 816, rotating the hollow conduit 820 to push the tissue away can be analogous to driving a screw into wood. With each rotation of the hollow conduit 820, the beveled tip of the hollow conduit 820 moves deeper into the tissue of the eye until it reaches a target region. The medicament container 850 can be fixedly coupled to the adapter 855 while the fluid container 813.

In some embodiments, the distal tip of the hollow conduit can be beveled at an angle of about 5 degrees (relative to an unbeveled tip), about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or about 90 degrees, inclusive of all values and ranges therebetween.

Figure 12C:
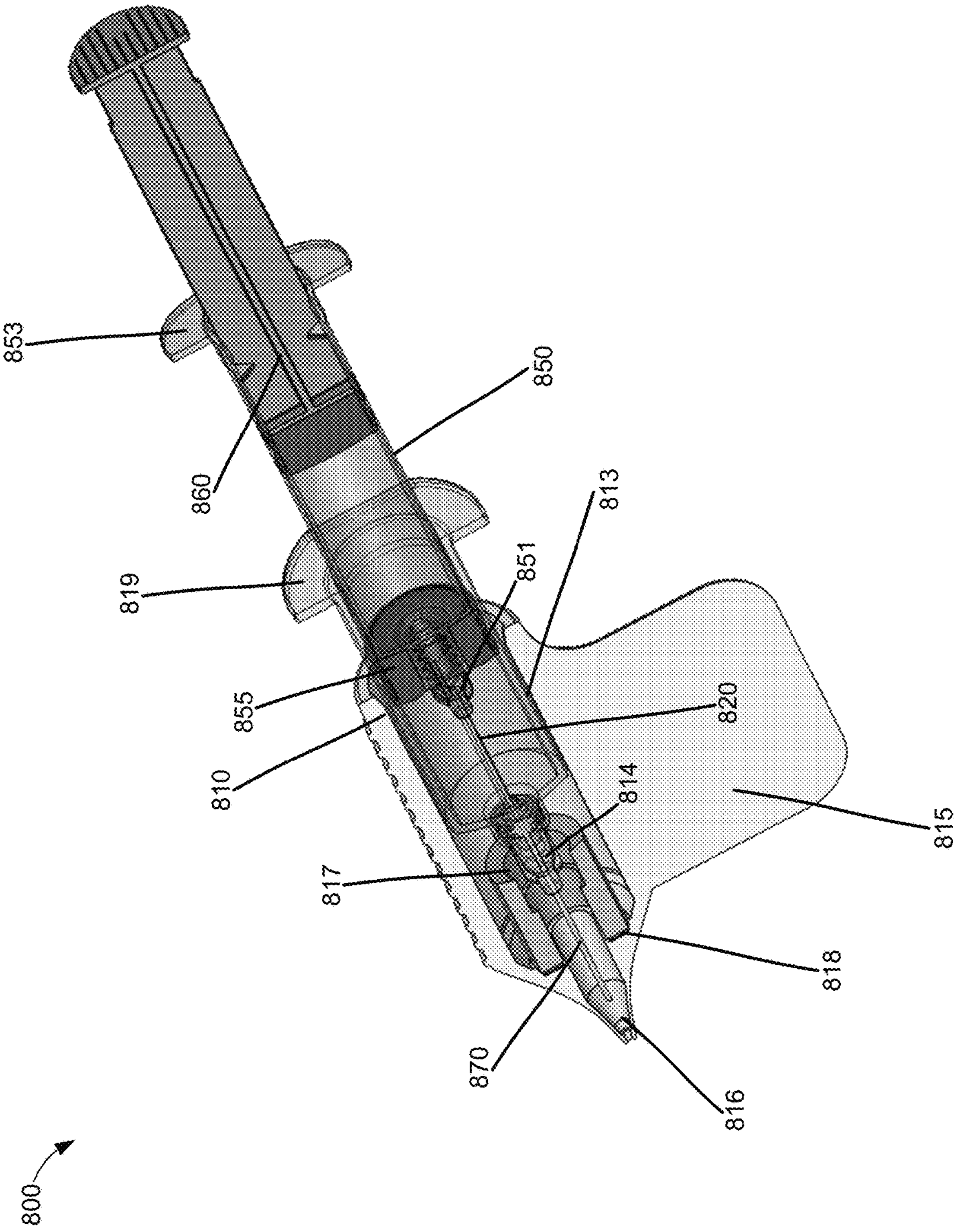
Figure 12D:
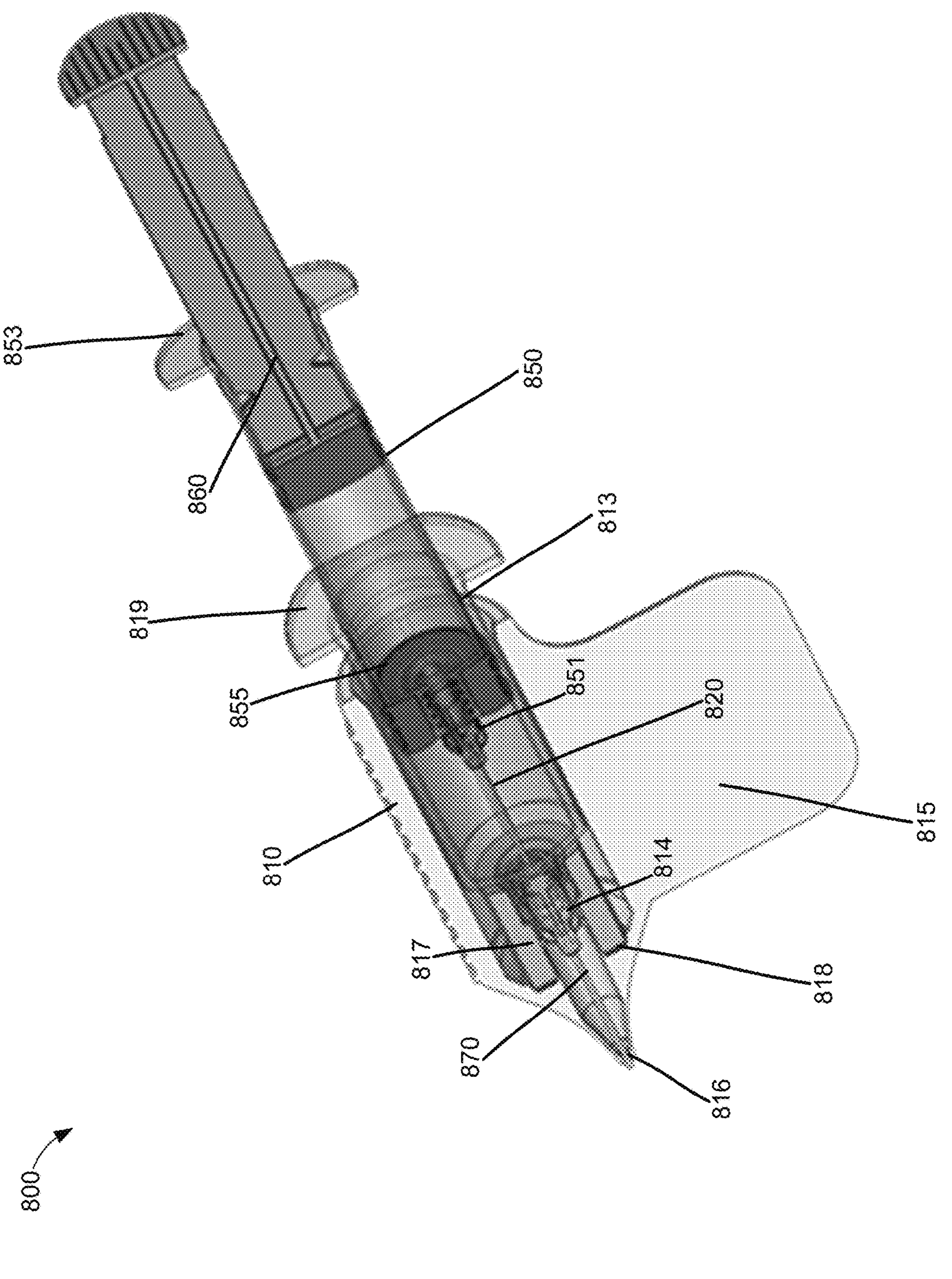

In use, the sclera (not shown) can be pre-scored. FIGS. 12C and 12D show the transition of the fluid container 813 from the first position to the second position. In some implementations, the clearance distance can be about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm, inclusive of all values and ranges therebetween. The fluid container flange 819 is pushed (e.g., by a finger) to seal the sealing surface 816 against the pre-scored sclera hole. In some embodiments, the fluid container 813 can be rotatable relative to the housing 810, as the outer diameter of the fluid container 813 can be smaller than the inner diameter of the housing 810. The catheter 870 is fixedly coupled to the fluid container 813. As the fluid container 813 rotates and/or slides relative to the housing 810, the catheter 870 can advance distally relative to the sealing surface 816 such that the distal end of the catheter 870 enters the sclera, the SCS, the choroid, the SRS, and/or the retina. In some embodiments, the fluid container 813 can be slidably removed from the housing 810.

Figure 12E:
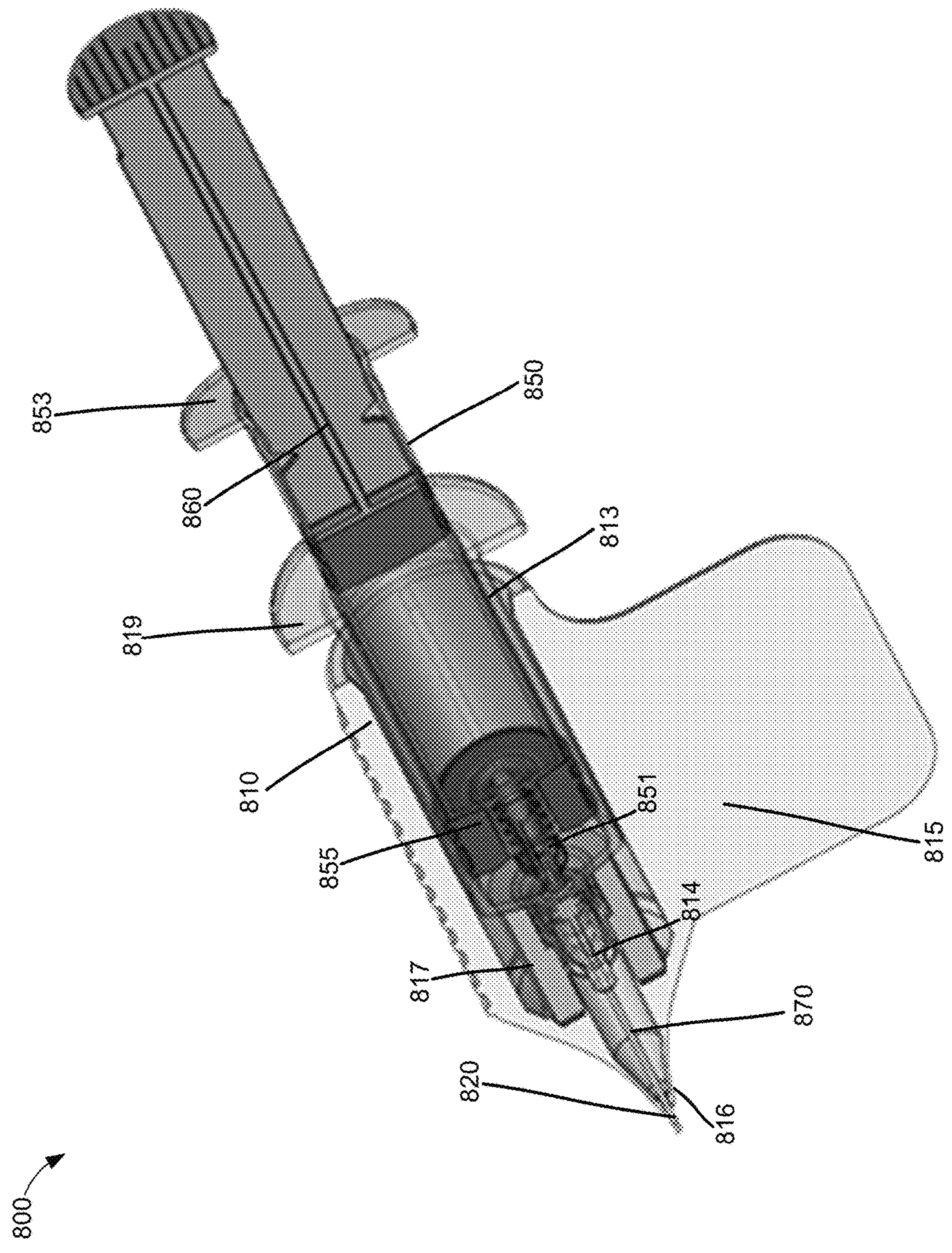
Figure 12F:
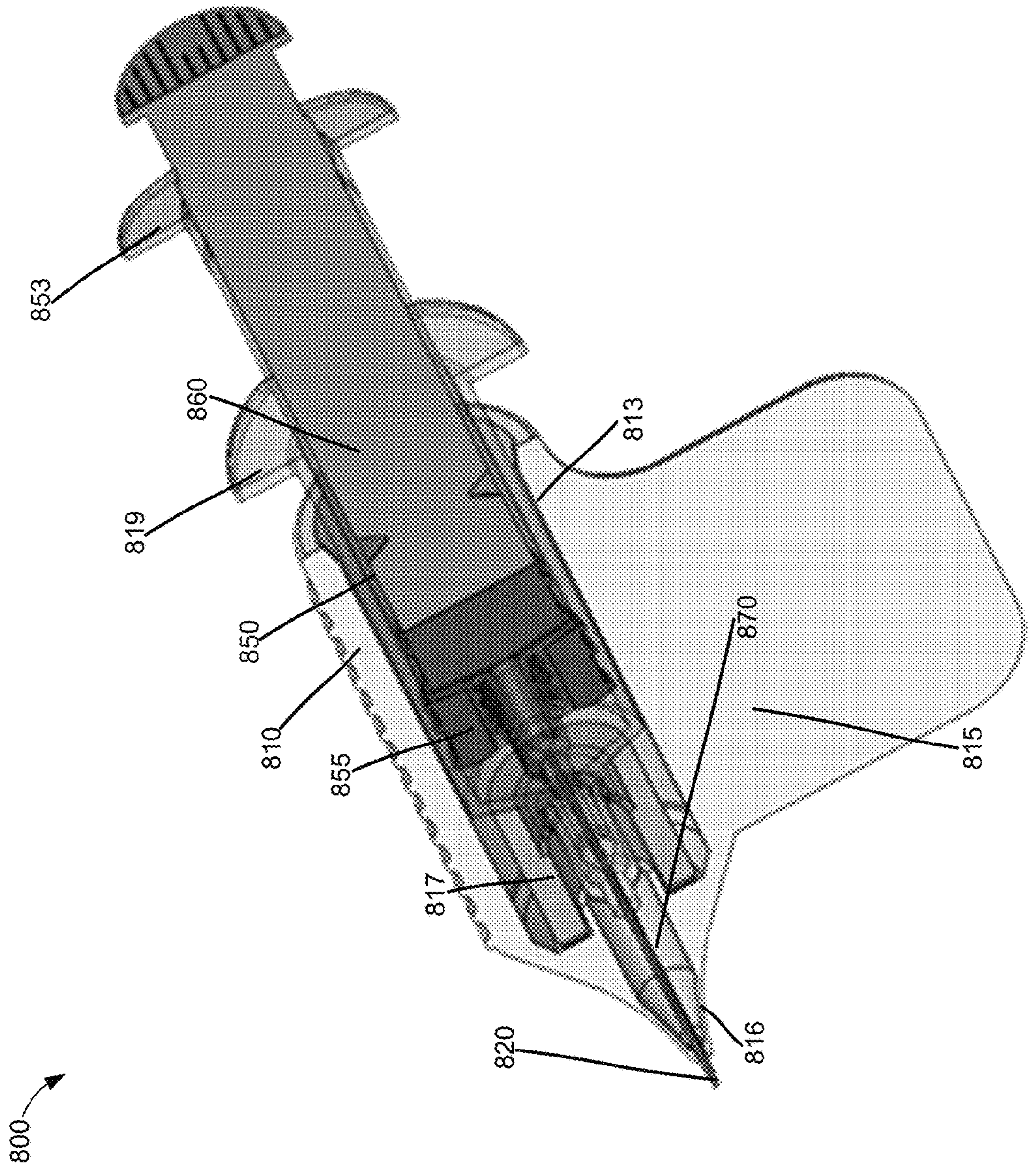

The medicament container 850 can then be gripped and pushed distally relative to the fluid container 813 (see FIG. 12E). In some implementations, the medicament container 850 can be moved by pushing on the medicament container flange 853 in a distal direction relative to the fluid container 813. In some implementations, the fluid container 813 can have a liquid (e.g., a saline solution) disposed therein. In some implementations, pushing the medicament container 850 can pressurize the liquid in the fluid container 813. In some implementations, the seal 817 can move with the medicament container 850 as the medicament container 850 is being advanced. Upon penetration of the sclera by the catheter 870 and entry of the distal end of the catheter 870 into the SCS, the liquid can flow from the fluid container 813 into the SCS via the catheter 870. The fluid that enters the SCS can separate the distal end of the catheter 870 from the choroid, reducing impact to the chorioid. The fluid can enter the space between the sclera and the choroid and hydrodissect the sclera and the choroid to create and/or expand the SCS.

In some embodiments, the liquid can flow from the fluid container 813 via a loss-of-resistance mechanism. In other words, the liquid can be pressurized in an appropriate pressure range such that the liquid is prevented from flowing through the catheter 870 when the distal end of the catheter is in the sclera and the liquid can flow through the catheter 870 when the distal end of the catheter 870 reaches a region (e.g., the SCS) of low pressure (e.g., relative to the sclera). In some implementations, the liquid in the fluid container 813 can be pressurized (e.g., via a force applied by relative distal movement of the medicament container 850. By pressurizing the liquid, the forces acting on the seal 817 can become unbalanced once the distal end opening of the catheter 870 reaches a low-density region (e.g., the SCS) relative to the sclera, causing the medicament container 850, the seal 817, and the catheter 870 to advance from the first position to the second position, thereby injecting the liquid into the SCS via the catheter 870.

As shown in FIGS. 12A-12F, the hollow conduit 820 is fixedly coupled to a distal end of the medicament container 850. The medicament container hub 851 positions and secures the hollow conduit 820 on the medicament container 850. In some implementations, the hollow conduit 820 can advance with the medicament container 850, such that the hollow conduit 820 moves through the catheter 870 and the distal end of the hollow conduit 820 extends beyond the distal end of the catheter 870 and into the injection site (e.g., the SRS). As the liquid dissipates throughout the SCS, the liquid can move the choroid and the choroid can relax against a distal end of the hollow conduit 820. The distal end opening of the hollow conduit 820 enters the SRS. Medicament can then be delivered to the SRS by pushing on the injection controller 860. More specifically, pushing on the injection controller 860 can cause the medicament to exit the medicament container 850 via the hollow conduit 820 and enter the SRS.

Figure 13A:
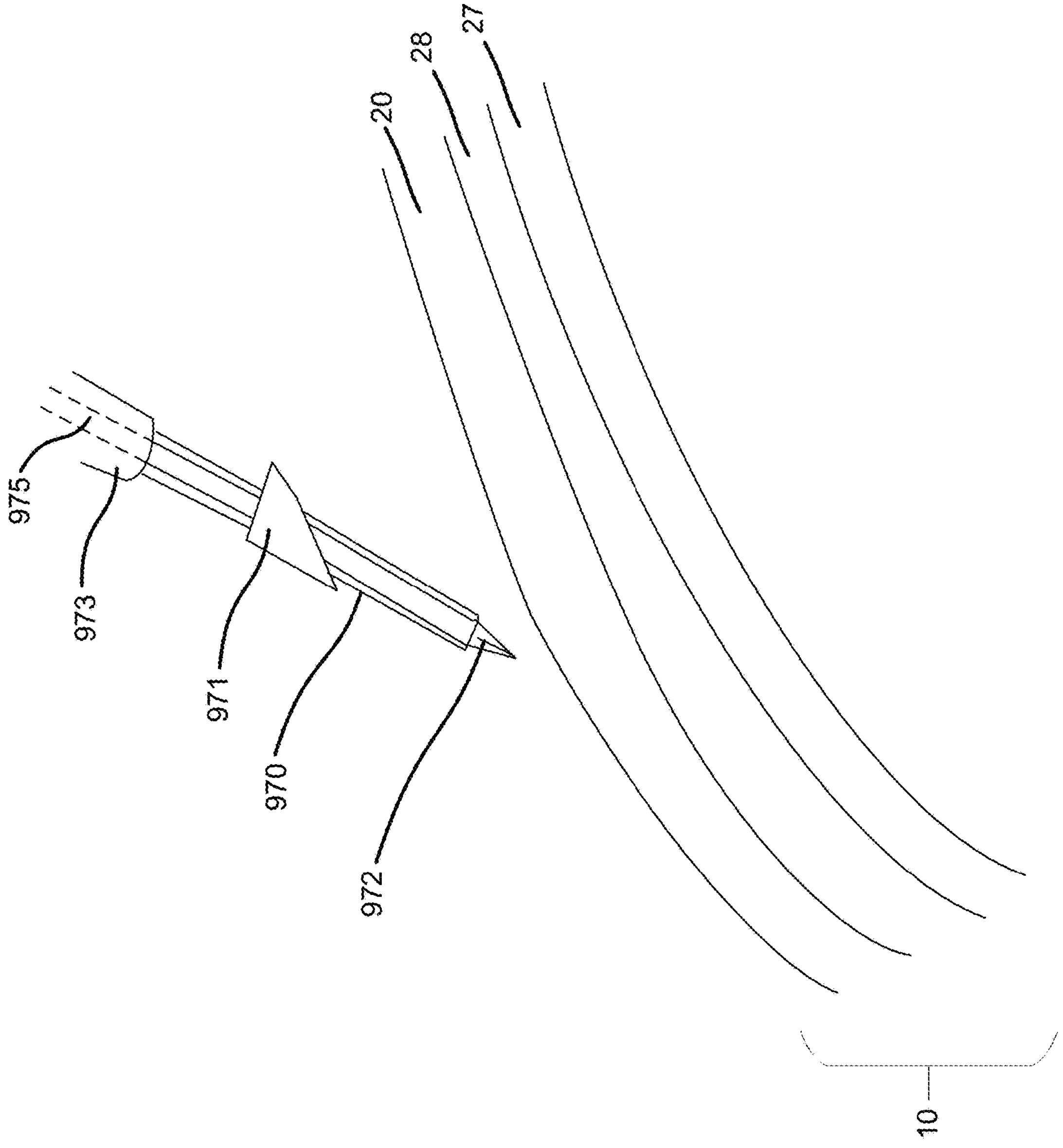
FIGS. 13A-13O illustrate methods and apparatus for performing an injection into the retinal tissue, according to various embodiments.
Figure 13B:
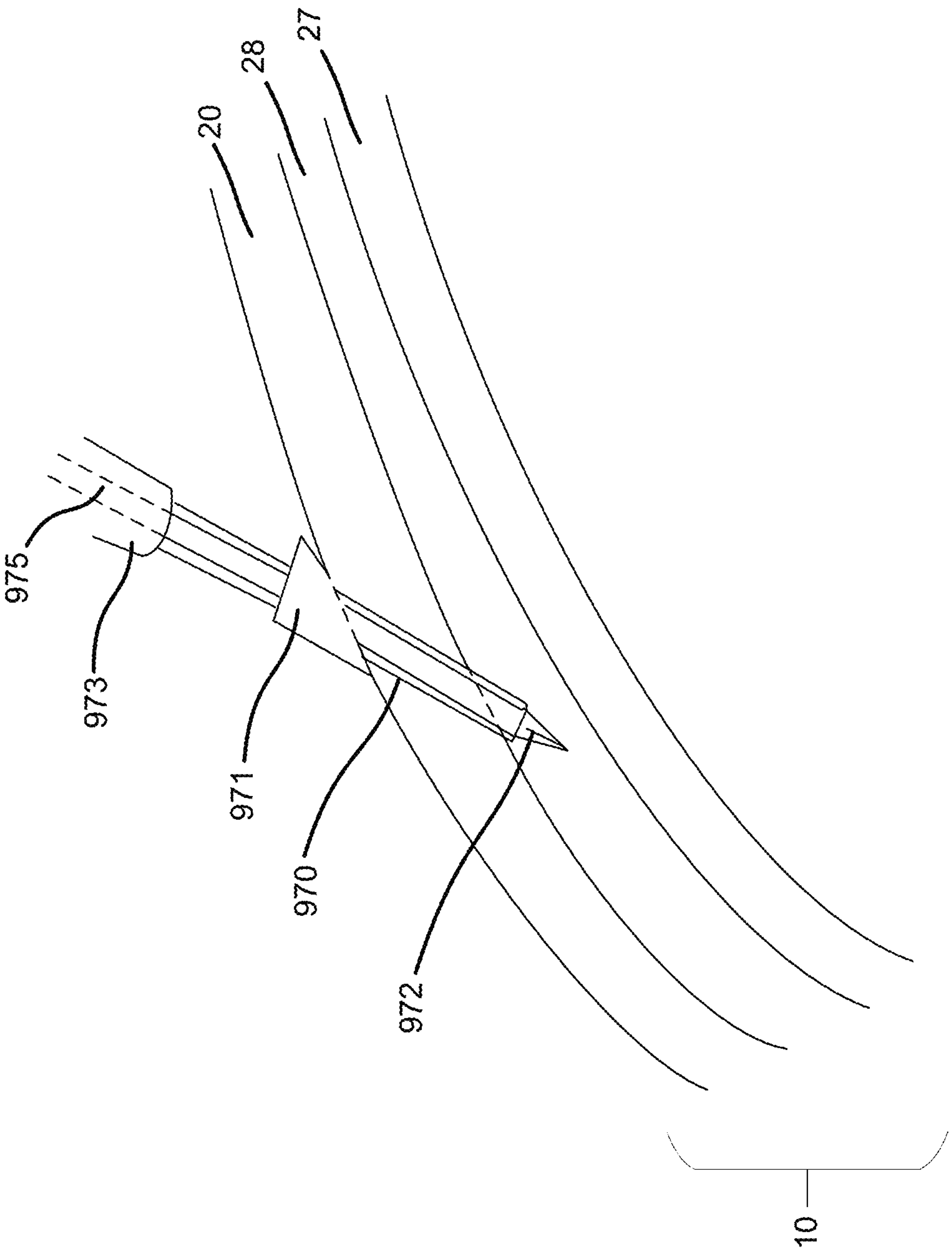
Figure 13C:
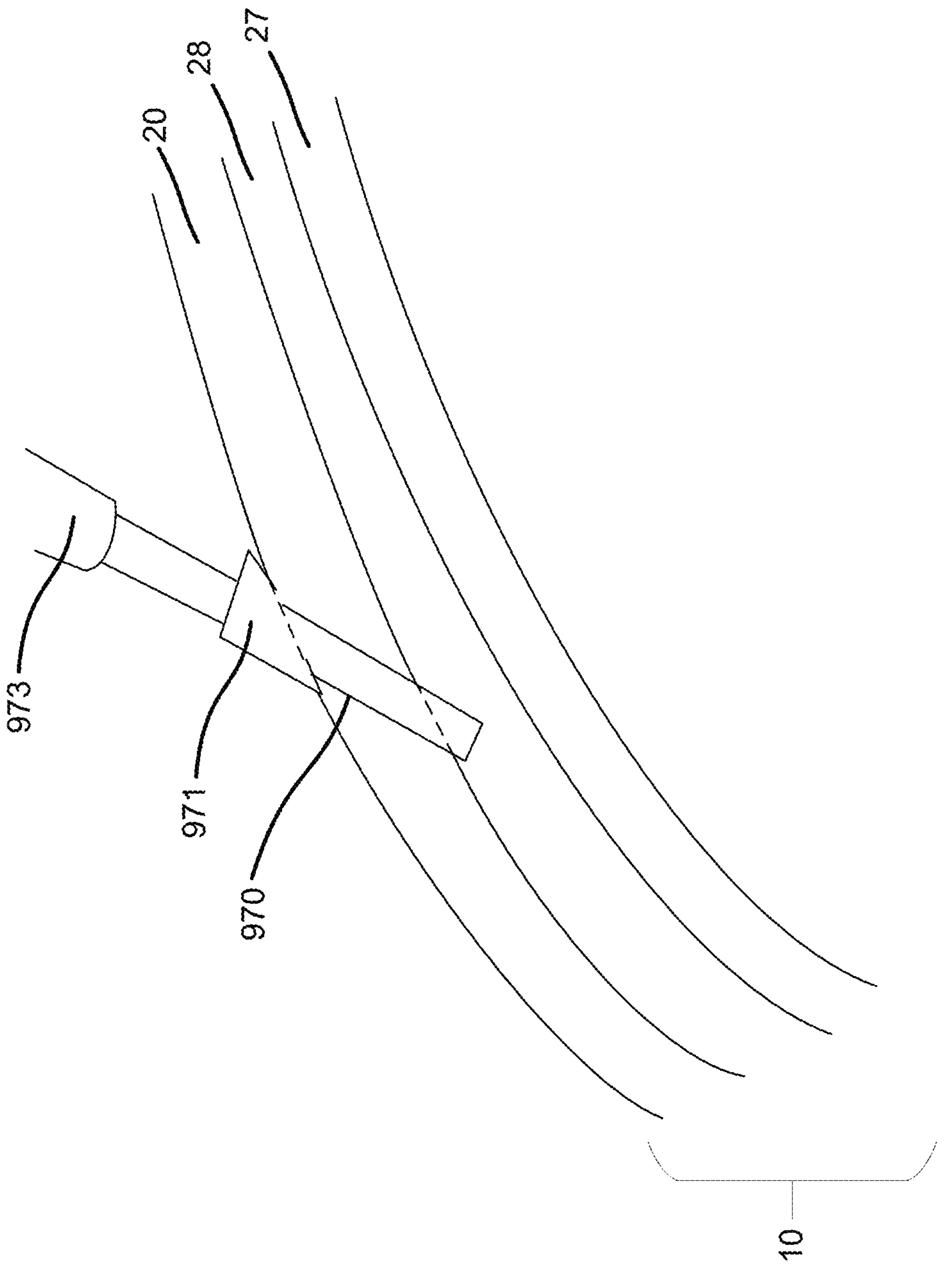
Figure 13D:
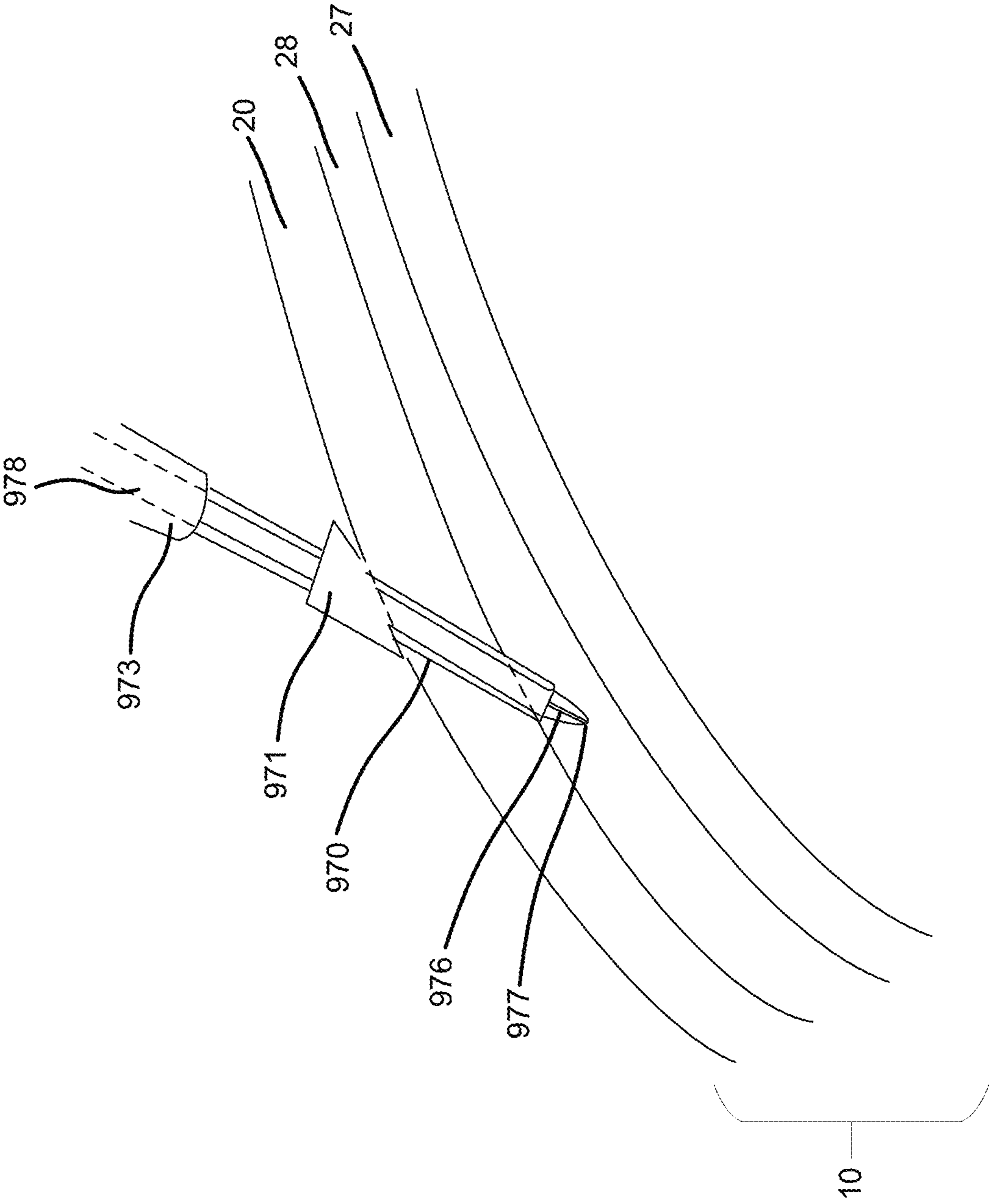
Figure 13E:
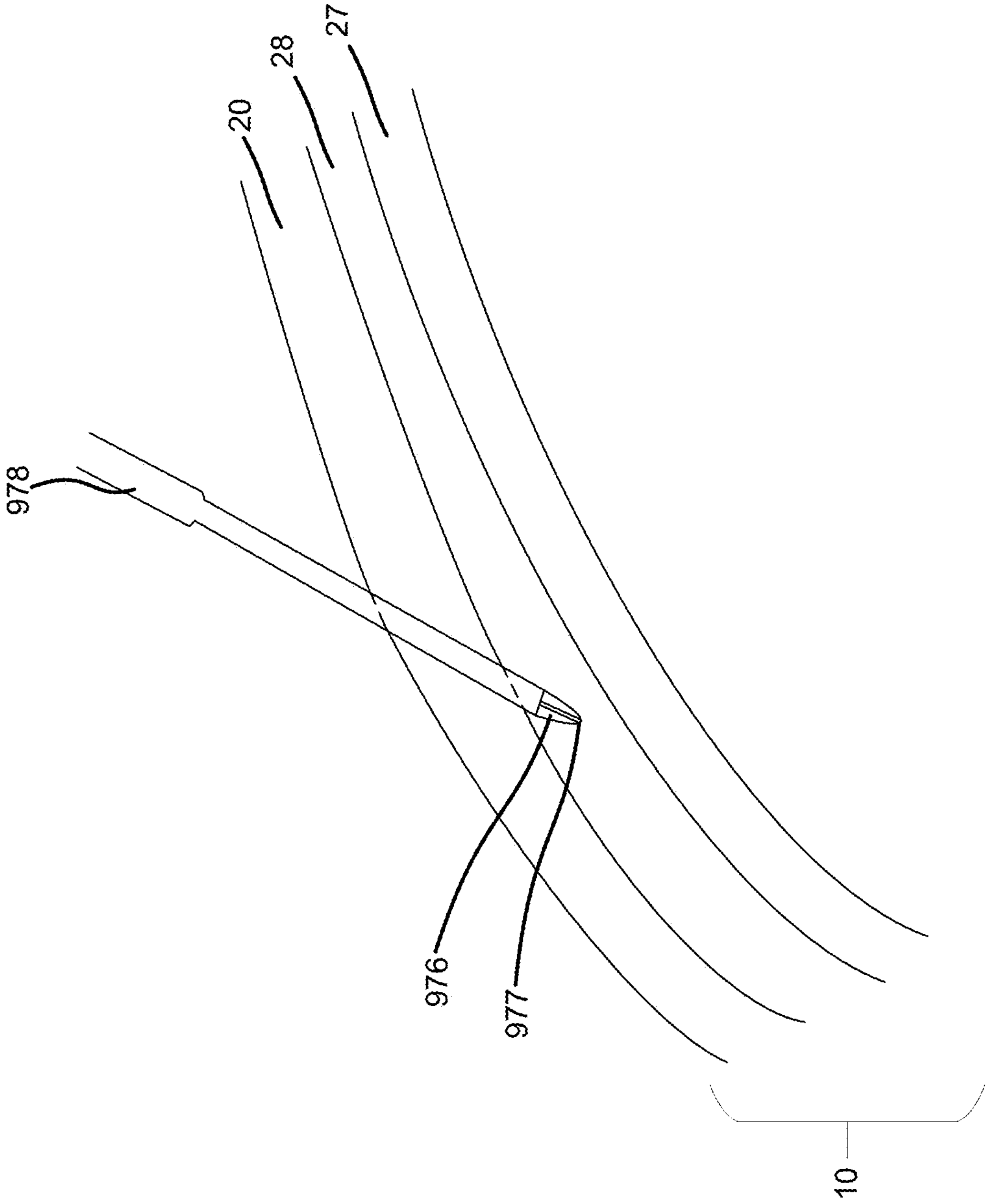
Figure 13F:
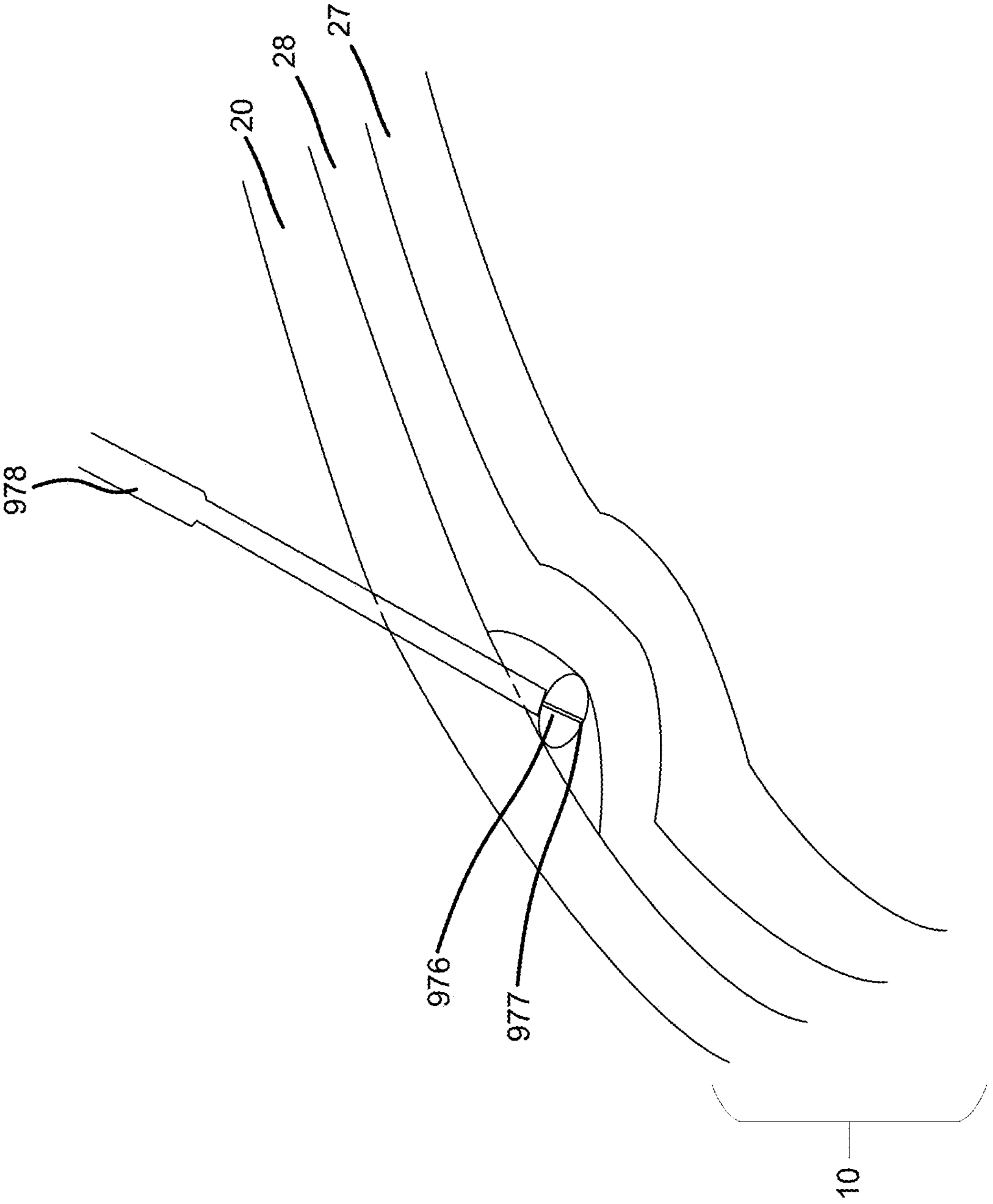
Figure 13G:
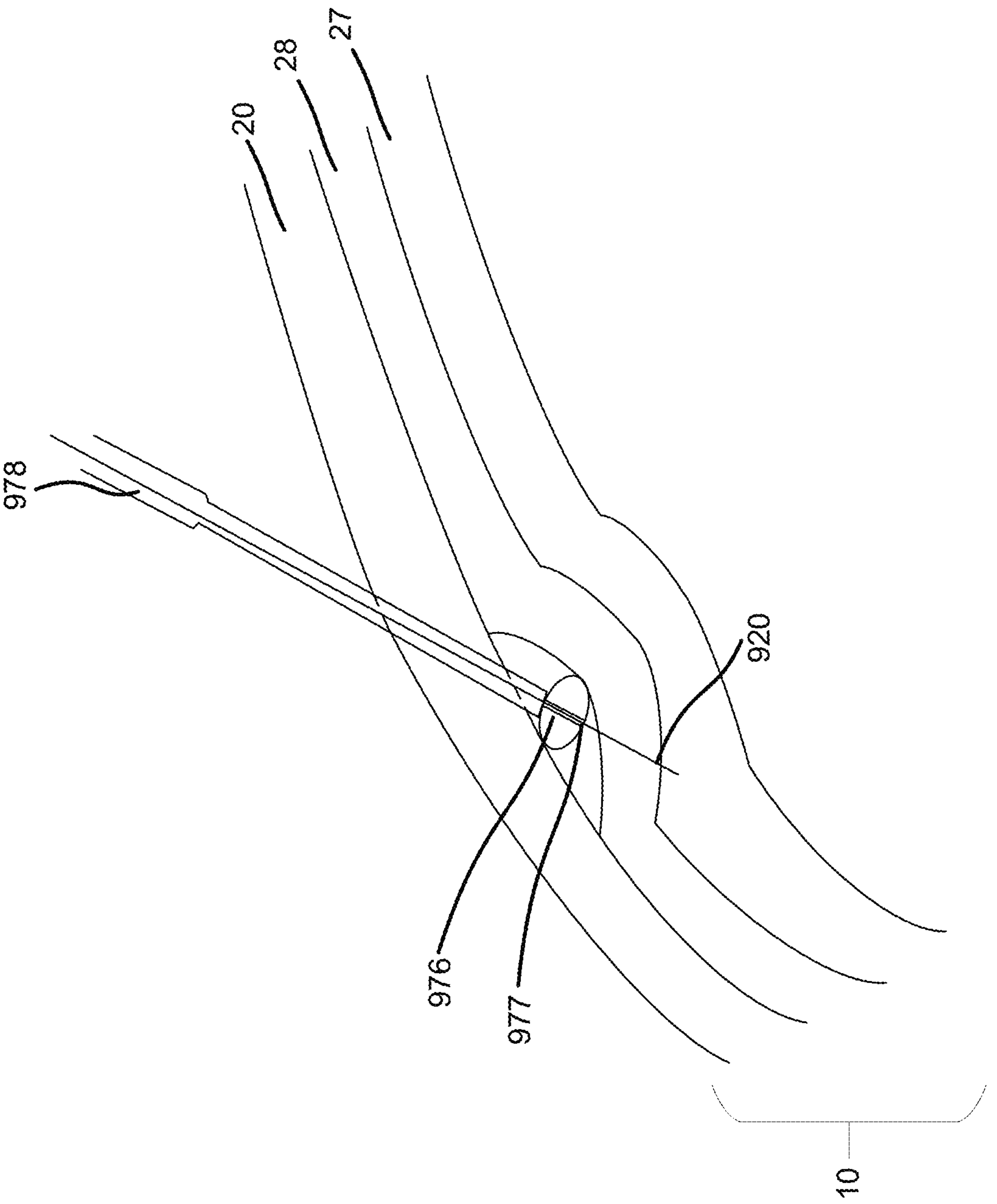
Figure 13H:
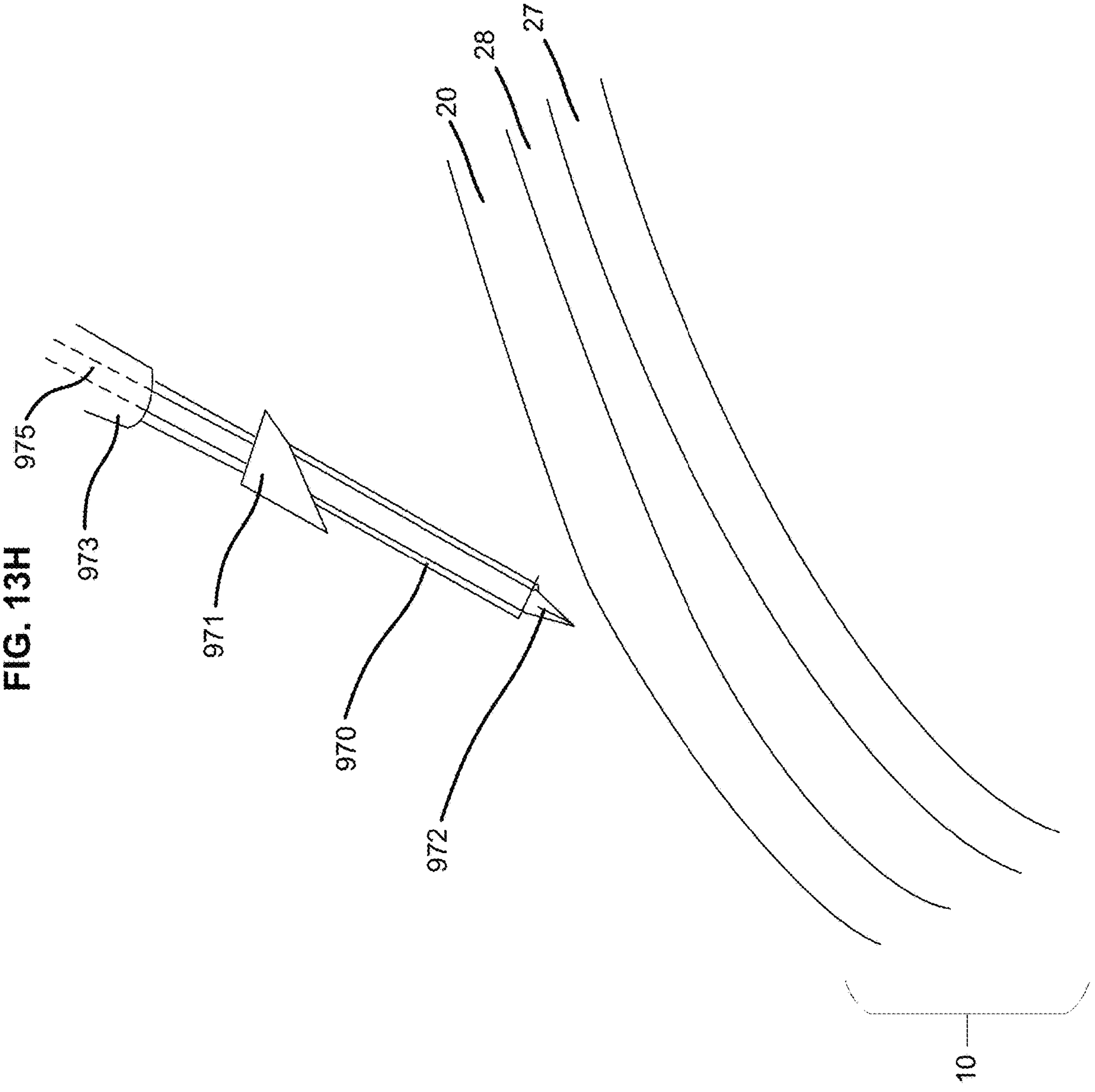
Figure 13I:
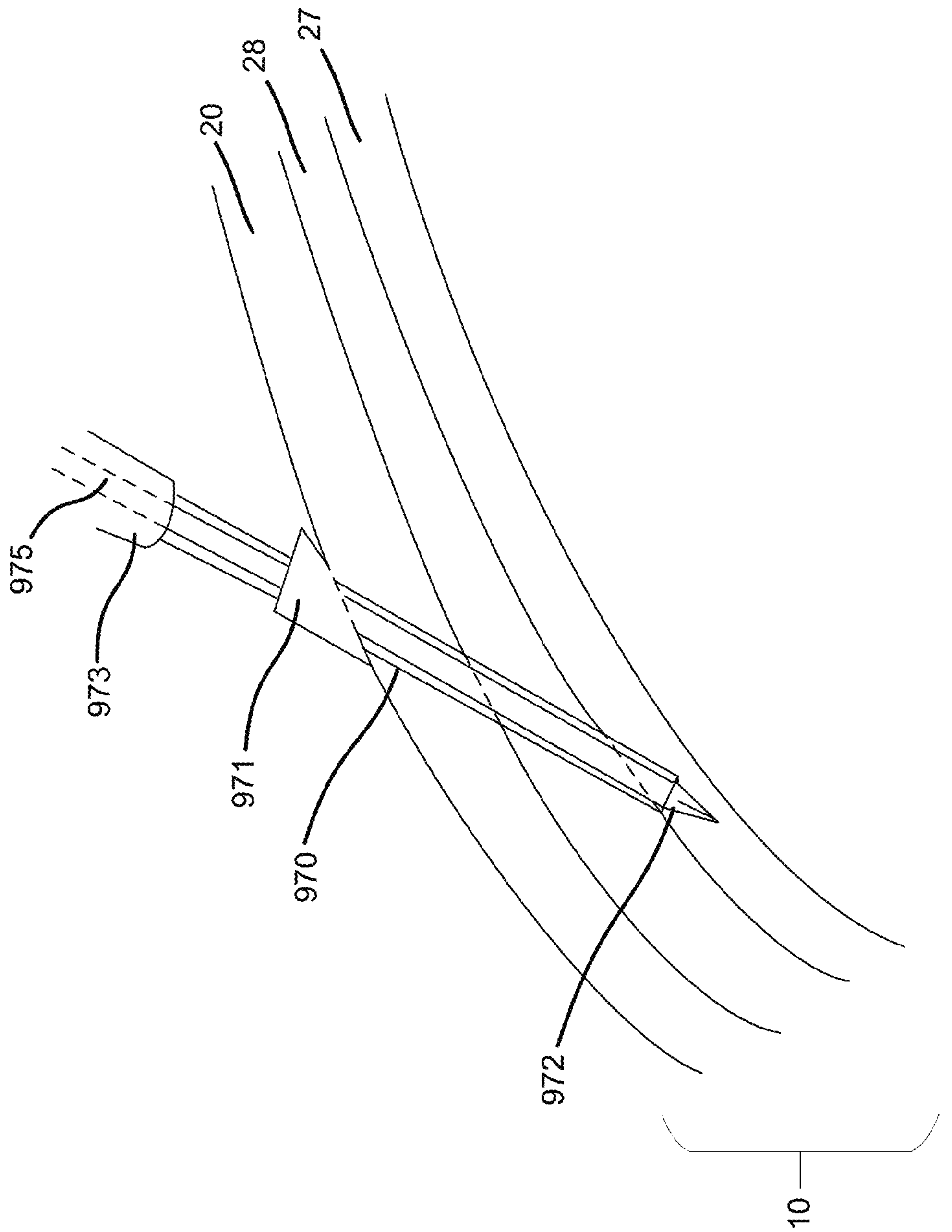
Figure 13J:
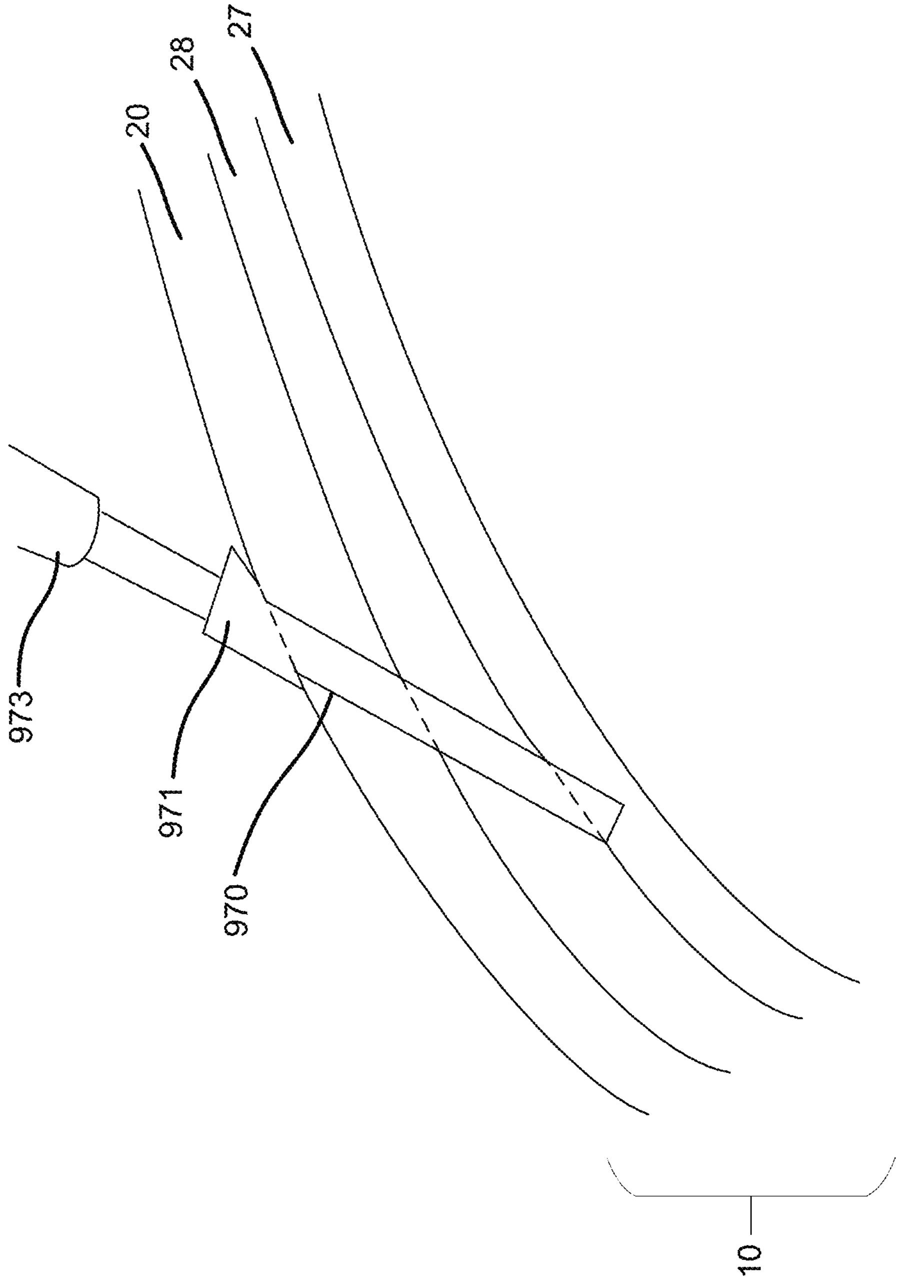
Figure 13K:
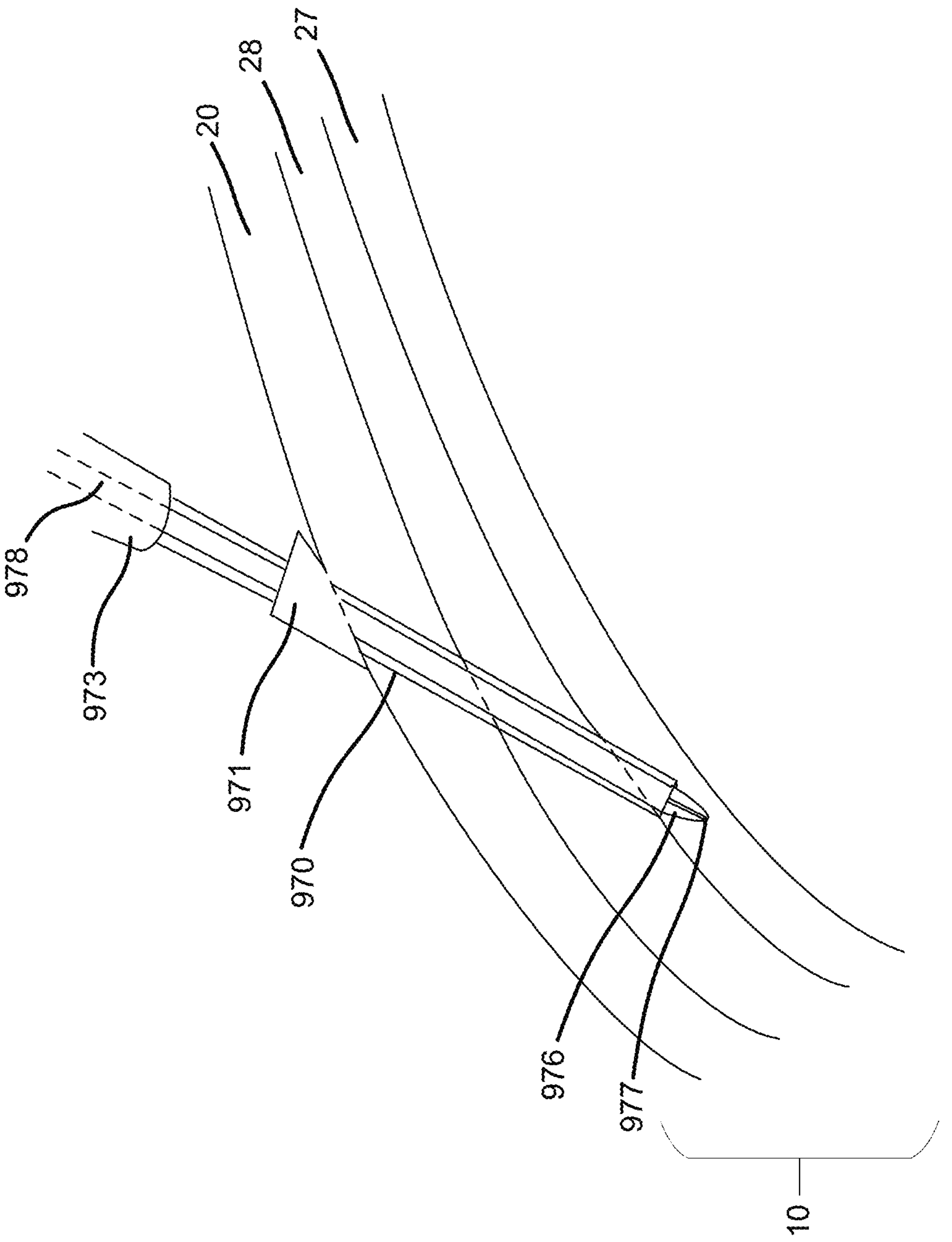
Figure 13L:
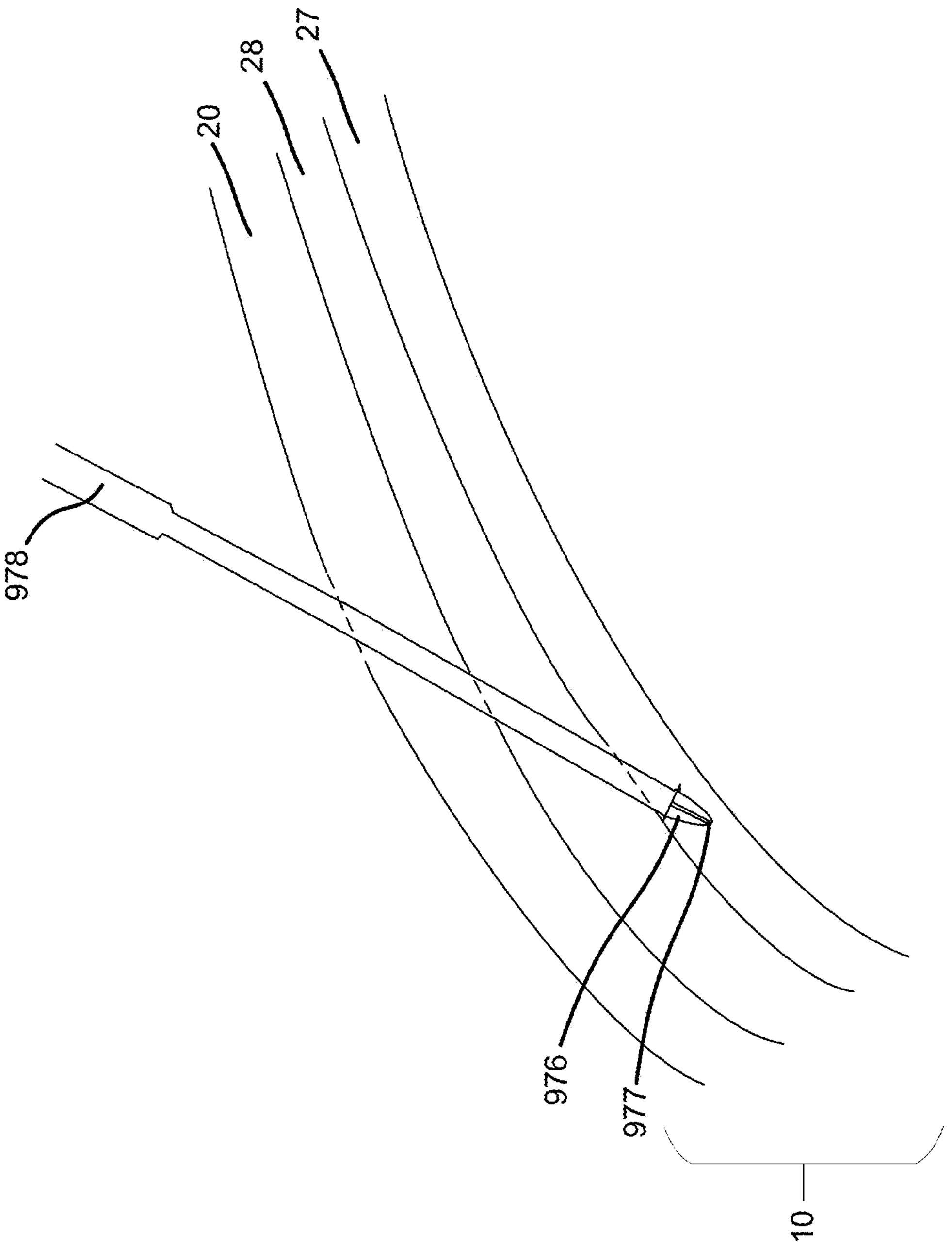
Figure 13M:
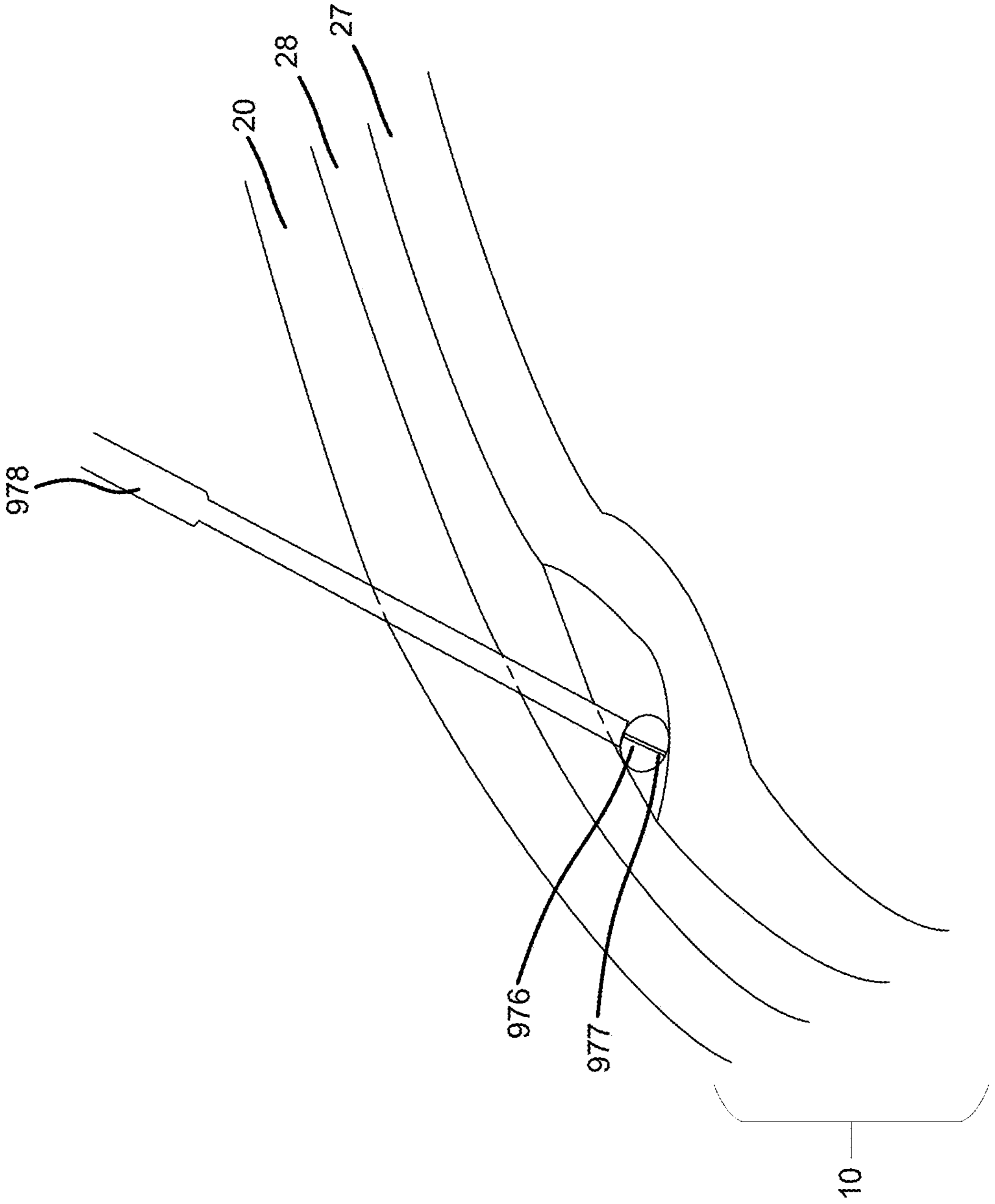
Figure 13N:
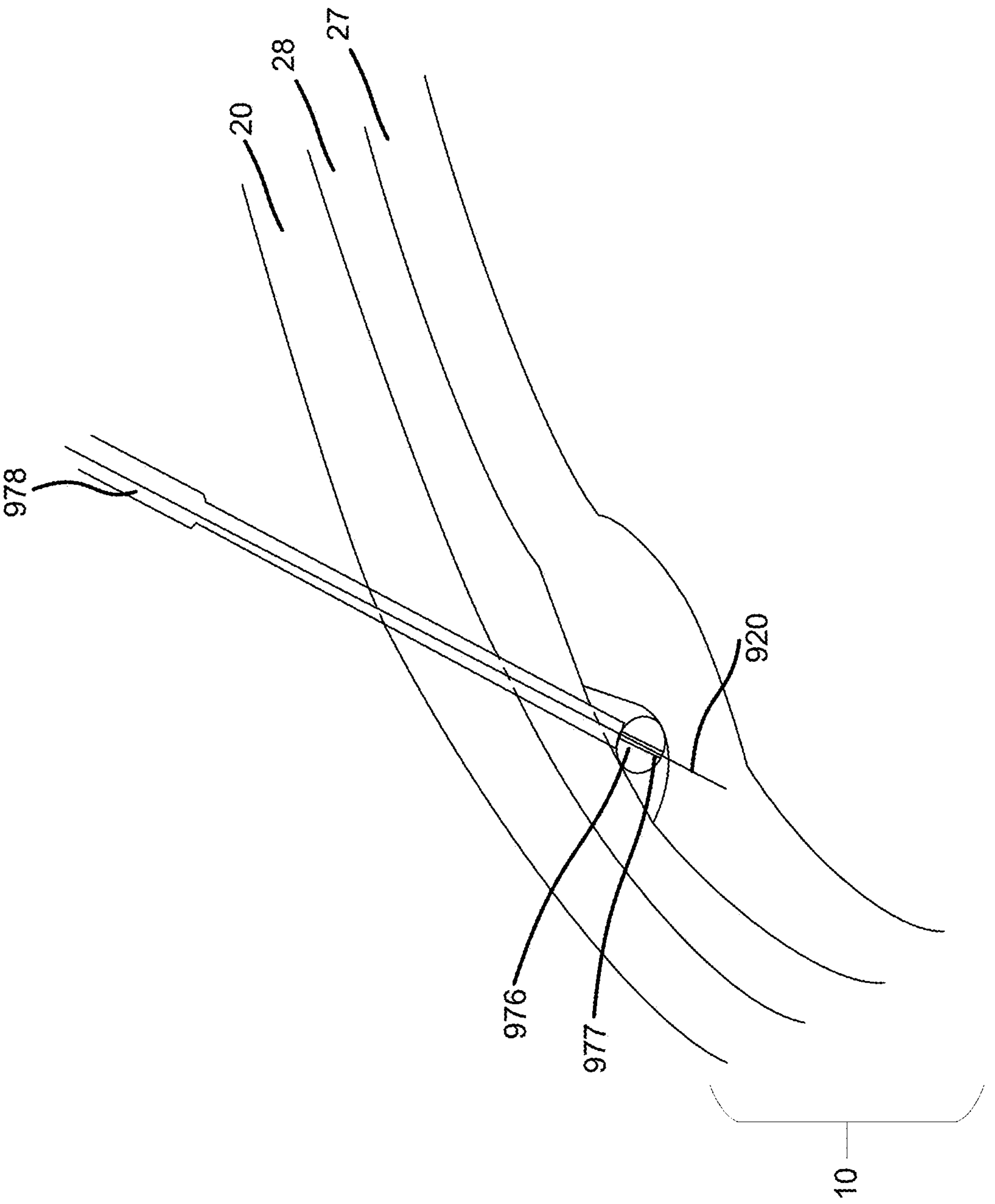
Figure 13O:
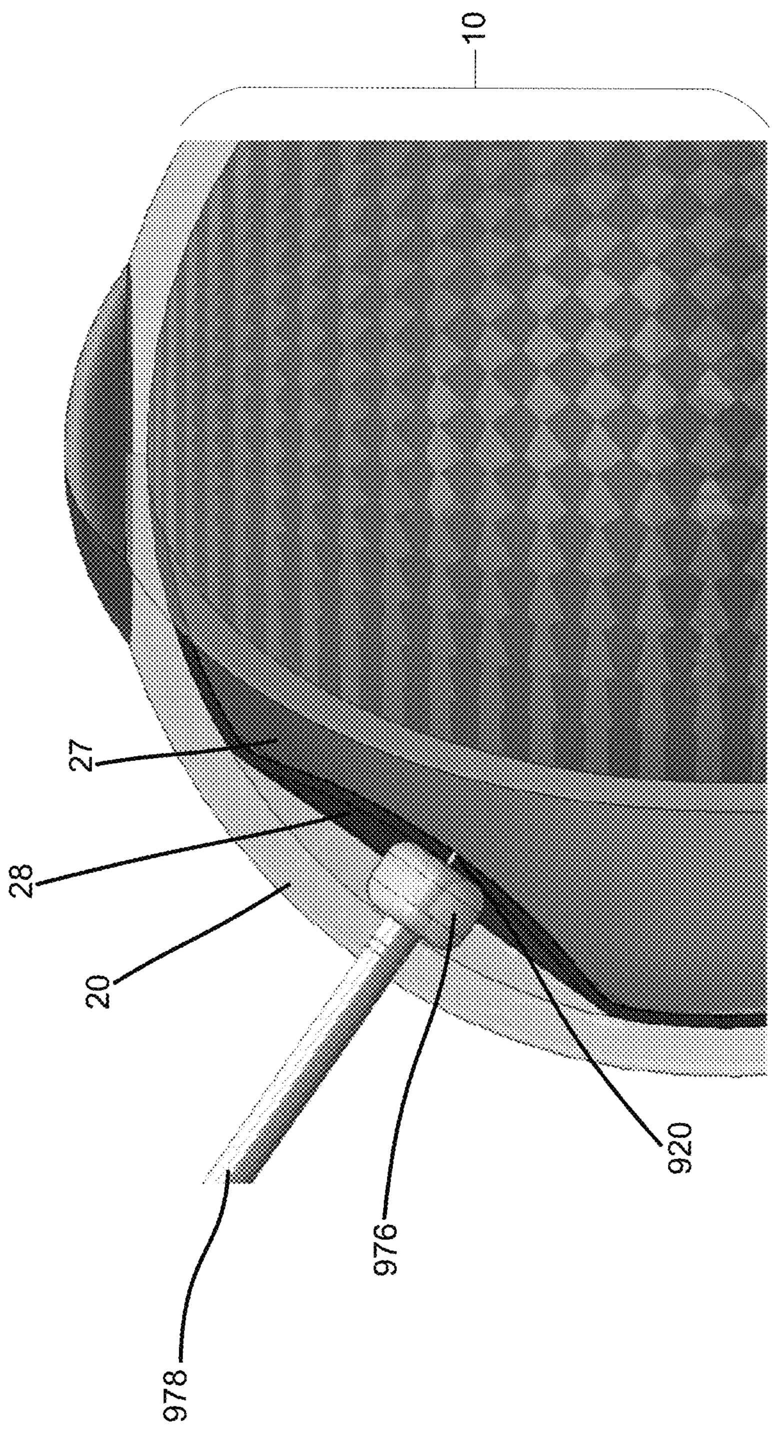

FIGS. 13A-13O illustrate methods and apparatus for performing an injection into the retinal tissue, according to various embodiments. Layers of the eye 10 depicted in FIGS. 13A-130 include the sclera 20, the choroid 28, and the retina 27. FIGS. 13A-13G show a method of spreading the sclera 20 apart from the choroid 28 for injection of medicament, while FIGS. 13H-13N show a method of spreading the chodoid 28 apart from the retina 27 for injection of medicament. As shown in FIGS. 13A-13C, a trocar 972 delivers an outer sleeve 970 to the eye 10. FIG. 13A shows the trocar 972 in the process of delivering the outer sleeve 970 to the eye 10. In FIG. 13B, the trocar 972 has penetrated the sclera 20 and placed the outer sleeve 970 in the eye 10. The outer sleeve 970 includes a stop 971. Once the stop 971 makes contact with the outer surface of the eye 10, the trocar 972 and the outer sleeve 970 are prevented from advancing further. Also depicted in FIGS. 13A and 13B are a sleeve handle 973 and a trocar handle 975. The sleeve handle 973 is coupled to the outer sleeve 970 and facilitates easy holding and advancement of the outer sleeve 970. The trocar handle 975 is coupled to the trocar 972 and facilitates easy holding and advancement of the trocar 972.

In some embodiments, the trocar 972 can include a measurement device that aids in determining proper placement of the outer sleeve 970. In some embodiments, the measurement device can include a pressure measurement device. In some embodiments, the measurement device can include an emissivity measurement device. In some embodiments, the the measurement device can include an OCT probe. In some embodiments, the measurement device can include an electrical impedance device. In some embodiments, the measurement device can include an acoustic wave measurement device. In some embodiments, the outer sleeve 970 can include hash marks to assist in measuring penetration depth of the outer sleeve 970. In some embodiments, the outer sleeve 970 can be placed or inserted into the eye 10 without the use of the trocar 972. In some embodiments, the outer sleeve 970 can be manually inserted into the eye 10 (e.g., via an operators hand(s)).

Figure 31A:
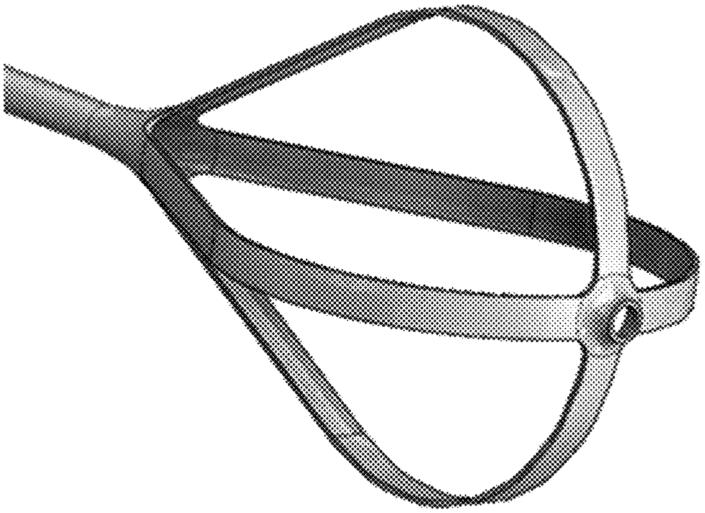
FIGS. 31A and 31B show example malecot cages, according to an embodiment
Figure 31B:
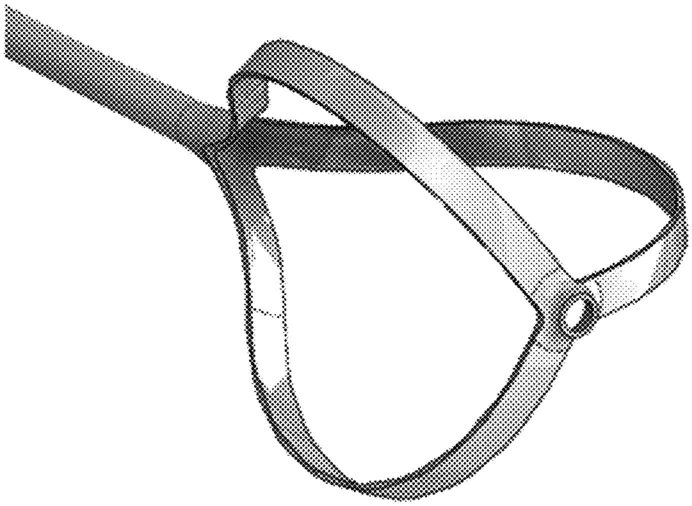

Once the outer sleeve 970 has been properly placed in the eye 10, the trocar 972 is removed from the outer sleeve 970 (e.g., by pulling the trocar 972 out of a lumen of the outer sleeve 970), leaving the outer sleeve 970 positioned with the stop 971 flush with the outside surface of the eye 10, as depicted in FIG. 13C. In some embodiments, the outer sleeve 970 can be delivered to the eye 10 without the trocar 972. For example, the outer sleeve 970 can be inserted into the eye 10 by manually pushing the outer sleeve 970 into the eye 10. FIG. 13D depicts insertion of a cannula 978 into the lumen of the outer sleeve 970 with an expandable member 976 disposed onto a distal end of the cannula 978. The expandable member 976 is an object that is able to expand (e.g., via inflation) to push apart two adjacent layers of eye tissue. The cannula 978 is inserted such that the expandable member 976 coupled to the distal end of the cannula 978 contacts an interface between two adjacent layers of eye tissue (e.g., the sclera 20 and the choroid 28) and pushes apart the adjacent layers of the eye tissue. As shown, in this embodiment, the expandable member 976 is a balloon. In some embodiments, the expandable member 976 can include any other expandable member that can be inserted having a first cross-sectional area, and expand to a second, larger cross-sectional area. In some embodiments, the expandable member 976 can be or include a stent and/or an inflatable tube. In some embodiments, the expandable member 976 can be or include one or more wings, similar to a Malecot catheter, a nephrostomy catheter, an expandable foam, a silicone foam, a slow-recovery foam, a stone retrieval basket, a nitinol cage, a shape memory cage, or any other suitable device that can be inserted and/or delivered into the eye in a relatively small, delivery configuration, and then transitioned to an expanded, relatively large, delivered configuration, as discussed in more detail here. Example malecot cages (e.g., formed of shape-memory material, like Nitinol) are shown in FIGS. 31A and 31B, each of which define an orifice at its distal end through which a puncture member can be advanced.

As shown, the balloon 976 is attached to a cannula 978 and includes an annulus 977 for insertion of a hollow conduit. Once the cannula 978 has been inserted into the eye 10 such that the balloon 976 contacts the interface between the two adjacent layers of eye tissue, the outer sleeve 970 can be removed from the eye 10 (e.g., by manually pulling the outer sleeve 970 out of the eye 10), as depicted in FIG. 13E. The balloon 976 can then be inflated, as shown in FIG. 13F. In some embodiments, the balloon 976 can be inflated via a conduit (not shown) fluidically coupling an inflation medium container (not shown) and the balloon 976. The conduit can fluidically couple the balloon 976 and the inflation medium container by extending through the length of the cannula 978. Inflation of the balloon 976 can aid in positioning and securing the balloon 976 and cannula 978 in a fixed location to prevent the balloon 976 from sliding around. Said another way, the inflation of the balloon 976 can create a tension or a taughtness in the sclera 20, the choroid 28, and the retina 27, such that an anchor point is created. Under tension of the layers of the eye 10, the balloon 976 is prevented from lateral movements.

In some embodiments, the balloon 976 can include a measurement device that aids in determining proper placement of the balloon 976. In some embodiments, the measurement device can include a pressure measurement device. In some embodiments, the measurement device can include an emissivity measurement device. In some embodiments, the measurement device can include an electrical impedance device. In some embodiments, the measurement device can include an acoustic wave measurement device. In some embodiments, the cannula 978 can include hash marks to assist in measuring the penetration depth of the balloon 976. In some embodiments, the balloon 976 can be placed on the end of a placement shaft that includes hash marks to assist in measuring the penetration depth of the balloon 976. In some embodiments, the balloon 976 can be placed independent of the trocar 972 and can include measurement marks along the cannula 978.

FIG. 13G depicts the insertion of a hollow conduit 920 into the retina 27 of the eye 10. The hollow conduit 920 is inserted through the annulus 977. The creation of the anchor point enables precise injection, as the hollow conduit 920 is able to enter the retina 27 via the annulus 977 through a stable reference point, rather than a reference point that slides around laterally. In some embodiments, the hollow conduit 920 can be the same or substantially similar to the hollow conduit 120, as described above with reference to FIG. 5. In some embodiments, the balloon 976 can be placed such that a distal end of the balloon 976 is at a reference location, such that the hollow conduit 920 can be inserted to move just past the reference location to a desired injection location. In some embodiments, the hollow conduit 920 can include a measurement device disposed on a distal end of the hollow conduit 920. In some embodiments, the measurement device can include a pressure measurement device. In some embodiments, the measurement device can include an emissivity measurement device. In some embodiments, the measurement device can include an OCT probe. In some embodiments, the measurement device can include an electrical impedance device. In some embodiments, the measurement device can include an acoustic wave measurement device.

In some embodiments, insertion of the hollow conduit 920 into the retina 27 can be such that the distal tip of the hollow conduit 920 extends beyond the balloon 976 by at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, or at least about 9.5 mm. In some embodiments, insertion of the hollow conduit 920 into the retina 27 can be such that the distal tip of the hollow conduit 920 extends beyond the balloon 976 by no more than about 1 cm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, no more than about 1.5 mm, or no more than about 1 mm. Combinations of the above-referenced distances are also possible (e.g., at least about 0.5 mm and no more than about 10 mm or at least about 2 mm and no more than about 6 mm), inclusive of all values and ranges therebetween. In some embodiments, insertion of the hollow conduit 920 into the retina 27 can be such that the distal tip of the hollow conduit 920 extends beyond the balloon 976 by about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 10 mm.

FIGS. 13H-13N show a method of spreading the choroid 28 apart from the retina 27 for injection of medicament. FIG. 13H shows the trocar 972 in the process of delivering the outer sleeve 970 to the eye 10. In FIG. 13I, the trocar 972 has penetrated the sclera 20 and the choroid 28 and placed the outer sleeve 970 in the eye 10. Once the stop 971 makes contact with the outer surface of the eye 10, the trocar 972 and the outer sleeve 970 are prevented from advancing further.

The outer sleeve 970 is placed in a desired location and depth in the eye via the trocar 972. For example, the outer sleeve 970 can be placed such that the distal end of the outer sleeve 970 straddles the boundary between the sclera 20 and the choroid 28. In some embodiments, the outer sleeve 970 can be placed such that the distal end of the outer sleeve 970 is proximal to the boundary between the sclera 20 and the choroid 28 by about 50 μm, about 100 μm, about 150 μm, about 200 μm, about 250 μm, or about 300 μm, inclusive of all values and ranges therebetween. As shown in FIG. 13I, the outer sleeve 970 is placed such that the distal end of the outer sleeve 970 straddles the boundary between the choroid 28 and the retina 27. In some embodiments, the outer sleeve 970 can be placed such that the distal end of the outer sleeve 970 is proximal to the boundary between the choroid 28 and the retina 27 by about 50 μm, about 100 μm, about 150 μm, about 200 μm, about 250 μm, or about 300 μm, inclusive of all values and ranges therebetween. Once the outer sleeve 970 has been properly placed in the eye 10, the trocar 972 is removed, leaving the outer sleeve 970 positioned with the stop 971 flush with the outside surface of the eye 10, as depicted in FIG. 13J. In some embodiments, the trocar 972 can be removed by manually pulling the trocar 972 out of the outer sleeve 970 by causing the trocar 972 to move proximally relative to the outer sleeve 970. FIG. 13K depicts insertion of the cannula 978 into the outer sleeve 970, with the balloon 976 coupled to the distal end of the cannula 978. The cannula 978 is inserted into the outer sleeve 970 such that the balloon 976 extends beyond the distal end of the outer sleeve 970. As shown, the balloon 976 includes an annulus 977 through which the hollow conduit 920 can pass. The outer sleeve 970 can be removed from the eye 10, as depicted in FIG. 13L. In some embodiments, the outer sleeve 970 can be removed from the eye 10 by manually pulling the outer sleeve 970 from the eye 10. In some embodiments, the outer sleeve 970 can be removed from the eye 10 by machine, or an automated process. The balloon 976 can then be inflated in a region at or near the interface of the choroid 28 and the retina 27, as shown in FIG. 13M. Inflation of the balloon 976 can aid in anchoring the distal end of the cannula 978 between the choroid 28 and the retina 27, such that a medicament can be delivered to or in the vicinity of the anchor point created by the inflation of the balloon 976. The inflated balloon 976 is securely placed at the anchor point due to back-pressure from the adjacent layers of the eye 10 (i.e., the choroid 28 and the retina 27). The back pressure from the choroid 28 and the retina 27 prevents the balloon 976 from sliding around. Said another way, the inflation of the balloon 976 can create a tension or a taughtness at the interface between the choroid 28 and the retina 27 that prevents sliding or lateral movements of the balloon 976 within the layers of the eye 10. With the inflated balloon 976 disposed between the choroid 28 and the retina 27, the hollow conduit 920 can be inserted into the retina 27, as shown in FIG. 13N. The hollow conduit 920 is inserted through the annulus 977, and medicament is injected into the retina 27 via the hollow conduit 920. The medicament can be injected from a medicament container (not shown) fluidically coupled to the hollow conduit 920. In some embodiments, the medicament container can include a syringe barrel. In some embodiments, the injection can be initiated via an injection controller (e.g., a plunger). In some embodiments, the hollow conduit 920 can be part of an injection apparatus (e.g., the injection apparatus 700, as described above with reference to FIG. 11). In other words, the hollow conduit 920 can be fluidically coupled to a medicament container (e.g., the medicament container 750), and medicament can be deployed from the medicament container via an injection controller (e.g., the injection controller 760). In some embodiments, the insertion of the hollow conduit 920 into the retina 27 of the eye 10 can involve manually advancing the hollow conduit 920 through the lumen of the cannula 978 and the annulus 977 of the balloon 976. In some embodiments, the hollow conduit 920 can be automatically inserted through the cannula 978 and the annulus 977.

Similar to FIGS. 13A-13G, FIG. 13O shows a perspective view of the balloon 976 inflated between the sclera 20 and the choroid 28. As shown, the balloon 976 is expanded in the SCS. In some embodiments, the balloon 976 can have a spherical or substantially spherical shape. In some embodiments, the balloon 976 can have a torus or donut shape, such that the hollow conduit 920 and/or the cannula 978 can fit through the annulus 977 in the middle of the balloon 976. In some embodiments, the balloon 976 can have a spheroid shape, an ellipsoid shape, an ellipsoid of revolution shape, or a rotational ellipsoid shape. In some embodiments, the balloon 976 can be illuminated for ease of monitoring. For example, a fiber optic cable can be incorporated into the cannula 978 and/or the conduit fluidically coupled to the balloon 976. In some embodiments, the balloon 976 can include a radio-opaque material (e.g., iodine, barium, tantalum, bismuth, gold, etc.) that can be visualized via any suitable imaging modality, such as, for example, X-ray. In some embodiments, the balloon 976 can be illuminated upon inflation. In some embodiments, the balloon 976 can be illuminated upon administration of medicament through the hollow conduit 920.

In some embodiments, the balloon 976 can be filled with a compressible medium (e.g., a gas). In some embodiments, the balloon 976 can be filled with nitrogen. In some embodiments, the balloon 976 can be filled with air. In some embodiments, the balloon 976 can be filled with an incompressible medium (e.g., a liquid). In some embodiments, the balloon 976 can be filled with water. In some embodiments, the balloon 976 can be filled with a saline solution. In some embodiments, the medium used to fill the balloon 976 can be selected to minimize poisoning danger to the patient if the balloon 976 ruptures. Filling the balloon 976 with air, for example, can have the advantage of reusability and ease of priming. In some instances, filling the balloon 976 with water or saline without gas can improve safety, as embolisms can be prevented.

In some embodiments, inflation of the balloon 976 can cause deformation of the eye 10. In some embodiments, the eye 10 can change from a substantially spherical shape to a spherical shape with a protrusion based on the inflation of the balloon 976. Reshaping and deforming of the eye 10 can be a visual indication of the effectiveness of the inflation of the balloon 976. In some embodiments, the outer surface of the eye 10 can be described by a first set of spherical coordinates prior to inflation of the balloon 976 and a second set of spherical coordinates after inflation of the balloon 976. The first set of spherical coordinates and the second set of spherical coordinates both use a common point inside the eye 10 as the origin in the spherical coordinate system. In some embodiments, the maximum r-value of the surface of the eye 10 in the second set of spherical coordinates can be greater than the maximum r-value of the surface of the eye 10 in the first set of spherical coordinates by at least about 50 μm, at least about 100 μm, at least about 150 μm, at least about 200 μm, at least about 250 μm, at least about 300 μm, at least about 350 μm, at least about 400 μm, at least about 450 μm, at least about 500 μm, at least about 550 μm, at least about 600 μm, at least about 650 μm, at least about 700 μm, at least about 750 μm, at least about 800 μm, at least about 850 μm, at least about 900 μm, at least about 950 μm, at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, or at least about 9.5 mm. In some embodiments, the maximum r-value in the second set of spherical coordinates can be greater than the maximum r-value in the first set of spherical coordinates by no more than about 1 cm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, no more than about 1.5 mm, no more than about 1 mm, no more than about 950 μm, no more than about 900 μm, no more than about 850 μm, no more than about 800 μm, no more than about 750 μm, no more than about 700 μm, no more than about 650 μm, no more than about 600 μm, no more than about 550 μm, no more than about 500 μm, no more than about 450 μm, no more than about 400 μm, no more than about 350 μm, no more than about 300 μm, no more than about 250 μm, no more than about 200 μm, no more than about 150 μm, or no more than about 100 μm.

Combinations of the above-referenced differences between the maximum value of the second set of spherical coordinates and the maximum value of the first set of spherical coordinates are also possible (e.g., at least about 50 μm and no more than about 1 cm or at least about 300 μm and no more than about 1 mm), inclusive of all values and ranges therebetween. In some embodiments, the maximum r-value in the second set of spherical coordinates can be greater than the maximum r-value in the first set of spherical coordinates by about 50 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 1 cm.

In some embodiments, the balloon 976 can have an interior capacity of at least about 100 μL, at least about 200 μL, at least about 300 μL, at least about 400 μL, at least about 500 μL, at least about 600 μL, at least about 700 μL, at least about 800 μL, at least about 900 μL, at least about 1 mL, at least about 1.1 mL, at least about 1.2 mL, at least about 1.3 mL, at least about 1.4 mL, at least about 1.5 mL, at least about 1.6 mL, at least about 1.7 mL, at least about 1.8 mL, at least about 1.9 mL, at least about 2 mL, at least about 2.1 mL, at least about 2.2 mL, at least about 2.3 mL, at least about 2.4 mL, at least about 2.5 mL, at least about 3 mL, at least about 3.5 mL, at least about 4 mL, or at least about 4.5 mL. In some embodiments, the balloon 976 can have an interior capacity of no more than about 5 mL, no more than about 4.5 mL, no more than about 4 mL, no more than about 3.5 mL, no more than about 3 mL, no more than about 2.5 mL, no more than about 2.4 mL, no more than about 2.3 mL, no more than about 2.2 mL, no more than about 2.1 mL, no more than about 2 mL, no more than about 1.9 mL, no more than about 1.8 mL, no more than about 1.7 mL, no more than about 1.6 mL, no more than about 1.5 mL, no more than about 1.4 mL, no more than about 1.3 mL, no more than about 1.2 mL, no more than about 1.1 mL, no more than about 1 mL, no more than about 900 μL, no more than about 800 μL, no more than about 700 μL, no more than about 600 μL, no more than about 500 μL, no more than about 400 μL, no more than about 300 μL, or no more than about 200 μL. Combinations of the above-referenced interior capacities of the balloon 976 are also possible (e.g., at least about 100 μL and no more than about 5 mL or at least about 1.5 mL and no more than about 2.5 mL), inclusive of all values and ranges therebetween. In some embodiments, the balloon 976 can have an interior capacity of about 100 μL, about 200 μL, about 300 μL, about 400 μL, about 500 μL, about 600 μL, about 700 μL, about 800 μL, about 900 μL, about 1 mL, about 1.1 mL, about 1.2 mL, about 1.3 mL, about 1.4 mL, about 1.5 mL, about 1.6 mL, about 1.7 mL, about 1.8 mL, about 1.9 mL, about 2 mL, about 2.1 mL, about 2.2 mL, about 2.3 mL, about 2.4 mL, about 2.5 mL, about 3 mL, about 3.5 mL, about 4 mL, about 4.5 mL, or about 5 mL.

In some embodiments, the flexibility of the hollow conduit 920 can be optimized to conform to the SCS, SRS, or any other desired space inside the eye 10, thereby allowing and/or enhancing the ability for and/or effectiveness of the injectate to hydrodissect and find, create, expand, etc. the SCS and/or SRS. The flexibility of the hollow conduit 920 can allow the hollow conduit 920 to rest at an interface between two adjacent tissue layers that do not strongly adhere to each other (e.g., the sclera 20 and the choroid 28 or the choroid 28 and the retina 27). Hydrodissection then creates and/or expands the potential space (e.g., the SCS or the SRS). In some embodiments, the hollow conduit 920 can have a specific stiffness of about $1*10^6$ $m^2/s^2$, about $2*10^6$ $m^2/s^2$, about $3*10^6$ $m^2/s^2$, about $4*10^6$ $m^2/s^2$, about $5*10^6$ $m^2/s^2$, about $6*10^6$ $m^2/s^2$, about $7*10^6$ $m^2/s^2$, about $8*10^6$ $m^2/s^2$, about $9*10^6$ $m^2/s^2$, about $1*10^7$ $m^2/s^2$, about $2*10^7$ $m^2/s^2$, about $3*10^7$ $m^2/s^2$, about $4*10^7$ $m^2/s^2$, about $5*10^7$ $m^2/s^2$, about $6*10^7$ $m^2/s^2$, about $7*10^7$ $m^2/s^2$, about $8*10^7$ $m^2/s^2$, about $9*10^7$ $m^2/s^2$, about $1*10^8$ $m^2/s^2$, about $2*10^8$ $m^2/s^2$, about $3*10^8$ $m^2/s^2$, about $4*10^8$ $m^2/s^2$, about $5*10^8$ $m^2/s^2$, about $6*10^8$ $m^2/s^2$, about $7*10^8$ $m^2/s^2$, about $8*10^8$ $m^2/s^2$, about $9*10^8$ $m^2/s^2$, inclusive of all values and ranges therebetween. In some embodiments, the flexibility of the hollow conduit 920 can be modified by bonding with an adhesive (e.g., superglue). In some embodiments, the flexibility of the hollow conduit 920 can be modified by bonding with a UV-cured adhesive. In some embodiments, the hollow conduit 920 can be absent of a pre-curvature, such that the hollow conduit 920 can take on the curvature of the retina 27.

In some embodiments, the hollow conduit 920 can have a Young's modulus of at least about 100 MPa, at least about 200 MPa, at least about 300 MPa, at least about 400 MPa, at least about 500 MPa, at least about 600 MPa, at least about 700 MPa, at least about 800 MPa, at least about 900 MPa, at least about 1 GPa, at least about 2 GPa, at least about 3 GPa, at least about 4 GPa, at least about 5 GPa, at least about 6 GPa, at least about 7 GPa, at least about 8 GPa, or at least about 9 GPa. In some embodiments, the hollow conduit 920 can have a Young's modulus of no more than about 10 GPa, no more than about 9 GPa, no more than about 8 GPa, no more than about 7 GPa, no more than about 6 GPa, no more than about 5 GPa, no more than about 4 GPa, no more than about 3 GPa, no more than about 2 GPa, no more than about 1 GPa, no more than about 900 MPa, no more than about 800 MPa, no more than about 700 MPa, no more than about 600 MPa, no more than about 500 MPa, no more than about 400 MPa, no more than about 300 MPa, or no more than about 200 MPa. Combinations of the above-referenced values of the Young's modulus of the hollow conduit 920 are also possible (e.g., at least about 100 MPa and no more than about 10 GPa or at least about 500 MPa and no more than about 5 GPa), inclusive of all values and ranges therebetween. In some embodiments, the hollow conduit 920 can have a Young's modulus of about 100 MPa, about 200 MPa, about 300 MPa, about 400 MPa, about 500 MPa, about 600 MPa, about 700 MPa, about 800 MPa, about 900 MPa, about 1 GPa, about 2 GPa, about 3 GPa, about 4 GPa, about 5 GPa, about 6 GPa, about 7 GPa, about 8 GPa, about 9 GPa, or about 10 GPa.

In some embodiments, injectate administration can be monitored in real time. In some embodiments, monitoring injectate administration can include illuminating the hollow conduit 920 and/or the balloon 976 during administration. In some embodiments, injectate administration can include incorporation of injectate material that can be excited via an external stimulation. In some embodiments, the external stimulation can include fluorescent excitation, infrared (IR) excitation, ultraviolet (UV) excitation, or any other suitable excitation method or combinations thereof.

FIGS. 14A-14D show an injection apparatus 1000 and a method of using the injection apparatus 1000, according to an embodiment. Layers of the eye 10 depicted in FIGS. 14A-14D include the sclera 20, the choroid 28, and the retina 27. As shown, the injection apparatus 1000 includes a hollow conduit 1020, an outer sleeve 1070 (also referred to as a sheath 1070), a catheter 1074, and a balloon 1076. In some embodiments, the hollow conduit 1020, the outer sleeve 1070, and the balloon 1076 can be the same or substantially similar to the hollow conduit 920, the outer sleeve 970, and the balloon 976, as described above with reference to FIGS. 13A-130. Thus, certain aspects of the hollow conduit 1020, the outer sleeve 1070, and the balloon 1076 are not described in greater detail herein.

Figure 14A:
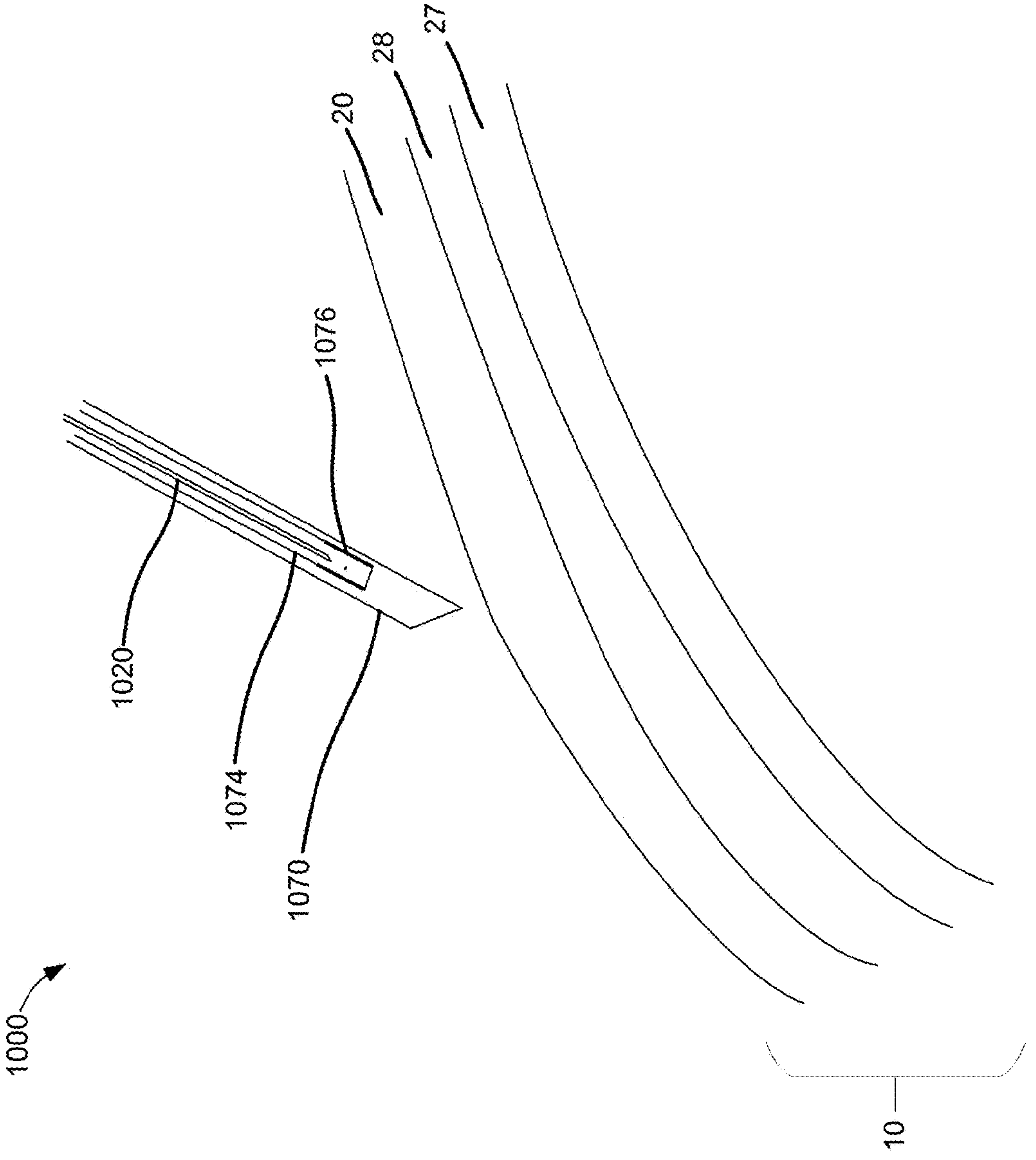
FIGS. 14A-14D illustrate a method and apparatus for performing an injection into the retinal tissue, according to an embodiment.
Figure 14B:
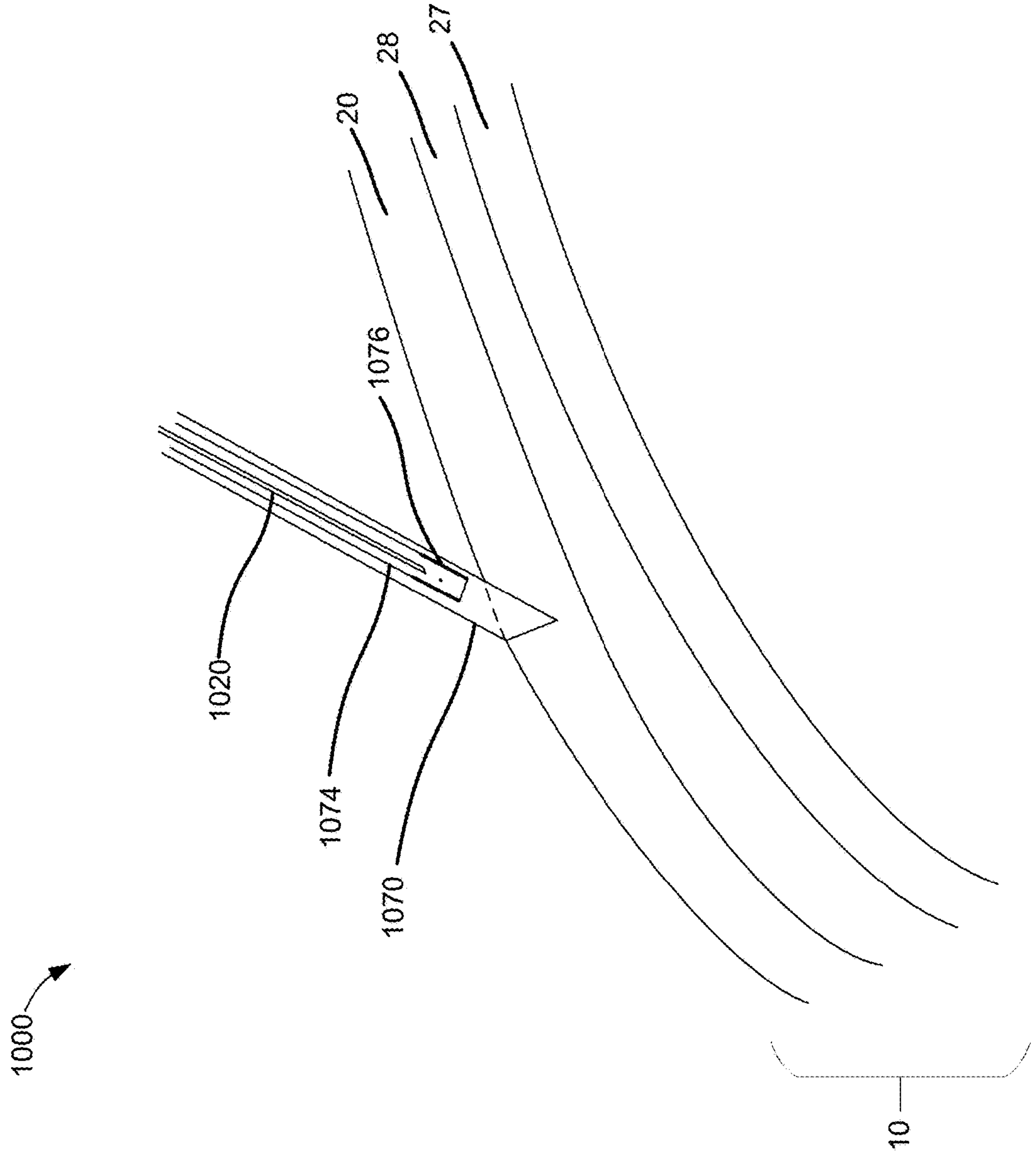

FIG. 14A shows the injection apparatus 1000 approaching the eye 10. In FIG. 14B, the sheath 1070 of the injection apparatus 1000 has begun to penetrate the sclera 20. In other words, the sheath 1070 punctures the sclera 20 to access the SCS. In some embodiments, the sheath 1070 can include a needle. In some embodiments, the sheath 1070 can include a hypotube needle. In some embodiments, the sheath 1070 can include a trocar. In some embodiments, the sheath 1070 can include a hypotube trocar. In some embodiments, the sheath 1070 can include a 17Ga needle, an 18Ga needle, a 19Ga needle, a 20Ga needle, a 21Ga needle, a 22Ga needle, a 23Ga needle, a 24Ga needle, a 25Ga needle, or any other suitable size needle. In some embodiments, the sheath 1070 can have a length of at least about 500 μm, at least about 600 μm, at least about 700 μm, at least about 800 μm, at least about 900 μm, at least about 1 mm, at least about 1.1 mm, at least about 1.2 mm, at least about 1.3 mm, or at least about 1.4 mm. In some embodiments, the sheath 1070 can have a length of no more than about 1.5 mm, no more than about 1.4 mm, no more than about 1.3 mm, no more than about 1.2 mm, no more than about 1.1 mm, no more than about 1 mm, no more than about 900 μm, no more than about 800 μm, no more than about 700 μm, or no more than about 600 μm. Combinations of the above-referenced lengths of the sheath 1070 are also possible (e.g., at least about 500 μm and no more than about 1.5 mm or at least about 900 μm and no more than about 1.1 mm), inclusive of all values and ranges therebetween. In some embodiments, the sheath 1070 can have a length of about 500 μm, about 600 μm, about 700 μm, about 800 μm, about 900 μm, about 1 mm, about 1.1 mm, about 1.2 mm, about 1.3 mm, about 1.4 mm, or about 1.5 mm.

Figure 14C:
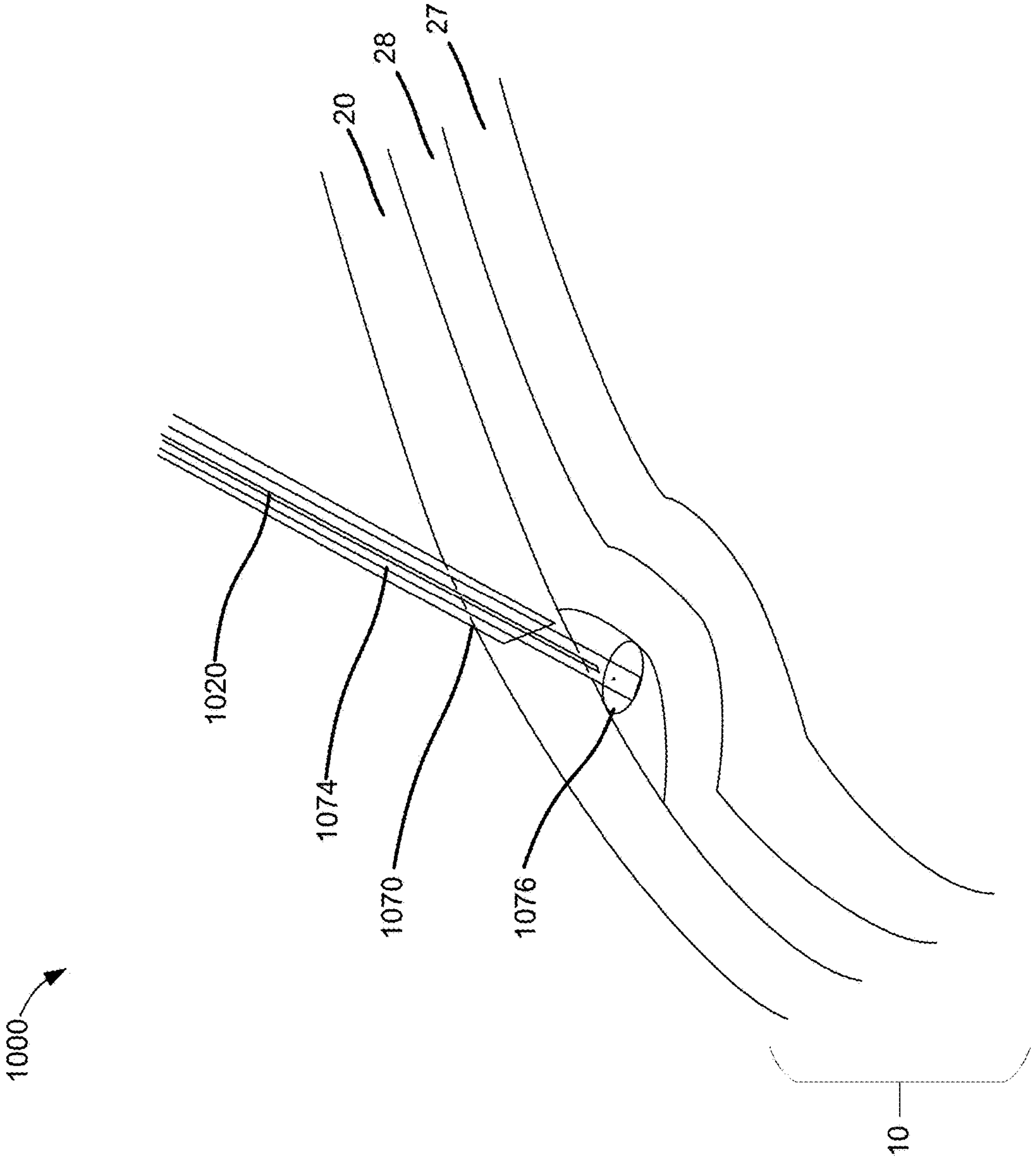

In FIG. 14C, the catheter 1074 is deployed from the sheath 1070, such that a distal end of the catheter 1070 is between the sclera 20 and the choroid 28. The balloon 1076 is inflated to secure the distal end of the catheter between the sclera 20 and the choroid 28. Inflation of the balloon 1076 can aid in preventing the balloon 1076 and the distal end of the catheter 1074 from moving around. In other words, inflation of the balloon 1076 can create tension on the choroid 28. In some embodiments, the catheter 1074 can be a multilumen balloon catheter. In some embodiments, the catheter 1074 can be a 1Fr, a 1.1 Fr, a 1.2 Fr, a 1.3 Fr, a 1.4 Fr, or a 1.5 Fr sized multilumen balloon catheter, inclusive of all sizes and size ranges therebetween. In some embodiments, the catheter 1074 can include a 72D Pebax® catheter, a 70D Pebax® catheter, a 63D Pebax® catheter, a 55D Pebax® catheter, a 40D Pebax® catheter, a 35D Pebax® catheter, or a 25D Pebax® catheter.

In some embodiments, the balloon 1076 can be composed of urethane. In some embodiments, the balloon 1076 can have a material thickness of about 10 μm, about 15 μm, about 20 μm, about 25 μm, about 30 μm, about 35 μm, about 40 μm, about 45 μm, about 50 μm, inclusive of all values and ranges therebetween. In some embodiments, a separation distance between the sclera 20 and the choroid 28 created by the inflation of the balloon 1076 can be about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm, inclusive of all values and ranges therebetween.

Figure 14D:
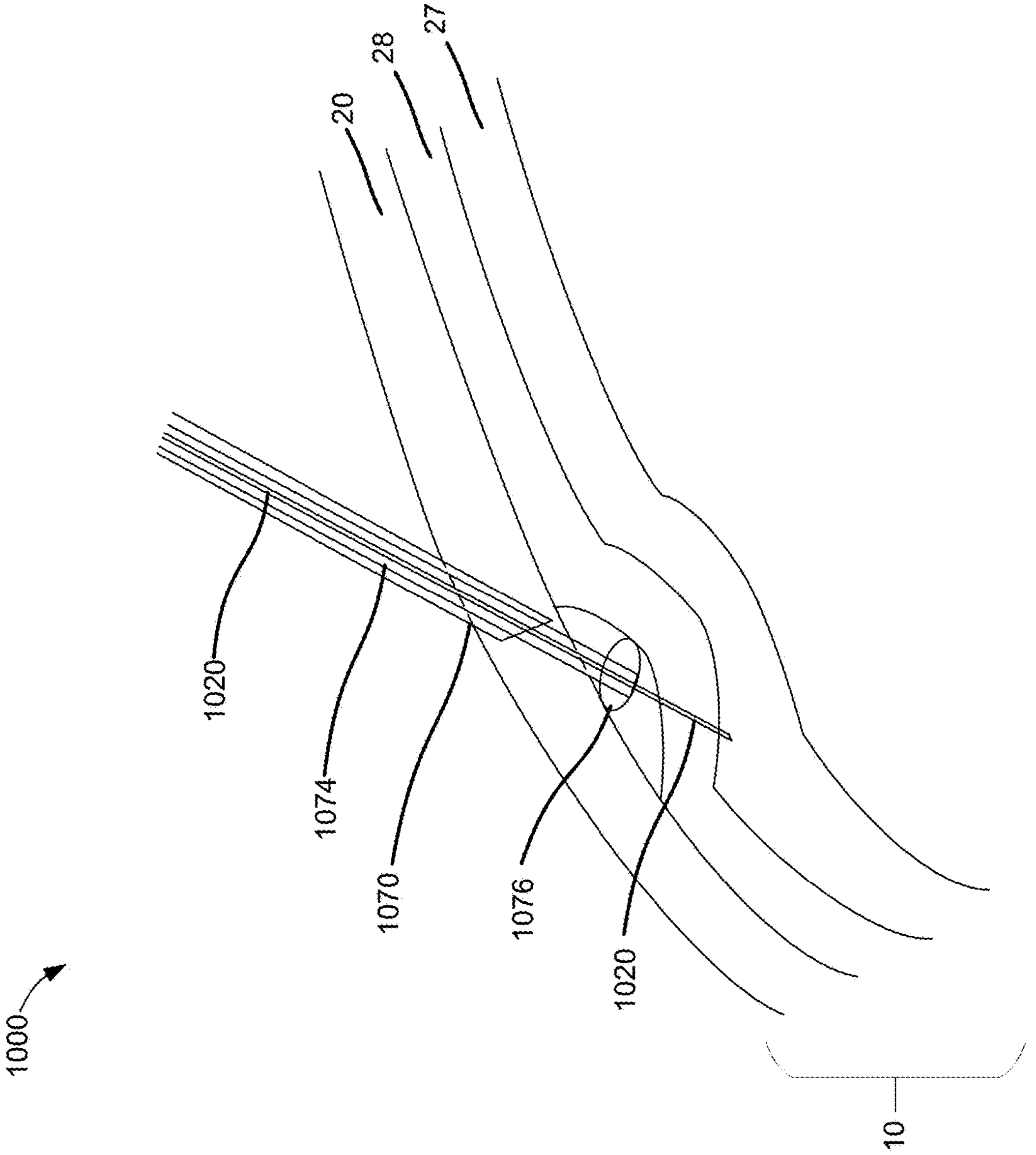

In FIG. 14D, the hollow conduit 1020 is deployed from the catheter 1074 and inserted into the retina 27 of the eye 10. In some embodiments, the hollow conduit 1020 can include a needle. In some embodiments, the hollow conduit 1020 can include a microneedle. In some embodiments, the hollow conduit 1020 can include a 35Ga microneedle, a 36Ga microneedle, a 37Ga microneedle, a 38Ga microneedle, a 39Ga microneedle, a 40Ga needle, a 41Ga needle, a 42Ga needle, a 43Ga needle, a 44Ga needle, a 45Ga needle, or any other suitable size microneedle. In some embodiments, the hollow conduit 1020 can be composed of a polymer, a metal, a polyamide, or any other suitable material. As shown, the balloon 1076 is inserted and inflated between the sclera 20 and the choroid 28. In some embodiments, the balloon 1076 can be inserted and inflated between the choroid 28 and the retina 27. Location of the insertion and inflation of the balloon 1076 can be selected based on the desired injection location. For example, if the desired injection location is in the SRS or in the retinal tissue, the balloon 1076 can be inserted and inflated between the choroid 28 and the retina 27. If the desired injection location is in the SCS or in the choroid, the balloon 1076 can be inserted and inflated between the sclera 20 and the choroid 28.

Figure 15A:
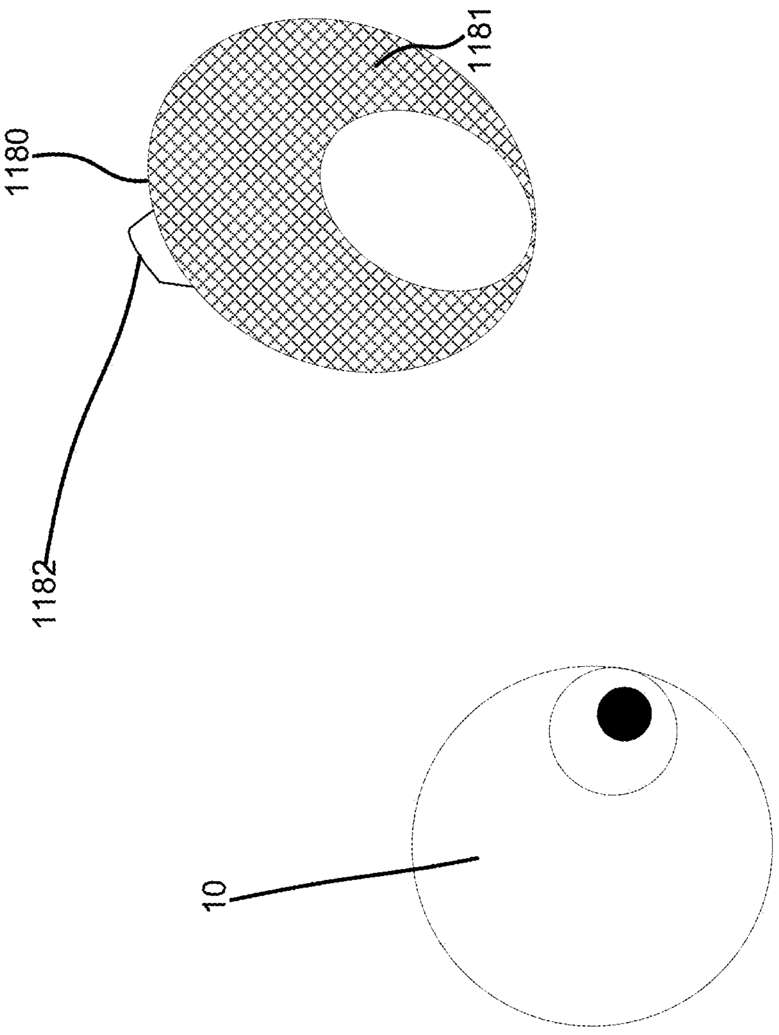
FIGS. 15A-15E illustrate an injection cover and the placement of the injection cover on the eye, according to an embodiment.
Figure 15B:
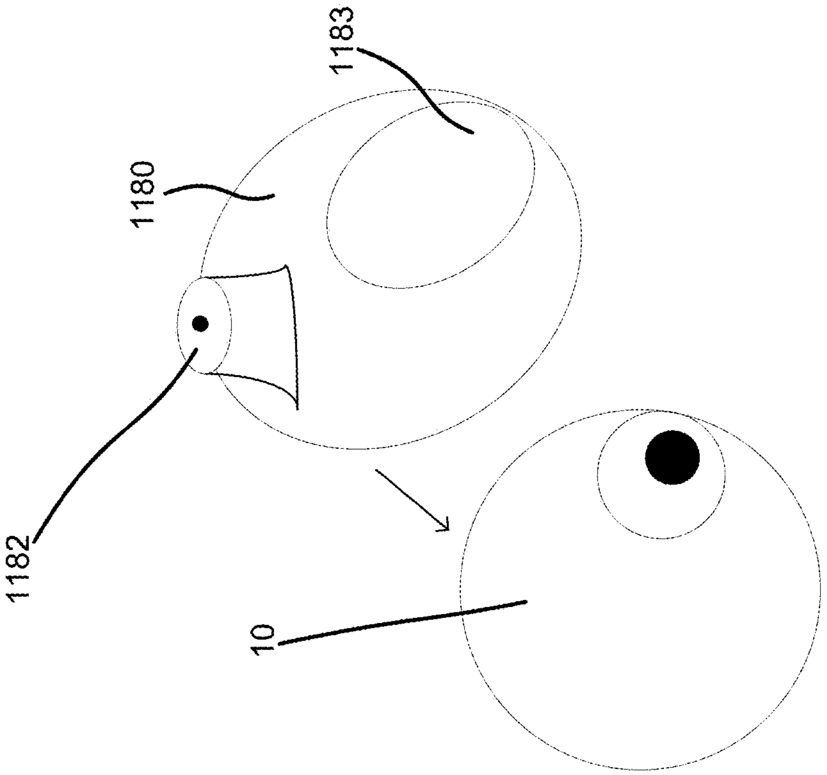
Figure 15C:
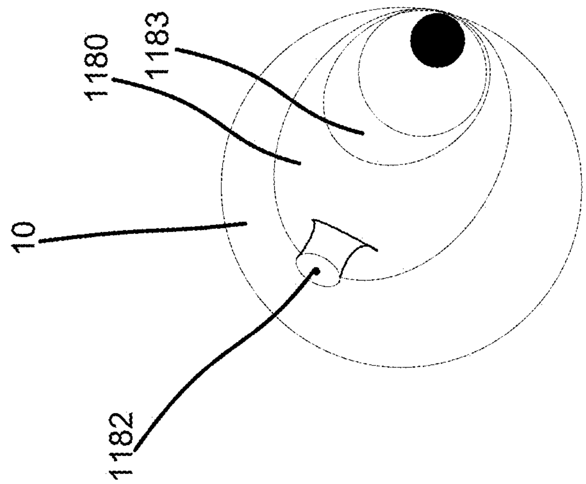
Figure 15D:
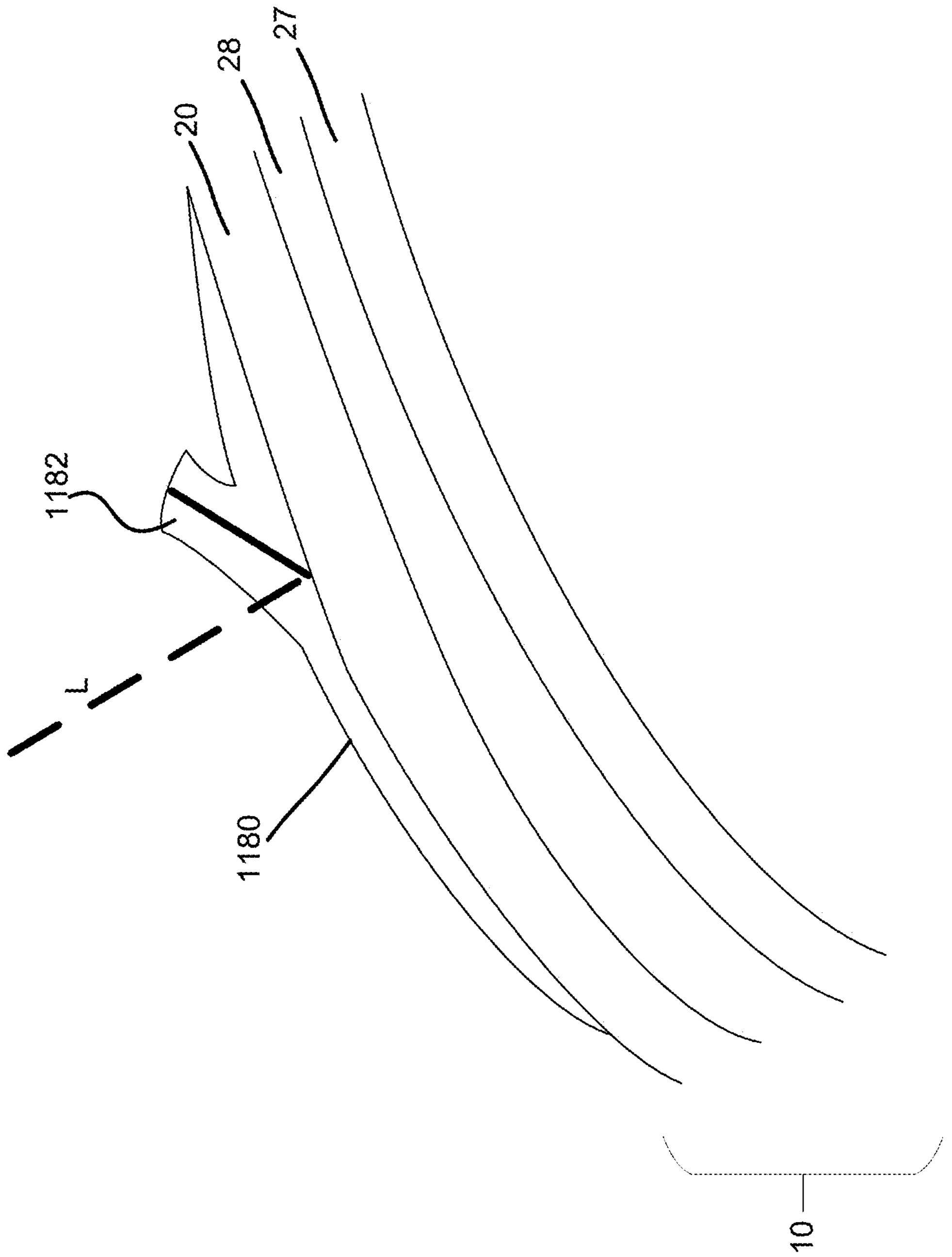
Figure 15E:
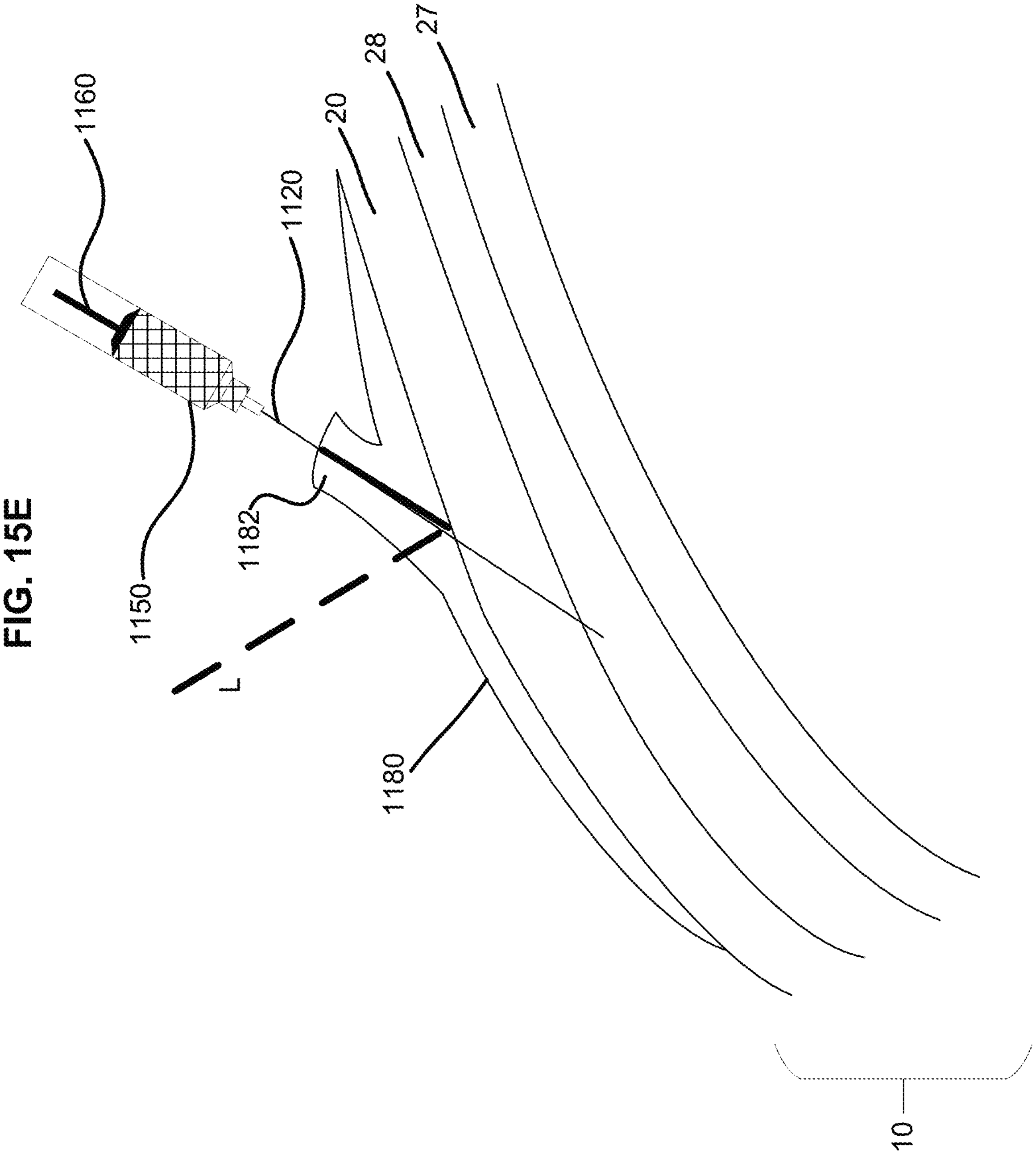

FIGS. 15A-15E illustrate an injection cover 1180 and the placement of the injection cover 1180 on the eye 10, according to an embodiment. As shown, the injection cover 1180 includes an adhesive backing 1181 and an injection port 1182. In some embodiments, the injection cover 1180 can include an iris hole 1183, such that placement of the injection cover 1180 on the eye 10 does not place the injection cover 1180 in contact with the iris. As shown in FIGS. 15A-15B, the adhesive backing can be removed from the injection cover 1180 and the injection cover 1180 can be placed on the eye 10. After removal of the adhesive backing 1181, the injection cover 1180 can be placed on the eye 10. FIG. 15C shows a top view of the injection cover 1180 placed on the eye 10. FIG. 15D shows a cross-sectional view of the injection cover 1180 placed on the eye 10. FIG. 15E shows a cross-sectional view of the injection cover 1180 placed on the eye 10 with a medicament container 1150 configured to inject a medicament into the eye 10 via an injection controller 1160 and a hollow conduit 1120. In some embodiments, the hollow conduit 1120, the medicament container 1150, and the injection controller 1160 can be the same or substantially similar to the hollow conduit 120, the medicament container 150, and the injection controller 160, as described above with reference to FIG. 5. Thus, certain aspects of the hollow conduit 1120, the medicament container 1150, and the injection controller 1160 are not described in greater detail herein.

In some embodiments, the injection port 1182 can form an angle with the outside surface of the eye 10 to guide the angle of entry of the hollow conduit 1120. In some embodiments, the injection port 1182 can form an angle with a line L extending perpendicular from the surface of the eye 10. In some embodiments, the angle formed between the line L and the injection port 1182 can be at least about 0 degrees, at least about 5 degrees, at least about 10 degrees, at least about 15 degrees, at least about 20 degrees, at least about 25 degrees, at least about 30 degrees, at least about 35 degrees, at least about 40 degrees, at least about 45 degrees, at least about 50 degrees, or at least about 55 degrees. In some embodiments, the angle formed between the the line L and the injection port 882 can be no more than about 60 degrees, no more than about 55 degrees, no more than about 50 degrees, no more than about 45 degrees, no more than about 40 degrees, no more than about 35 degrees, no more than about 30 degrees, no more than about 25 degrees, no more than about 20 degrees, no more than about 15 degrees, no more than about 10 degrees, or no more than about 5 degrees. Combinations of the above-referenced angles formed between the line L and the injection port 1182 are also possible (e.g., at least about 0 degrees and no more than about 60 degrees or at least about 10 degrees and no more than about 45 degrees), inclusive of all values and ranges therebetween. In some embodiments, the angle formed between the line L and the injection port 1182 can be about 0 degrees, about 5 degrees, about 10 degrees, about 15 degrees, about 20 degrees, about 25 degrees, about 30 degrees, about 35 degrees, about 40 degrees, about 45 degrees, about 50 degrees, about 55 degrees, or about 60 degrees.

FIGS. 16A-16E are illustrations of an injection apparatus 1200 and a method of operating the injection apparatus 1200, according to an embodiment. As shown, the injection apparatus 1200 includes a housing 1210, a vacuum handle 1213, a vacuum space 1214, a flange 1215, a hollow conduit 1220, a medicament container 1250, and an injection controller 1260. In some embodiments, the housing 1210, the hollow conduit 1220, the medicament container 1250, and the injection controller 1260 can be the same or substantially similar to the housing 110, the hollow conduit 120, the medicament container 150, and the injection controller 160, as described above with reference to FIG. 5. Thus, certain aspects of the housing 1210, the hollow conduit 1220, the medicament container 1250, and the injection controller 1260 are not described in greater detail herein.

Figure 16A:
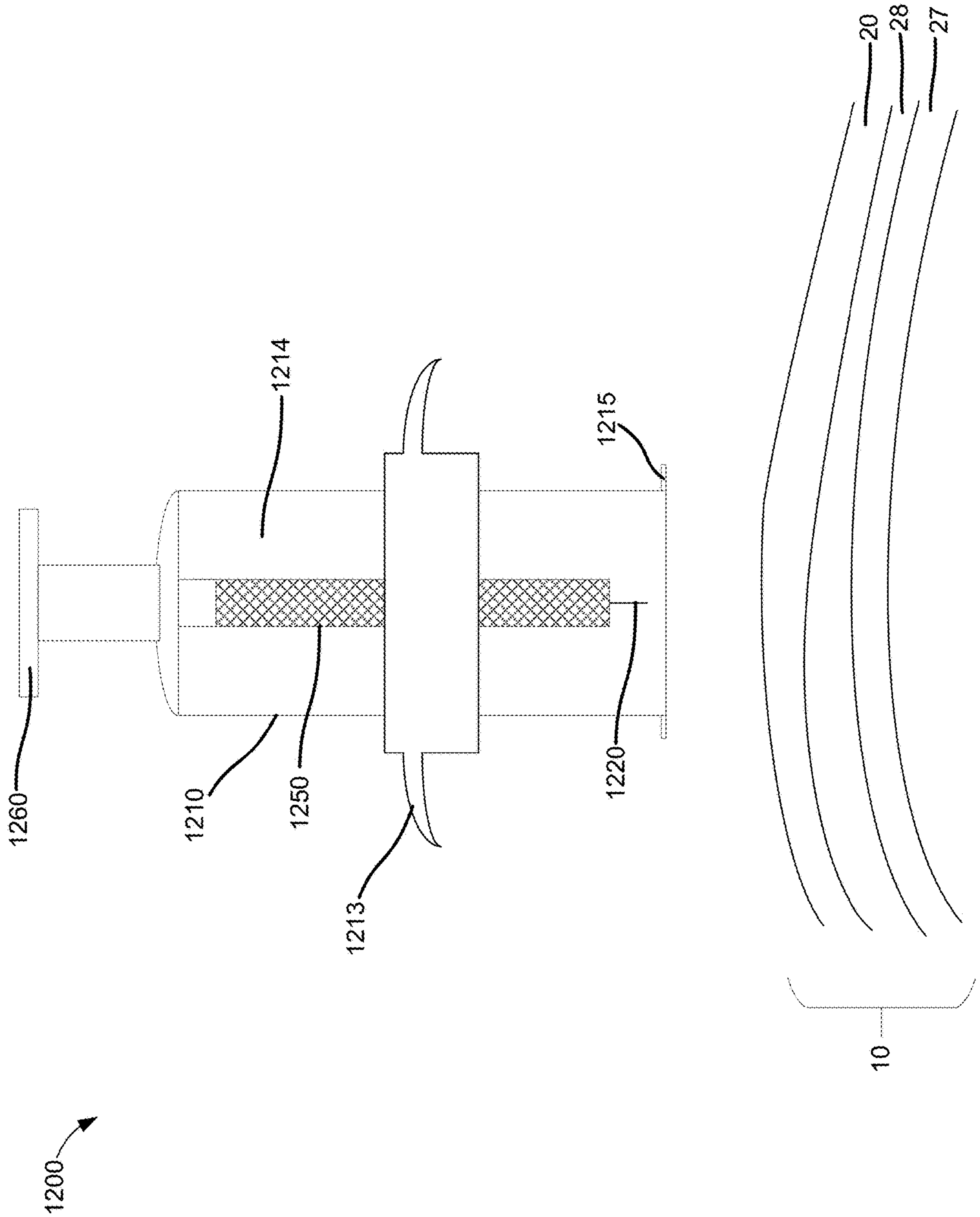
FIGS. 16A-16E are illustrations an injection apparatus and a method of operating the injection apparatus, according to an embodiment.
Figure 16B:
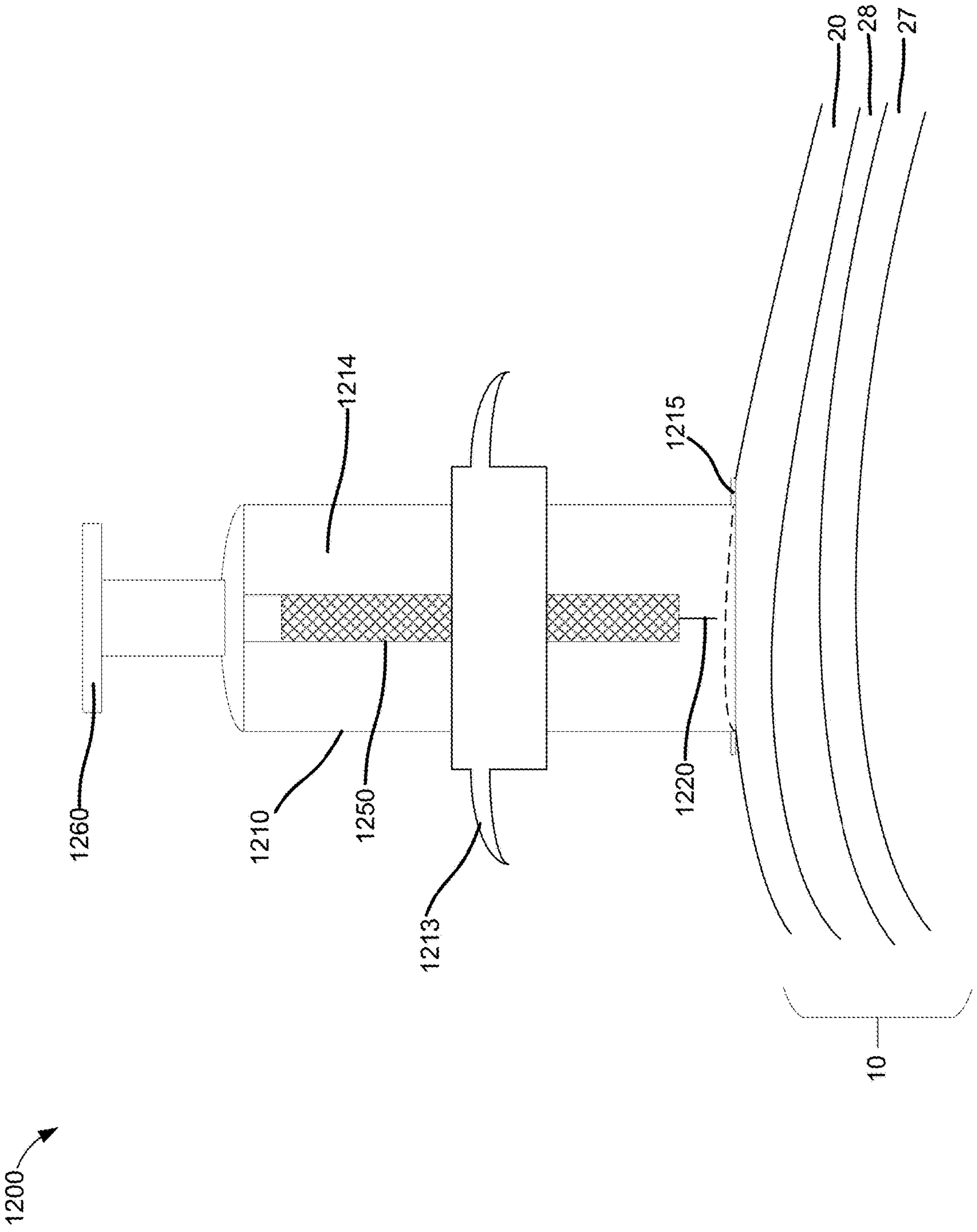

FIG. 16A shows the injection apparatus 1200 spaced apart from the eye 10. FIG. 16B shows the injection apparatus

Figure 16C:
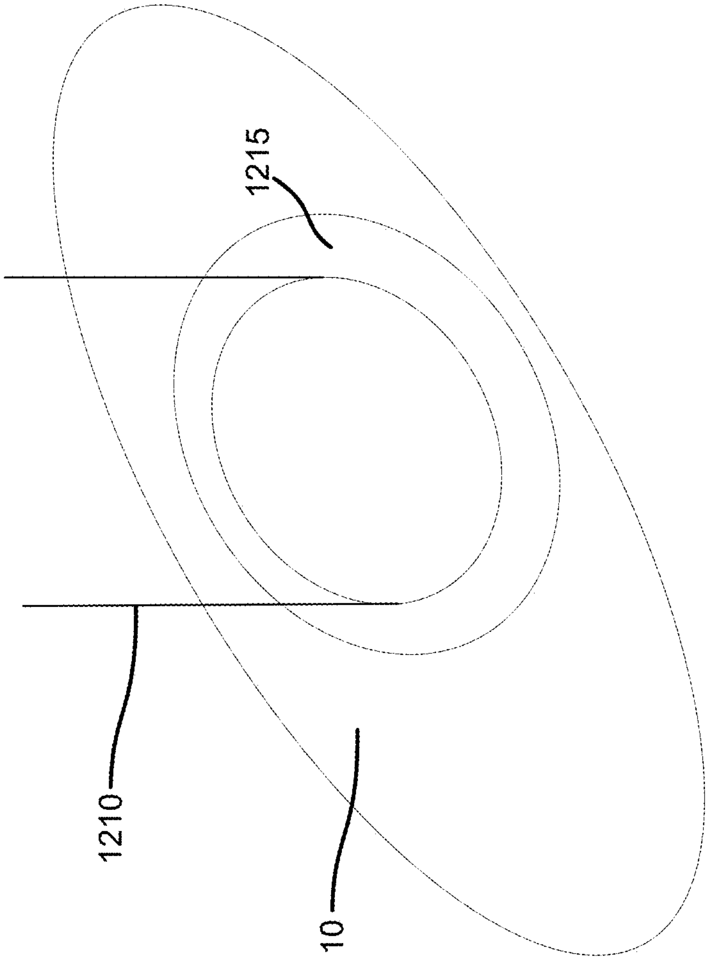
Figure 16D:
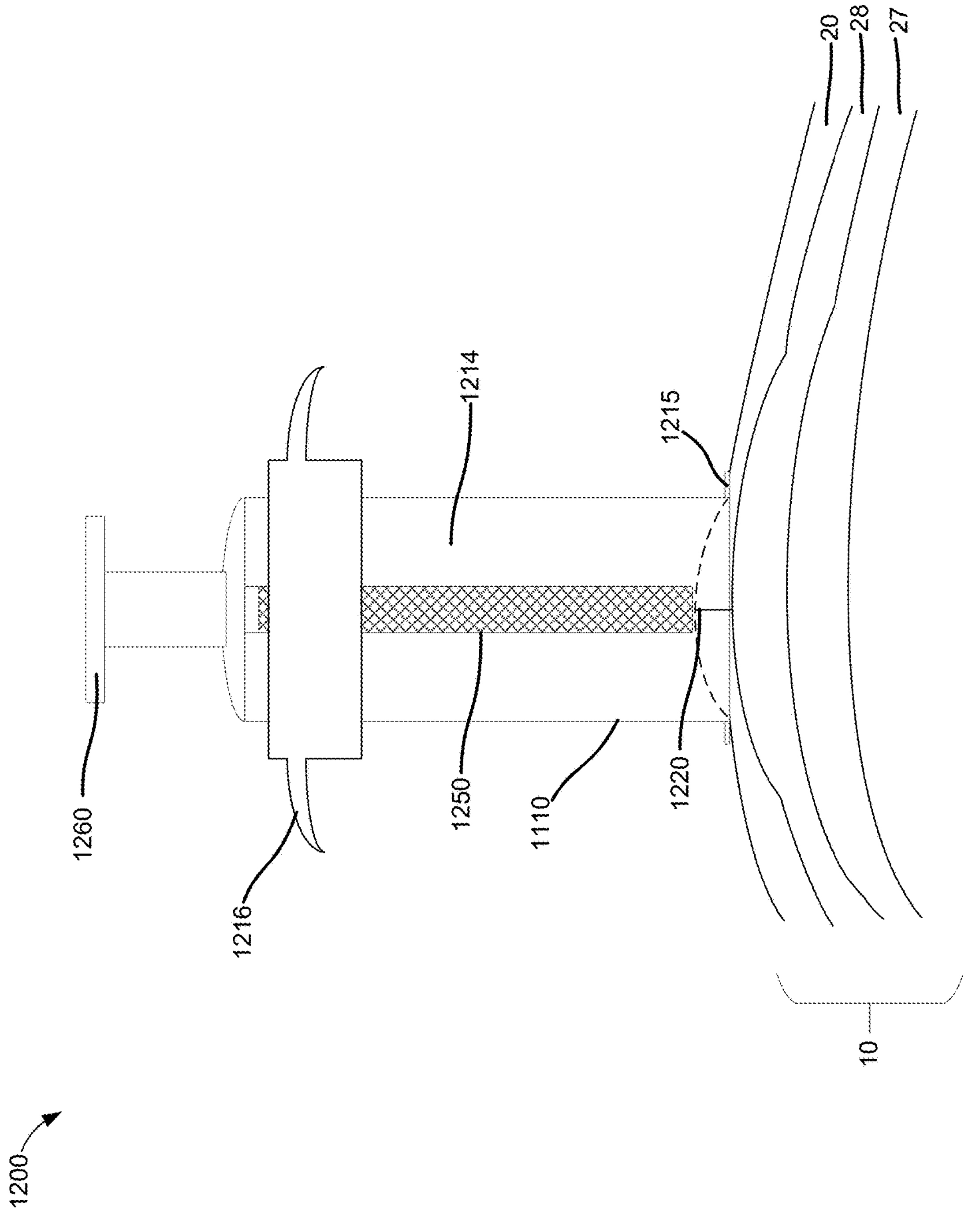
Figure 16E:
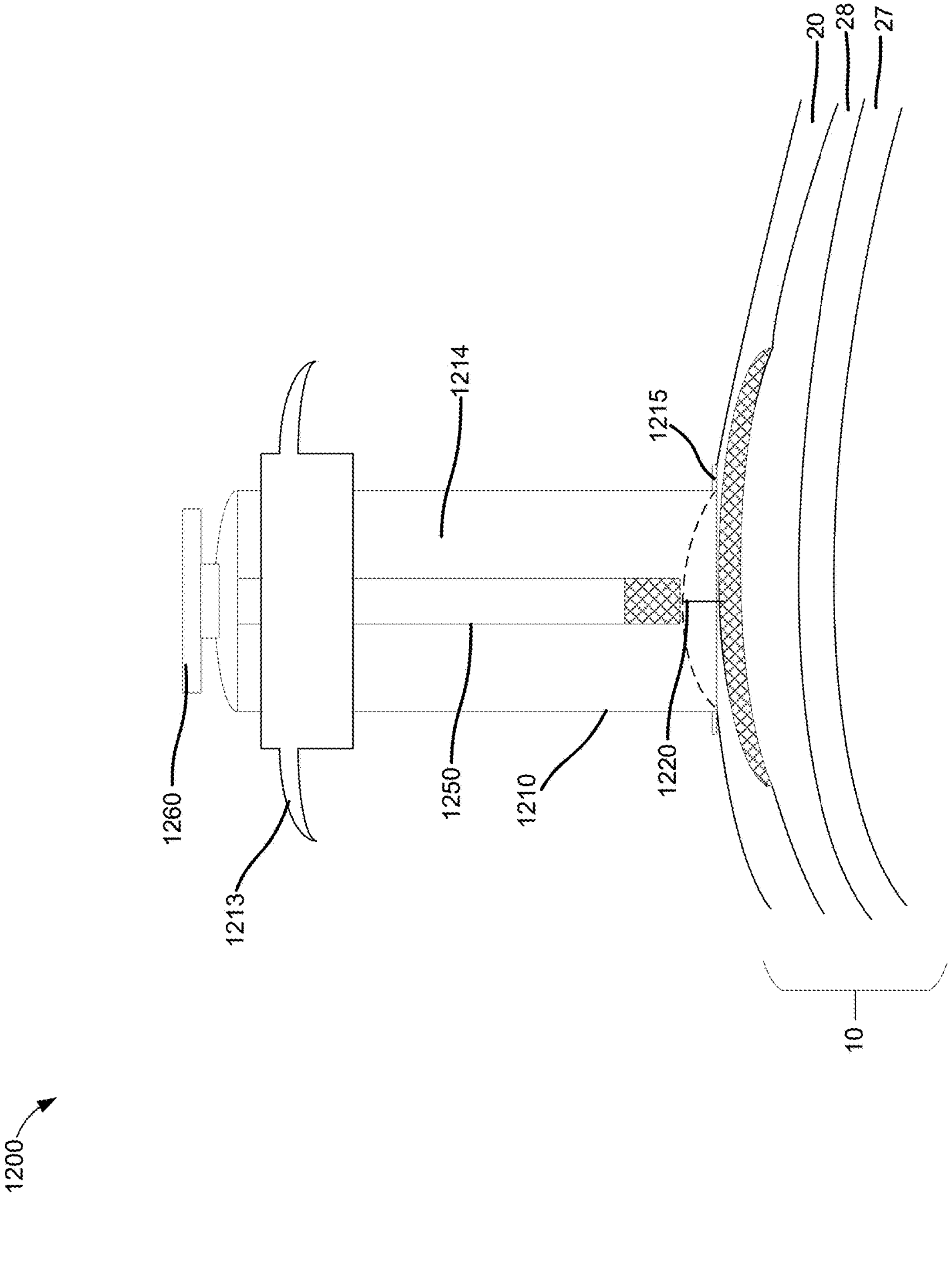

1200 contacting the outer surface of the eye. As shown in FIG. 16C, the flange 1215 forms a seal with the outer surface of the eye 10. After contact is made with the outer surface of the eye, the vacuum handle 1213 is pulled to reduce the pressure in the vacuum space 1214. This reduction in pressure in the vacuum space 1214 draws the sclera 20, the choroid 28, and the retina 27 toward the injection apparatus 1200. The vacuum created aids in keeping the sclera 20, the choroid 28, and the retina 27 in a fixed position relative to the injection apparatus 1200, such that the injection apparatus 1200 does not slide along the surface of the eye 10 during injection of the medicament. FIG. 16D shows the sclera 20, the choroid 28, and the retina 27 drawn to the vacuum created by pulling the vacuum handle 1213. Once the vacuum is pulled and the hollow conduit 1220 is placed properly, the injection controller 1260 can be pressed to deploy the medicament into the desired space in the eye 10. In some embodiments, the injection controller 1260 can be pressed to deploy the medicament and the vacuum handle 1213 can be pulled to reduce the pressure in the vacuum space 1214 simultaneously. In some embodiments, the vacuum handle 1213 can be pulled to reduce the pressure in the vacuum space 1214 during a first time period and the injection controller 1260 can be pressed to deploy the medicament during a second time period. In some embodiments, the first time period can be completely different from the second time period (i.e., no overlap). In some embodiments, the first time period can have some overlap with the second time period. In some embodiments, there can be significant overlap between the first time period and the second time period, such that they occur simultaneously. In some embodiments, the injection controller 1260 can act as an actuator to advance the hollow conduit 1220 toward the eye 10. In some embodiments, the injection controller 1260 can both advance the hollow conduit 1220 toward the eye 10 and inject the medicament into the eye 10.

In some embodiments, the vacuum pulled in the vacuum space 1214 can result in a pressure reduction in the vacuum space 1214 of at least about 0 bar, at least about 0.1 bar, at least about 0.2 bar, at least about 0.3 bar, at least about 0.4 bar, at least about 0.5 bar, at least about 0.6 bar, at least about 0.7 bar, at least about 0.8 bar, at least about 0.9 bar, or at least about 1 bar. In some embodiments, the vacuum pulled in the vacuum space 1214 can result in a pressure reduction in the vacuum space of no more than about 1 bar, no more than about 0.9 bar, no more than about 0.8 bar, no more than about 0.7 bar, no more than about 0.6 bar, no more than about 0.5 bar, no more than about 0.4 bar, no more than about 0.3 bar, no more than about 0.2 bar, or no more than about 0.1 bar. Combinations of the above-referenced pressure reductions in the vacuum space are also possible (e.g., at least about 0 bar and no more than about 1 bar or at least about 0.3 bar and no more than about 0.7 bar), inclusive of all values and ranges therebetween. In some embodiments, the vacuum pulled in the vacuum space 914 can result in a pressure reduction in the vacuum space 914 of about 0 bar, about 0.1 bar, about 0.2 bar, about 0.3 bar, about 0.4 bar, about 0.5 bar, about 0.6 bar, about 0.7 bar, about 0.8 bar, about 0.9 bar, or about 1 bar.

In some embodiments, the hollow conduit 1220 can include a measurement disposed on the distal end of the hollow conduit 1220. In some embodiments, the measurement device can include a pressure measurement device. In some embodiments, the measurement device can include an emissivity measurement device. In some embodiments, the measurement device can include an OCT probe. In some embodiments, the measurement device can include an electrical impedance device. In some embodiments, the measurement device can include an acoustic wave measurement device.

Figure 17A:
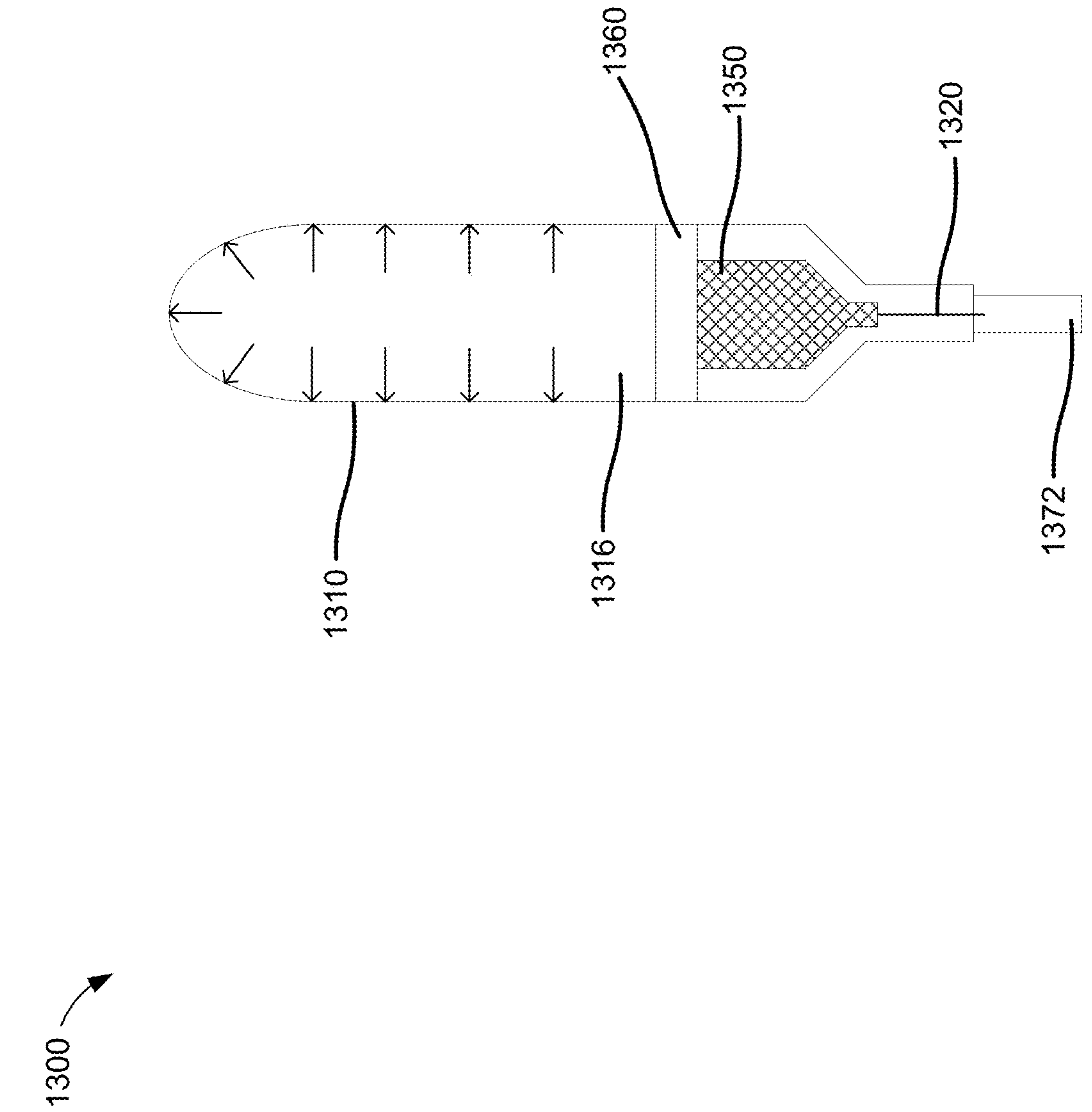
FIGS. 17A-17B are illustrations of an injection apparatus, according to an embodiment.
Figure 17B:
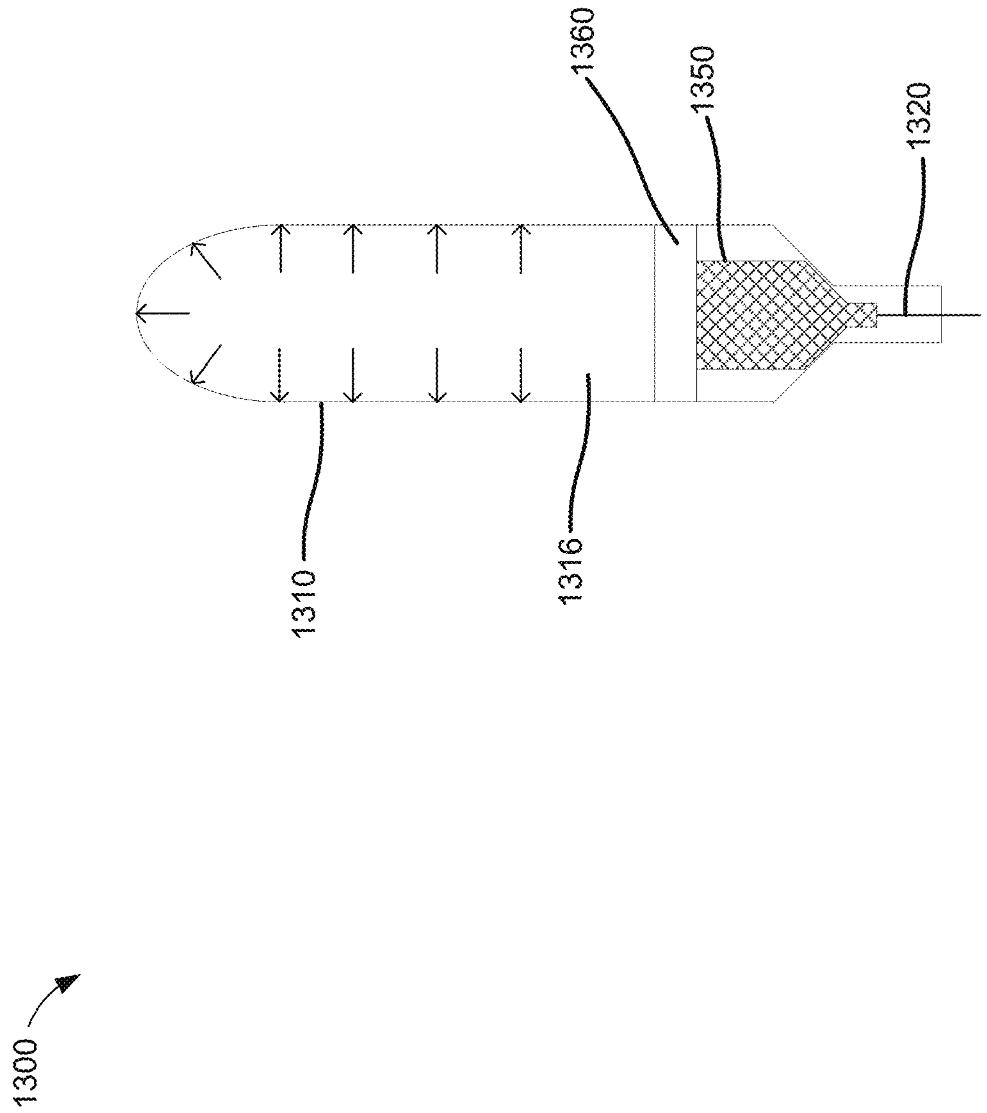

FIGS. 17A-17B show an injection apparatus 1300, according to an embodiment. As shown, the injection apparatus 1300 includes a housing 1310, a pressure chamber 1316, a hollow conduit 1320, a medicament container 1350, an injection controller 1360, and a trocar 1372. In some embodiments, the housing 1310, the hollow conduit 1320, the medicament container 1350, and the injection controller 1360 can be the same or substantially similar to the housing 110, the hollow conduit 120, the medicament container 150, and the injection controller 160, as described above with reference to FIG. 5. In some embodiments, the trocar 1372 can be the same or substantially similar to the trocar 972, as described above with reference to FIGS. 13A-13E. Thus, certain aspects of the housing 1310, the hollow conduit 1320, the medicament container 1350, the injection controller 1360, and the trocar 1372 are not described in greater detail herein.

In use, the injection apparatus 1300 is placed near the surface of the eye and the the trocar 1372 can aid in placement of any guiding apparatus on the eye, as shown in FIG. 17A. Once the injection apparatus is properly placed, the trocar 1372 can be removed, as shown in FIG. 17B. The pressure chamber 1316 can aid in advancement of the medicament container 1350 and the hollow conduit 1320, such that a distal end portion of the hollow conduit 1320 is placed at a desired location in the eye. Once the distal end portion of the hollow conduit 1320 is placed at the desired location in the eye, the medicament can be injected into the eye. In some embodiments, the injection controller 1360 can move relative to the medicament container 1350 to inject the medicament into the desired location within the eye. In some embodiments, the pressure chamber 1316 can apply a force to the injection controller 1360, such that the injection controller 1360 deploys the medicament via the hollow conduit 1320 when the distal end of the hollow conduit 1320 reaches an area of low resistance (e.g., when the distal end of the hollow conduit 1320 passes from the sclera to the SCS). This loss of resistance mechanism is described in greater detail in the '139 patent.

In some embodiments, the pressure chamber 1316 can be maintained at a constant pressure. In some embodiments, the pressure chamber 1316 can be maintained at constant pressure via an internal pumping mechanism. In some embodiments, the pressure chamber 1316 can be pressurized via manual actuation (e.g., via a mechanical hand pump). In some embodiments, a mechanical pump that pressurizes the pressure chamber 1316 can include a one-way valve to restrict flow of gas out of the pressure chamber. In some embodiments, the pressure chamber 1316 can be pressurized via an automatic mechanical pump. In some embodiments, the pressure chamber can be pressurized via a fluidic coupling with a high pressure gas (e.g., a $CO_2$ cartridge). In some embodiments, the pressure chamber 1316 can be maintained at a pressure of at least about 0.1 bar gauge, at least about 0.2 bar gauge, at least about 0.3 bar gauge, at least about 0.4 bar gauge, at least about 0.5 bar gauge, at least about 0.6 bar gauge, at least about 0.7 bar gauge, at least about 0.8 bar gauge, at least about 0.9 bar gauge, at least about 1 bar gauge, at least about 2 bar gauge, at least about 3 bar gauge, at least about 4 bar gauge, at least about 5 bar gauge, at least about 6 bar gauge, at least about 7 bar gauge, at least about 8 bar gauge, or at least about 9 bar gauge. In some embodiments, the pressure chamber 1316 can be maintained at a pressure of no more than about 9 bar gauge, no more than about 8 bar gauge, no more than about 7 bar gauge, no more than about 6 bar gauge, no more than about 5 bar gauge, no more than about 4 bar gauge, no more than about 3 bar gauge, no more than about 2 bar gauge, no more than about 1 bar gauge, no more than about 0.9 bar gauge, no more than about 0.8 bar gauge, no more than about 0.7 bar gauge, no more than about 0.6 bar gauge, no more than about 0.5 bar gauge, no more than about 0.4 bar gauge, no more than about 0.3 bar gauge, no more than about 0.2 bar gauge, or no more than about 0.1 bar gauge. Combinations of the above-referenced pressures in the pressure chamber 1316 are also possible (e.g., at least about 0.1 bar gauge and no more than about 10 bar gauge or at least about 0.3 bar gauge and no more than about 1 bar gauge), inclusive of all values and ranges therebetween. In some embodiments, the pressure chamber 1316 can be maintained at a pressure of about 0.1 bar gauge, about 0.2 bar gauge, about 0.3 bar gauge, about 0.4 bar gauge, about 0.5 bar gauge, about 0.6 bar gauge, about 0.7 bar gauge, about 0.8 bar gauge, about 0.9 bar gauge, about 1 bar gauge, about 2 bar gauge, about 3 bar gauge, about 4 bar gauge, about 5 bar gauge, about 6 bar gauge, about 7 bar gauge, about 8 bar gauge, about 9 bar gauge, or about 10 bar gauge.

Figure 18A:
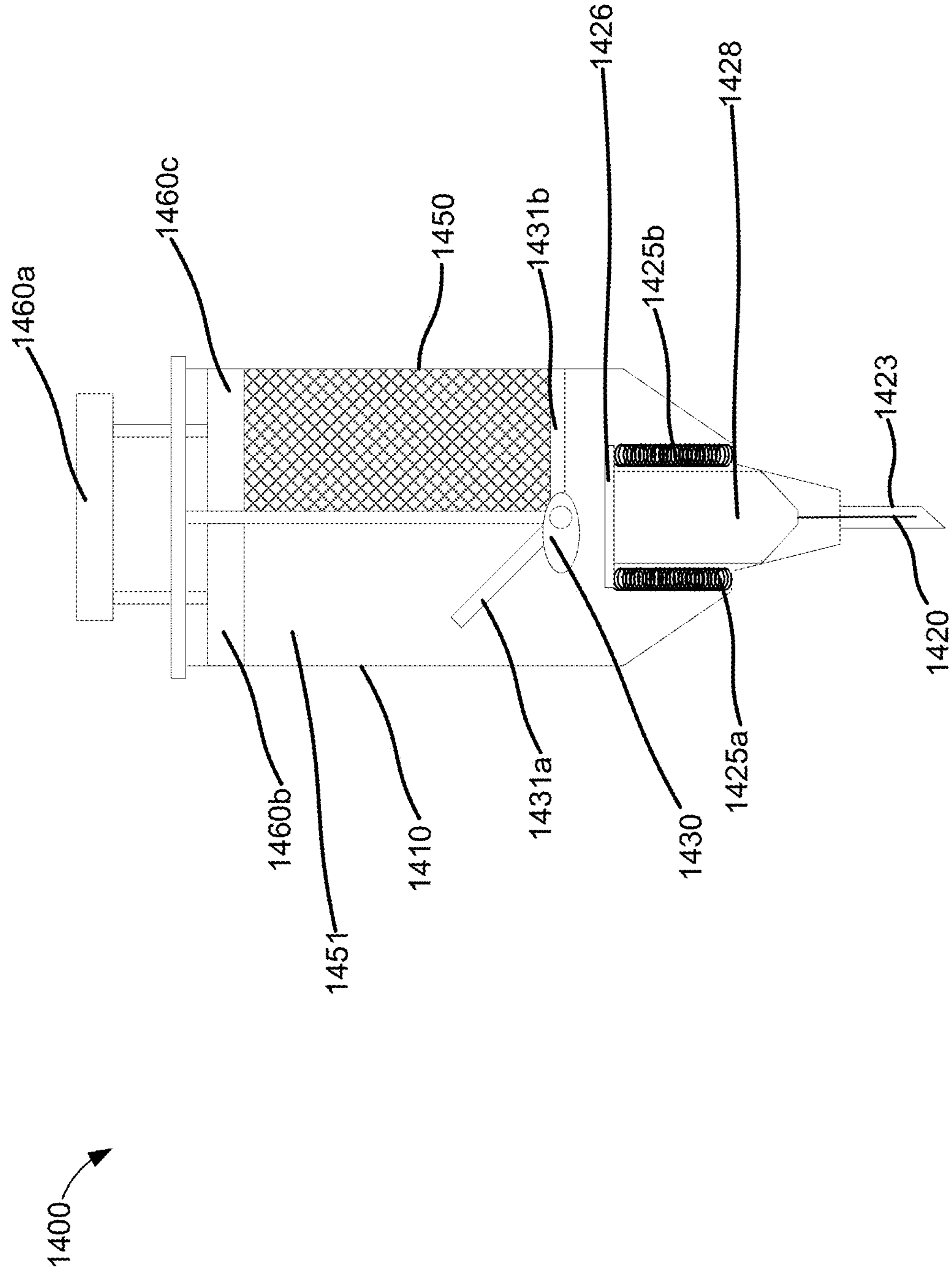
FIGS. 18A-18C are illustrations of an injection apparatus, according to an embodiment.
Figure 18B:
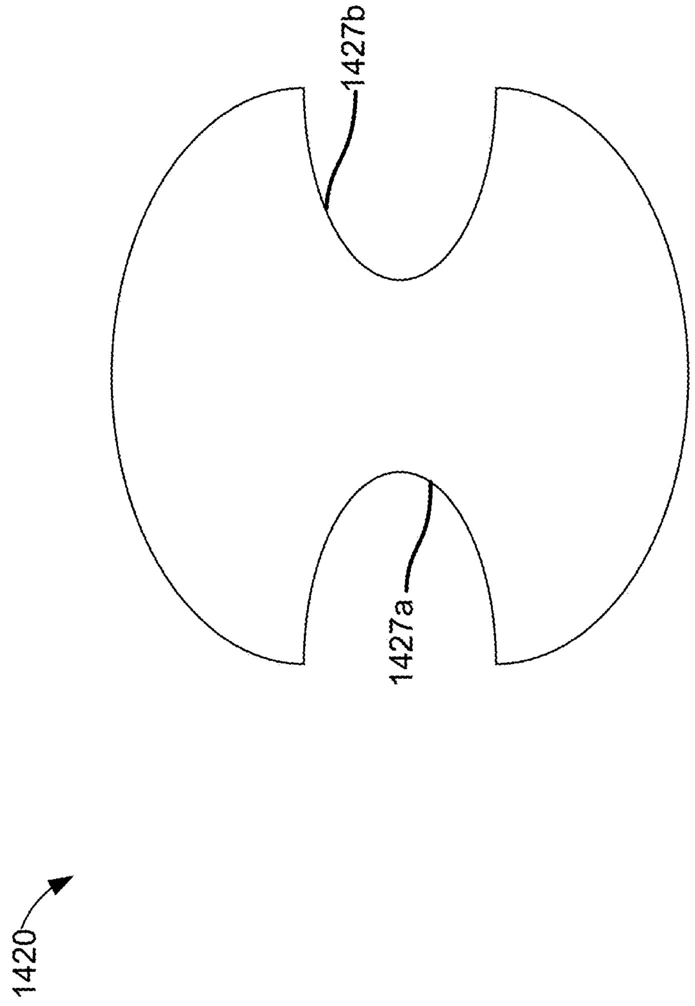
Figure 18C:
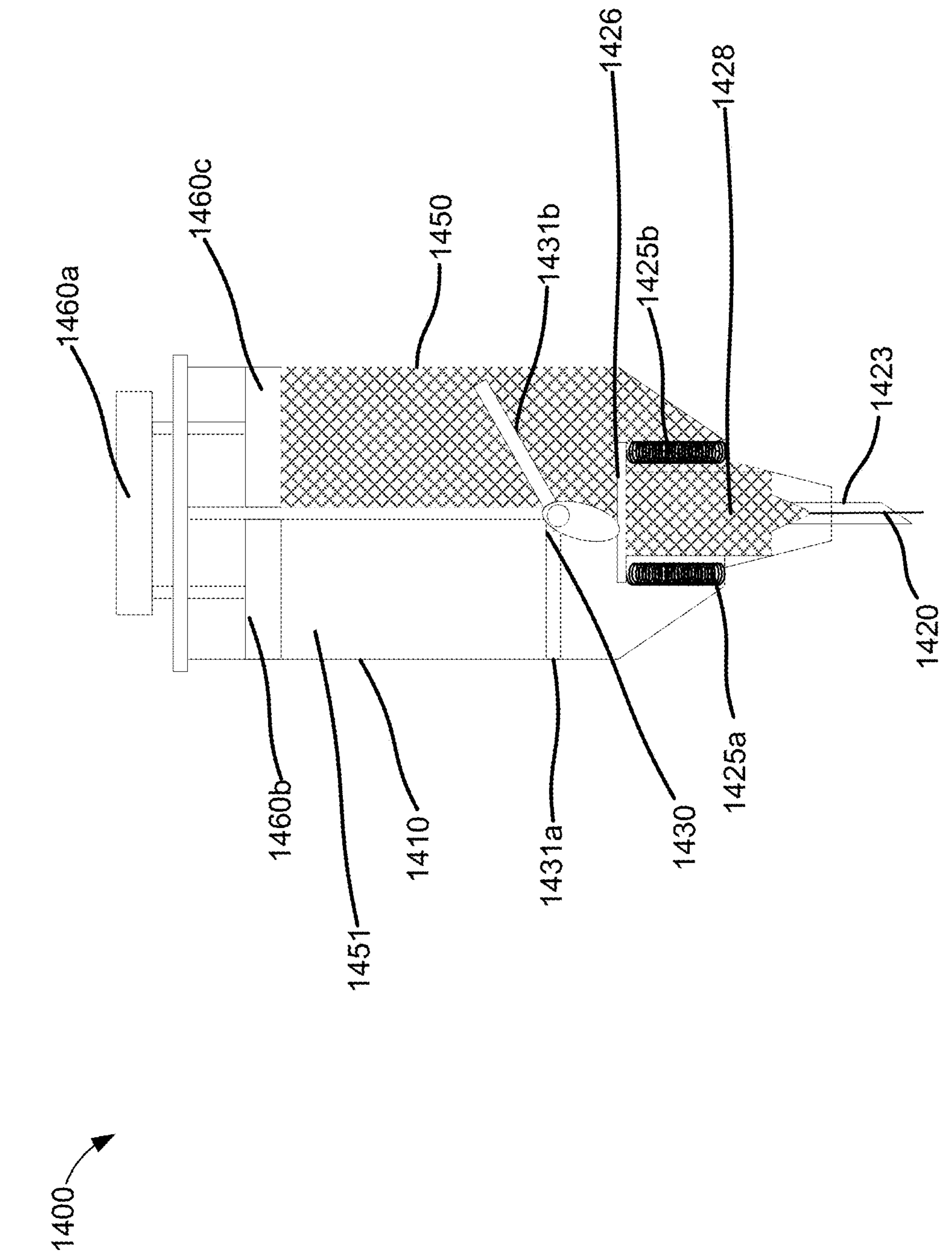

FIGS. 18A-18C show an injection apparatus 1400, according to an embodiment. FIG. 18A shows the injection apparatus 1400 before the injection begins. FIG. 18B shows a cross section of a portion of a hollow conduit 1420 of the injection apparatus 1400. FIG. 18C shows the injection apparatus 1400 after the injection has begun. As shown, the injection apparatus 1400 includes a housing 1410, the hollow conduit 1420, a sheath 1423, springs 1425*a*, 1425*b* (collectively referred to as springs 1425), an actuator contact surface 1426, a deployment chamber 1428, an actuator 1430, trap doors 1431*a*, 1431*b* (collectively referred to as trap doors 1431), a medicament container 1450, a void space 1451, injection controllers 1460*a*, 1460*b*, 1460*c* (collectively referred to as injection controllers 1460). The hollow conduit 1420 includes entry ridges 1427*a*, 1427*b* (collectively referred to as entry ridges 1427). In some embodiments, the housing 1410, the hollow conduit 1420, the actuator 1430, the medicament container 1450, and the injection controllers 1460 can be the same or substantially similar to the housing 110, the hollow conduit 120, the actuator 130, the medicament container 150, and the injection controller 160, as described above with reference to FIG. 5. Thus, certain aspects of the housing 1410, the hollow conduit 1420, the actuator 1430, the medicament container 1450, and the injection controllers 1460 are not described in greater detail herein.

In some embodiments, the sheath 1423 can provide a protective shell for the hollow conduit 1420 to protect the hollow conduit 1420 from damage. In some embodiments, the sheath 1423 can provide a more rigid body than the hollow conduit 1420 to penetrate tougher layers of the eye (e.g., sclera). Once the sclera has been penetrated, the hollow conduit 1420 can be advanced to reach the desired injection site. In some embodiments, the entry ridges 1427 can create a dual-lumen cannula for movement of medicament through the hollow conduit 1420. In some embodiments, the entry ridge 1427*b* can provide a flow path for the medicament while the entry ridge 1427*a* can provide a flow path for gas. In some embodiments, the entry ridge 1427*a* can provide a flow path for gas when the trap door 1431*a* is open. In some embodiments, the entry ridge 1427*b* can provide a flow path for medicament when the trap door 1431*b* is open.

As shown, the actuator 1430 has an elliptical shape, such that the actuator 1430 can rotate to make contact with and push the actuator contact surface 1426 (i.e., compressing the springs 1425). Pushing the actuator contact surface 1426 can advance the hollow conduit 1420 within the eye. In some embodiments, the rotation of the actuator 1430 can simultaneously move the trap doors 1431. As shown, the trap door 1431*b* contains the medicament while the trap door 1431*a* can contain the void space 1451. In some embodiments, rotation of the actuator 1430 can shift the trap door 1431*b* that contains the medicament to an open position. In some embodiments, the rotation of the actuator 1430 can shift the trap door 1431*a* that can contain the void space 1451 to a closed position, such that the trap door 1431*a* forms a seal with a wall of the housing and contains the void space 1451. Forming the seal with the wall of the housing 1410 can prevent gas from flowing into the void space 1451, thereby maintaining a high pressure in the medicament container 1450. Upon opening of the trap door 1431*b*, the medicament can flow into the hollow conduit 1420 via the deployment chamber 1428. In some embodiments, the actuator contact surface 1426 can include one or more holes to fluidically couple the medicament container 1450 to the deployment chamber 1428 and allow flow of medicament into the deployment chamber 1428. In some embodiments, the actuator contact surface 1426 and the deployment chamber 1428 can act as a female Luer-Lock® fitting. Movement of the medicament can be facilitated by movement of the injection controller 1460*c* through the medicament container 1450. As shown, the injection controller 1460*a* is physically coupled to the injection controller 1460*b* and the injection controller 1460*c*. In some embodiments, the injection controller 1460*a* can control the movement of the injection controller 1460*c* and the injection controller 1460*b*. The dual-chamber configuration of the injection apparatus 1400 can have several advantages. In some embodiments, force applied to the injection controller 1460*a* can increase the pressure in the void space 1451 and provide pressure at the distal end of the hollow conduit 1420 to create space in the target tissue (e.g., suprachoroidal space, retinal space). Once a space has been created in the target tissue, the actuator 1430 can rotate to open the trap door 1431*b* while closing the trap door 1431*a*, and the medicament can flow into the space created. In some embodiments, the injection apparatus 1400 can include a measurement device (not shown). In some embodiments, the measurement device can have the same or substantially similar properties to the measurement device 140, as described above with reference to FIG. 5.

Figure 19A:
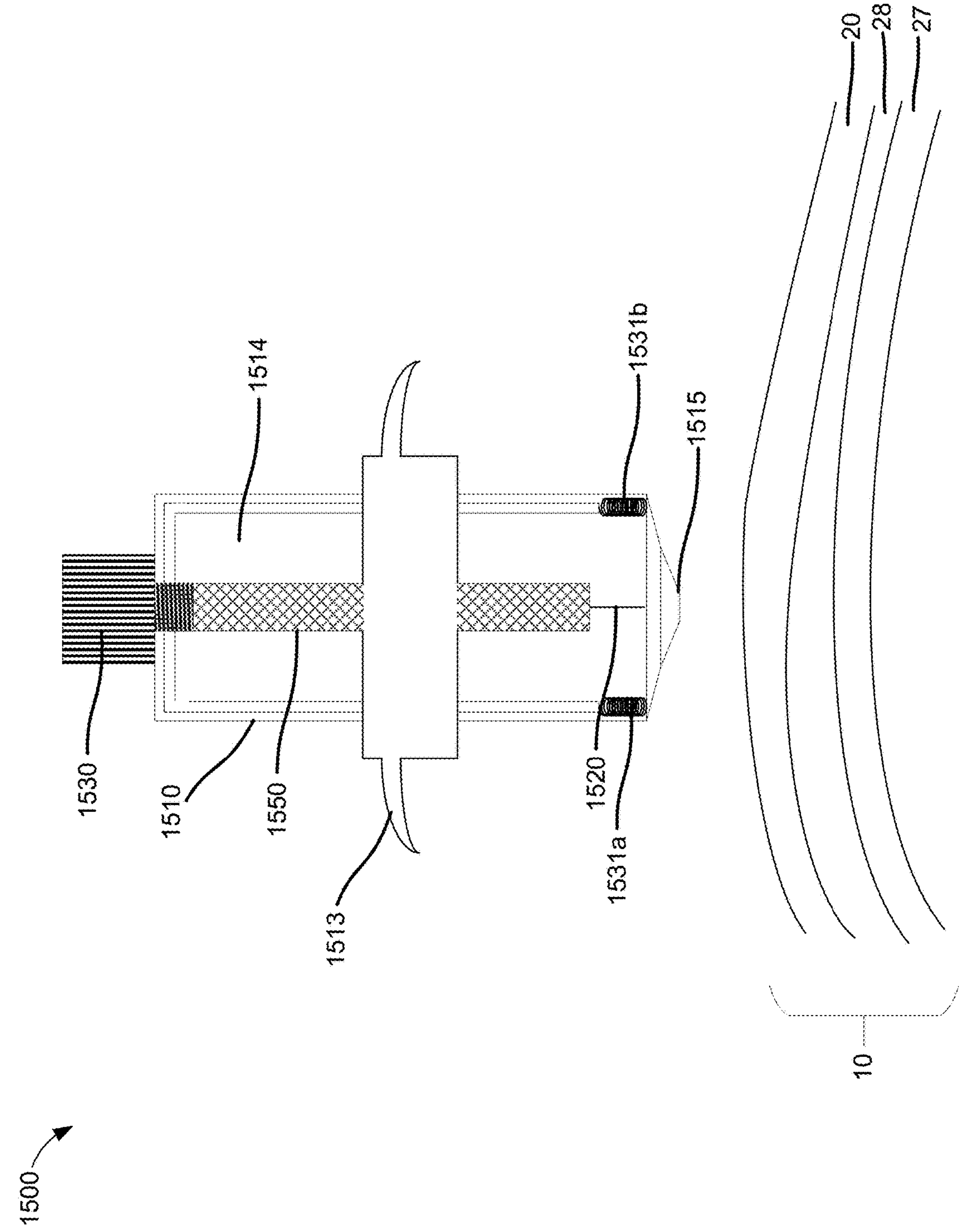
FIGS. 19A-19C are illustrations of an injection apparatus and a method of operating the injection apparatus, according to an embodiment.
Figure 19B:
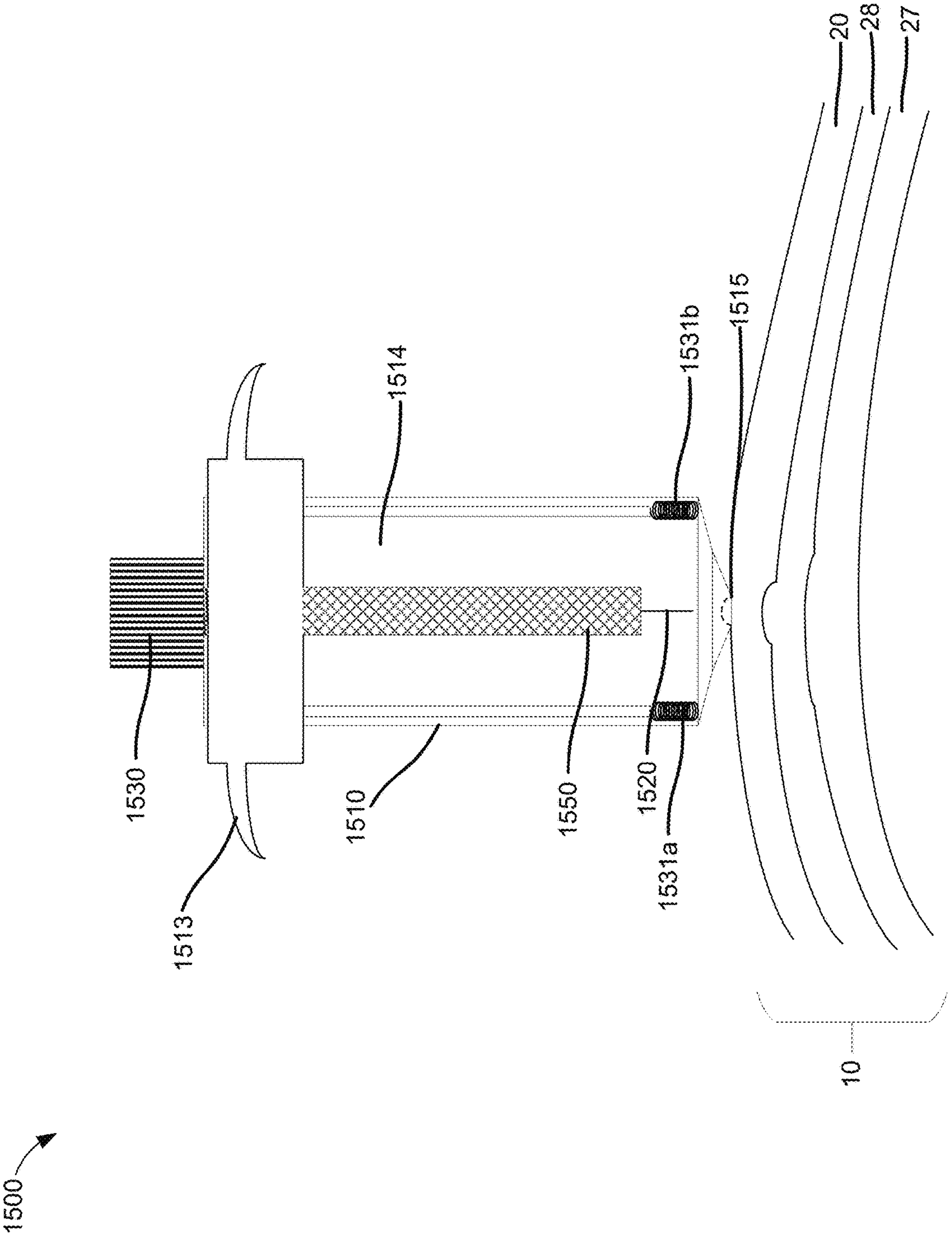
Figure 19C:
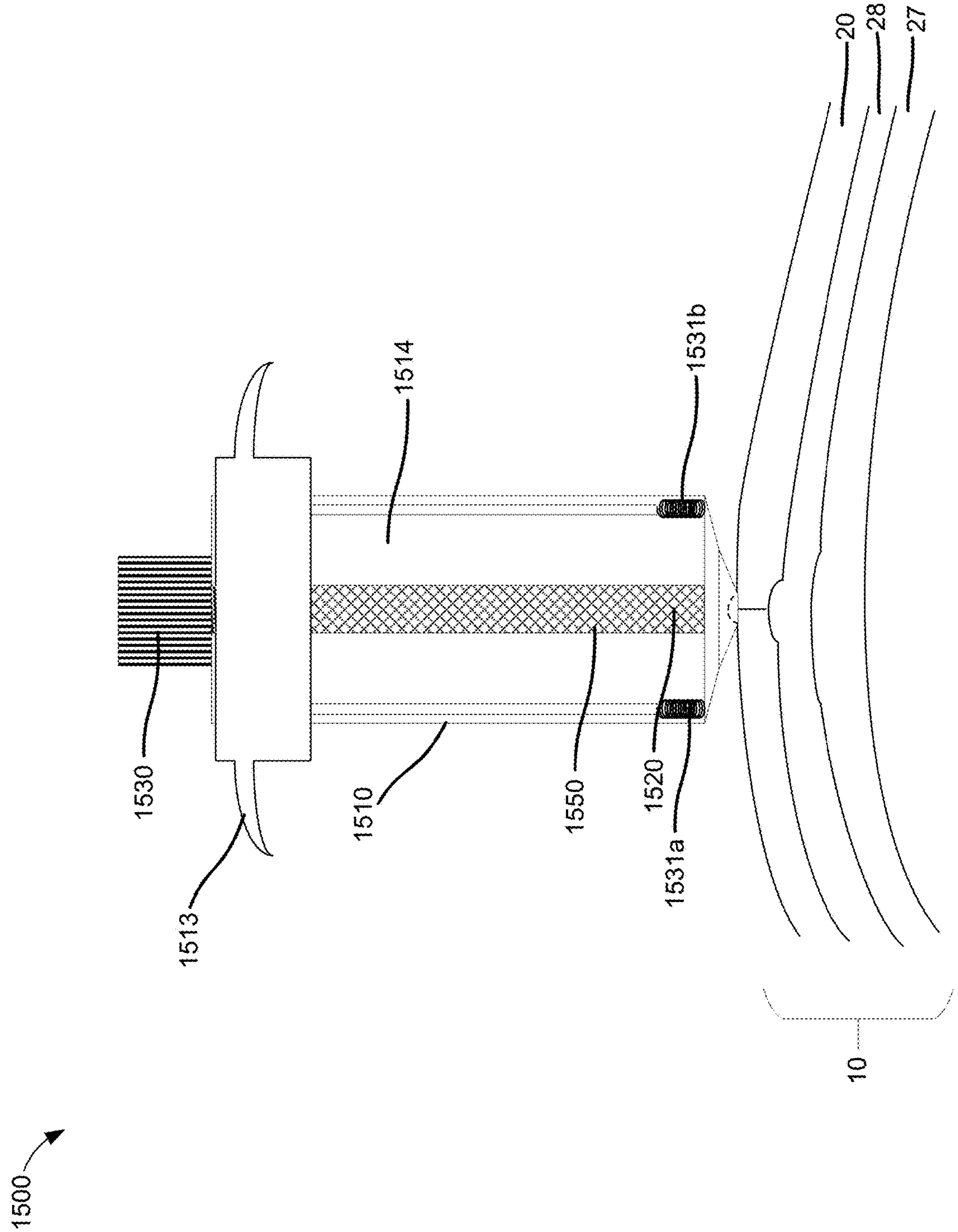

FIGS. 19A-19C show an injection apparatus 1500 and a method of using the injection apparatus 1500, according to an embodiment. As shown, the injection apparatus 1500 includes a housing 1510, a vacuum handle 1513, a vacuum space 1514, a vacuum nozzle 1515, a hollow conduit 1520, an actuator 1530, and actuator springs 1531*a*, 1531*b* (collectively referred to as actuator springs 1531). In some embodiments, the housing 1510, the hollow conduit 1520, and the actuator 1530 can be the same or substantially similar to the housing 110, the hollow conduit 120, and the actuator 130, as described above with reference to FIG. 5. In some embodiments, the vacuum handle 1513 and the vacuum space 1514 can be the same or substantially similar to the vacuum handle 1213 and the vacuum space 1214, as described above with reference to FIGS. 16A-16E. Thus certain aspects of the housing 1510, the vacuum handle 1513, the vacuum space 1514, the hollow conduit 1520, and the actuator 1530 are not described in greater detail herein. In some embodiments, the injection apparatus 1500 can include an injection controller (not shown). In some embodiments, the injection controller can be the same or substantially similar to the injection controller 160, as described above with reference to FIG. 5.

FIG. 19A shows the injection apparatus 1500 spaced apart from the eye 10. In FIG. 19B, the injection apparatus 1500 is contacting the eye 10, and the vacuum handle 1513 is engaged to pull a portion of the sclera 20 through the vacuum nozzle 1515. In FIG. 19C, the hollow conduit 1520 has been advanced such that a distal end of the hollow conduit 1520 is at a desired injection site.

In use, the injection apparatus 1500 is placed such that the vacuum nozzle 1515 contacts the eye 10. The vacuum handle 1513 is then pulled to lower the pressure in the vacuum space 1514. Pulling the vacuum on a portion of the outer surface of the eye 10 can keep the layers of the eye 10 secured during injection. The actuator 1530 then advances the medicament container 1550 and the hollow conduit 1520 such that the distal end of the hollow conduit 1520 is at a desired injection site in the eye 10. As shown, advancement of the medicament container 1550 and the hollow conduit 1520 is performed against a force imposed by the actuator springs 1531. In some embodiments, the actuator 1530 can be a micrometer. After the distal end of the hollow conduit 1520 is at the desired injection site in the eye 10, the medicament is deployed via the hollow conduit 1520.

Figure 20:
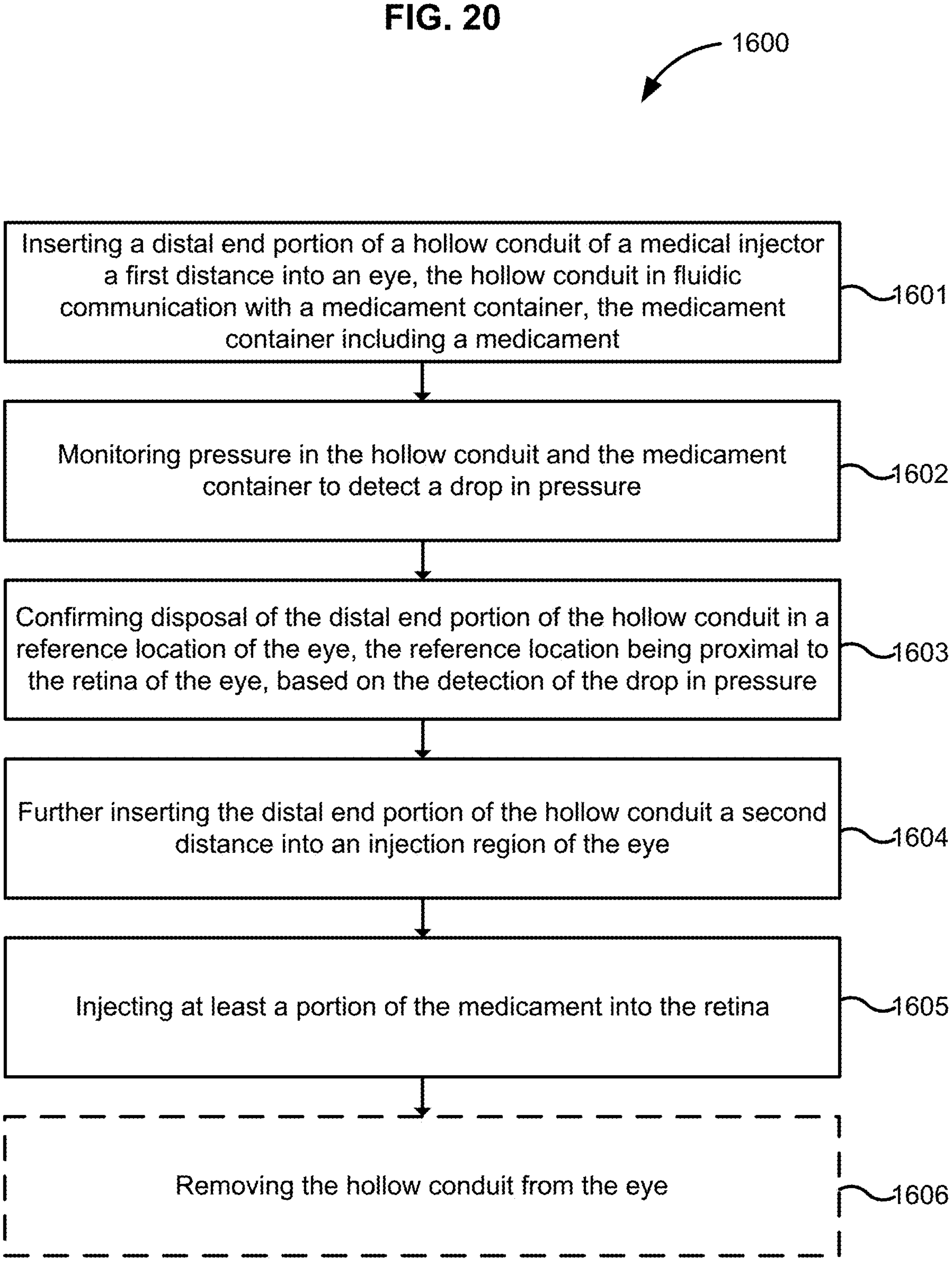
FIG. 20 shows a flow diagram of a method for performing an injection into the retinal tissue, according to an embodiment.

FIG. 20 shows a flow diagram of a method 1600 for performing an injection into the retinal tissue, according to an embodiment. At step 1601, the method 1600 includes inserting a distal end portion of a hollow conduit of a medical injector a first distance into an eye. The hollow conduit is in fluidic communication with a medicament container, and the medicament container includes a medicament. In some embodiments, insertion of the distal tip of the hollow conduit can be automatic. In some embodiments, insertion of the distal tip of the hollow conduit can be manual. In some embodiments, the medicament can include one or more of the medicaments listed in the '139 patent.

In some embodiments, the first distance can be sufficient to reach the SCS. In some embodiments, the first distance can be at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, at least about 9.5 mm, at least about 1 cm, at least about 1.5 cm, at least about 2 cm, at least about 2.5 cm, at least about 3 cm, at least about 3.5 cm, at least about 4 cm, or at least about 4.5 cm. In some embodiments, the first distance can be no more than about 5 cm, no more than about 4.5 cm, no more than about 4 cm, no more than about 3.5 cm, no more than about 3 cm, no more than about 2.5 cm, no more than about 2 cm, no more than about 1.5 cm, no more than about 1 cm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, or no more than about 1.5 mm.

Combinations of the above-referenced values for the first distance are also possible (e.g., at least about 1 mm and no more than about 5 cm or at least about 5 mm and no more than about 1 cm), inclusive of all values and ranges therebetween. In some embodiments, the first distance can be about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 1 cm, about 1.5 cm, about 2 cm, about 2.5 cm, about 3 cm, about 3.5 cm, about 4 cm, about 4.5 cm, or about 5 cm.

In some embodiments, the insertion can be performed such that a centerline of the hollow conduit and a surface line tangential to a target surface of the eye defines an angle of entry. If the angle of entry is too small or zero degrees, this can potentially deform the sclera and put the retina under tension. In some embodiments, the beveling of the distal end of the hollow conduit and the angle of entry can be selected to minimize deformation of the sclera and tension upon the retina. In some embodiments, the angle of entry can be at least about 30 degrees, at least about 35 degrees, at least about 40 degrees, at least about 45 degrees, at least about 50 degrees, at least about 55 degrees, at least about 60 degrees, at least about 65 degrees, at least about 70 degrees, at least about 75 degrees, at least about 80 degrees, at least about 85 degrees, at least about 90 degrees, at least about 95 degrees, at least about 100 degrees, at least about 105 degrees, at least about 110 degrees, at least about 115 degrees, at least about 120 degrees, at least about 125 degrees, at least about 130 degrees, at least about 135 degrees, at least about 140 degrees, or at least about 145 degrees. In some embodiments, the angle of entry can be no more than about 150 degrees, no more than about 145 degrees, no more than about 140 degrees, no more than about 135 degrees, no more than about 130 degrees, no more than about 125 degrees, no more than about 120 degrees, no more than about 115 degrees, no more than about 110 degrees, no more than about 105 degrees, no more than about 100 degrees, no more than about 95 degrees, no more than about 90 degrees, no more than about 85 degrees, no more than about 80 degrees, no more than about 75 degrees, no more than about 70 degrees, no more than about 65 degrees, no more than about 60 degrees, no more than about 55 degrees, no more than about 50 degrees, no more than about 45 degrees, no more than about 40 degrees, or no more than about 35 degrees.

Combinations of the above-referenced angles of entries are also possible (e.g., at least about 30 degrees and no more than about 150 degrees), inclusive of all values and ranges therebetween. In some embodiments, the angle of entry can be about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 95 degrees, about 100 degrees, about 105 degrees, about 110 degrees, about 115 degrees, about 120 degrees, about 125 degrees, about 130 degrees, about 135 degrees, about 140 degrees, about 145 degrees, or about 150 degrees. In some embodiments, an angle control device can be placed on the outer surface of the eye to guide the movement of the hollow conduit and guide the angle of entry.

The method 1600 further includes monitoring pressure in the hollow conduit and the medicament container at step 1602. In some embodiments, the pressure in the hollow conduit can be monitored to detect a change (e.g., drop) in pressure in the hollow conduit. In some embodiments, a seal between the hollow conduit and the medicament container can be broken prior to monitoring the pressure in the hollow conduit and the medicament container. In some embodiments, monitoring the pressure in the hollow conduit and the medicament container can be via a manometer, a digital pressure transducer, a barometer, a pressure tube, a piezometer, a bourdon gauge, a diaphragm pressure gauge, a micromanometer, or any other suitable pressure measurement device, or combinations thereof.

The method 1600 further includes confirming disposal or positioning of the distal end portion of the hollow conduit in a reference location of the eye at step 1603. The reference location is proximal to the retina of the eye, and can be detected based on the detected change in pressure. In some embodiments, the reference location can be an interface between a choroid tissue and the RPE. In some embodiments, the reference location can be in the RPE. In some embodiments, the reference location can be in the SCS. In some embodiments, the reduction in pressure can be at least about 5 mmHg, at least about 10 mmHg, at least about 20 mmHg, at least about 30 mmHg, at least about 40 mmHg, at least about 50 mmHg, at least about 60 mmHg, at least about 70 mmHg, at least about 80 mmHg, at least about 90 mmHg, at least about 100 mmHg, at least about 125 mmHg, at least about 150 mmHg, at least about 175 mmHg, at least about 200 mmHg, at least about 225 mmHg, at least about 250 mmHg, at least about 275 mmHg, at least about 300 mmHg, at least about 325 mmHg, at least about 350 mmHg, at least about 375 mmHg, at least about 400 mmHg, at least about 425 mmHg, at least about 450 mmHg, at least about 475 mmHg, at least about 500 mmHg, at least about 525 mmHg, at least about 550 mmHg, at least about 575 mmHg, at least about 600 mmHg, at least about 625 mmHg, at least about 650 mmHg, at least about 675 mmHg, at least about 700 mmHg, at least about 725 mmHg, at least about 750 mmHg, at least about 760 mmHg, at least about 775 mmHg, at least about 800 mmHg, at least about 825 mmHg, at least about 850 mmHg, at least about 875 mmHg, at least about 900 mmHg, at least about 925 mmHg, at least about 950 mmHg, or at least about 975 mmHg. In some embodiments, the reduction in pressure can be no more than about 1,000 mmHg, no more than about 975 mmHg, no more than about 950 mmHg, no more than about 925 mmHg, no more than about 900 mmHg, no more than about 875 mmHg, no more than about 850 mmHg, no more than about 825 mmHg, no more than about 800 mmHg, no more than about 775 mmHg, no more than about 760 mmHg, no more than about 750 mmHg, no more than about 725 mmHg, no more than about 700 mmHg, no more than about 675 mmHg, no more than about 650 mmHg, no more than about 625 mmHg, no more than about 600 mmHg, no more than about 575 mmHg, no more than about 550 mmHg, no more than about 525 mmHg, no more than about 500 mmHg, no more than about 475 mmHg, no more than about 450 mmHg, no more than about 425 mmHg, no more than about 400 mmHg, no more than about 375 mmHg, no more than about 350 mmHg, no more than about 325 mmHg, no more than about 300 mmHg, no more than about 275 mmHg, no more than about 250 mmHg, no more than about 225 mmHg, no more than about 200 mmHg, no more than about 175 mmHg, no more than about 150 mmHg, no more than about 125 mmHg, no more than about 100 mmHg, no more than about 90 mmHg, no more than about 80 mmHg, no more than about 70 mmHg, no more than about 60 mmHg, no more than about 50 mmHg, no more than about 40 mmHg, no more than about 30 mmHg, no more than about 20 mmHg, or no more than about 10 mmHg.

Combinations of the above-referenced values of the reduction in pressure are also possible (e.g., at least about 5 mmHg and no more than about 1,000 mmHg or at least about 50 mmHg and no more than about 500 mmHg), inclusive of all values and ranges therebetween. In some embodiments, the reduction in pressure can be about 5 mmHg, about 10 mmHg, about 20 mmHg, about 30 mmHg, about 40 mmHg, about 50 mmHg, about 60 mmHg, about 70 mmHg, about 80 mmHg, about 90 mmHg, about 100 mmHg, about 125 mmHg, about 150 mmHg, about 175 mmHg, about 200 mmHg, about 225 mmHg, about 250 mmHg, about 275 mmHg, about 300 mmHg, about 325 mmHg, about 350 mmHg, about 375 mmHg, about 400 mmHg, about 425 mmHg, about 450 mmHg, about 475 mmHg, about 500 mmHg, about 525 mmHg, about 550 mmHg, about 575 mmHg, about 600 mmHg, about 625 mmHg, about 650 mmHg, about 675 mmHg, about 700 mmHg, about 725 mmHg, about 750 mmHg, about 760 mmHg, about 775 mmHg, about 800 mmHg, about 825 mmHg, about 850 mmHg, about 875 mmHg, about 900 mmHg, about 925 mmHg, about 950 mmHg, or about 975 mmHg, or about 1,000 mmHg.

In some embodiments, the reference location can be identified based on a gauge pressure value in the hollow conduit and the medicament container (i.e., the difference between the pressure in the hollow conduit and medicament container and atmospheric pressure). In some embodiments, the reference location can be identified upon the gauge pressure reaching a threshold pressure value. In some embodiments, the threshold pressure value can be at least about 5 mmHg gauge, at least about 10 mmHg gauge, at least about 20 mmHg gauge, at least about 30 mmHg gauge, at least about 40 mmHg gauge, at least about 50 mmHg gauge, at least about 60 mmHg gauge, at least about 70 mmHg gauge, at least about 80 mmHg gauge, at least about 90 mmHg gauge, at least about 100 mmHg gauge, at least about 125 mmHg gauge, at least about 150 mmHg gauge, at least about 175 mmHg gauge, at least about 200 mmHg gauge, at least about 225 mmHg gauge, at least about 250 mmHg gauge, at least about 275 mmHg gauge, at least about 300 mmHg gauge, at least about 325 mmHg gauge, at least about 350 mmHg gauge, at least about 375 mmHg gauge, at least about 400 mmHg gauge, at least about 425 mmHg gauge, at least about 450 mmHg gauge, at least about 475 mmHg gauge, at least about 500 mmHg gauge, at least about 525 mmHg gauge, at least about 550 mmHg gauge, at least about 575 mmHg gauge, at least about 600 mmHg gauge, at least about 625 mmHg gauge, at least about 650 mmHg gauge, at least about 675 mmHg gauge, at least about 700 mmHg gauge, at least about 725 mmHg gauge, at least about 750 mmHg gauge, at least about 775 mmHg gauge, at least about 800 mmHg gauge, at least about 825 mmHg gauge, at least about 850 mmHg gauge, or at least about 875 mmHg gauge. In some embodiments, the threshold pressure value can be no more than about 900 mmHg gauge, no more than about 875 mmHg gauge, no more than about 850 mmHg gauge, no more than about 825 mmHg gauge, no more than about 800 mmHg gauge, no more than about 775 mmHg gauge, no more than about 760 mmHg gauge, no more than about 750 mmHg gauge, no more than about 725 mmHg gauge, no more than about 700 mmHg gauge, no more than about 675 mmHg gauge, no more than about 650 mmHg gauge, no more than about 625 mmHg gauge, no more than about 600 mmHg gauge, no more than about 575 mmHg gauge, no more than about 550 mmHg gauge, no more than about 525 mmHg gauge, no more than about 500 mmHg gauge, no more than about 475 mmHg gauge, no more than about 450 mmHg gauge, no more than about 425 mmHg gauge, no more than about 400 mmHg gauge, no more than about 375 mmHg gauge, no more than about 350 mmHg gauge, no more than about 325 mmHg gauge, no more than about 300 mmHg gauge, no more than about 275 mmHg gauge, no more than about 250 mmHg gauge, no more than about 225 mmHg gauge, no more than about 200 mmHg gauge, no more than about 175 mmHg gauge, no more than about 150 mmHg gauge, no more than about 125 mmHg gauge, no more than about 100 mmHg gauge, no more than about 90 mmHg gauge, no more than about 80 mmHg gauge, no more than about 70 mmHg gauge, no more than about 60 mmHg gauge, no more than about 50 mmHg gauge, no more than about 40 mmHg gauge, no more than about 30 mmHg gauge, no more than about 20 mmHg gauge, or no more than about 10 mmHg gauge.

Combinations of the above-referenced threshold pressure values are also possible (e.g., at least about 5 mmHg gauge and no more than about 900 mmHg gauge or at least about 50 mmHg gauge and no more than about 100 mmHg gauge), inclusive of all values and ranges therebetween. In some embodiments, the reference location can be identified based on a gauge pressure value in the hollow conduit and the medicament container (i.e., the difference between the pressure in the hollow conduit and medicament container and atmospheric pressure). In some embodiments, the reference location can be identified upon the gauge pressure reaching a threshold pressure value. In some embodiments, the threshold pressure value can be about 5 mmHg gauge, about 10 mmHg gauge, about 20 mmHg gauge, about 30 mmHg gauge, about 40 mmHg gauge, about 50 mmHg gauge, about 60 mmHg gauge, about 70 mmHg gauge, about 80 mmHg gauge, about 90 mmHg gauge, about 100 mmHg gauge, about 125 mmHg gauge, about 150 mmHg gauge, about 175 mmHg gauge, about 200 mmHg gauge, about 225 mmHg gauge, about 250 mmHg gauge, about 275 mmHg gauge, about 300 mmHg gauge, about 325 mmHg gauge, about 350 mmHg gauge, about 375 mmHg gauge, about 400 mmHg gauge, about 425 mmHg gauge, about 450 mmHg gauge, about 475 mmHg gauge, about 500 mmHg gauge, about 525 mmHg gauge, about 550 mmHg gauge, about 575 mmHg gauge, about 600 mmHg gauge, about 625 mmHg gauge, about 650 mmHg gauge, about 675 mmHg gauge, about 700 mmHg gauge, about 725 mmHg gauge, about 750 mmHg gauge, about 775 mmHg gauge, about 800 mmHg gauge, about 825 mmHg gauge, about 850 mmHg gauge, or about 875 mmHg gauge, or about 900 mmHg gauge.

The method 1600 includes further inserting the distal end portion of the hollow conduit a second distance into an injection region of the eye at step 1604. In some embodiments, the second distance can be sufficient for the distal tip of the hollow conduit to reach the injection region. In some embodiments, the second distance can be sufficient for the distal tip of the hollow conduit to reach a region between the SCS and a boundary layer between a retinal layer and vitreous space. In some embodiments, the second distance can be at least about 50 μm, at least about 75 μm, at least about 100 μm, at least about 125 μm, at least about 150 μm, at least about 175 μm, at least about 200 μm, at least about 225 μm, at least about 250 μm, at least about 275 μm, at least about 300 μm, at least about 350 μm, at least about 400 μm, at least about 450 μm, at least about 500 μm, at least about 550 μm, at least about 600 μm, at least about 650 μm, at least about 700 μm, at least about 750 μm, at least about 800 μm, at least about 850 μm, at least about 900 μm, at least about 950 μm, at least about 1 mm, at least about 1.1 mm, at least about 1.2 mm, at least about 1.3 mm, at least about 1.4 mm, at least about 1.5 mm, at least about 1.6 mm, at least about 1.7 mm, at least about 1.8 mm, or at least about 1.9 mm. In some embodiments, the second distance can be no more than about 2 mm, no more than about 1.9 mm, no more than about 1.8 mm, no more than about 1.7 mm, no more than about 1.6 mm, no more than about 1.5 mm, no more than about 1.4 mm, no more than about 1.3 mm, no more than about 1.2 mm, no more than about 1.1 mm, no more than about 1 mm, no more than about 950 μm, no more than about 900 μm, no more than about 850 μm, no more than about 800 μm, no more than about 750 μm, no more than about 700 μm, no more than about 650 μm, no more than about 600 μm, no more than about 550 μm, no more than about 500 μm, no more than about 450 μm, no more than about 400 μm, no more than about 350 μm, no more than about 300 μm, no more than about 275 μm, no more than about 250 μm, no more than about 225 μm, no more than about 200 μm, no more than about 175 μm, no more than about 150 μm, no more than about 125 μm, no more than about 100 μm, or no more than about 75 μm. Combinations of the above-referenced values for the second distance are also possible (e.g., at least about 50 μm and no more than about 2 mm or at least about 100 μm and no more than about 150 μm), inclusive of all values and ranges therebetween. In some embodiments, the second distance can be about 50 μm, about 75 μm, about 100 μm, about 125 μm, about 150 μm, about 175 μm, about 200 μm, about 225 μm, about 250 μm, about 275 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm.

The method 1600 further includes injecting at least a portion of the medicament into the injection region at step 1605. In some embodiments, the injection region can be in the retina. In some embodiments, the injection region can be within a region between the SCS and the boundary layer between the retinal layer and vitreous space. In some embodiments, the injection region can be between the choroid and the boundary layer between the retinal tissue and the vitreous body. In some embodiments, the injection region can be between the RPE and the boundary layer between the retinal tissue and the vitreous body. In some embodiments, the injection region can be between the rods and cones of the retina and the boundary layer between the retinal tissue and the vitreous body. In some embodiments, the injection region can be between the bipolar cells of the retina and the boundary layer between the retinal tissue and the vitreous body. In some embodiments, the injection region can be between the ganglion cells of the retina and the boundary layer between the retinal tissue and the vitreous body. In some embodiments, the injection region can be between the SCS and the ganglion cells. In some embodiments, the injection region can be between the choroid and the ganglion cells. In some embodiments, the injection region can be between the RPE and the ganglion cells. In some embodiments, the injection region can be between the rods and cones of the retina and the ganglion cells. In some embodiments, the injection region can be between the bipolar cells of the retina and the ganglion cells. In some embodiments, the injection region can be between the SCS and the bipolar cells of the retina. In some embodiments, the injection region can be between the choroid and the bipolar cells of the retina. In some embodiments, the injection region can be between the rods and cones of the retina and the bipolar cells of the retina. In some embodiments, the injection region can be between the SCS and the rods and cones of the retina. In some embodiments, the injection region can be between the choroid and the rods and cones of the retina. In some embodiments, the injection region can be between the RPE and the rods and cones of the retina. In some embodiments, the injection region can be between the RPE and the rod and cone outer segments of the retina. In some embodiments, the injection region can be between the RPE and the rod and cone nuclei of the retina. In some embodiments, the injection region can be between the SCS and the RPE. In some embodiments, the injection region can include the choroid and the retina (i.e., the injection region can straddle the RPE).

In some embodiments, all or substantially all of the medicament can be injected. In some embodiments, a portion of the medicament can be injected. In some embodiments, the portion of the medicament injected can be at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, the portion of the medicament injected can be no more than about 99%, no more than about 95%, no more than about 90%, no more than about 85%, no more than about 80%, no more than about 75%, no more than about 70%, no more than about 65%, no more than about 60%, no more than about 55%, no more than about 50%, no more than about 45%, no more than about 40%, no more than about 35%, no more than about 30%, no more than about 25%, no more than about 20%, no more than about 15%, or no more than about 10%.

Combinations of the above referenced portions of the medicament injected are also possible (e.g., at least about 1% and no more than about 99% or at least about 50% and no more than about 75%), inclusive of all values and ranges therebetween. In some embodiments, the portion of the medicament injected can be about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%.

In some embodiments, a volume of the medicament can be injected. In some embodiments, the volume can be at least about 10 μL, at least about 20 μL, at least about 30 μL, at least about 40 μL, at least about 50 μL, at least about 60 μL, at least about 70 μL, at least about 80 μL, at least about 90 μL, at least about 100 μL, at least about 200 μL, at least about 300 μL, at least about 400 μL, at least about 500 μL, at least about 600 μL, at least about 700 μL, at least about 800 μL, at least about 900 μL, at least about 1 mL, at least about 2 mL, at least about 3 mL, or at least about 4 mL. In some embodiments, the volume can be no more than about 5 mL, no more than about 4 mL, no more than about 3 mL, no more than about 2 mL, no more than about 1 mL, no more than about 900 μL, no more than about 800 μL, no more than about 700 μL, no more than about 600 μL, no more than about 500 μL, no more than about 400 μL, no more than about 300 μL, no more than about 200 μL, no more than about 100 μL, no more than about 90 μL, no more than about 80 μL, no more than about 70 μL, no more than about 60 μL, no more than about 50 μL, no more than about 40 μL, no more than about 30 μL, or no more than about 20 μL. Combinations of the above-referenced volumes are also possible (e.g., at least about 10 μL and no more than about 5 mL or at least about 50 μL and no more than about 100 μL), inclusive of all values and ranges therebetween. In some embodiments, the volume can be about 10 μL, about 20 μL, about 30 μL, about 40 μL, about 50 μL, about 60 μL, about 70 μL, about 80 μL, about 90 μL, about 100 μL, about 200 μL, about 300 μL, about 400 μL, about 500 μL, about 600 μL, about 700 μL, about 800 μL, about 900 μL, about 1 mL, about 2 mL, about 3 mL, about 4 mL, or about 5 mL.

In some embodiments, the method 1600 can further include removing the hollow conduit from the eye at step 1606. In some embodiments, the removal can be manual. In some embodiments, the removal can be automatic. In some embodiments, the removal can be actuated (e.g., via a piezo motor).

Figure 21:
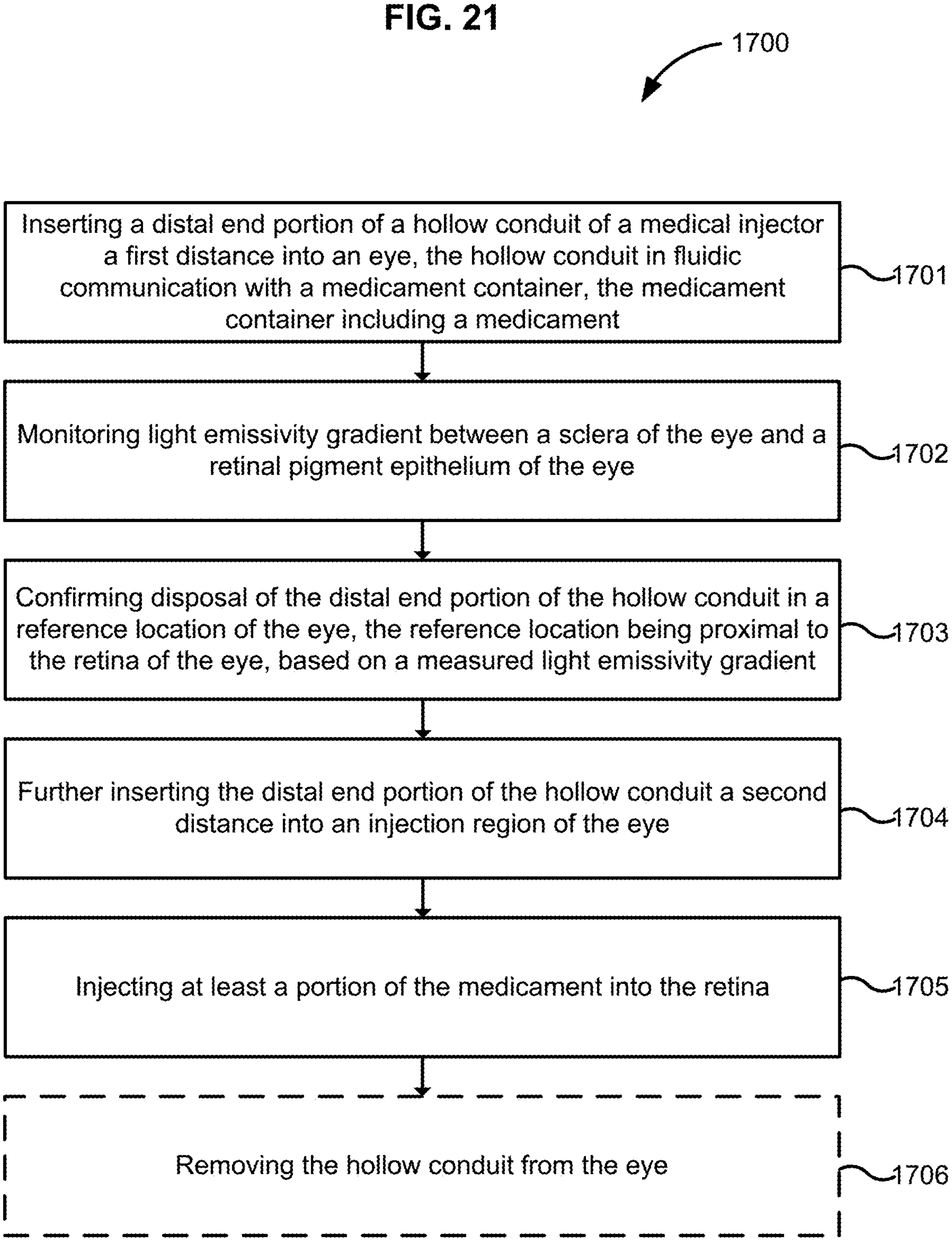
FIG. 21 shows a flow diagram of a method for performing an injection into the retinal tissue, according to an embodiment.

The aforementioned methods include performing an injection into retinal tissue using pressure measurements. FIG. 21 shows a flow diagram of a method 1700 for performing an injection into the retinal tissue using light emissivity measurements, according to an embodiment. The method includes inserting a distal end portion of a hollow conduit of a medical injector a first distance into an eye at step 1701. The method 1700 further includes monitoring a light emissivity gradient between the sclera and the RPE at step 1702, confirming disposal of the distal end portion of the hollow conduit in a reference location of the eye, based on a measured light emissivity gradient at step 1703, further inserting the distal tip of the needle a second distance into the eye at step 1704, injecting at least a portion of the medicament into the retina at step 1705, and removing the hollow conduit from the eye at step 1706. In some embodiments, step 1701, step 1704, step 1705, and step 1706 can be the same or substantially similar to step 1601, step 1604, step 1605, and step 1606, respectively, as described above with reference to FIG. 20. Thus, certain elements of step 1701, step 1704, step 1705, and step 1706 are not described in greater detail herein.

In some embodiments, step 1702 can include a constant measurement of emissivity at the distal end of the hollow conduit. In some embodiments, step 1702 can include a periodic measurement of emissivity at the distal end of the hollow conduit. In some embodiments, the measurement of emissivity at the distal end of the hollow conduit can be implemented throughout the execution of the method 1700. In some embodiments, the measurement can begin as soon as the distal end of the hollow conduit enters the sclera. In some embodiments, the measurement can begin before the distal end of the hollow conduit enters the sclera. In some embodiments, the measurement can begin before the distal end of the hollow conduit enters the SCS. In some embodiments, the measurement can begin as soon as the distal end of the hollow conduit enters the SCS. In some embodiments, the measurement can begin before the distal end of the hollow conduit enters the choroid. In some embodiments, the measurement can begin as soon as the distal end of the hollow conduit enters the choroid. In some embodiments, the measurement can begin before the distal end of the hollow conduit enters the RPE. In some embodiments, the measurement can begin as soon as the distal end of the hollow conduit enters the RPE.

In some embodiments, the reference location identified in step 1703 can be in the RPE. In some embodiments, locating the RPE can be reliably done via light emissivity measurements. In some embodiments, locating the RPE can be reliably done via OCT probe imaging. In some embodiments, the reference location can be an interface between a choroid tissue and a retinal pigment epithelium. In some embodiments, the reference location can be in the SCS. In some embodiments, identifying the reference location at step 1703 can be based on a light emissivity gradient between a sclera of the eye and a retinal pigment epithelium of the eye.

In some embodiments, the reference location can be identified based on a single light emissivity value, such as the fraction of light emitted through the pupil (or light emitted from the medical injector) that reaches the distal end of the hollow conduit. In some embodiments, the emissivity value can be at least about 0.05, at least about 0.1, at least about 0.15, at least about 0.2, at least about 0.25, at least about 0.3, at least about 0.35, at least about 0.4, at least about 0.45, at least about 0.5, at least about 0.55, at least about 0.60, at least about 0.65, at least about 0.7, at least about 0.75, at least about 0.80, at least about 0.85, at least about 0.90, or at least about 0.95. In some embodiments, the emissivity value can be no more than about 0.99, no more than about 0.95, no more than about 0.9, no more than about 0.85, no more than about 0.8, no more than about 0.75, no more than about 0.7, no more than about 0.65, no more than about 0.6, no more than about 0.55, no more than about 0.5, no more than about 0.45, no more than about 0.4, no more than about 0.35, no more than about 0.3, no more than about 0.25, no more than about 0.2, no more than about 0.15, or no more than about 0.1. Combinations of the above referenced emissivity values are also possible (e.g., at least about 0.05 and no more than about 0.99 or at least about 0.5 and no more than about 0.75), inclusive of all values and ranges therebetween. In some embodiments, the emissivity value can be about 0.05, about 0.1, about 0.15, about 0.2, about 0.25, about 0.3, about 0.35, about 0.4, about 0.45, about 0.5, about 0.55, about 0.60, about 0.65, about 0.7, about 0.75, about 0.80, about 0.85, about 0.90, about 0.95, or about 0.99.

In some embodiments, the reference location can be identified by a sudden change in emissivity while inserting the distal end of the hollow conduit into the eye. In some embodiments, the change in emissivity can be a change value per μm of insertion depth into the eye. In some embodiments, the change in emissivity indicating reaching the reference location can be at least about 0.00014 μm, at least about 0.00054 μm, at least about 0.0014 μm, at least about 0.0054 μm, at least about 0.014 μm, at least about 0.024 μm, at least about 0.034 μm, at least about 0.044 μm, at least about 0.054 μm, at least about 0.064 μm, at least about 0.074 μm, at least about 0.084 μm, or at least about 0.094 μm. In some embodiments, the change in emissivity indicating reaching the reference location can be no more than about 0.14 μm, no more than about 0.094 μm, no more than about 0.084 μm, no more than about 0.074 μm, no more than about 0.064 μm, no more than about 0.054 μm, no more than about 0.044 μm, no more than about 0.034 μm, no more than about 0.024 μm, no more than about 0.014 μm, no more than about 0.0054 μm, no more than about 0.0014 μm, or no more than about 0.00054 μm. Combinations of the above-referenced changes in emissivity values are also possible (e.g., at least about 0.00014 μm and no more than about 0.14 μm or at least about 0.024 μm and no more than about 0.054 μm), inclusive of all values and ranges therebetween. In some embodiments, the change in emissivity indicating reaching the reference location can be about 0.00014 μm, about 0.00054 μm, about 0.0014 μm, about 0.0054 μm, about 0.014 μm, about 0.024 μm, about 0.03/μm, about 0.04/μm, about 0.05/μm, about 0.06/μm, about 0.07/μm, about 0.08/μm, about 0.09/μm, or about 0.1/μm.

Figure 22:
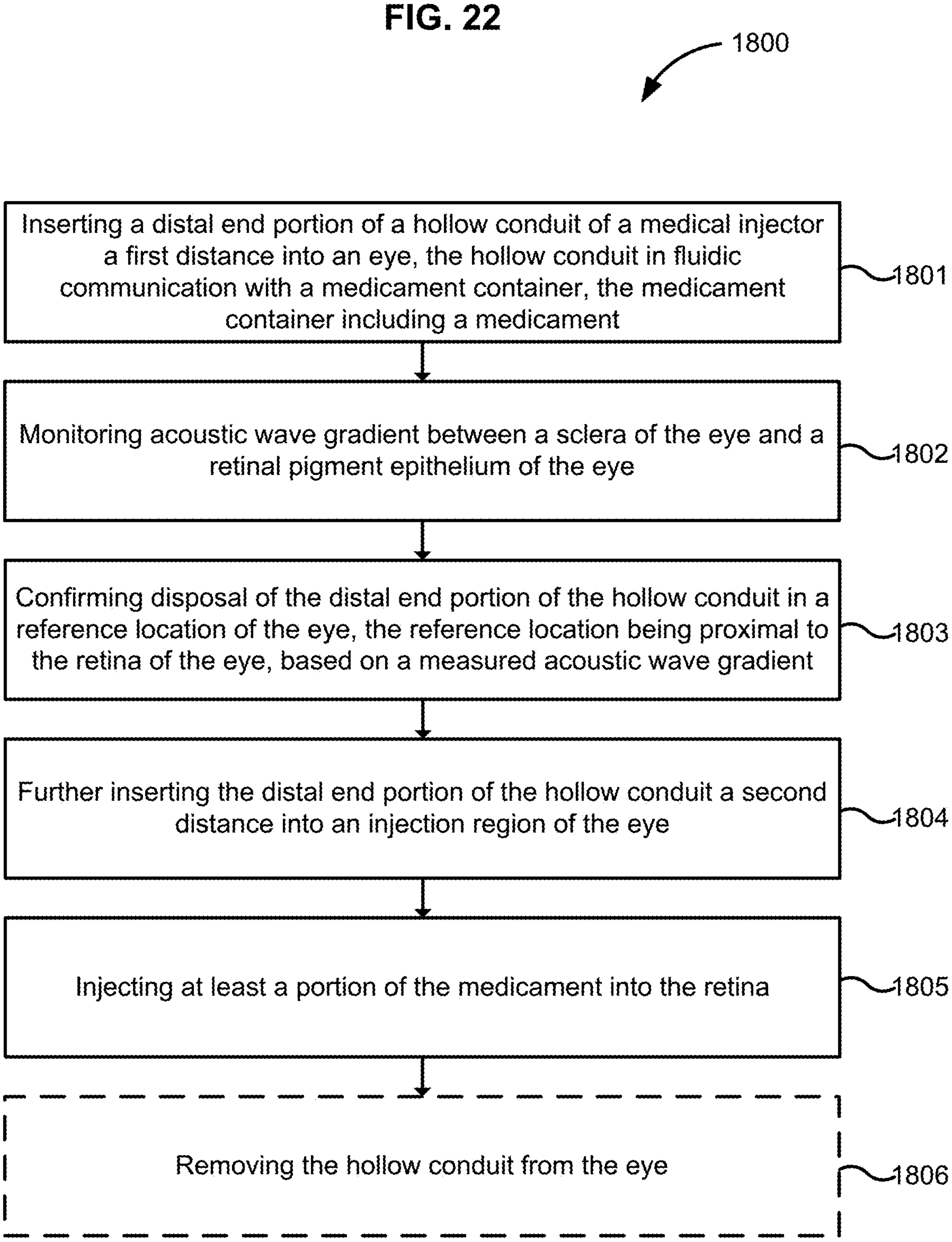
FIG. 22 shows a flow diagram of a method for performing an injection into the retinal tissue, according to an embodiment.

FIG. 22 shows a flow diagram of a method 1800 for performing an injection into the retinal tissue, according to an embodiment. The method includes inserting a distal end portion of a hollow conduit of a medical injector a first distance into an eye at step 1801. The method 1800 further includes monitoring an acoustic wave gradient between the sclera and the RPE at step 1802, confirming disposal of the distal end portion of the hollow conduit in a reference location of the eye, based on a measured acoustic wave gradient at step 1803, further inserting the distal tip of the needle a second distance into the eye at step 1804, injecting at least a portion of the medicament into the retina at step 1805, and removing the hollow conduit from the eye at step 1806. In some embodiments, step 1801, step 1804, step 1805, and step 1806 can be the same or substantially similar to step 1601, step 1604, step 1605, and step 1606, respectively, as described above with reference to FIG. 20. Thus, certain elements of step 1801, step 1804, step 1805, and step 1806 are not described in greater detail herein.

In some embodiments, step 1802 can include a constant measurement of emissivity at the distal end of the hollow conduit. In some embodiments, step 1802 can include generating tomography images with an OCT probe disposed within the hollow conduit. In some embodiments, step 1802 can include a periodic acoustic wave measurement at the distal end of the hollow conduit. In some embodiments, the acoustic wave measurement at the distal end of the hollow conduit can be implemented throughout the execution of the method 1800. In some embodiments, the measurement can begin as soon as the distal end of the hollow conduit enters the sclera. In some embodiments, the measurement can begin before the distal end of the hollow conduit enters the sclera. In some embodiments, the measurement can begin before the distal end of the hollow conduit enters the SCS. In some embodiments, the measurement can begin as soon as the distal end of the hollow conduit enters the SCS. In some embodiments, the measurement can begin before the distal end of the hollow conduit enters the choroid. In some embodiments, the measurement can begin as soon as the distal end of the hollow conduit enters the choroid. In some embodiments, the measurement can begin before the distal end of the hollow conduit enters the RPE. In some embodiments, the measurement can begin as soon as the distal end of the hollow conduit enters the RPE.

In some embodiments, the reference location identified in step 1803 can be in the RPE. In some embodiments, locating the RPE can be reliably done via acoustic wave measurements. In some embodiments, the reference location can be an interface between a choroid tissue and a retinal pigment epithelium. In some embodiments, the reference location can be in the SCS. In some embodiments, identifying the reference location at step 1803 can be based on an acoustic wave gradient between a sclera of the eye and a retinal pigment epithelium of the eye.

In some embodiments, the reference location can be identified based on a single threshold acoustic wave measurement. In some embodiments, the reference location can be identified by a sudden acoustic wave change while inserting the distal end of the hollow conduit into the eye. In some embodiments, the acoustic wave change can be a change value per μm of insertion depth into the eye.

Figure 23:
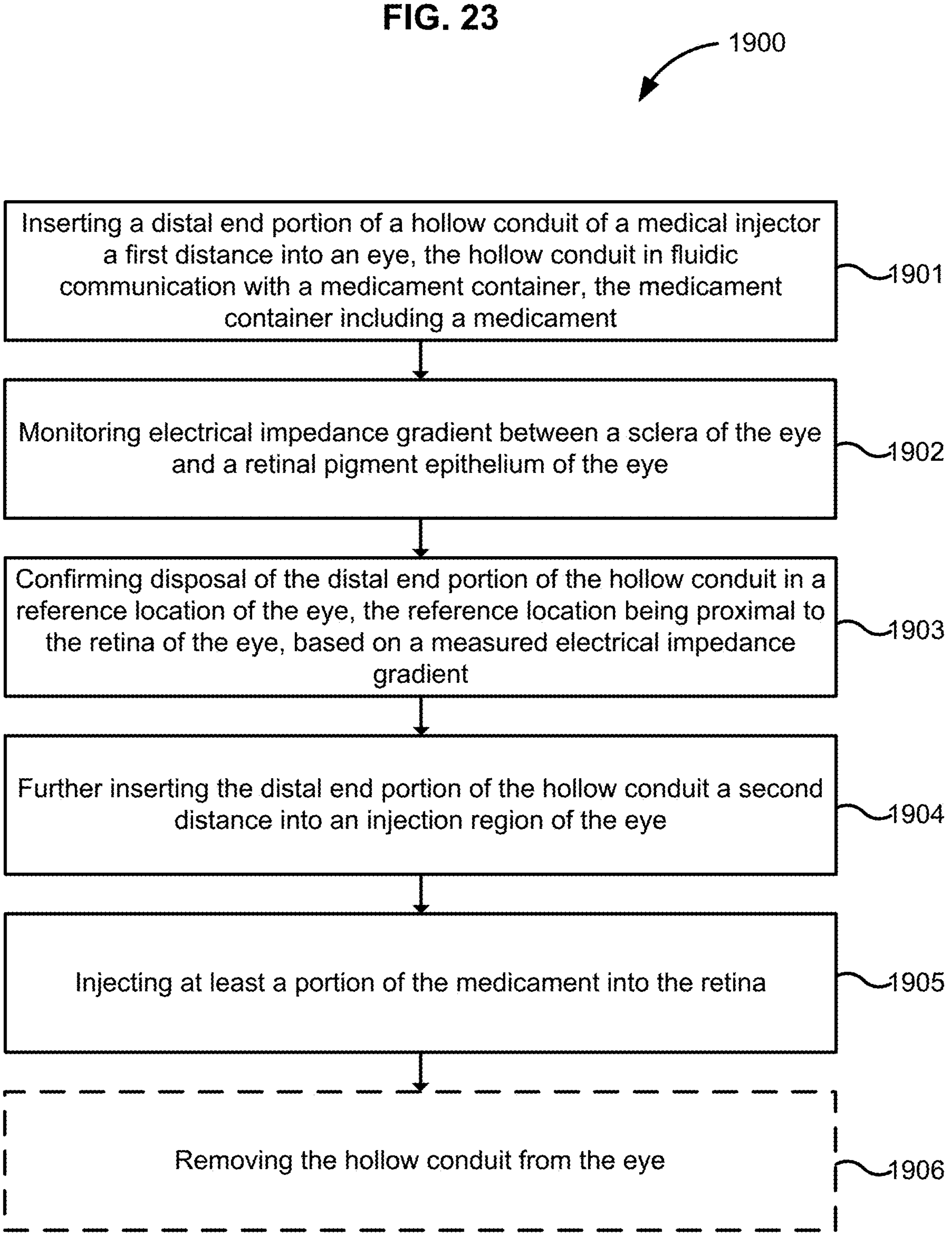
FIG. 23 shows a flow diagram of a method for performing an injection into the retinal tissue, according to an embodiment.

FIG. 23 shows a flow diagram of a method 1900 for performing an injection into the retinal tissue, according to an embodiment. The method includes inserting a distal end portion of a hollow conduit of a medical injector a first distance into an eye at step 1901. The method 1900 further includes monitoring an electrical impedance gradient between the sclera and the RPE at step 1902, confirming disposal of the distal end portion of the hollow conduit in a reference location of the eye, based on a measured electrical impedance gradient at step 1903, further inserting the distal tip of the needle a second distance into the eye at step 1904, injecting at least a portion of the medicament into the retina at step 1905, and removing the hollow conduit from the eye at step 1906. In some embodiments, step 1901, step 1904, step 1905, and step 1906 can be the same or substantially similar to step 1601, step 1604, step 1605, and step 1606, respectively, as described above with reference to FIG. 20. Thus, certain elements of step 1901, step 1904, step 1905, and step 1906 are not described in greater detail herein.

In some embodiments, step 1902 can include a constant measurement of electrical impedance at the distal end of the hollow conduit. In some embodiments, step 1902 can include a periodic electrical impedance measurement at the distal end of the hollow conduit. In some embodiments, the electrical impedance measurement at the distal end of the hollow conduit can be implemented throughout the execution of the method 1900. In some embodiments, the measurement can begin as soon as the distal end of the hollow conduit enters the sclera. In some embodiments, the measurement can begin before the distal end of the hollow conduit enters the sclera. In some embodiments, the measurement can begin before the distal end of the hollow conduit enters the SCS. In some embodiments, the measurement can begin as soon as the distal end of the hollow conduit enters the SCS. In some embodiments, the measurement can begin before the distal end of the hollow conduit enters the choroid. In some embodiments, the measurement can begin as soon as the distal end of the hollow conduit enters the choroid. In some embodiments, the measurement can begin before the distal end of the hollow conduit enters the RPE. In some embodiments, the measurement can begin as soon as the distal end of the hollow conduit enters the RPE.

In some embodiments, the reference location identified in step 1903 can be in the RPE. In some embodiments, locating the RPE can be reliably done via electrical impedance measurements. In some embodiments, the reference location can be an interface between a choroid tissue and a retinal pigment epithelium. In some embodiments, the reference location can be in the SCS. In some embodiments, identifying the reference location at step 1903 can be based on an electrical impedance gradient between a sclera of the eye and a retinal pigment epithelium of the eye.

Figure 24:
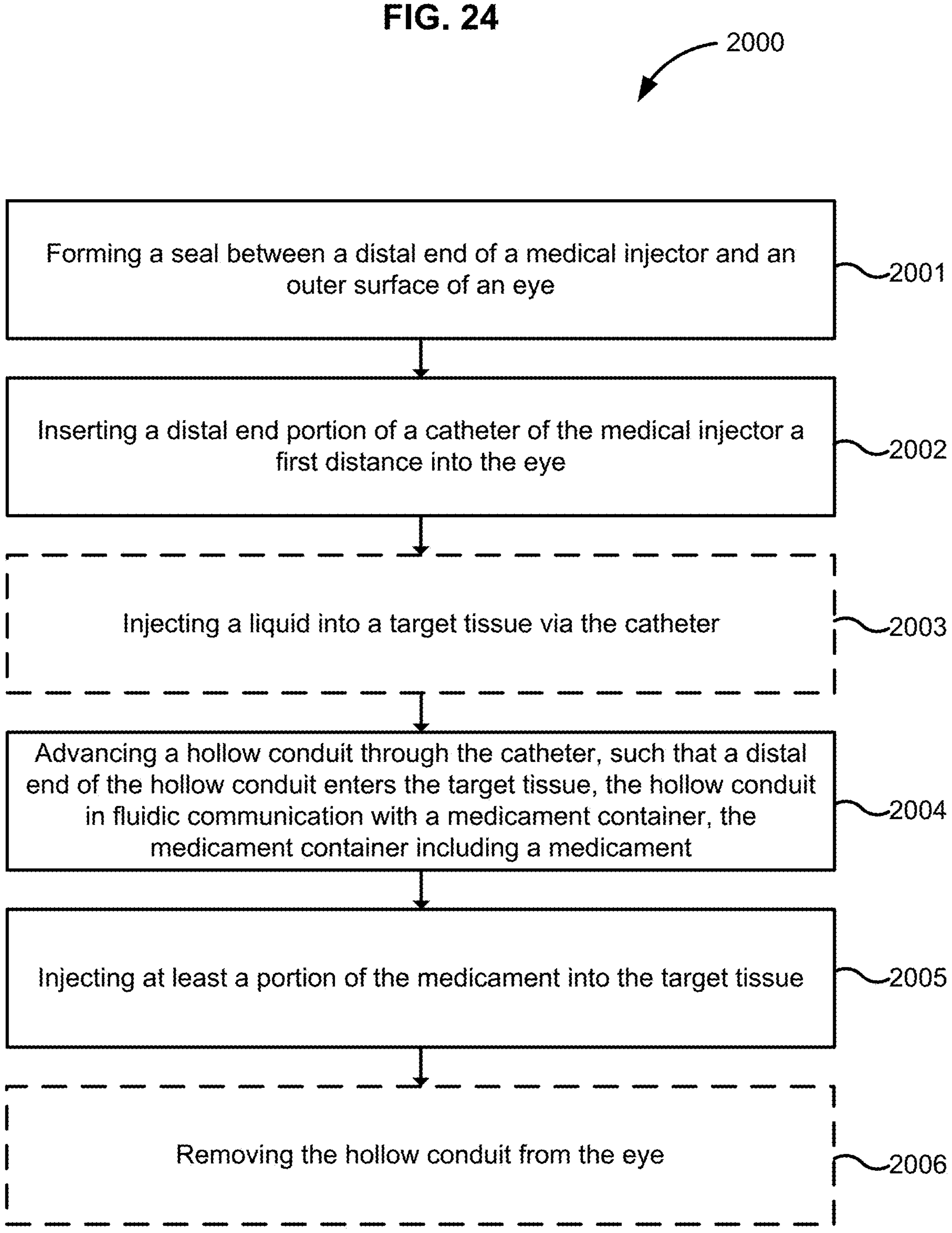
FIG. 24 shows a flow diagram of a method for performing an injection into a target region of the eye, according to an embodiment.

FIG. 24 shows a flow diagram of a method 2000 for performing an injection into the retinal tissue, according to an embodiment. As shown, the method 2000 includes forming a seal between a distal end of a medicament container and an outer surface of an eye at step 2001 and inserting a distal end portion of a catheter of the medical injector a first distance into the eye at step 2002. The method 2000 then optionally includes injecting a liquid into a target tissue via the catheter at step 2003. The method 2000 further includes advancing a hollow conduit through the catheter, such that a distal end of the hollow conduit enters the target tissue, the hollow conduit in fluidic communication with a medicament container, the medicament container including a medicament at step 2004 and injecting at least a portion of the medicament into the target tissue at step 2005. The method 2000 optionally includes removing the hollow conduit from the eye in step 2006.

In some embodiments, step 2001 can include scoring the sclera of the eye. In some embodiments, forming the seal between the distal end of the medical injector and the outer surface of the eye can include advancing a medicament container such that a distal end of the medicament container contacts the sclera. In some embodiments, the catheter inserted in step 2002 can be in fluidic communication with a fluid container. In some embodiments, the fluid container can include a liquid. Step 2003 optionally includes injecting the liquid into a target tissue via the catheter. In some embodiments, the liquid can include a saline solution a carboxymethyl cellulose (CMC) solution, and/or a hyaluronic acid (HA) solution. In some embodiments, injection of the liquid into the target tissue can occur simultaneously to advancement of a medicament container. In some embodiments, advancement of the medicament container can also cause the liquid to be injected into the target tissue. In some embodiments, advancement of the medicament container can be manual. In some embodiments, the medicament container can advance automatically (e.g., via a loss-of-resistance mechanism).

Step 2004 includes advancing a hollow conduit through the catheter. In some embodiments, the hollow conduit can include a needle. The hollow conduit is in fluidic communication with a medicament container and the medicament container includes a medicament. In some embodiments, the hollow conduit can include a microneedle. Step 2005 includes injecting at least a portion of the medicament into the target tissue. In some embodiments, step 2005 can include manual injection of the medicament into the target tissue. In some embodiments, step 2005 can include automatic injection of the medicament into the target tissue (i.e., via a loss-of-resistance mechanism). Step 2006 includes optionally removing the hollow conduit from the eye.

Figure 25:
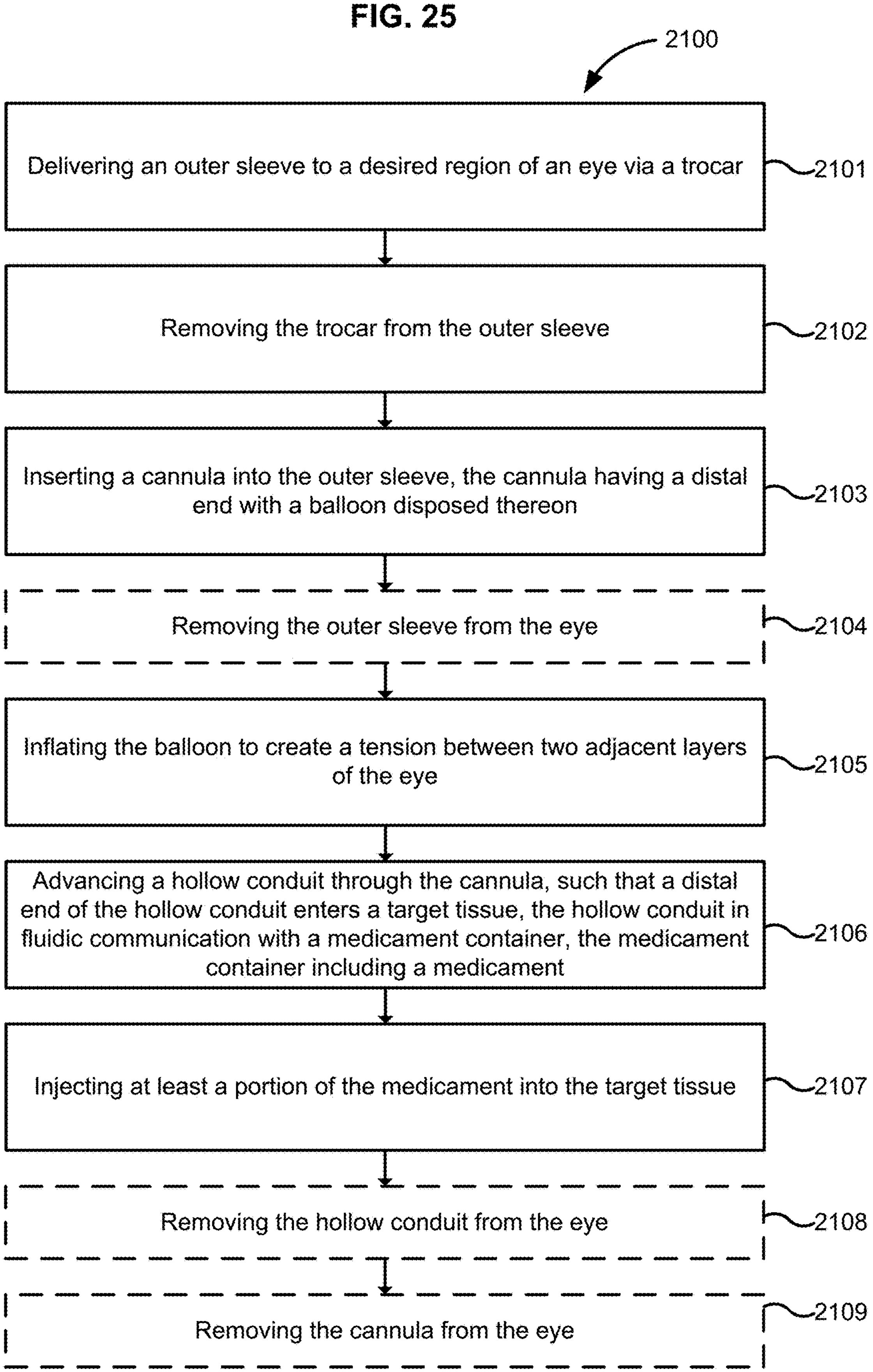
FIG. 25 shows a flow diagram of a method for performing an injection into a target region of the eye, according to an embodiment.

FIG. 25 shows a flow diagram of a method 2100 for performing an injection into the target tissue, according to an embodiment. As shown, the method 2100 includes delivering an outer sleeve to a desired region of an eye via a trocar at step 2101. The method 2100 includes removing the trocar from the outer sleeve at step 2102, inserting a cannula into the outer sleeve at step 2103. The cannula has a distal end with a balloon disposed thereon. The method 2100 optionally includes removing the outer sleeve from the eye at step 2104. The method 2100 includes inflating the balloon to create a tension between two adjacent layers of the eye at step 2105. The method 2100 includes advancing a hollow conduit through the cannula at step 2106, such that a distal end of the hollow conduit enters a target tissue, the hollow conduit in fluidic communication with a medicament container. The medicament container includes a medicament. The method 2100 includes injecting at least a portion of the medicament into the target tissue at step 2107, optionally removing the hollow conduit from the eye at step 2108, and optionally removing the cannula from the eye at step 2109.

Step 2101 includes delivering an outer sleeve to an eye via a trocar. In some embodiments, the trocar can have a sharp distal surface that can penetrate the sclera of the eye. The trocar can be positioned in a lumen of the outer sleeve. In other words, the outer sleeve can be situated around the outside of the trocar. By inserting the trocar into the eye, the outer sleeve is also inserted into the eye. In some embodiments, the outer sleeve can have a sharp distal surface that can penetrate the sclera of the eye. In some embodiments, the outer sleeve can include a stop to stop the outer sleeve from advancing any further once the distal end of the outer sleeves reaches a desired depth inside the eye.

Step 2102 includes removing the trocar from the outer sleeve. Upon the removal of the trocar, the outer sleeve remains disposed in the eye. In some embodiments, removal of the trocar from the outer sleeve can include pulling the trocar manually from the eye. In some embodiments, removal of the trocar from the outer sleeve can be automated.

Step 2103 includes inserting a cannula into the outer sleeve. The cannula can be inserted into the lumen of the outer sleeve. The distal end of the cannula has a balloon disposed thereon. In some embodiments, the cannula can be inserted into the outer sleeve such that balloon is between the sclera and the retina. In some embodiments, the cannula can be inserted into the outer sleeve such that balloon is between the sclera and the choroid. In some embodiments, the cannula can be inserted into the outer sleeve such that balloon is between the choroid and the retina. In some embodiments, the cannula can include a conduit therein, the conduit fluidically coupled to the balloon. The conduit can allow for flow of fluid (e.g., gas, liquid) to inflate the balloon.

Step 2104 is optional and includes removing the outer sleeve from the eye. In some embodiments, removing the outer sleeve can be via manual pulling of the outer sleeve. In some embodiments, removing the outer sleeve can be automated.

Step 2105 includes inflating the balloon to create a tension between between two adjacent layers of the eye. In some embodiments, inflating the balloon can create a tension between the sclera and the choroid. In some embodiments, inflating the balloon can create a tension between the choroid and the retina. The tension can aid in securing the placement of the distal end of the balloon at the desired location in the eye (e.g., between the choroid and the retina or between the sclera and the choroid) and preventing lateral movements of the eye. The inflation and securement of the balloon creates a stable anchor point, and the medicament can be injected into a location at a specified distance distal to the stable anchor point (e.g., about 50 μm, about 100 μm, about 150 μm, about 200 μm, about 250 μm, about 300 μm, about 350 μm, about 400 μm, about 450 μm, or about 500 μm distal to the stable anchor point, inclusive of all values and ranges therebetween).

Step 2106 includes advancing a hollow conduit through the cannula, such that a distal end of the hollow conduit enters the target tissue. The hollow conduit is in fluidic communication with a medicament container and the medicament container includes a medicament. In some embodiments, the hollow conduit can be a part of an injection apparatus. In some embodiments, the hollow conduit can be advanced such that a distal end of the hollow conduit is in the retinal tissue of the eye. In some embodiments, the hollow conduit can be advanced such that the distal end of the hollow conduit is in the choroidal tissue of the eye.

Step 2107 includes injecting at least a portion of the medicament into the target tissue. In some embodiments, the injecting can be via pushing on an injection controller. Step 2108 is optional and includes removing the hollow conduit from the eye. In some embodiments, removing the hollow conduit from the eye can be done by manually pulling the hollow conduit from the cannula. In some embodiments, removing the hollow conduit from the eye can be automated. In some embodiments, step 2107 can include automatic injection of the medicament into the target tissue (i.e., via a loss-of-resistance mechanism).

Step 2109 is optional and includes removing the cannula from the eye. In some embodiments, removing the cannula can be done by manually pulling the cannula from the eye. In some embodiments, the removal of the cannula can be automated. In some embodiments, the balloon can be deflated prior to removing the cannula from the eye.

Figure 26:
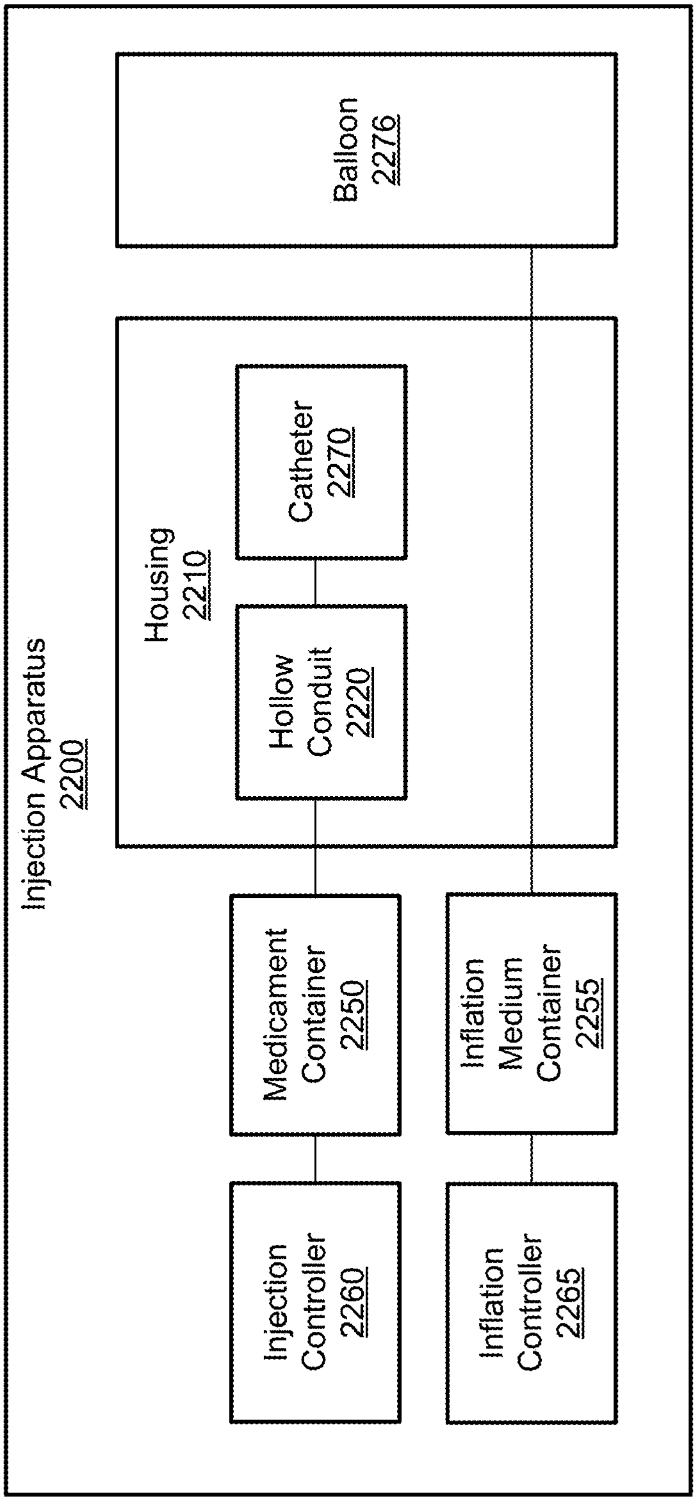
FIG. 26 is a schematic illustration of an injection apparatus, according to an embodiment.

FIG. 26 is a schematic illustration of an injection apparatus 2200, according to an embodiment. As shown, the injection apparatus 2200 includes a housing 2210, a hollow conduit 2220, a medicament container 2250, an inflation medium container 2255, an injection controller 2260, an inflation controller 2265, a catheter 2270, and a balloon 2276. In some embodiments, the hollow conduit 2220, the catheter 2270, and the balloon 2276 can be the same or substantially similar to, in form and/or in function, the hollow conduit 920, the outer sleeve 970, and the balloon 976, as described above with reference to FIGS. 13A-13O. In some embodiments, the medicament container 2250 and the injection controller 2260 can be the same or substantially similar to, in form and/or in function, the housing 110, the medicament container 150, and the injection controller 160, as described above with reference to FIG. 5. Thus, certain aspects of the housing 2210, the hollow conduit 2220, the medicament container 2250, the injection controller 2260, the catheter 2270, and the balloon 2276 are not described in greater detail herein.

In some embodiments, the balloon 2276 can be disposed at a distal end of the housing 2210. In some embodiments, the balloon 2276 can be disposed at a distal end of the catheter 2270. As shown, the inflation medium container 2255 is fluidically coupled to the balloon 2276, such that the inflation medium container 2255 dispenses an inflation medium to inflate the balloon 2276. The inflation controller 2265 moves the inflation medium from the inflation medium container 2255 to the balloon 2276. In some embodiments, the inflation controller 2265 can include a plunger. In some embodiments, the inflation medium can be transferred to the balloon 2276 manually (e.g., by pushing on the inflation controller 2265). In some embodiments, the inflation medium can be transferred to the balloon 2276 automatically. In some embodiments, the inflation medium container 2255 can be fluidically coupled to the balloon 2276 via a conduit. In some embodiments, the inflation medium can be a gas. In some embodiments, the inflation medium can be a liquid. In some embodiments, the inflation medium can have any of the properties described above with reference to FIGS. 13A-13O.

In some embodiments, the balloon 2276 can have an annular shape, such that the hollow conduit 2220 can advance through the annulus of the balloon 2276.

Figure 27:
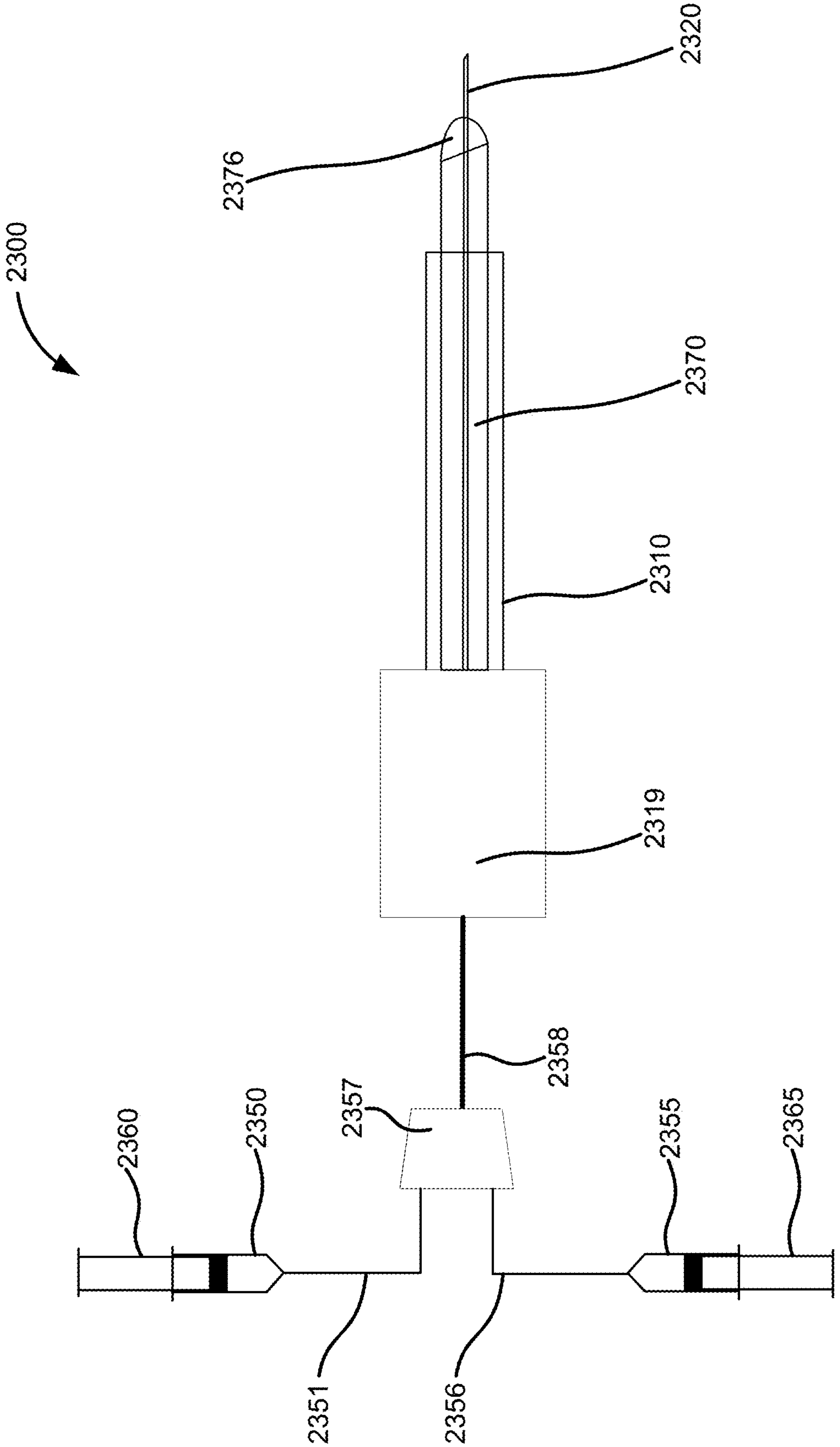
FIG. 27 illustrates an injection apparatus, according to an embodiment.

FIG. 27 is an illustration of an injection apparatus 2300, according to an embodiment. As shown, the injection apparatus 2300 includes a housing 2310, a handle 2319 coupled to the housing 2310, a hollow conduit 2320, a medicament container 2350, a medicament conduit 2351, an inflation medium container 2355, an inflation medium conduit 2356, a conduit union 2357, a conduit casing 2358, an injection controller 2360, an inflation controller 2265, a catheter 2370, and a balloon 2376. In some embodiments, the housing 2310, the hollow conduit 2320, the medicament container 2350, the inflation medium container 2355, the injection controller 2360, the inflation controller 2365, the catheter 2370, and the balloon 2376 can be the same or substantially similar to, in form and/or in function, the housing 2210, the hollow conduit 2220, the medicament container 2250, the inflation medium container 2255, the injection controller 2260, the inflation controller 2265, the catheter 2270, and the balloon 2276, as described above with reference to FIG. 26. Thus, certain aspects of the housing 2310, the hollow conduit 2320, the medicament container 2350, the inflation medium container 2355, the injection controller 2360, the inflation controller 2365, the catheter 2370, and the balloon 2376 are not described in greater detail herein.

The handle 2319 is an optional feature that allows the user to grip the housing 2310 more easily. The medicament conduit 2351 fluidically couples the medicament container 2350 to the hollow conduit 2320. The inflation medium conduit 2356 fluidically couples the inflation medium container 2355 to the balloon 2376. The conduit union 2357 joins the medicament conduit 2351 and the inflation medium conduit 2356 in the conduit casing 2358, without fluidically coupling the the medicament conduit 2351 and the inflation medium conduit 2356. In some embodiments, the conduit casing 2358 can include a tube that connects the conduit union 2357 and the housing 2310 (e.g., via the handle 2319). Upon entering the housing 2310, the medicament conduit 2351 and the inflation medium conduit 2356 can separate from each other, as the medicament conduit 2351 joins with the hollow conduit 2320. In some embodiments, the inflation medium conduit 2356 can run lengthwise along an interior of the housing 2310 and couple to the balloon 2376. In some embodiments, the inflation medium conduit 2356 can run lengthwise along the interior of the catheter 2370 and couple with the balloon 2376.

Figure 28A:
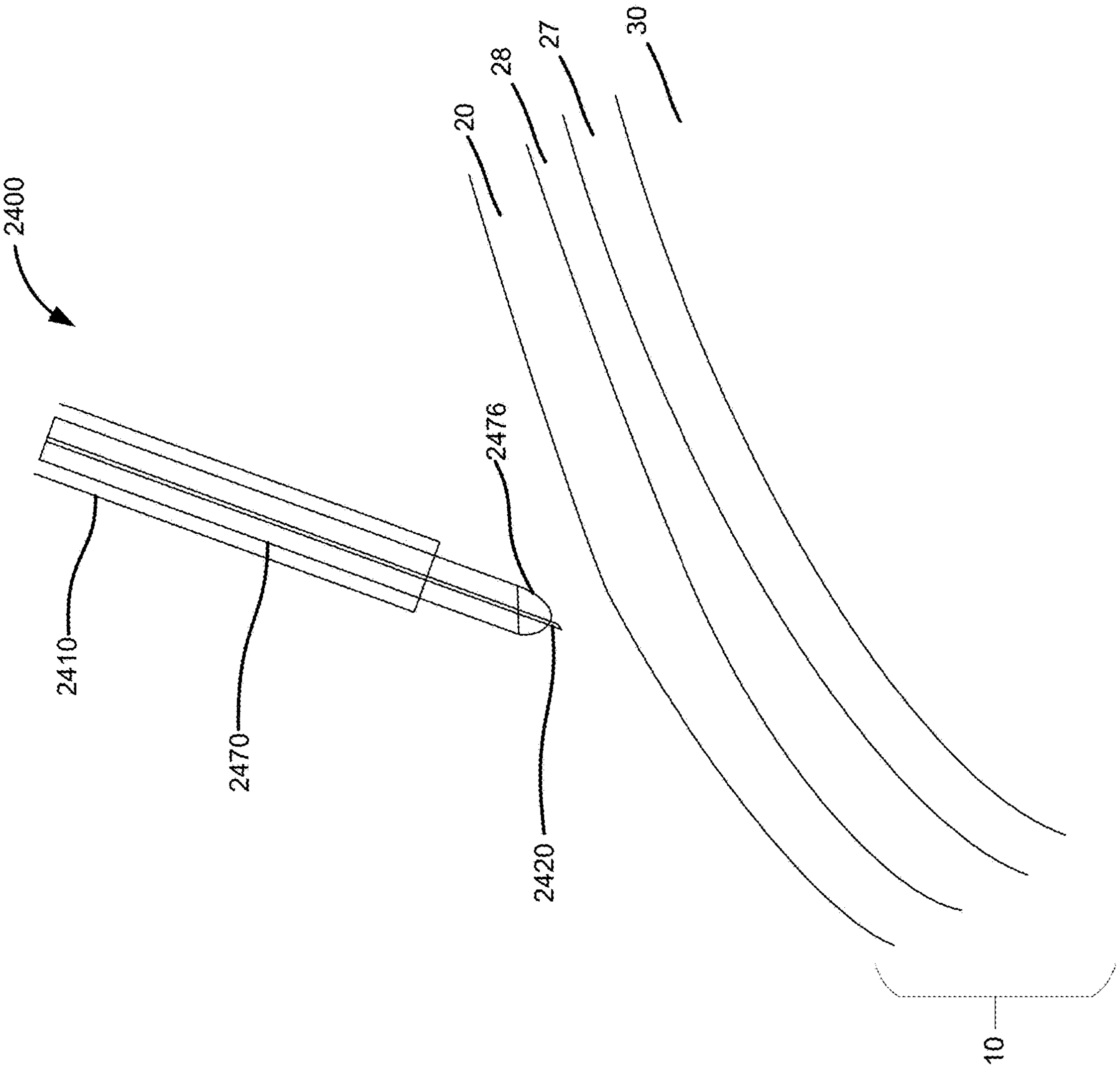
FIGS. 28A-28F illustrate methods and apparatus for performing an injection into ocular tissue, according to various embodiments.
Figure 28B:
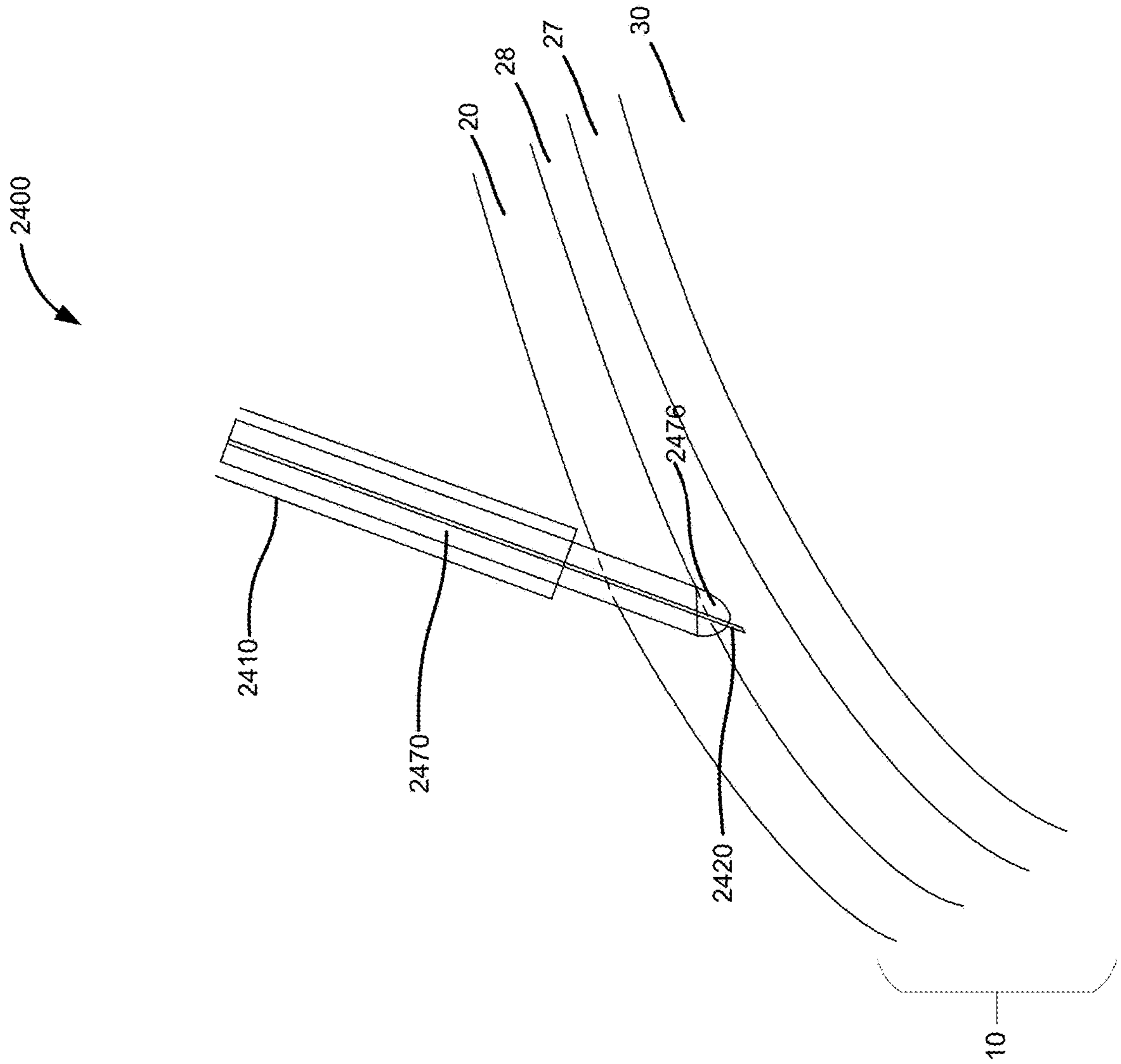
Figure 28C:
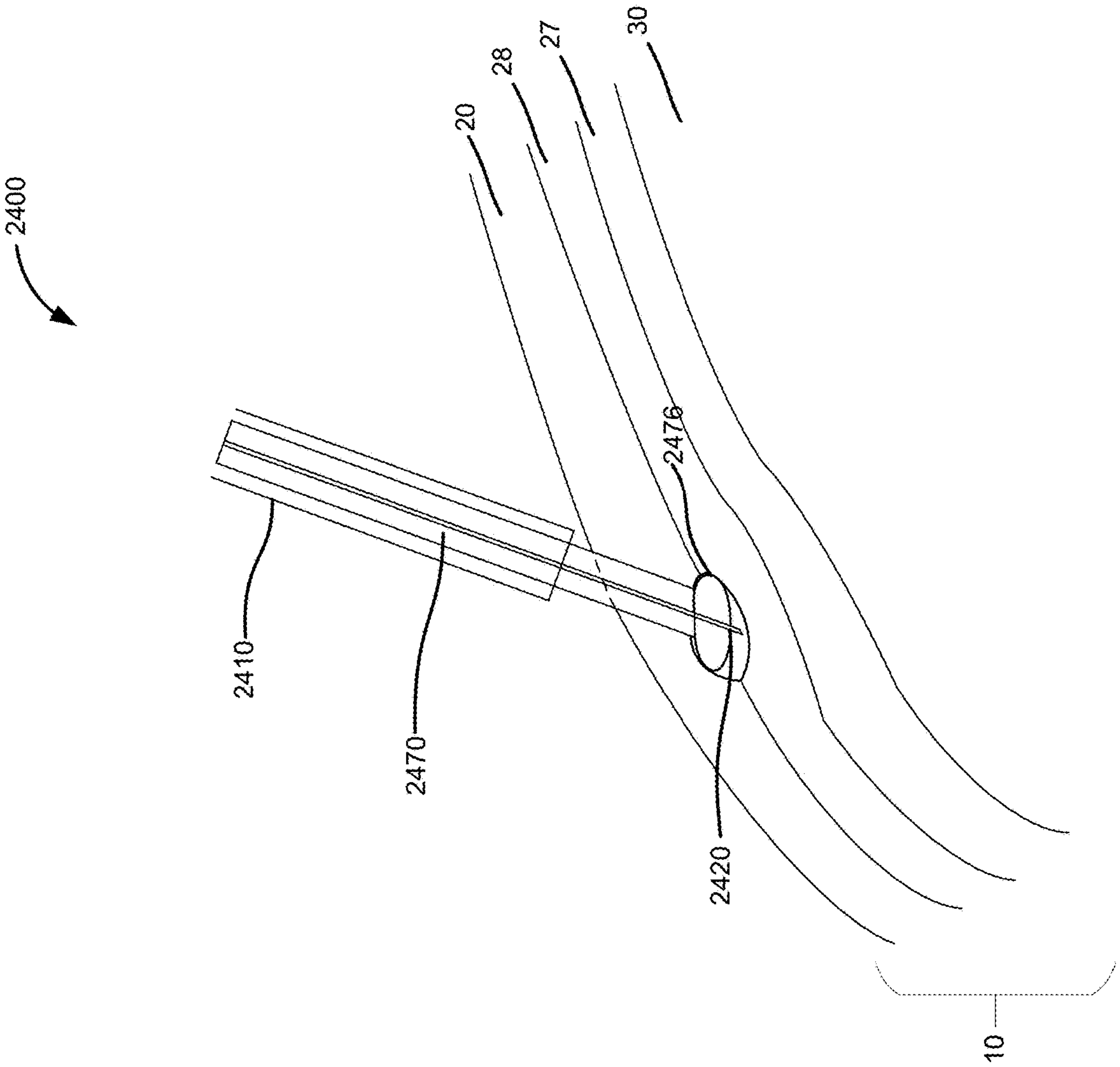
Figure 28D:
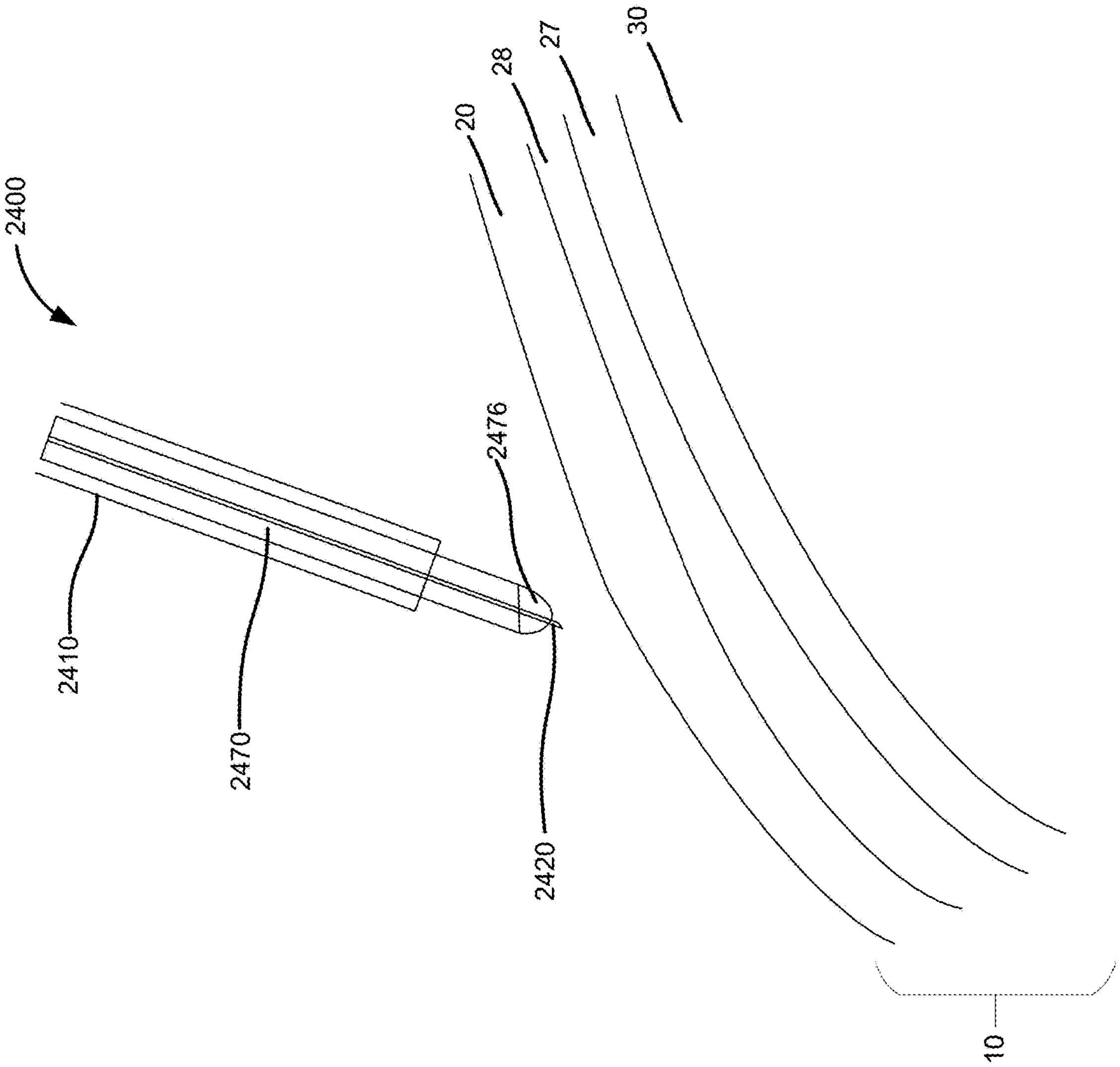
Figure 28E:
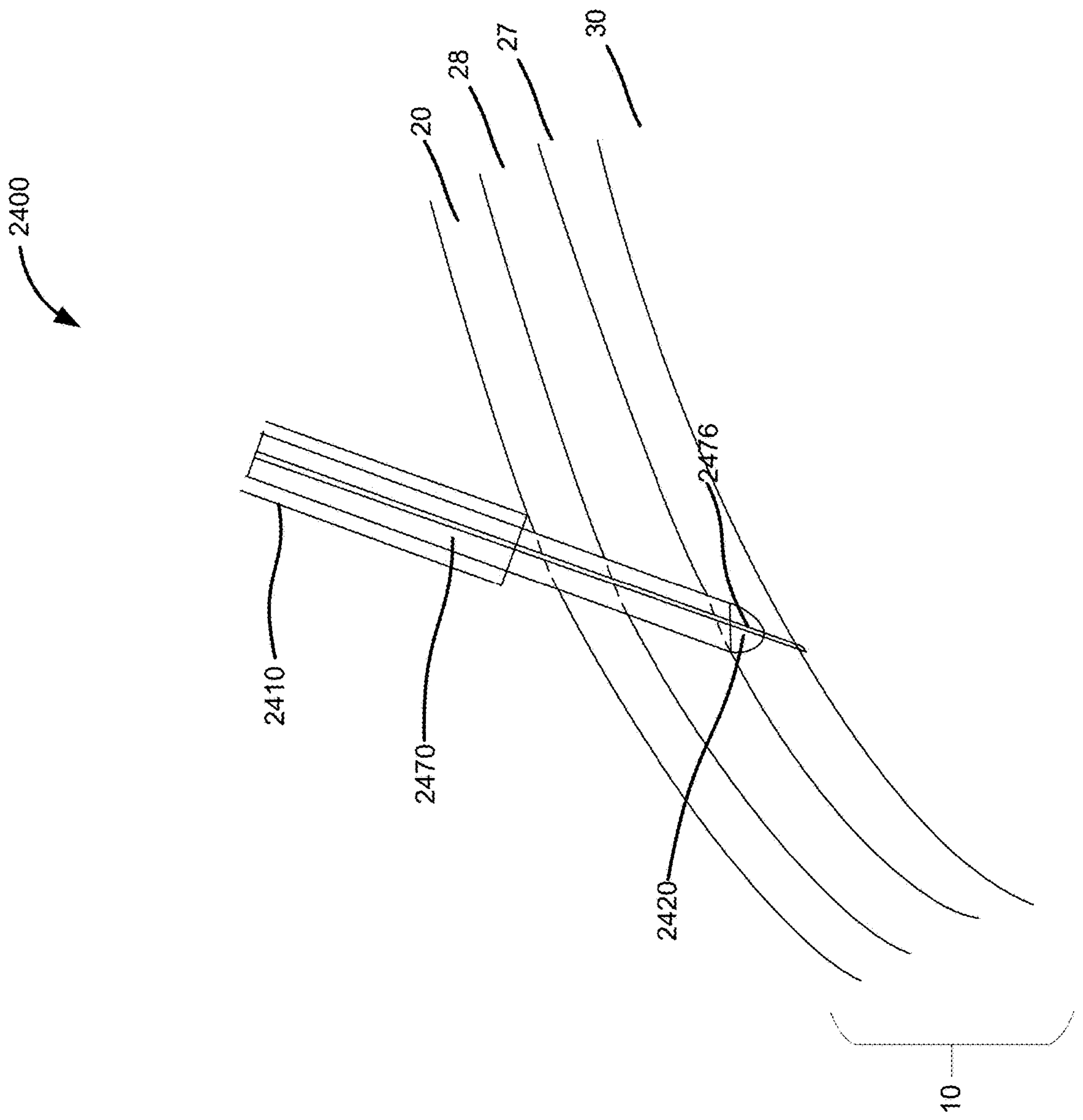
Figure 28F:
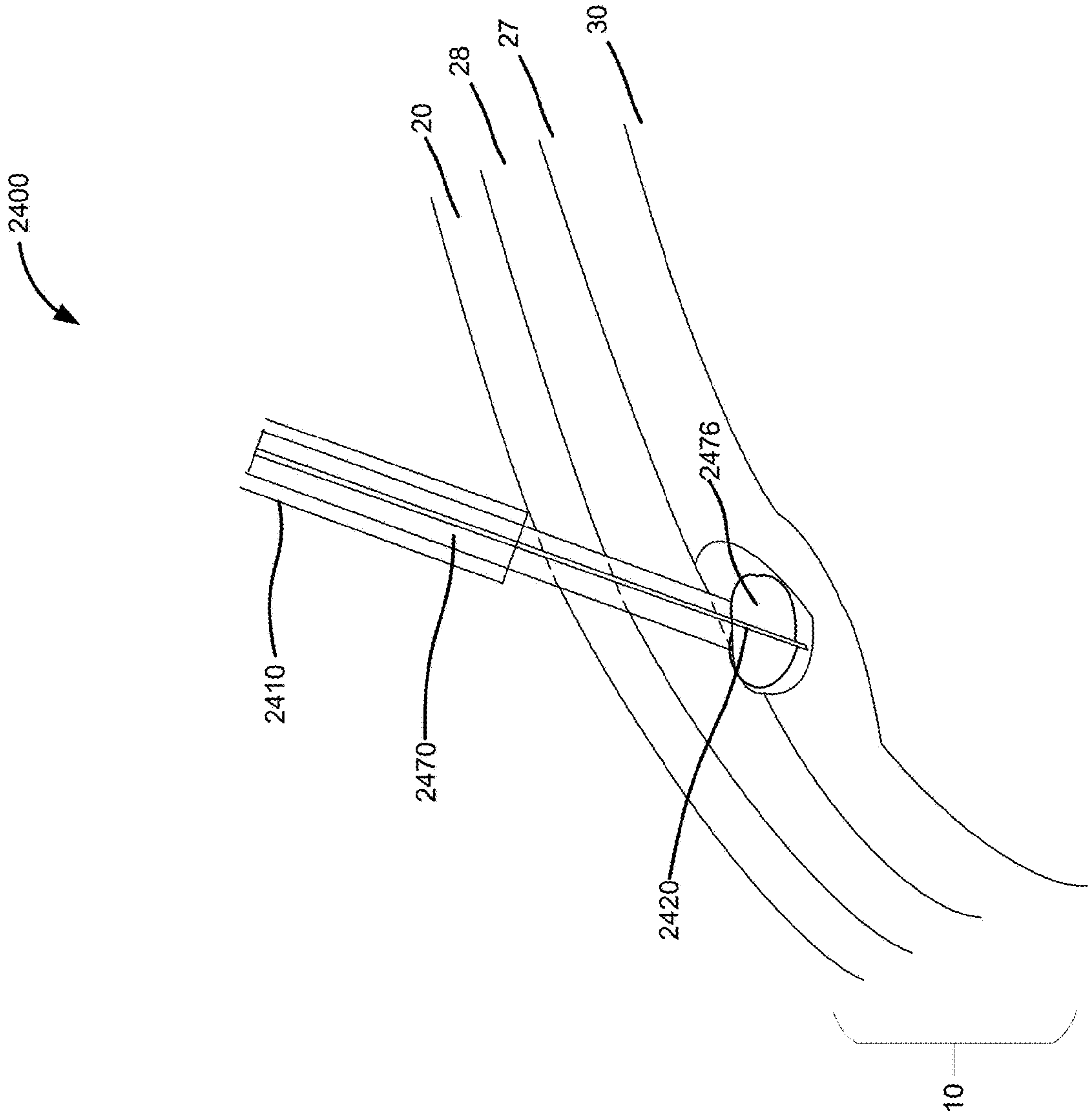

FIGS. 28A-28F illustrate methods and apparatus for performing an injection into ocular tissue, according to various embodiments. As shown, an injection apparatus 2400 includes a housing 2410, a hollow conduit 2420, a catheter 2470, and a balloon 2476. In some embodiments, the injection apparatus 2400, the housing 2410, the hollow conduit 2420, the catheter 2470, and the balloon 2476 can be the same or substantially similar to, in form and/or in function, the injection apparatus 2300, the housing 2310, the hollow conduit 2320, the catheter 2370, and the balloon 2376, as described above with reference to FIG. 27, and/or other embodiments described herein. The injection apparatus 2400 can also include the additional components of the injection apparatus 2300 (e.g., the medicament container 2350, the injection medium container 2355, etc.) not shown in FIGS. 28A-28F. FIGS. 28A-28C show a process of injecting a medicament into the SCS or the choroid 28, while FIGS. 28D-28F show a process of injecting the medicament into the SRS or the retina 27.

FIG. 28A shows the injection apparatus 2400 approaching the eye 10. In FIG. 28B, the catheter 2470 and the hollow conduit 2420 have advanced such that the balloon 2476 is at an interface between the sclera 20 and the choroid 28. As shown, the catheter 2470 is coupled to the housing 2410. In some embodiments, the catheter 2470 can be fixedly coupled to the housing 2410, such that the catheter 2470 moves with the housing 2410. In some embodiments, the catheter 2470 can be slidably coupled to the housing 2410, such that the catheter 2470 can move independently of the housing 2410. As shown, the hollow conduit 2420 is fixedly coupled to the catheter 2470. In some embodiments, the hollow conduit 2420 can be slidably coupled to the catheter 2470. As shown, the advancement of the catheter and the hollow conduit 2420 has caused the hollow conduit 2420 to advance into the choroid 28. In some embodiments, the position of the opening of the hollow conduit 2420 relative to the sclera 20 and the choroid 28 can be measured via any of the aforementioned methods (e.g., pressure, emissivity, OCT probe). As shown, the opening of the hollow conduit is positioned at the distal end of the hollow conduit 2420. In some embodiments, the opening of the hollow conduit 2420 can be proximal to the distal end of the hollow conduit 2420. The distal end of the hollow conduit 2420 can then be inserted slightly further into the eye 10, based on the distance between the balloon 2476 and the distal end of the hollow conduit 2420. In some embodiments, the opening of the hollow conduit 2420, while the hollow conduit 2420 is fixedly coupled to the catheter 2470, can extend beyond the distal end of the uninflated balloon 2476 by about 50 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1 mm, about 1.5 mm, about 2 mm, about 2.5 mm, about 3 mm, about 3.5 mm, about 4 mm, about 4.5 mm, or about 5 mm, inclusive of all values and ranges therebetween. In some embodiments, the hollow conduit 2420 can slide, such that the opening of the hollow conduit 2420 extends beyond the distal end of the uninflated balloon 2476 by about 50 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1 mm, about 1.5 mm, about 2 mm, about 2.5 mm, about 3 mm, about 3.5 mm, about 4 mm, about 4.5 mm, or about 5 mm, inclusive of all values and ranges therebetween.

FIG. 28C shows the balloon 2476 in an inflated state. The balloon 2476 can be inflated by conveying an inflation medium from an inflation medium container (not shown) to the balloon 2476 via a conduit (not shown) that fluidically couples the inflation medium container and the balloon 2476. The inflation of the balloon 2476 has caused the layers of the eye 10 to move relative to the hollow conduit 2420 and has created, expanded, and/or opened up the SCS between the sclera 20 and the choroid 28. As shown, the position of the opening of the hollow conduit 2420 has retreated relative to the layers of the eye 10 upon inflation of the balloon 2476. Prior to the inflation of the balloon 2476, the opening of the hollow conduit 2420 is in the choroid 28, and after the inflation of the balloon 2476, the opening of the hollow conduit 2420 has retreated to the SCS. As shown, the opening of the hollow conduit 2420 is disposed in the SCS after the inflation of the balloon 2476. In some embodiments, the opening of the hollow conduit 2420 can be disposed in the choroid 28 after inflation of the balloon 2476. In some embodiments, the hollow conduit 2420 can be flexible, such that the hollow conduit 2420 slides more easily in the interfaces between the layers of the eye 10 and does not get caught on various surfaces of the eye 10. In some embodiments, the balloon 2476 can be pressurized prior to entering the SCS (e.g., while in the sclera 20), and the balloon 2476 can expand (e.g., automatically) upon entering the relatively low-pressure region of the SCS. In other words, the balloon 2476 can inflate via a loss-of-resistance mechanism, such that the balloon 2476 inflates when it moves from a region with a relatively high resistance to expansion to a region with a relatively low resistance to expansion. In this manner, inflation of the balloon 2476 (or other type of expandable member) can serve as an indicator to the user (e.g., by visual confirmation) that the balloon 2476 as reached the SCS (or in other instances, the SRS, retina, or other target region of the eye).

In some embodiments, in its expanded state, the balloon 2476 can have a diameter or a dimension perpendicular to the length of the hollow conduit 2420 of at least about 1 mm, at least about 1.5 mm, at least about 2 mm, at least about 2.5 mm, at least about 3 mm, at least about 3.5 mm, at least about 4 mm, at least about 4.5 mm, at least about 5 mm, at least about 5.5 mm, at least about 6 mm, at least about 6.5 mm, at least about 7 mm, at least about 7.5 mm, at least about 8 mm, at least about 8.5 mm, at least about 9 mm, or at least about 9.5 mm. In some embodiments, in its expanded state, the balloon 2476 can have a diameter or a dimension perpendicular to the length of the hollow conduit 2420 of no more than about 10 mm, no more than about 9.5 mm, no more than about 9 mm, no more than about 8.5 mm, no more than about 8 mm, no more than about 7.5 mm, no more than about 7 mm, no more than about 6.5 mm, no more than about 6 mm, no more than about 5.5 mm, no more than about 5 mm, no more than about 4.5 mm, no more than about 4 mm, no more than about 3.5 mm, no more than about 3 mm, no more than about 2.5 mm, no more than about 2 mm, or no more than about 1.5 mm. Combinations of the above-referenced diameters are also possible (e.g., at least about 1 mm and no more than about 10 mm or at least about 2 mm and no more than about 7 mm), inclusive of all values and ranges therebetween. In some embodiments, in its expanded state, the balloon 2476 can have a diameter or a dimension perpendicular to the length of the hollow conduit 2420 of about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 10 mm.

In some cases, the injection of medicament into a target region can hydrodissect the sclera 20 and the choroid 28 to create the SCS. In other words, the injection of the medicament can create a pressure, such that the sclera 20 and the choroid 28 separate to create the SCS.

FIGS. 28D-28F show a process of injecting a medicament into the SRS or the retina 27. FIG. 28D shows the injection apparatus approaching the eye 10. In FIG. 28E, catheter 2470 and the hollow conduit 2420 have advanced relative to the layers of the eye 10, such that the balloon 2476 is at an interface between the choroid 28 and the retina 27 and the opening of the hollow conduit 2420 is in the vitreous space 30. FIG. 28F shows the balloon 2476 in an inflated state. The balloon 2476 can be inflated by conveying an inflation medium from an inflation medium container (not shown) to the balloon 2476 via a conduit (not shown) that fluidically couples the inflation medium container and the balloon 2476. The inflation of the balloon 2476 has caused the layers of the eye 10 to retreat relative to the hollow conduit 2420 and has created, expanded, and/or opened up the SRS between the choroid 28 and the retina 27. As shown, the position of the opening of the hollow conduit 2420 has changed relative to the layers of the eye 10 upon inflation of the balloon 2476, i.e., its position has moved proximally away from the vitreous space 30 and into the SRS. The location of the opening of the hollow conduit 2420 after inflation of that balloon 2476 can be a function of the location of the opening of the hollow conduit 2420 prior to inflation of the balloon 2476 and the volume of the balloon 2476 upon inflation. As shown, the opening of the hollow conduit 2420 has moved relative to the eye 10 from the vitreous space 30 to the SRS due to the inflation of the balloon 2476. In some embodiments, the opening of the hollow conduit 2420 can move from the vitreous space 30 to the retina 27 due to the inflation of the balloon 2476. In some embodiments, the balloon 2476 can be pressurized prior to entering the SRS (e.g., while in the choroid 28), and the balloon 2476 can expand upon entering the relatively low-pressure region of the SRS, similar to as described above with respect to the SCS.

Figure 29:
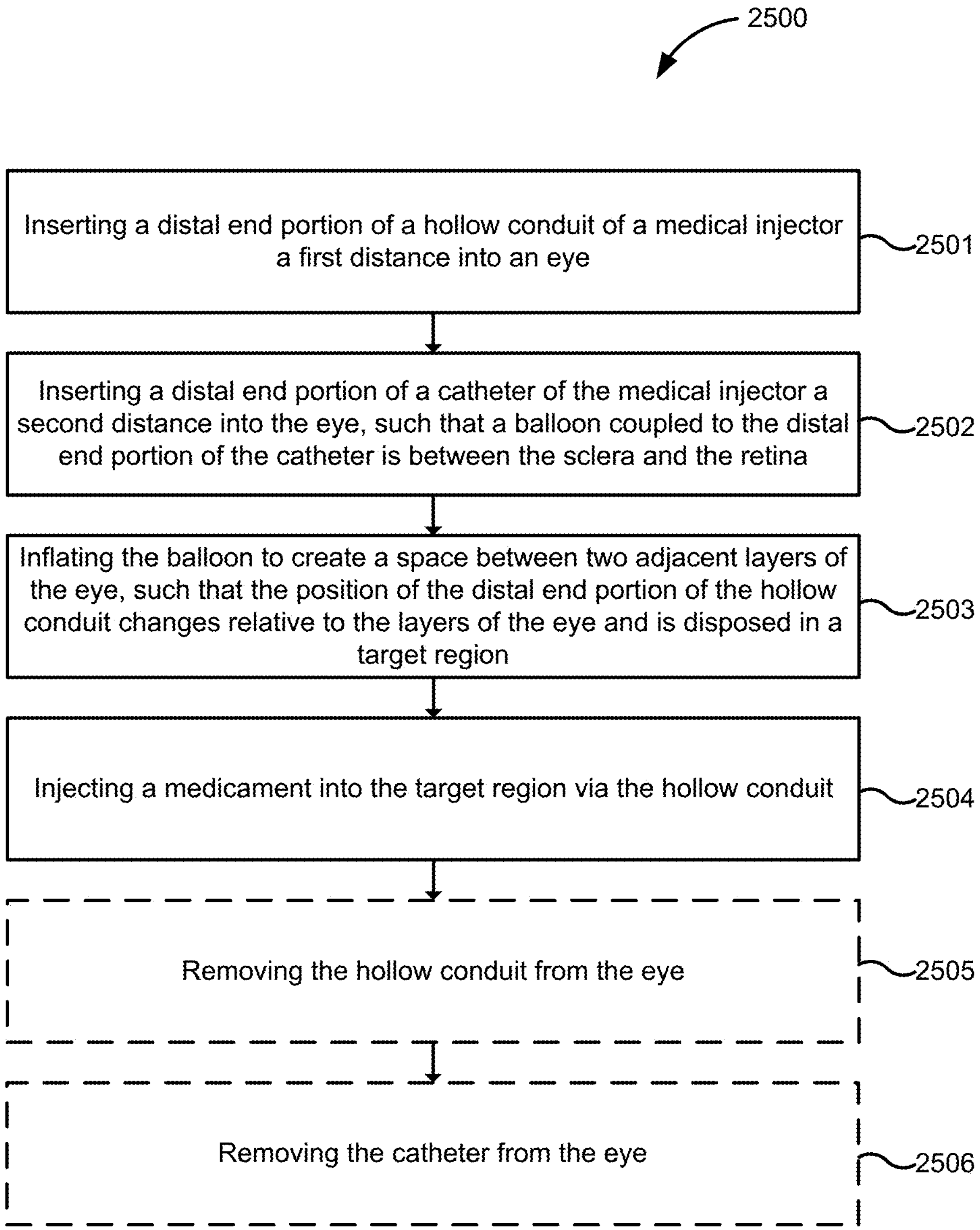
FIG. 29 shows a flow diagram of a method for performing an injection into a target region of the eye, according to an embodiment.

FIG. 29 shows a flow diagram of a method 2500 for performing an injection into a target region of the eye, according to an embodiment. As shown, the method 2500 includes inserting a distal end portion of a hollow conduit of a medical injector a first distance into an eye at step 2501, inserting a distal end portion of a catheter of the medical injector a second distance into the eye, such that a balloon coupled to the distal end portion of the catheter is between the sclera and the retina at step 2502, inflating the balloon to create a space between two adjacent layers of the eye, such that the position of the distal end portion of the hollow conduit changes relative to the layers of the eye and is disposed in a target region at step 2503, and injecting a medicament into the target region via the hollow conduit at step 2504. The method 2500 optionally includes removing the hollow conduit from they eye at step 2505 and removing the catheter from the eye at step 2506.

Step 2501 includes inserting a distal end portion of a hollow conduit of a medical injector a first distance into an eye. Inserting the distal end portion of the hollow conduit the first distance into the eye places the distal end of the hollow conduit in a first location in the eye. In some embodiments, the first location can be in the vitreous space. In some embodiments, the first location can be in the retina. In some embodiments, the first location can be in the SRS. In some embodiments, the first location can be in the choroid. In some embodiments, the first location can be in the SCS. In some embodiments, the first location can be in the sclera.

Step 2502 includes inserting a distal end portion of the catheter a second distance into the eye. In some embodiments, the second distance can be less than the first distance. In some embodiments, the inserting of the distal end portion of the catheter and the inserting of the distal end portion of the hollow conduit can be part of the same motion. In other words, the catheter and the hollow conduit can be coupled to each other such that they advance together.

Step 2503 includes inflating the balloon to create a space between two adjacent layers and/or potential space of the eye. In some embodiments, the two adjacent layers can include the sclera and the choroid. In some embodiments, the two adjacent layers can include the choroid and the retina. In some embodiments, the potential space can include the SCS. In some embodiments, the potential space can include the SRS. Inflating the balloon causes the distal end of the hollow conduit to change position from the first location to a second location, relative to the layers of the eye. This relative movement of the distal end of the hollow conduit can be caused by deformation of the layers of the eye due to the inflation of the balloon. In some embodiments, the second location can be in the retina. In some embodiments, the second location can be in the SRS. In some embodiments, the second location can be in the choroid. In some embodiments, the second location can be in the SCS. In some embodiments, the second location can be in the sclera.

Step 2504 includes injecting a medicament into the target region via the hollow conduit. In some embodiments, the target region can be the second location, as described above with reference to step 2503. In some embodiments, the hollow conduit can be fluidically coupled to a medicament container, and at least a portion of the medicament in the medicament container can be delivered to the target region. Step 2505 is optional and includes removing the hollow conduit from the eye. Step 2506 is optional and includes removing the catheter from the eye. In some embodiments, removal of the hollow conduit and the catheter from the eye can be accomplished in one motion. In some embodiments, the hollow conduit and/or the catheter can be removed from the eye via manual pulling. In some embodiments, the hollow conduit and/or the catheter can be removed from the eye via automation. In some embodiments, the balloon can be deflated prior to removing the catheter from the eye. In some embodiments, step 2504 can include automatic injection of the medicament into the target tissue (i.e., via a loss-of-resistance mechanism).

In some embodiments, an injection apparatus can be configured to administer a drug to a target region, such as, e.g., the retina, following a sclerotomy to expose a portion of the eye beyond the sclera. Such an injection apparatus 2600 is shown in and described with respect to FIGS. 30A-D, according to an embodiment. Certain components of the injection apparatus 2600 can be the same as or similar to, in form and/or function, any of the injection apparatuses described herein. Thus, certain aspects of the injection apparatus 2600 are not described in greater detail herein.

Figure 30B:
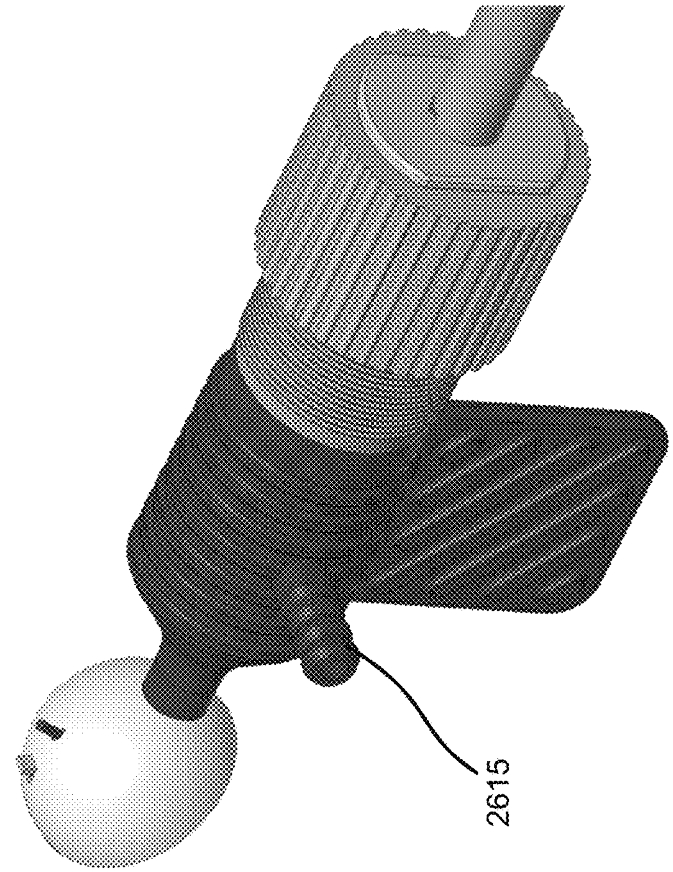
FIGS. 30A-30D shows an injection apparatus that uses vacuum to administer a medicament to retinal tissue, according to an embodiment.
Figure 30A:
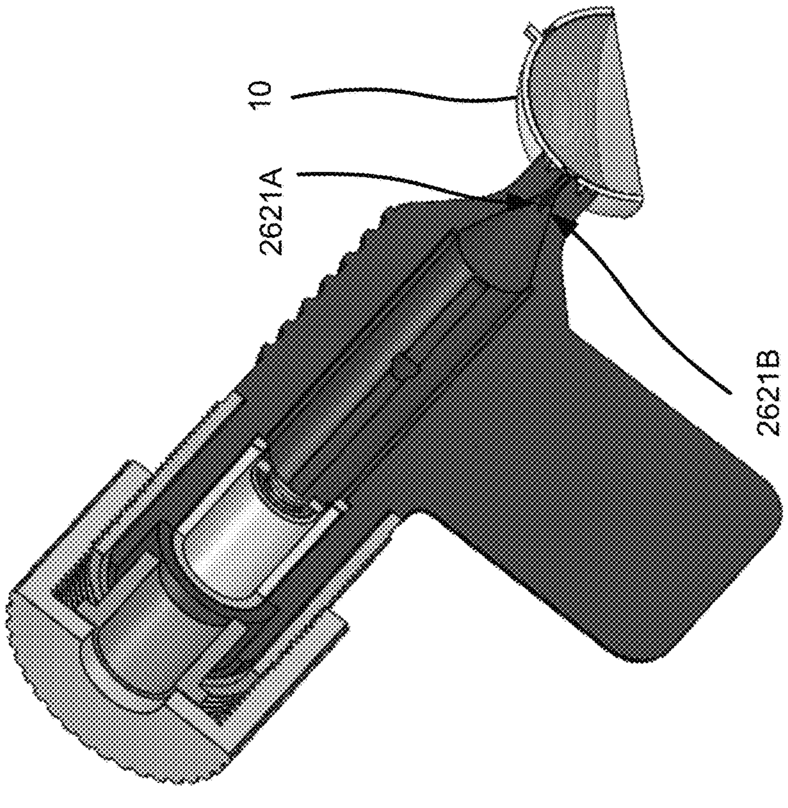
Figure 30C:
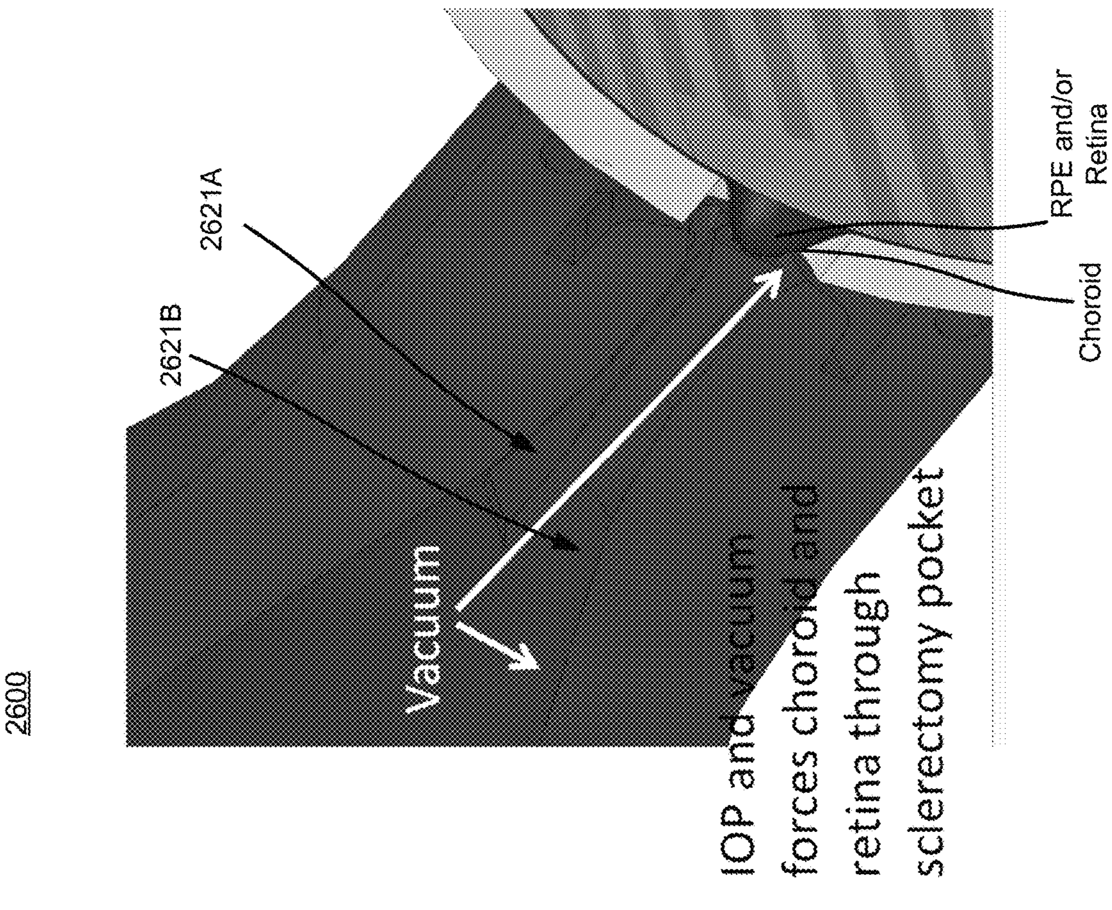
Figure 30D:
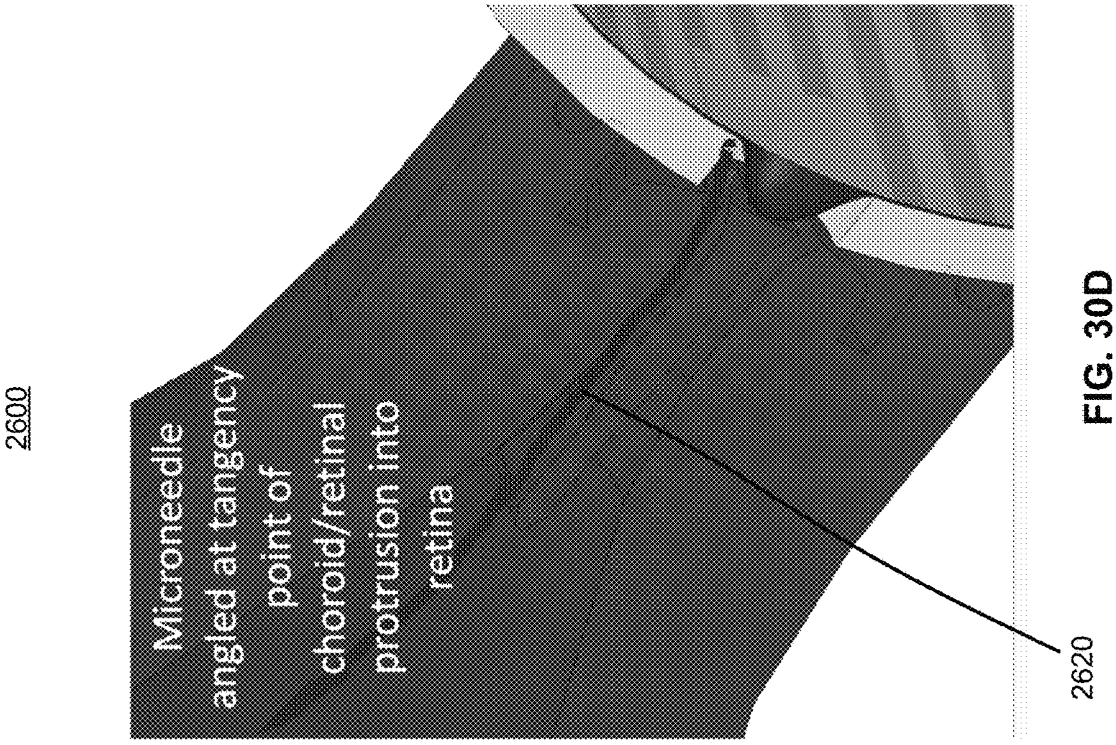

A sclerectomy is a procedure that creates an incision in the sclera of the eye, thereby exposing the underlying tissue(s), including the choroid, and the RPE just under the choroid. Eyes have a naturally occurring interocular pressure (IOP) that is greater than ambient pressure, such that when the sclera of the eye is cut, the IOP of the eye can bias or urge the choroid, RPE, and/or retinal tissue through the opening in the sclera. The injection apparatus 2600 is configured to capitalize on this phenomenon influenced by the IOP by providing a vacuum about the opening to pull or withdraw, or maintain, the tissue through the opening of the sclera, in a dome-like shape, as shown in FIGS. 30C and 30D. The injection apparatus 2600 can define a dome-like recess to receive the choroid and RPE in the dome-like form, and with the application of vacuum (applied through vacuum port or nozzle 2615), the injection apparatus 2600 can stabilize the choroid, RPE, and retinal tissue in that dome-like form within the recess (i.e., maintains the tissue in a fixed position relative to the injection apparatus 2600), at which point a puncture member 2620 can be advanced through a puncture member guide 2621 defined within the injection apparatus 2600 to puncture the tissue at a tanget point in the dome (+/− about a few degrees). Such a tangential entry limits the distal advancement of the puncture member 2620 and thereby limits inadvertent puncturing through the retina and into the vitreous. With a distal end opening of the puncture member 2620 then disposed within the retina, a medicament (not shown) housed within a medicament container (not shown) of the injection apparatus 2600 can be conveyed through a lumen of the puncture member 2620 and into the retina. As an additional feature to prevent the puncture member 2620 from advancing beyond the retina, the injection apparatus 2600 may optionally include a puncture member 2620 stop member (not shown) to limit a distance the puncture member 2620 can travel beyond the distal end of the injection apparatus 2600 and into the eye.

As shown, in this embodiment, the injection apparatus 2600 includes two puncture member guides 2621A, 2621B such that an operator can administer a medicament to one or both sides of the domed tissue. In some implementations, the injection apparatus 2600 can include two puncture members 2620, each configured to advance through one of the two puncture member guides 2621A, 2621B whereas in some implementations, the injection apparatus 2600 may include only one puncture member 2620 configured to advance through one or both of the two puncture member guides 2621A, 2621B. In some embodiments, an injection apparatus may include only one puncture member guide 2621. In some implementations, the puncture member 2620 can be manually advanced by an operator, while in some implementations, the puncture member 2620 can be automatically advanced with the help of an energy storage member (e.g., spring-actuated) operably coupled to the puncture member 2620.

In some embodiments, combinations of the above-referenced methods and systems can be employed for retinal injection. In some embodiments, an apparatus can include both a pressure measurement device and a light emissivity device for finding the reference location. In some embodiments, an apparatus can include both a pressure measurement device and an acoustic wave measurement device for finding the reference location. In some embodiments, an apparatus can include both a pressure measurement device and an electrical impedance measurement device for finding the reference location. In some embodiments, an apparatus can include both a pressure measurement device and an acoustic wave measurement device for finding the reference location. In some embodiments, an apparatus can include both a light emissivity device and an electrical impedance measurement device for finding the reference location. In some embodiments, an apparatus can include both a light emissivity device and an acoustic wave measurement device for finding the reference location. In some embodiments, an apparatus can include both an electrical impedance measurement and an acoustic wave measurement for finding the reference location. In some embodiments, an apparatus can include both an OCT probe device and a light emissivity device for finding the reference location. In some embodiments, an apparatus can include both an OCT probe device and an acoustic wave measurement device for finding the reference location. In some embodiments, an apparatus can include both an OCT probe device and an electrical impedance measurement device for finding the reference location. In some embodiments, an apparatus can include both an OCT probe device and an acoustic wave measurement device for finding the reference location. In some embodiments, an apparatus can include a pressure measurement device, a light emissivity device, an OCT probe device, an acoustic wave measurement device, an electrical impedance device, or any combinations thereof.

In one embodiment, an angiogenesis inhibitor is delivered via the methods and devices described herein, in one embodiment, is interferon gamma 1β, interferon gamma 1β (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PB14050, PB14419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260 or XV615.

In one embodiment, a VEGF modulator is delivered via one of the devices described herein. In one embodiment, the VEGF modulator is a VEGF antagonist. In one embodiment, the VEGF modulator is a VEGF-receptor kinase antagonist, an anti-VEGF antibody or fragment thereof, an anti-VEGF receptor antibody, an anti-VEGF aptamer, a small molecule VEGF antagonist, a thiazolidinedione, a quinoline or a designed ankyrin repeat protein (DARPin). In one embodiment, the VEGF antagonist is an antagonist of a VEGF receptor (VEGFR), i.e., a drug that inhibits, reduces, or modulates the signaling and/or activity of a VEGFR. The VEGFR may be a membrane-bound or soluble VEGFR. In a further embodiment, the VEGFR is VEGFR-1, VEGFR-2 or VEGFR-3. In one embodiment, the VEGF antagonist targets the VEGF-C protein. In another embodiment, the VEGF modulator is an antagonist of a tyrosine kinase or a tyrosine kinase receptor. In another embodiment, the VEGF modulator is a modulator of the VEGF-A protein. In yet another embodiment, the VEGF antagonist is a monoclonal antibody. In a further embodiment, the monoclonal antibody is a humanized monoclonal antibody.

In one embodiment, the VEGF modulator is one or more of the following: AL8326, 2C3 antibody, AT001 antibody, HyBEV, bevacizumab (Avastin®), ANG3070, APX003 antibody, APX004 antibody, ponatinib (AP24534), BDM-E, VGX100 antibody (VGX100 CIRCADIAN), VGX200 (c-fos induced growth factor monoclonal antibody), VGX300, COSMIX, DLX903/1008 antibody, ENMD2076, sunitinib malate (Sutent®), INDUS815C, R84 antibody, KD019, NM3, allogenic mesenchymal precursor cells combined with an anti-VEGF antagonist (e.g., anti-VEGF antibody), MGCD265, MG516, VEGF-Receptor kinase inhibitor, MP0260, NT503, anti-DLL4/VEGF bispecific antibody, PAN90806, Palomid 529, BD0801 antibody, XV615, lucitanib (AL3810, E3810), AMG706 (motesanib diphosphate), AAV2-sFLT01, soluble Flt1 receptor, cediranib (Recentin™), AV-951, tivozanib (KRN-951), regorafenib (Stivarga®), volasertib (BI6727), CEP11981, KH903, lenvatinib (E7080), lenvatinib mesylate, terameprocol (EM1421), ranibizumab (Lucentis®), pazopanib hydrochloride (Votrient™), PF00337210, PRS050, SPO1 (curcumin), carboxyamidotriazole orotate, hydroxychloroquine, linifanib (ABT869, RG3635), fluocinolone acetonide (Iluvien®), ALG1001, AGN150998, DARPin MP0112, AMG386, ponatinib (AP24534), AVA101, nintedanib (Vargatef™), BMS690514, KH902, golvatinib (E7050), everolimus (Afinitor®), dovitinib lactate (TKI258, CHIR258), ORA101, ORA102, axitinib (Inlyta®, AG013736), plitidepsin (Aplidin®), PTC299, aflibercept (Zaltrap®, Eylea®), pegaptanib sodium (Macugen™, LI900015), verteporfin (Visudyne®), bucillamine (Rimatil, Lamin, Brimani, Lamit, Boomiq), R3 antibody, AT001/r84 antibody, troponin (BLS0597), EG3306, vatalanib (PTK787), Bmab100, GSK2136773, Anti-VEGFR Alterase, Avila, CEP7055, CLT009, ESBA903, HuMax-VEGF antibody, GW654652, HMPL010, GEM220, HYB676, JNJ17029259, TAK593, XtendVEGF antibody, Nova21012, Nova21013, CP564959, Smart Anti-VEGF antibody, AG028262, AG13958, CVX241, SU14813, PRS055, PG501, PG545, PTI101, TG100948, ICS283, XL647, enzastaurin hydrochloride (LY317615), BC194, quinolines, COT601M06.1, COT604M06.2, MabionVEGF, SIR-Spheres coupled to anti-VEGF or VEGF-R antibody, Apatinib (YN968D1), and AL3818. In addition, delivery of a VEGF antagonist using the microneedle devices and non-surgical methods disclosed herein may be combined with one or more agents listed herein or with other agents known in the art, either in a single or multiple formulations.

In one embodiment, an immunosuppressive agent is delivered via one of the devices described herein. In a further embodiment, the immunosuppressive agent is a glucocorticoid, cytokine inhibitor, cytostatic, alkylating agent, anti-metabolite, folic acid analogue, cytotoxic antibiotic, interferon, opioid, T-cell receptor directed antibody or an IL-2 receptor directed antibody. In one embodiment, the immunosuppressive agent is an anti-metabolite and the anti-metabolite is a purine analog, pyrimidine analogue, folic acid analogue or a protein synthesis inhibitor. In another embodiment, the immunosuppressive agent is an interleukin-2 inhibitor (e.g., basiliximab or daclizumab). Other immunosuppressive agents amenable for use with the methods and formulations described herein include, but are not limited to cyclophosphamide, nitrosourea, methotrexate, azathioprine, mercaptopurine, fluorouracil, dactinomycin, anthracycline, mitomycin C, bleomycin, mithramycin, muromonab-CD3, cyclosporine, tacrolimus, sirolimus or mycophenolate. In one embodiment, the drug formulation comprises an effective amount mycophenolate.

In one embodiment, the drug formulation delivered via one of the devices described herein comprises an effective amount of vascular permeability inhibitor. In one embodiment, the vascular permeability inhibitor is a vascular endothelial growth factor (VEGF) antagonist or an angiotensin converting enzyme (ACE) inhibitor. In a further embodiment, the vascular permeability inhibitor is an angiotensin converting enzyme (ACE) inhibitor and the ACE inhibitor is captopril.

In one embodiment, the drug is a steroid or a non-steroid anti-inflammatory drug (NSAID). In another embodiment, the anti-inflammatory drug is an antibody or fragment thereof, an anti-inflammatory peptide(s) or an anti-inflammatory aptamer(s).

Steroidal compounds that can be administered via the methods provided herein include hydrocortisone, hydrocortisone-17-butyrate, hydrocortisone-17-aceponate, hydrocortisone-17-buteprate, cortisone, tixocortol pivalate, prednisolone, methylprednisolone, prednisone, triamcinolone, triamcinolone acetonide, mometasone, amcinonide, budesonide, desonide, fluocinonide, halcinonide, bethamethasone, bethamethasone dipropionate, dexamethasone, fluocortolone, hydrocortisone-17-valerate, halometasone, alclometasone dipropionate, prednicarbate, clobetasone-17-butyrate, clobetasol-17-propionate, fluocortolone caproate, fluocortolone pivalate, fluprednidene acetate and prednicarbate.

Specific classes of NSAIDs that can be administered via the methods provided herein include salicylates, propionic acid derivatives, acetic acid derivatives, enolic acid derivatives, fenamic acid derivatives and cyclooxygenase-2 (COX-2) inhibitors. In one embodiment, the methods provided herein are used to deliver one or more of the following NSAIDs to the eye of a patient in need thereof: acetylsalicylic acid, diflunisal, salsalate, ibuprofen, dexibuprofen, naproxen, fenoprofen, keotoprofen, dexketoprofen, flurbiprofen, oxaprozin, loxaprofen, indomethacin, tolmetin, sulindac, etodolac, ketorolac, diclofenac or nabumetone, piroxicam, meloxicam, tenoxicam, droxicam, lornoxicam or isoxicam, mefanamic acid, meclofenamic acid, flufenamic acid, tolfenamic acid, celecoxib, refecoxib, valdecoxib, parecoxib, lumiracoxib, etoricoxib or firocoxib.

Other examples of anti-inflammatory drugs include, but are not limited to: mycophenolate, remicase, nepafenac, 19AV agonist(s), 19GJ agonists, 2MD analogs, 4SC101, 4SC102, 57-57, 5-HT2 receptor antagonist, 64G12, A804598, A967079, AAD2004, AB1010, AB224050, abatacept, etaracizumab (Abegrin™), Abevac®, AbGn134, AbGn168, Abki, ABN912, ABR215062, ABR224050, cyclosporine (Abrammune®), docosanol (behenyl alcohol, Abreva®), ABS15, ABS4, ABS6, ABT122, ABT325, ABT494, ABT874, ABT963, ABXIL8, ABXRB2, AC430, Accenetra, lysozyme chloride (Acdeam®), ACE772, aceclofenac (Acebloc, Acebid, Acenac), acetaminophen, chlorzoxazone, serrapeptase, tizanidine hydrochloride, betadex, Aceclogesic Plus, Aceclon, Acecloren, Aceclorism, acecrona, Aceffein, acemetacin, asprin (Acenterine), Acetal-SP (Aceclofenac—combination, ibuprofen, Acetyl-G, acetylsalicylate dl-lysine, acetylsalicylic acid, Acicot, Acifine, Acik, Aclocen, Acloflam-P, Aclomore, Aclon, A-CQ, ACS15, actarit, Actemra, Acthelea liofilizado, Actifast, Actimab-B, Actiquim, Actirin, Actis PLUS, activated leukocyte cell adhesion molecule antibody, Acular X, AD452, adalimumab, ADAMTS5 inhibitor, ADC1001, Adco-Diclofenac, Adco-Indomethacin, Adco-Meloxicam, Adco-Naproxen, Adco-Piroxicam, Adcort, Adco-Sulindac, adenosine triphosphate disodium, AdenosineA2a Receptor Agonist, Adimod, Adinos, Adioct, Adiodol, Adipoplus, adipose derived stem and/or regenerative cells, Adizen, Adpep, Advacan, Advagraf, Advel, Adwiflam, AEB071, Aental, Afenac, Affen Plus, Afiancen, Afinitor, Aflamin, Aflazacort, Aflogen, Afloxan, AFM15, AFM16, AFM17, AFM23, Afpred-Dexa, AFX200, AG011, Agafen, aganirsen, AGI1096, Agidex, AGS010, Agudol, A-Hydrocort, AIK1, AIN457, Airtal, AIT110, AJM300, ajulemic acid, AK106, AL-24-2A1, AL4-1A1, Ala Cort, Alanz, Albumin immune-globulin, alclometasone dipropionate, ALD518, aldesleukin, Aldoderma, alefacept, alemtuzumab, Alequel™, Alergolon, Alergosone, Aletraxon, Alfenac, Algason, Algin vek coat, Algioflex, Algirex, Algivin Plus, alicaforsen sodium, Alin, Alinia, Aliviodol, Aliviosin, alkaline phosphatase, ALKS6931, allantoin, Allbupen, Allmol, Allochrysine, allogeneic endothelial cells, allogeneic mesenchymal precursor cells, allogeneic mesenchymal stem cells, alminoprofen, alpha 1 antitrypsin, Alpha 7 nicotinic agonists, alpha amylase, alpha chymotrypsin, alpha fetoprotein, alpha linolenic acid, alpha-1-antitrypsin, a2β1 integrin inhibitor, a2β1 integrin inhibitor, avβ3 inhibitor, avβ5 inhibitor, avβ1 inhibitor, a4β1 inhibitor, a4β7 inhibitor Alphacort, Alphafen, alpha-hexidine, alphatrypsin, Alphintern, Alpinamed mobility omega 3, Alpoxen, AL-Rev1, Alterase, ALX0061, ALX0761, ALXN1007, ALXN1102, AM3840, AM3876, AMAB, AMAP102, Amason, Ambene, AmbezimG, amcinonide, AME133v, Amecin, Ameloteks, A-Methapred, Amevive, AMG108, AMG139, AMG162, AMG181, AMG191, AMG220, AMG623, AMG674, AMG714, AMG719, AMG729, AMG827, Amidol, amifampridine phosphate, diclofenac (Emifenac®), Amimethacin, amiprilose hydrochloride, Amiprofen, Ammophos, Amoflam, AMP110, Ampikyy, Ampion, ampiroxicam, amtolmetin guacil, AMX256, AN6415, ANA004, ANA506, Anabu, Anacen, Anaflam, Anaflex ACI, Anaida, anakinra, Analgen Artritis, Anapan, Anaprox, Anavan, Anax, Anco, andrographis, Aneol, Anergix, Anervax.RA™ (therapeutic peptide vaccine), Anflene, ANG797, Anilixin, Anmerushin, Annexin 1 peptides, annexin A5, Anodyne, Ansaid, Anspirin, Antarene, anti BST2 antibody, anti C5a MAb, anti ILT7 antibody, anti VLA1 antibody, anti-alpha11 antibody, anti-CD4 802-2, anti-CD86 monoclonal antibody, anti-chemokine, anti-DC-SIGN, anti-HMGB-1 MAb, anti-IL-18 Mab, anti-IL-1R MAb, anti-IL-1R MAb, anti-IL23 BRISTOL, anti-interleukin-1β antibody, anti-LIGHT antibody, anti-MIF antibody, anti-MIF antibody, anti-miR181a, antioxidant inflammation modulators, Antiphlamine, AntiRAGE MAb, antithrombin III, Anti-TIRC-7 MAb, Anusol-HC, Anyfen, AP105, AP1089, AP1189, AP401, AP501, apazone, APD334, Apentac, APG103, Apidone, apilimod mesylate, Apitac, Apitoxin, Apizel, APN inhibitor, apo-azathioprine, Apo-dexamethasone, ApoE mimetics, ApoFasL, apo-Indomethacin, apo-mefenamic, apo-methotrexate, apo-nabumetone, Apo-Napro-NA, apo-Naproxen, aponidin, apo-Phenylbutazone, apo-Piroxicam, apo-Sulin, Apo-Tenoxicam, apo-Tiaprofenic, Apranax, apremilast, apricoxib, Aprofen, Aprose, Aproxen, APX001 antibody, APX007 antibody, APY0201, AqvoDex, AQX108, AQX1125, AQX131135, AQX140, AQX150, AQX200, AQX356, AQXMN100, AQXMN106, ARA290, Arava, Arcalyst, Arcoxia, Arechin, Arflur, ARG098, ARG301, arginine aescin, arginine deiminase (pegylated), ARGX109 antibody, ARGX110, Arheuma, Aristocort, Aristospan, Ark-AP, ARN4026, Arofen, Aroff EZ, Arolef, Arotal, Arpibru, Arpimune, Arpu Shuangxin, ARQ101, Arrestin SP, Arrox, ARRY162, ARRY371797, ARRY614, ARRY872, ART621, Artamin, Arthfree, Artho Tech, Arthrexin, Arthrispray, Arthrotec, aeterna shark cartilage extract (Arthrovas™, Neoretna™, Psovascar™) Artifit, Artigo, Artin, Artinor, Artisid, Artoflex, Artren Hipergel, Artridol, Artrilase, Artrocaptin, Artrodiet, Artrofen, Artropan, Artrosil, Artrosilene, Artrotin, Artrox, Artyflam, Arzerra, AS604850, AS605858, Asacol, ASA-Grindeks, Asazipam, Aseclo, ASF1096, ASF1096, ASK8007, ASKP1240, ASLAN003, Asmo ID, Asonep, ASP015K, ASP2408, ASP2409, Aspagin, Aspeol, Aspicam, Aspirimex, AST120, astaxanthin, AstroCort, Aszes, AT002 antibody, AT007, AT008 antibody, AT008 antibody, AT010, AT1001, atacicept, Ataspin, Atepadene, Atgam, ATG-Fresenius, Athrofen, ATI003, atiprimod, ATL1222, ATN103, ATN192, ATR107, *Atri*, Atrmin, Atrosab antibody, ATX3105, AU801, auranofin, Aurobin, Auropan, Aurothio, aurotioprol, autologous adipose derived regenerative cells, Autonec, Avandia, AVE9897, AVE9940, Avelox, Avent, AVI3378, Avloquin, AVP13546, AVP13748, AVP28225, AVX002, Axcel Diclofenac, Axcel Papain, Axen, AZ17, AZ175, Azacortid, AZA-DR, Azafrine, Azamun, Azanin, Azap, Azapin, Azapren, Azaprin, Azaram, Azasan, azathioprine, AZD0275, AZD0902, AZD2315, AZD5672, AZD6703, AZD7140, AZD8309, AZD8566, AZD9056, Azet, Azintrel, azithromycin, Az-od, Azofit, Azolid, Azoran, Azulene, Azulfidine, Azulfin, B1 antagonists, Baclonet, BAF312, BAFF Inhibitor, Bages, Baily S.P., Baleston, Balsolone, baminercept alfa, bardoxolone methyl, baricitinib, Barotase, Basecam, basiliximab, Baxmune, Baxo, BAY869766, BB2827, BCX34, BCX4208, Becfine, Beclate-C, Beclate-N, Beclolab Q, beclomethasone dipropionate, Beclorhin, Becmet-CG, Begita, Begti, belatacept, belimumab, Belosalic, Bemetson, Ben, Benevat, Benexam, Benflogin, Benisan, Benlysta, Benlysta, benorilate, Benoson, benoxaprofen, Bentol, benzydamine hydrochloride, Benzymin, Beofenac, Berafen, Berinert, Berlofen, Bertanel, Bestamine, Bestofen, Beta Nicip, Betacort, Betacorten G, Betafoam, beta-glucan, Betalar, Beta-M, Betamed, Betamesol, betamethasone, betamethasone dipropionate, betamethasone sodium, betamethasone sodium phosphate, betamethasone valerate, Betane, Betanex, Betapanthen, Betapar, Betapred, Betason, Betasonate, Betasone, Betatrinta, Betaval, Betazon, Betazone, Betesil, Betnecort, Betnesol, Betnovate, Bextra, BFPC13, BFPC18, BFPC21, BFPT6864, BG12, BG9924, BI695500, BI695501, BIA12, Big-Joint-D, BIIB023 antibody, Bi-ksikam, Bingo, BioBee, Bio-Cartilage, Bio-C-Sinkki, Biodexone, Biofenac, Bioreucam, Biosone, Biosporin, BIRB796, Bitnoval, Bitvio, Bivigam, BKT140, BKTP46, BL2030, BL3030, BL4020, BL6040, BL7060, BLI1300, blisibimod, Blokium B12, Blokium Gesic, Blokium, BMS066, BMS345541, BMS470539, BMS561392, BMS566419, BMS582949, BMS587101, BMS817399, BMS936557, BMS945429, BMS-A, BN006, BN007, BNP166, Bonacort, Bonas, bone marrow stromal cell antigen 2 antibody, Bonflex, Bonifen, Boomiq, Borbit, Bosong, BR02001, BR3-FC, Bradykinin B1 Receptor Antagonist, Bredinin, Brexecam, Brexin, Brexodin, briakinumab, Brimani, briobacept, Bristaflam, Britten, Broben, brodalumab, Broen-C, bromelains, Bromelin, Bronax, Bropain, Brosiral, Bruace, Brufadol, Brufen, Brugel, Brukil, Brusil, BT061, BTI9, BTK kinase inhibitors, BTT1023 antibody, BTT1507, bucillamine, Bucillate, Buco Reigis, bucolome, Budenofalk, budesonide, Budex, Bufect, Bufencon, Bukwang Ketoprofen, Bunide, Bunofen, Busilvex, busulfan, Busulfex, Busulipo, Butartrol, Butarut B12, Butasona, Butazolidin, Butesone, Butidiona, BVX10, BXL628, BYM338, B-Zone, C1 esterase inhibitor, C243, c4462, c5997, C5aQb, c7198, c9101, C9709, c9787, CAB101, cadherin 11 antibody, caerulomycin A, CAL263, Calcort, Calmatel, CAM3001, Camelid Antibodies, Camlox, Camola, Campath, Camrox, Camtenam, canakinumab, *Candida albicans* antigen, Candin, cannabidiol, CAP1.1, CAP1.2, CAP2.1, CAP2.2, CAP3.1, CAP3.2, Careram, Carimune, Cariodent, Cartifix, CartiJoint, Cartilago, Carti-safe-DN, Cartishine, Cartivit, Cartril-S, Carudol, CaspaClDe, CaspaClDe, Casyn, CAT1004, CAT1902, CAT2200, Cataflam, Cathepsin S inhibitor, Catlep, CB0114, CB2 agonist, CC0478765, CC10004, CC10015, CC1088, CC11050, CC13097, CC15965, CC16057, CC220, CC292, CC401, CC5048, CC509, CC7085, CC930, CCR1 antagonist, CCR6 inhibitor, CCR7 antagonist, CCRL2 antagonist, CCX025, CCX354, CCX634, CD Diclofenac, CD102, CD103 antibody, CD103 antibody, CD137 antibody, CD16 antibody, CD18 antibody, CD19 antibody, CD1d antibody, CD20 antibody, CD200Fc, CD209 antibody, CD24, CD3 antibody, CD30 antibody, CD32A antibody, CD32B antibody, CD4 antibody, CD40 ligand, CD44 antibody, CD64 antibody, CDC839, CDC998, CDIM4, CDIM9, CDK9-Inhibitor, CDP146, CDP323, CDP484, CDP6038, CDP870, CDX1135, CDX301, CE224535, Ceanel, Cebedex, Cebutid, Ceclonac, Ceex, CEL2000, Celact, Celbexx, Celcox, Celebiox, Celebrex, Celebrin, Celecox, celecoxib, Celedol, Celestone, Celevex, Celex, CELG4, Cell adhesion molecule antagonists, CellCept, Cellmune, Celosti, Celoxib, Celprot, Celudex, cenicriviroc mesylate, cenplacel-1, CEP11004, CEP37247, CEP37248, Cephyr, Ceprofen, Certican, certolizumab pegol, Cetofenid, Cetoprofeno, cetylpyridinium chloride, CF101, CF402, CF502, CG57008, CGEN15001, CGEN15021, CGEN15051, CGEN15091, CGEN25017, CGEN25068, CGEN40, CGEN54, CGEN768, CGEN855, CGI1746, CGI560, CGI676, Cgtx-Peptides, CH1504, CH4051, CH4446, chaperonin 10, chemokine C-C motif ligand 2, chemokine C-C motif ligand 2 antibody, chemokine C-C motif ligand 5 antibody, chemokine C-C motif receptor 2 antibody, chemokine C-C motif receptor 4 antibody, chemokine C-X-C motif ligand 10 antibody, chemokine C-X-C motif ligand 12 aptamer, Chemotaxis Inhibitor, Chillmetacin, chitinase 3-like 1, Chlocodemin, Chloquin, chlorhexidine gluconate, chloroquine phosphate, choline magnesium trisalicylate, chondroitin sulfate, Chondroscart, CHR3620, CHR4432, CHR5154, Chrysalin, Chuanxinlian, Chymapra, Chymotase, chymotrypsin, Chytmutrip, CI202, CI302, Cicloderm-C, Ciclopren, Cicporal, Cilamin, Cimzia, cinchophen, cinmetacin, cinnoxicam, Cinoderm, Cinolone-S, Cinryze, Cipcorlin, cipemastat, Cipol-N, Cipridanol, Cipzen, Citax F, Citogan, Citoken T, Civamide, CJ042794, CJ14877, c-Kit monoclonal antibody, cladribine, Clafen, Clanza, Claversal, clazakizumab, Clearoid, Clease, Clevegen, Clevian, Clidol, Clindac, Clinoril, Cliptol, Clobenate, Clobequad, clobetasol butyrate, clobetasol propionate, Clodol, clofarabine, Clofen, Clofenal LP, Clolar, Clonac, Clongamma, clonixin lysine, Clotasoce, Clovacort, Clovana, Cloxin, CLT001, CLT008, C-MAF Inhibitor, CMPX1023, Cnac, CNDO201, CNI1493, CNTO136, CNTO148, CNT01959, Cobefen, CoBenCoDerm, Cobix, Cofenac, Cofenac, COG241, COL179, colchicine, *Colchicum* Dispert, Colchimax, Colcibra, Coledes A, Colesol, Colifoam, Colirest, collagen, type V, Comcort, complement component (3b/4b) receptor 1, Complement Component C1s Inhibitors, complement component C3, complement factor 5a receptor antibody, complement factor 5a receptor antibody, complement factor D antibody, Condrosulf, Condrotec, Condrothin, conestat alfa, connective tissue growth factor antibody, Coolpan, Copaxone, Copiron, Cordefla, Corhydron, Cort S, Cortan, Cortate, Cort-Dome, Cortecetine, Cortef, Corteroid, Corticap, Corticas, Cortic-DS, corticotropin, Cortiderm, Cortidex, Cortiflam, Cortinet M, Cortinil, Cortipyren B, Cortiran, Cortis, Cortisolu, cortisone acetate, Cortival, Cortone acetate, Cortopin, Cortoral, Cortril, Cortypiren, Cosamine, Cosone, cosyntropin, COT Kinase Inhibitor, Cotilam, Cotrisone, Cotson, Covox, Cox B, COX-2/5-LO Inhibitors, Coxeton, Coxflam, Coxicam, Coxitor, Coxtral, Coxypar, CP195543, CP412245, CP424174, CP461, CP629933, CP690550, CP751871, CPSI2364, C-quin, CR039, CR074, CR106, CRA102, CRAC channel inhibitor, CRACM ion channel inhibitor, Cratisone, CRB15, CRC4273, CRC4342, C-reactive protein 2-methoxyethyl phosphorothioate oligonucleotide, CreaVax-RA, CRH modulators, critic-aid, Crocam, Crohnsvax, Cromoglycic acid, cromolyn sodium, Cronocorteroid, Cronodicasone, CRTX803, CRx119, CRx139, CRx150, CS502, CS670, CS706, CSF1R Kinase Inhibitors, CSL324, CSL718, CSL742, CT112, CT1501R, CT200, CT2008, CT2009, CT3, CT335, CT340, CT5357, CT637, CTP05, CTP10, CT-P13, CTP17, Cuprenil, Cuprimine, Cuprindo, Cupripen, Curaquin, Cutfen, CWF0808, CWP271, CX1020, CX1030, CX1040, CX5011, Cx611, Cx621, Cx911, CXC chemokine receptor 4 antibody, CXCL13 antibodies, CXCR3 antagonists, CXCR4 antagonist, Cyathus 1104 B, Cyclo-2, Cyclocort, cyclooxygenase-2 inhibitor, cyclophosphamide, Cyclorine, Cyclosporin A Prodrug, Cyclosporin analogue A, cyclosporine, Cyrevia, Cyrin CLARIS, CYT007TNFQb, CYT013IL1bQb, CYT015IL17Qb, CYT020TNFQb, CYT107, CYT387, CYT99007, cytokine inhibitors, Cytopan, Cytoreg, CZC24832, D1927, D9421C, daclizumab, danazol, Danilase, Dantes, Danzen, dapsone, Dase-D, Daypro, Daypro Alta, Dayrun, Dazen, DB295, DBTP2, D-Cort, DD1, DD3, DE096, DE098, Debio0406, Debio0512, Debio0615, Debio0618, Debio1036, Decaderm, Decadrale, Decadron, Decadronal, Decalon, Decan, Decason, Decdan, Decilone, Declophen, Decopen, Decorex, Decorten, Dedema, Dedron, Deexa, Defcort, De-flam, Deflamat, Deflan, Deflanil, Deflaren, Deflaz, deflazacort, Defnac, Defnalone, Defnil, Defosalic, Defsure, Defza, Dehydrocortison, Dekort, Delagil, delcasertib, delmitide, Delphicort, Deltacorsolone prednisolone (Deltacortril), Deltafluorene, Deltasolone, Deltasone, Deltastab, Deltonin, Demarin, Demisone, Denebola, denileukin diftitox, denosumab, Denzo, Depocortin, Depo-medrol, Depomethotrexate, Depopred, Deposet, Depyrin, Derinase, Dermol, Dermolar, Dermonate, Dermosone, Dersone, Desketo, desonide, desoxycorticosterone acetate, Deswon, Dexa, Dexabene, Dexacip, Dexacort, dexacortisone, Dexacotisil, dexadic, dexadrin, Dexadron, Dexafar, Dexahil, Dexalab, Dexalaf, Dexalet, Dexalgen, dexallion, dexalocal, Dexalone, Dexa-M, Dexamecortin, Dexamed, Dexamedis, dexameral, Dexameta, dexamethasone, dexamethasone acetate, dexamethasone palmitate, dexamethasone phosphate, dexamethasone sodium metasulfobenzoate, dexamethasone sodium phosphate, Dexamine, Dexapanthen, Dexa-S, Dexason, Dexatab, Dexatopic, Dexaval, Dexaven, Dexazolidin, Dexazona, Dexazone, Dexcor, Dexibu, dexibuprofen, Dexico, Dexifen, Deximune, dexketoprofen, dexketoprofen trometamol, Dexmark, Dexomet, Dexon I, Dexonalin, Dexonex, Dexony, Dexoptifen, Dexpin, Dextan-Plus, dextran sulfate, Dezacor, Dfz, diacerein, Diannexin, Diastone, Dicarol, Dicasone, Dicknol, Diclo, Diclobon, Diclobonse, Diclobonzox, Diclofast, Diclofen, diclofenac, diclofenac beta-dimethylaminoethanol, diclofenac deanol, diclofenac diethylamine, diclofenac epolamine, diclofenac potassium, diclofenac resinate, diclofenac sodium, Diclogen AGIO, Diclogen Plus, Diclokim, Diclomed, Diclo-NA, Diclonac, Dicloramin, Dicloran, Dicloreum, Diclorism, Diclotec, Diclovit, Diclowal, Diclozem, Dico P, Dicofen, Dicoliv, Dicorsone, Dicron, Dicser, Difena, Diffutab, diflunisal, dilmapimod, Dilora, dimethyl sulfone, Dinac, D-Indomethacin, Dioxaflex Protect, Dipagesic, Dipenopen, Dipexin, Dipro AS, Diprobeta, Diprobetasone, Diproklenat, Dipromet, Dipronova, Diprosone, Diprovate, Diproxen, Disarmin, Diser, Disopain, Dispain, Dispercam, Distamine, Dizox, DLT303, DLT404, DM199, DM99, DMI9523, dnaJP1, DNX02070, DNX04042, DNX2000, DNX4000, docosanol, Docz-6, Dolamide, Dolaren, Dolchis, Dolex, Dolflam, Dolfre, Dolgit, Dolmax, Dolmina, Dolo Ketazon, Dolobest, Dolobid, Doloc, Dolocam, Dolocartigen, Dolofit, Dolokind, Dolomed, Dolonac, Dolonex, Dolotren, Dolozen, Dolquine, Dom0100, Dom0400, Dom0800, Domet, Dometon, Dominadol, Dongipap, Donica, Dontisanin, doramapimod, Dorixina Relax, Dormelox, Dorzine Plus, Doxatar, Doxtran, DP NEC, DP4577, DP50, DP6221, D-Penamine, DPIV/APN Inhibitors, DR1 Inhibitors, DR4 Inhibitors, DRA161, DRA162, Drenex, DRF4848, DRL15725, Drossadin, DSP, Duexis, Duo-Decadron, Duoflex, Duonase, DV1079, DV1179, DWJ425, DWP422, Dymol, DYN15, Dynapar, Dysmen, E5090, E6070, Easy Dayz, Ebetrexat, EBI007, ECO286, EC0565, EC0746, Ecax, *Echinacea purpurea* extract, EC-Naprosyn, Econac, Ecosprin 300, Ecosprin 300, Ecridoxan, eculizumab, Edecam, efalizumab, Efcortesol, Effigel, Eflagen, Efridol, EGFR Antibody, EGS21, eIF5A1 siRNA, Ekarzin, elafin, Eldoflam, Elidel, Eliflam, Elisone, Elmes, Elmetacin, ELND001, ELND004, elocalcitol, Elocom, elsibucol, Emanzen, Emcort, Emifen, Emifenac, emorfazone, Empynase, emricasan, Emtor, Enable, Enbrel, Enceid, EncorStat, Encortolon, Encorton, Endase, Endogesic, Endoxan, Enkorten, Ensera, Entocort, Enzylan, Epanova, Eparang, Epatec, Epicotil, epidermal growth factor receptor 2 antibody, epidermal growth factor receptor antibody, Epidixone, Epidron, Epiklin, EPPA1, epratuzumab, EquiO, Erac, Erazon, ERB041, ERB196, Erdon, EryDex, *Escherichia coli* enterotoxin B subunit, Escin, E-Selectin Antagonists, Esfenac, ESN603, esonarimod, Esprofen, estetrol, Estopein, Estrogen Receptor beta agonist, etanercept, etaracizumab, ETC001, ethanol propolis extract, ETI511, etiprednol dicloacetate, Etodin, Etodine, Etodol, etodolac, Etody, etofenamate, Etol Fort, Etolac, Etopin, etoricoxib, Etorix, Etosafe, Etova, Etozox, Etura, Eucob, Eufans, eukaryotic translation initiation factor 5A oligonucleotide, Eunac, Eurocox, Eurogesic, everolimus, Evinopon, EVT401, Exaflam, EXEL9953, Exicort, Expen, Extra Feverlet, Extrapan, Extrauma, Exudase, F16, F991, Falcam, Falcol, Falzy, Farbovil, Farcometacin, Farnerate, Farnezone, Farnezone, Farotrin, fas antibody, Fastflam, FasTRACK, Fastum, Fauldmetro, FcgammaRIA antibody, FE301, Febrofen, Febrofid, felbinac, Feldene, Feldex, Feloran, Felxicam, Fenac, Fenacop, Fenadol, Fenaflan, Fenamic, Fenaren, Fenaton, Fenbid, fenbufen, Fengshi Gutong, Fenicort, Fenopine, fenoprofen calcium, Fenopron, Fenris, Fensupp, Fenxicam, fepradinol, Ferovisc, Feverlet, fezakinumab, FG3019, FHT401, FHTCT4, FID114657, figitumumab, Filexi, filgrastim, Fillase, Final, Findoxin, fingolimod hydrochloride, firategrast, Firdapse, Fisiodar, Fivasa, FK778, Flacoxto, Fladalgin, Flagon, Flamar, Flamcid, Flamfort, Flamide, Flaminase, Flamirex Gesic, Flanid, Flanzen, Flaren, Flaren, Flash Act, Flavonoid Anti-inflammatory Molecule, Flebogamma DIF, Flenac, Flex, Flexafen 400, Flexi, Flexidol, Flexium, Flexon, Flexono, Flogene, Flogiatrin B12, Flogomin, Flogoral, Flogosan, Flogoter, Flo-Pred, Flosteron, Flotrip Forte, Flt3 inhibitors, fluasterone, Flucam, Flucinar, fludrocortisone acetate, flufenamate aluminum, flumethasone, Flumidon, flunixin, fluocinolone, fluocinolone acetonide, fluocinonide, fluocortolone, Fluonid, fluorometholone, Flur, flurbiprofen, Fluribec, Flurometholone, Flutal, fluticasone, fluticasone propionate, Flutizone, Fluzone, FM101 antibody, fms-related tyrosine kinase 1 antibody, Folitrax, fontolizumab, formic acid, Fortecortin, Fospeg, fostamatinib disodium, FP1069, FP13XX, FPA008, FPA031, FPT025, FR104, FR167653, Framebin, Frime, Froben, Frolix, FROUNT Inhibitors, Fubifen PAP, Fucole ibuprofen, Fulamotol, Fulpen, Fungifin, Furotalgin, fusidate sodium, FX002, FX141L, FX201, FX300, FX87L, Galectin modulators, gallium maltolate, Gamimune N, Gammagard, Gamma-I.V., GammaQuin, Gamma-Venin, Gamunex, Garzen, Gaspirin, Gattex, GBR500, GBR500 antibody, GBT009, G-CSF, GED0301, GED0414, Gefenec, Gelofen, Genepril, Gengraf, Genimune, Geniquin, Genotropin, Genz29155, Gerbin, Gerbin, gevokizumab, GF01564600, Gilenia, Gilenya, givinostat, GL0050, GL2045, glatiramer acetate, Globulin, Glortho Forte, Glovalox, Glovenin-I, GLPG0259, GLPG0555, GLPG0634, GLPG0778, GLPG0974, Gluco, Glucocerin, glucosamine, glucosamine hydrochloride, glucosamine sulfate, Glucotin, Gludex, Glutilage, GLY079, GLY145, Glycanic, Glycefort up, Glygesic, Glysopep, GMCSF Antibody, GMI1010, GMI1011, GMI1043, GMR321, GN4001, Goanna Salve, Goflex, gold sodium thiomalate, golimumab, GP2013, GPCR modulator, GPR15 Antagonist, GPR183 antagonist, GPR32 antagonist, GPR83 antagonist, G-protein Coupled Receptor Antagonists, Graceptor, Graftac, granulocyte colony-stimulating factor antibody, granulocyte-macrophage colony-stimulating factor antibody, Gravx, GRC4039, Grelyse, GS101, GS9973, GSC100, GSK1605786, GSK1827771, GSK2136525, GSK2941266, GSK315234, GSK681323, GT146, GT442, Gucixiaotong, Gufisera, Gupisone, gusperimus hydrochloride, GW274150, GW3333, GW406381, GW856553, GWB78, GXP04, Gynestrel, Haloart, halopredone acetate, Haloxin, HANALL, Hanall Soludacortin, Havisco, Hawon Bucillamin, HB802, HC31496, HCQ 200, HD104, HD203, HD205, HDAC inhibitor, HE2500, HE3177, HE3413, Hecoria, Hectomitacin, Hefasolon, Helen, Helenil, HemaMax, Hematom, hematopoietic stem cells, Hematrol, Hemner, Hemril, heparinoid, Heptax, HER2 Antibody, Herponil, hESC Derived Dendritic Cells, hESC Derived Hematopoietic stem cells, Hespercorbin, Hexacorton, Hexadrol, hexetidine, Hexoderm, Hexoderm Salic, HF0220, HF1020, HFT-401, hG-CSFR ED Fc, Hiberna, high mobility group box 1 antibody, Hiloneed, Hinocam, hirudin, Hirudoid, Hison, Histamine H4 Receptor Antagonist, Hitenercept, Hizentra, HL036, HL161, HMPL001, HMPL004, HMPL004, HMPL011, HMPL342, HMPL692, honey bee venom, Hongqiang, Hotemin, HPH116, HTI101, HuCAL Antibody, Human adipose mesenchymal stem cells, anti-MHC class II monoclonal antibody, Human Immunoglobulin, Human Placenta Tissue Hydrolysate, HuMaxCD4, HuMax-TAC, Humetone, Humicade, Humira, Huons Betamethasone sodium phosphate, Huons dexamethasone sodium phosphate, Huons Piroxicam, Huons Talniflumate, Hurofen, Huruma, Huvap, HuZAF, HX02, Hyalogel, hyaluronate sodium, hyaluronic acid, hyaluronidase, Hyaron, Hycocin, Hycort, Hy-Cortisone, hydrocortisone, hydrocortisone acetate, hydrocortisone butyrate, hydrocortisone hemisuccinate, hydrocortisone sodium phosphate, hydrocortisone sodium succinate, Hydrocortistab, Hydrocortone, Hydrolin, Hydroquine, Hydro-Rx, Hydrosone HIKMA, hydroxychloroquine, hydroxychloroquine sulfate, Hylase Dessau, HyMEX, Hypen, HyQ, Hysonate, HZN602, I.M.75, IAP Inhibitors, Ibalgin, Ibalgin, Ibex, ibrutinib, IBsolvMIR, Ibu, Ibucon, Ibudolor, Ibufen, Ibuflam, Ibuflex, Ibugesic, Ibu-Hepa, Ibukim, Ibumal, Ibunal, Ibupental, Ibupril, Ibuprof, ibuprofen, Ibuscent, Ibusoft, Ibusuki Penjeong, Ibususpen, Ibutard, Ibutop, Ibutop, Ibutrex, IC487892, ichthammol, ICRAC Blocker, IDEC131, IDECCE9.1, Ides, Idicin, Idizone, IDN6556, Idomethine, IDR1, Idyl SR, Ifen, iguratimod, IK6002, IKK-beta inhibitor, IL17 Antagonist, IL-17 Inhibitor, IL-17RC, IL18, IL1Hy1, IL1R1, IL-23 Adnectin, IL23 Inhibitor, IL23 Receptor Antagonist, IL-31 mAb, IL-6 Inhibitor, IL6Qb, Ilacox, Ilaris, ilodecakin, ILV094, ILV095, Imaxetil, IMD0560, IMD2560, Imesel Plus, Iminoral, Immodin, IMMU103, IMMU106, Immucept, Immufine, Immunex Syrup, immunoglobulin, immunoglobulin G, Immunoprin, ImmunoRel, Immurin, IMO8400, IMP731 antibody, Implanta, Imunocell, Imuran, Imurek, Imusafe, Imusporin, Imutrex, IN0701, Inal, INCB039110, INCB18424, INCB28050, INCB3284, INCB3344, Indexon, Indic, Indo, Indo-A, Indobid, Indo-Bros, Indocaf, Indocarsil, Indocid, Indocin, Indomehotpas, Indomen, Indomet, Indometacin, indomethacin, Indomethasone, Indometin, Indomin, Indopal, Indoron, Indotroxin, INDUS830, INDUS83030, Infladase, Inflamac, Inflammasome inhibitor, Inflavis, Inflaxen, Inflectra, infliximab, Ingalipt, Inicox dp, Inmecin, Inmunoartro, Innamit, InnoD06006, INO7997, Inocin, Inoten, Inovan, Inpra, Inside Pap, Insider-P, Instacyl, Instracool, Intafenac, Intaflam, Inteban, Inteban Spansule, integrin, alpha 1 antibody, integrin, alpha 2 antibody, Intenurse, interferon alfa, interferon beta-1a, interferon gamma, interferon gamma antibody, Interking, interleukin 1 Hy1, interleukin 1 antibody, interleukin 1 receptor antibody, interleukin 1, beta antibody, interleukin 10, interleukin 10 antibody, interleukin 12, interleukin 12 antibody, interleukin 13 antibody, interleukin 15 antibody, interleukin 17 antibody, interleukin 17 receptor C, interleukin 18, interleukin 18 binding protein, interleukin 18 antibody, interleukin 2 receptor, alpha antibody, interleukin 20 antibody, Interleukin 21 mAb, interleukin 23 aptamer, interleukin 31 antibody, interleukin 34, Interleukin 6 Inhibitor, interleukin 6 antibody, interleukin 6 receptor antibody, interleukin 7, interleukin 7 receptor antibody, interleukin 8, interleukin 8 antibody, interleukin-18 antibody, Intidrol, Intradex, Intragam P, Intragesic, Intraglobin F, Intratect, Inzel, Iomab B, IOR-T3, IP751, IPH2201, IPH2301, IPH24, IPH33, IPI145, Ipocort, IPP201007, I-Profen, Iprox, Ipson, Iputon, IRAK4 Inhibitor, Iremod, Irtonpyson, IRX3, IRX5183, ISA247, ISIS104838, ISIS2302, ISISCRPRx, Ismafron, IsoQC inhibitor, Isox, ITF2357, Iveegam EN, Ivepred, IVIG-SN, IW001, Izilox, J607Y, J775Y, JAK Inhibitor, JAK3 inhibitor, JAK3 kinase inhibitor, JI3292, JI4135, Jinan Lida, JNJ10329670, JNJ18003414, JNJ26528398, JNJ27390467, JNJ28838017, JNJ31001958, JNJ38518168, JNJ39758979, JNJ40346527, JNJ7777120, JNT-Plus, Joflam, Joint Glucosamin, Jointec, Jointstem, Joinup, JPE1375, JSM10292, JSM7717, JSM8757, JTE051, JTE052, JTE522, JTE607, Jusgo, K412, K832, Kaflam, KAHR101, KAHR102, KAI9803, Kalymin, Kam Predsol, Kameton, KANAb071, Kappaproct, KAR2581, KAR3000, KAR3166, KAR4000, KAR4139, KAR4141, KB002, KB003, KD7332, KE298, keliximab, Kemanat, Kemrox, Kenacort, Kenalog, Kenaxir, Kenketsu Venoglobulin-IH, Keplat, Ketalgipan, Keto Pine, Keto, Ketobos, Ketofan, Ketofen, Ketolgan, Ketonal, Ketoplus Kata Plasma, ketoprofen, Ketores, Ketorin, ketorolac, ketorolac tromethamine, Ketoselect, Ketotop, Ketovail, Ketricin, Ketroc, Ketum, Keyi, Keyven, KF24345, K-Fenac, K-Fenak, K-Gesic, Kifadene, Kilcort, Kildrol, KIM127, Kimotab, Kinase Inhibitor 4SC, Kinase N, Kincort, Kindorase, Kineret, Kineto, Kitadol, Kitex, Kitolac, KLK1 Inhibitor, Klofen-L, Klotaren, KLS-40 or, KLS-40ra, KM277, Knavon, Kodolo orabase, Kohakusanin, Koide, Koidexa, Kolbet, Konac, Kondro, Kondromin, Konshien, Kontab, Kordexa, Kosa, Kotase, KPE06001, KRP107, KRP203, KRX211, KRX252, KSB302, K-Sep, Kv 1.3 Blocker, Kv1.3 4SC, Kv1.3 inhibitor, KVK702, Kynol, L156602, Labizone, Labohydro, Labopen, Lacoxa, Lamin, Lamit, Lanfetil, laquinimod, larazotide acetate, LAS186323, LAS187247, LAS41002, Laticort, LBEC0101, LCP3301, LCP-Siro, LCP-Tacro, LCsA, LDP392, Leap-S, Ledercort, Lederfen, Lederlon, Lederspan, Lefenine, leflunomide, Leflux, Lefno, Lefra, Leftose, Lefumide, Lefunodin, Lefva, lenalidomide, lenercept, LentiRA, LE015520, Leodase, Leukine, Leukocyte function-associated antigen-1 antagonist, leukocyte immunoglobulin-like receptor, subfamily A, member 4 antibody, Leukothera, leuprolide acetate, levalbuterol, levomenthol, LFA-1 Antagonist, LFA451, LFA703, LFA878, LG106, LG267 Inhibitors, LG688 Inhibitors, LGD5552, Li Life, LidaMantle, Lidex, lidocaine, lidocaine hydrochloride, Lignocaine hydrochloride, LIM0723, LIM5310, Limethason, Limus, Limustin, Lindac, Linfonex, Linola acute, Lipcy, lisofylline, Listran, Liver X Receptor modulator, Lizak, LJP1207, LJP920, Lobafen, Lobu, Locafluo, Localyn, Locaseptil-Neo, Locpren, Lodine, Lodotra, Lofedic, Loflam, Lofnac, Lolcam, Lonac, lonazolac calcium, Loprofen, Loracort, Lorcam, Lorfenamin, Lorinden Lotio, Lorncrat, lornoxicam, Lorox, losmapimod, loteprednol etabonate, Loteprednol, Lotirac, Low Molecular *Ganoderma Lucidum* Polysaccharide, Loxafen, Loxfenine, Loxicam, Loxofen, Loxonal, Loxonin, loxoprofen sodium, Loxoron, LP183A1, LP183A2, LP204A1, LPCN1019, LT1942, LT1964, LTNS101, LTNS103, LTNS106, LTNS108, LTS1115, LTZMP001, Lubor, lumiracoxib, Lumitect, LX2311, LX2931, LX2932, LY2127399, LY2189102, LY2439821, LY294002, LY3009104, LY309887, LY333013, lymphocyte activation gene 3 antibody, Lymphoglobuline, Lyser, lysine aspirin, Lysobact, Lysoflam, Lysozyme hydrochloride, M3000, M834, M923, mAb hG-CSF, MABP1, macrophage migration inhibitory factor antibody, Maitongna, Majamil prolongatum, major histocompatibility complex class II DR antibody, major histocompatibility complex class II antibody, Malidens, Malival, mannan-binding lectin, mannan-binding lectin-associated serine protease-2 antibody, MapKap Kinase 2 Inhibitor, maraviroc, Marlex, masitinib, Maso, MASP2 antibody, MAT304, Matrix Metalloprotease Inhibitor, mavrilimumab, Maxiflam, Maxilase, Maximus, Maxisona, Maxius, Maxpro, Maxrel, Maxsulid, Maxy12, Maxy30, MAXY4, Maxy735, Maxy740, Mayfenamic, MB11040, MBPY003b, MCAF5352A, McCam, McRofy, MCS18, MD707, MDAM, MDcort, MDR06155, MDT012, Mebicam, Mebuton, meclofenamate sodium, Meclophen, Mecox, Medacomb, Medafen, Medamol, Medesone, MEDI2070, MEDI5117, MEDI541, MEDI552, MEDI571, Medicox, Medifen, Medisolu, Medixon, Mednisol, Medrol, Medrolon, medroxyprogesterone acetate, Mefalgin, mefenamic acid, Mefenix, Mefentan, Meflen, Mefnetra forte, Meftagesic-DT, Meftal, Megakaryocyte Growth and Development Factor, Megaspas, Megaster, megestrol acetate, Meite, Meksun, Melbrex, Melcam, Melcam, Melflam, Melic, Melica, Melix, Melocam, Melocox, Mel-One, Meloprol, Melosteral, Melox, Meloxan, Meloxcam, Meloxic, Meloxicam, Meloxifen, Meloxin, Meloxiv, Melpred, Melpros, Melurjin, Menamin, Menisone, Menthomketo, Menthoneurin, Mentocin, Mepa, Mepharen, meprednisone, Mepresso, Mepsolone, mercaptopurine, Mervan, Mesadoron, mesalamine, Mesasal, Mesatec, Mesenchymal Precursor Cells, mesenchymal stem cell, Mesipol, Mesren, Mesulan, Mesulid, Metacin, Metadaxan, Metaflex, Metalcaptase, metalloenzyme inhibitors, Metapred, Metax, Metaz, Meted, Metedic, Methacin, Methaderm, Methasone, Methotrax, methotrexate, methotrexate sodium, Methpred, Methyl prednisolone acetate, methyl salicylate, methyl sulphonyl methane, Methylon, Methylpred, methylprednisolone, methylprednisolone acetate, methylprednisolone sodium succinate, methylprednisolone succinate, Methylprednisolone, Methysol, Metindol, Metoart, Metoject, Metolate, Metoral, Metosyn, Metotab, Metracin, Metrex, metronidazole, Metypred, Mevamox, Mevedal, Mevilox, Mevin SR, Mexilal, Mexpharm, Mext, Mextran, MF280, M-FasL, MHC class II beta chain peptide, Micar, Miclofen, Miclofenac, Micofenolato Mofetil, Micosone, Microdase, microRNA 181a-2 oligonucleotide, MIF Inhibitors, MIFQb, MIKA-Ketoprofen, Mikametan, milodistim, Miltax, Minafen, Minalfen, Minalfene, Minesulin, Minocort, Mioflex, Miolox, Miprofen, Miridacin, Mirloks, Misoclo, Misofenac, MISTB03, MISTB04, Mitilor, mizoribine, MK409, MK0359, MK0812, MK0873, MK2 Inhibitors, MK50, MK8457, MK8808, MKC204, MLN0002, MLN0415, MLN1202, MLN273, MLN3126, MLN3701, MLN3897, MLNM002, MM093, MM7XX, MN8001, Mobic, Mobicam, Mobicox, Mobifen Plus, Mobilat, Mobitil, Mocox, Modigraf, Modrasone, Modulin, Mofecept, Mofetyl, mofezolac sodium, Mofilet, Molace, molgramostim, Molslide, Momekin, Momen Gele, Moment 100, Momesone, Momesun, Mometamed, mometasone, mometasone furoate, Monimate, monosodium alpha-luminol, Mopik, MOR103, MOR104, MOR105, MOR208 antibody, MORAb022, Moricam, morniflumate, Mosuolit, Motoral, Movaxin, Mover, Movex, Movix, Movoxicam, Mox Forte, Moxen, moxifloxacin hydrochloride, Mozobil, MP, MP0210, MP0270, MP1000, MP1031, MP196, MP435, MPA, mPGES-1 inhibitor, MPSS, MRX7EAT, MSL, MT203, MT204, mTOR Inhibitor, MTRX1011A, Mucolase, Multicort, MultiStem, muramidase, muramidase, muramidase hydrochloride, muromonab-CD3, Muslax, Muspinil, Mutaze, Muvera, MX68, Mycept, Mycocell, Mycocept, Mycofenolatmofetil Actavis, Mycofet, Mycofit, Mycolate, Mycoldosa, Mycomun, Myconol, mycophenolate mofetil, mycophenolate sodium, mycophenolic acid, Mycotil, myeloid progenitor cells, Myfenax, Myfetil, Myfortic, Mygraft, Myochrysine, Myocrisin, Myprodol, Mysone, nab-Cyclosporine, Nabentac, nabiximols, Nabton, Nabuco, Nabucox, Nabuflam, Nabumet, nabumetone, Nabuton, Nac Plus, Nacta, Nacton, Nadium, Naklofen SR, NAL1207, NAL1216, NAL1219, NAL1268, NAL8202, Nalfon, Nalgesin S, namilumab, Namsafe, nandrolone, Nanocort, Nanogam, Nanosomal Tacrolimus, Napageln, Napilac, Naprelan, Napro, Naprodil, Napronax, Napropal, Naproson, Naprosyn, Naproval, Naprox, naproxen, naproxen sodium, Naproxin, Naprozen, Narbon, Narexsin, Naril, Nasida, natalizumab, Naxdom, Naxen, Naxin, Nazovel, NC2300, ND07, NDC01352, Nebumetone, NecLipGCSF, Necsulide, Necsunim, Nelsid-S, Neo Clobenate, Neo Swiflox FC, Neocoflan, Neo-Drol, Neo-Eblimon, Neo-Hydro, Neoplanta, Neoporine, Neopreol, Neoprox, Neoral, Neotrexate, Neozen, Nepra, Nestacort, Neumega, Neupogen, Neuprex, Neurofenac, Neurogesic, Neurolab, Neuroteradol, Neuroxicam, Neutalin, neutrazumab, Neuzym, New Panazox, Newfenstop, New-Gam, Newmafen, Newmatal, Newsicam, NEX1285, sFcRIIB, Nextomab, NF-kappaB Inhibitor, NF-kB inhibitor, NGD20001, NHP554B, NHP554P, NI0101 antibody, NI0401, NI0501 antibody, NI0701, NI071, NI1201 antibody, NI1401, Nicip, Niconas, Nicool, NiCord, Nicox, Niflumate, Nigaz, Nikam, Nilitis, Nimace, Nimaid, Nimark-P, Nimaz, Nimcet Juicy, Nime, Nimed, Nimepast, nimesulide, Nimesulix, Nimesulon, Nimica Plus, Nimkul, Nimlin, Nimnat, Nimodol, Nimpidase, Nimsaid-S, Nimser, Nimsy-SP, Nimupep, Nimusol, Nimutal, Nimuwin, Nimvon-S, Nincort, Niofen, Nipan, Nipent, Nise, Nisolone, Nisopred, Nisoprex, Nisulid, nitazoxanide, Nitcon, nitric oxide, Nizhvisal B, Nizon, NL, NMR1947, NN8209, NN8210, NN8226, NN8555, NN8765, NN8828, NNC014100000100, NNC051869, Noak, Nodevex, Nodia, Nofenac, Noflagma, Noflam, Noflamen, Noflux, Non-antibacterial Tetracyclines, Nonpiron, Nopain, Normferon, Notpel, Notritis, Novacort, Novagent, Novarin, Novigesic, NOXA12, NOXD19, Noxen, Noxon, NPI1302a-3, NPI1342, NPI1387, NPI1390, NPRCS1, NPRCS2, NPRCS3, NPRCS4, NPRCS5, NPRCS6, NPS3, NPS4, nPT-ery, NU3450, nuclear factor NF-kappa-B p65 subunit oligonucleotide, Nucort, Nulojix, Numed-Plus, Nurokind Ortho, Nusone-H, Nutrikemia, Nuvion, NV07alpha, NX001, Nyclobate, Nyox, Nysa, Obarcort, 00002417, OC2286, ocaratuzumab, OCTSG815, Oedemase, Oedemase-D, ofatumumab, Ofgyl-O, Ofvista, OHR118, OKi, Okifen, Oksamen, Olai, olokizumab, Omeprose E, Omnacortil, Omneed, Omniclor, Omnigel, Omniwel, onercept, 0N04057, ONS1210, ONS1220, Ontac Plus, Ontak, ONX0914, OPC6535, opebacan, OPN101, OPN201, OPN302, OPN305, OPN401, oprelvekin, OPT66, Optifer, Optiflur, OptiMIRA, Orabase Hca, Oradexon, Oraflex, OralFenac, Oralog, Oralpred, Ora-sed, Orasone, orBec, Orbone forte, Orcl, ORE10002, ORE10002, Orencia, Org214007, Org217993, Org219517, Org223119, Org37663, Org39141, Org48762, Org48775, Orgadrone, Ormoxen, Orofen Plus, Oromylase Biogaran, Orthal Forte, Ortho Flex, Orthoclone OKT3, Orthofen, Orthoflam, Orthogesic, Orthoglu, Ortho-II, Orthomac, Ortho-Plus, Ortinims, Ortofen, Orudis, Oruvail, OS2, Oscart, Osmetone, Ospain, Ossilife, Ostelox, Osteluc, Osteocerin, osteopontin, Osteral, otelixizumab, Otipax, Ou Ning, OvaSave, OX40 Ligand Antibody, Oxa, Oxagesic CB, Oxalgin DP, oxaprozin, OXCQ, Oxeno, Oxib MD, Oxibut, Oxicam, Oxiklorin, Oximal, Oxynal, oxyphenbutazone, Oxyphenbutazone, ozoralizumab, P13 peptide, P1639, P21, P2X7 Antagonists, p38 Alpha Inhibitor, p38 Antagonist, p38 MAP kinase inhibitor, p38alpha MAP Kinase Inhibitor, P7 peptide, P7170, P979, PA401, PA517, Pabi-dexamethasone, PAC, PAC10649, paclitaxel, Painoxam, Paldon, Palima, pamapimod, Pamatase, Panafcort, Panafcortelone, Panewin, PanGraf, Panimun Bioral, Panmesone, Panodin SR, Panslay, Panzem, Panzem NCD, PAP1, papain, Papirzin, Pappen K Pap, Paptinim-D, paquinimod, PAR2 Antagonist, Paracetamol, Paradic, Parafen TAJ, Paramidin, Paranac, Parapar, Parci, parecoxib, Parixam, Parry-S, Partaject Busulfan, pateclizumab, Paxceed, PBI0032, PBI1101, PBI1308, PBI1393, PBI1607, PBI1737, PBI2856, PBI4419, PBI4419, P-Cam, PCI31523, PCI32765, PCI34051, PCI45261, PCI45292, PCI45308, PD360324, PD360324, PDA001, PDE4 inhibitor, PDE-IV Inhibitor, PDL241 antibody, PDL252, Pediapred, Pefree, pegacaristim, Peganix, Peg-Interleukin 12, pegsunercept, Pegsunercept, PEGylated arginine deiminase, peldesine, pelubiprofen, Penacle, penicillamine, Penostop, Pentalgin, Pentasa, Pentaud, pentostatin, Peon, Pepdase, Pepser, Peptirase, Pepzen, Pepzol, Percutalgine, Periochip, Peroxisome Proliferator Activated Receptor gamma modulators, Petizene, PF00344600, PF04171327, PF04236921, PF04308515, PF05230905, PF05280586, PF251802, PF3475952, PF3491390, PF3644022, PF4629991, PF4856880, PF5212367, PF5230896, PF547659, PF755616, PF9184, PG27, PG562, PG760564, PG8395, PGE3935199, PGE527667, PH5, PH797804, PHA408, Pharmaniaga Mefenamic acid, Pharmaniaga Meloxicam, Pheldin, Phenocept, phenylbutazone, PHY702, PI3K delta inhibitor, PI3K Gamma/Delta Inhibitor, PI3K Inhibitor, Picalm, pidotimod, piketoprofen, Pilelife, Pilopil, Pilovate, pimecrolimus, Pipethanen, Piractam, Pirexyl, Pirobet, Piroc, Pirocam, Pirofel, Pirogel, Piromed, Pirosol, Pirox, Piroxen, Piroxicam, piroxicam betadex, Piroxifar, Piroxil, Piroxim, Pixim, Pixykine, PKC Theta Inhibitor, PL3100, PL5100 Diclofenac, Placenta Polypeptide, Plaquenil, plerixafor, Plocfen, PLR14, PLR18, Plutin, PLX3397, PLX5622, PLX647, PLX-BMT, pms-Diclofenac, pms-Ibuprofen, pms-Leflunomide, pms-Meloxicam, pms-Piroxicam, pms-Prednisolone, pms-Sulfasalazine, pms-Tiaprofenic, PMX53, PN0615, PN100, PN951, podofilox, POL6326, Polcortolon, Polyderm, Polygam S/D, Polyphlogin, Poncif, Ponstan, Ponstil Forte, Porine-A Neoral, Potaba, potassium aminobenzoate, Potencort, Povidone, povidone iodine, pralnacasan, Prandin, Prebel, Precodil, Precortisyl Forte, Precortyl, Predfoam, Predicort, Predicorten, Predilab, Predilone, Predmetil, Predmix, Predna, Prednesol, Predni, prednicarbate, Prednicort, Prednidib, Prednifarma, Prednilasca, prednisolone, Deltacortril (prednisolone), prednisolone acetate, prednisolone sodium phosphate, prednisolone sodium succinate, prednisolone sodium succinate, prednisone, prednisone acetate, Prednitop, Prednol-L, Prednox, Predone, Predonema, Predsol, Predsolone, Predsone, Predval, Preflam, Prelon, Prenaxol, Prenolone, Preservex, Preservin, Presol, Preson, Prexige, Priliximab, Primacort, Primmuno, Primofenac, prinaberel, Privigen, Prixam, Probuxil, Procarne, Prochymal, Procider-EF, Proctocir, Prodase, Prodel B, Prodent, Prodent Verde, Proepa, Profecom, Profenac L, Profenid, Profenol, Proflam, Proflex, Progesic Z, proglumetacin, proglumetacin maleate, Prograf, Prolase, Prolixan, promethazine hydrochloride, Promostem, Promune, PronaB, pronase, Pronat, Prongs, Pronison, Prontoflam, Propaderm-L, Propodezas, Propolisol, Proponol, propyl nicotinate, Prostaloc, Prostapol, Protacin, Protase, Protease Inhibitors, Protectan, Proteinase Activated Receptor 2 Inhibitor, Protofen, Protrin, Proxalyoc, Proxidol, Proxigel, Proxil, Proxym, Prozym, PRT062070, PRT2607, PRTX100, PRTX200, PRX106, PRX167700, Prysolone, PS031291, PS375179, PS386113, PS540446, PS608504, PS826957, PS873266, Psorid, PT, PT17, PTL101, P-Transfer Factor peptides, PTX3, Pulminiq, Pulsonid, Purazen, Pursin, PVS40200, PX101, PX106491, PX114, PXS2000, PXS2076, PYM60001, Pyralvex, Pyranim, pyrazinobutazone, Pyrenol, Pyricam, Pyrodex, Pyroxi-Kid, QAX576, Qianbobiyan, QPI1002, QR440, qT3, Quiacort, Quidofil, R107s, R125224, R1295, R132811, R1487, R1503, R1524, R1628, R333, R348, R548, R7277, R788, rabeximod, Radix *Isatidis*, Radofen, Raipeck, Rambazole, Randazima, Rapacan, Rapamune, Raptiva, Ravax, Rayos, RDEA119, RDEA436, RDP58, Reactine, Rebif, REC200, Recartix-DN, receptor for advanced glycation end products antibody, Reclast, Reclofen, recombinant HSA-TIMP-2, recombinant human alkaline Phosphatase, recombinant Interferon Gamma, Recominant human alkaline phosphatase, Reconil, Rectagel HC, Recticin, Recto Menaderm, Rectos, Redipred, Redolet, Refastin, Regenica, REGN88, Relafen, Relaxib, Relev, Relex, Relifen, Relifex, Relitch, Rematof, remestemcel-1, Remesulidum, Remicade® (infliximab), Remsima, Remsima, Remsima, ReN1869, Renacept, Renfor, Renodapt, Renodapt-S, Renta, Reosan, Repare-AR, Reparilexin, reparixin, Repertaxin, Repisprin, Resochin, Resol, resolvin E1, Resurgil, Re-tin-colloid, Retoz, Reumacap, Reumacon, Reumadolor, Reumador, Reumanisal, Reumazin, Reumel, Reumotec, Reuquinol, revamilast, Revascor, Reviroc, Revlimid, Revmoksikam, Rewalk, Rexalgan, RG2077, RG3421, RG4934 antibody, RG7416, RG7624, Rheila, Rheoma, Rheprox, Rheudenolone, Rheufen, Rheugesic, Rheumacid, Rheumacort, Rheumatrex, Rheumesser, Rheumid, Rheumon, Rheumox, Rheuoxib, Rhewlin, Rhucin, RhuDex, Rhulef, Ribox, Ribunal, Ridaura, rifaximin, rilonacept, rimacalib, Rimase, Rimate, Rimatil, Rimesid, risedronate sodium, Ritamine, Rito, Rituxan, rituximab, RNS60, R01138452, Ro313948, R03244794, R05310074, Rob803, Rocamix, Rocas, Rofeb, rofecoxib, Rofee, Rofewal, Roficip Plus, Rojepen, Rokam, Rolodiquim, Romacox Fort, Romatim, romazarit, Ronaben, ronacaleret, Ronoxcin, ROR Gamma T Antagonist, ROR gamma t inverse agonists, Rosecin, rosiglitazone, Rosmarinic acid, Rotan, Rotec, Rothacin, Roxam, Roxib, Roxicam, Roxopro, Roxygin DT, RP54745, RPI78, RPI78M, RPI78MN, RPIMN, RQ00000007, RQ00000008, RTA402, R-Tyflam, Rubicalm, Rubifen, Ruma pap, Rumalef, Rumidol, Rumifen, Runomex, rusalatide acetate, ruxolitinib, RWJ445380, RX10001, Rycloser MR, Rydol, S1P Receptor Agonists, S1P Receptor Modulators, S1P1 Agonist, S1P1 receptor agonist, 52474, S3013, SA237, SA6541, Saaz, S-adenosyl-L-methionine-sulfate-p-toluene sulfonate, Sala, Salazidin, Salazine, Salazopyrin, Salcon, Salicam, salsalate, Sameron, SAN300, Sanaven, Sandimmun, Sandoglobulin, Sanexon, SangCya, SAR153191, SAR302503, SAR479746, Sarapep, sargramostim, Sativex, Savantac, Save, Saxizon, Sazo, SB1578, SB210396, SB217969, SB242235, SB273005, SB281832, SB683698, SB751689, SBI087, SC080036, SC12267, SC409, Scaflam, SCD ketoprofen, SCIO323, SCIO469, SD-15, SD281, SDP051 antibody, Sd-rxRNA, secukinumab, Sedase, Sedilax, Sefdene, Seizyme, SEL113, Seladin, Selecox, selectin P ligand antibody, Glucocorticoid Receptor Agonist, Selectofen, Selektine, SelK1 antibody, Seloxx, Selspot, Selzen, Selzenta, Selzentry, semapimod, semapimod hydrochloride, semparatide, Semparatide, Senafen, Sendipen, Senterlic, SEP119249, Sepdase, Septirose, Seractil, Serafen-P, Serase, Seratid D, Seratiopeptidase, Serato-M, Seratoma Forte, Serazyme, Serezon, Sero, Serodase, Serpicam, Serra, serrapeptase, Serratin, Serratiopeptidase, Serrazyme, Servisone, Seven E P, SGI1252, SGN30, SGN70, SGX203, shark cartilage extract, Sheril, Shield, Shifazen, Shifazen-Fort, Shincort, Shincort, Shiosol, ShK186, Shuanghuangxiaoyan, 51615, 51636, Sigmasporin, Sigmasporin, SIM916, Simpone, Simulect, Sinacort, Sinalgia, Sinapol, Sinatrol, Sinsia, siponimod, Sirolim, sirolimus, Siropan, Sirota, Sirova, sirukumab, Sistal Forte, SKF105685, SKF105809, SKF106615, SKF86002, Skinalar, Skynim, Skytrip, SLAM family member 7 antibody, Slo-indo, SM101, SM201 antibody, SM401, SMAD family member 7 oligonucleotide, SMART Anti-IL-12 Antibody, SMP114, SNO030908, SNO070131, sodium aurothiomalate, sodium chondroitin sulfate, sodium deoxyribonucleotide, sodium gualenate, sodium naproxen, sodium salicylate, Sodixen, Sofeo, Soleton, Solhidrol, Solicam, Soliky, Soliris, Sol-Melcort, Solomet, Solondo, Solone, Solu-Cort, Solu-Cortef, Solu-Decortin H, Solufen, Solu-Ket, Solumark, Solu-Medrol, Solupred, Somalgen, somatropin, Sonap, Sone, sonepcizumab, Sonexa, Sonim, Sonim P, Soonil, Soral, Sorenil, sotrastaurin acetate, SP-10, SP600125, Spanidin, SP-Cortil, SPD550, Spedace, sperm adhesion molecule 1, Spictol, spleen tyrosine kinase oligonucleotide, Sporin, S-prin, SPWF1501, SQ641, SQ922, SR318B, SR9025, SRT2104, SSR150106, SSR180575, SSSO7 antibody, ST1959, STA5326, stabilin 1 antibody, Stacort, Stalogesic, stanozolol, Staren, Starmelox, Stedex IND-SWIFT, Stelara, Stemin, Stenirol, Sterapred, Steriderm S, Sterio, Sterisone, Steron, *stichodactyla helianthus* peptide, Stickzenol A, Stiefcortil, Stimulan, STNM01, Store Operated Calcium Channel (SOCC) Modulator, STP432, STP900, Stratasin, Stridimmune, Strigraf, SU Medrol, Subreum, Subuton, Succicort, Succimed, Sulan, Sulcolon, Sulfasalazin Heyl, Sulfasalazin, sulfasalazine, Sulfovit, Sulidac, Sulide, sulindac, Sulindex, Sulinton, Sulphafine, Sumilu, SUN597, Suprafen, Supretic, Supsidine, Surgam, Surgamine, Surugamu, Suspen, Suton, Suvenyl, Suwei, SW Dexasone, Syk Family Kinase Inhibitor, Syn1002, Synacran, Synacthen, Synalar C, Synalar, Synavive, Synercort, Sypresta, T cell cytokine-inducing surface molecule antibody, T cell receptor antibody, T5224, T5226, TA101, TA112, TA383, TA5493, tabalumab, Tacedin, Tacgraf, TACIFc5, Tacrobell, Tacrograf, Tacrol, tacrolimus, Tadekinig alpha, Tadolak, TAFA93, Tafirol Artro, Taizen, TAK603, TAK715, TAK783, Takfa, Taksta, talarozole, Talfin, Talmain, talmapimod, Talmea, Talnif, talniflumate, Talos, Talpain, Talumat, Tamalgen, Tamceton, Tamezon, Tandrilax, tannins, Tannosynt, Tantum, tanzisertib, Tapainbeta, Tapoein, Tarenac, tarenflurbil, Tarimus, Tarproxen, Tauxib, Tazomust, TBR652, TC5619, T-cell, immune regulator 1, ATPase, H+ transporting, lysosomal VO subunit A3 antibody, TCK1, T-cort, T-Dexa, Tecelac, Tecon, teduglutide, Teecort, Tegeline, Tementil, temoporfin, Tencam, Tendrone, Tenefuse, Tenfly, tenidap sodium, Tenocam, Tenoflex, Tenoksan, Tenotil, tenoxicam, Tenoxim, Tepadina, Teracort, Teradol, tetomilast, TG0054, TG1060, TG20, TG20, tgAAC94, Th1/Th2 Cytokine Synthase Inhibitor, Th-17 cell inhibitors, Thalido, thalidomide, Thalomid, Themisera, Thenil, Therafectin, Therapyace, thiarabine, Thiazolopyrimidines, thioctic acid, thiotepa, THR090717, THR0921, Threenofen, Thrombate III, Thymic peptide, Thymodepressin, Thymogam, Thymoglobulin, Thymoglobuline, Thymoject thymic peptides, thymomodulin, thymopentin, thymopolypetides, tiaprofenic acid, tibezonium iodide, Ticoflex, tilmacoxib, Tilur, T-immune, Timocon, Tiorase, Tissop, TKB662, TL011, TLR4 antagonists, TLR8 inhibitor, TM120, TM400, TMX302, TNF Alpha inhibitor, TNF alpha-TNF receptor antagonist, TNF antibody, TNF receptor superfamily antagonists, TNF TWEAK Bi-Specific, TNF-Kinoid, TNFQb, TNFR1 antagonist, TNR001, TNX100, TNX224, TNX336, TNX558, tocilizumab, tofacitinib, Tokuhon happ, TOL101, TOL102, Tolectin, TolerimAb, Tolerostem, Tolindol, toll-like receptor 4 antibody, toll-like receptor antibody, tolmetin sodium, Tongkeeper, Tonmex, Topflame, Topicort, Topleucon, Topnac, Toppin Ichthammol, toralizumab, Toraren, Torcoxia, Toroxx, Tory, Toselac, Totaryl, Touch-med, Touchron, Tovok, Toxic apis, Toyolyzom, TP4179, TPCA1, TPI526, TR14035, Tradil Fort, Traficet-EN, Tramace, tramadol hydrochloride, tranilast, Transimune, Transporina, Tratul, Trexall, Triacort, Triakort, Trialon, Triam, triamcinolone, triamcinolone acetate, triamcinolone acetonide, triamcinolone acetonide acetate, triamcinolone hexacetonide, Triamcort, Triamsicort, Trianex, Tricin, Tricort, Tricortone, TricOs T, Triderm, Trilac, Trilisate, Trinocort, Trinolone, Triolex, triptolide, Trisfen, Trivaris, TRK170, TRK530, Trocade, trolamine salicylate, Trolovol, Trosera, Trosera D, Troycort, TRX1 antibody, TRX4, Trymoto, Trymoto-A, TT301, TT302, TT32, TT32, TT33, TTI314, tumor necrosis factor, tumor necrosis factor 2-methoxyethyl phosphorothioate oligonucleotide, tumor necrosis factor antibody, tumor necrosis factor kinoid, tumor necrosis factor oligonucleotide, tumor necrosis factor receptor superfamily, member 1B antibody, tumor necrosis factor receptor superfamilylB oligonucleotide, tumor necrosis factor superfamily, member 12 antibody, tumor necrosis factor superfamily, member 4 antibody, tumor protein p53 oligonucleotide, tumour necrosis factor alpha antibody, TuNEX, TXA127, TX-RAD, TYK2 inhibitors, Tysabri, ubidecarenone, Ucerase, ulodesine, Ultiflam, Ultrafastin, Ultrafen, Ultralan, U-Nice-B, Uniplus, Unitrexate, Unizen, Uphaxicam, UR13870, UR5269, UR67767, Uremol-HC, Urigon, U-Ritis, ustekinumab, V85546, Valcib, Valcox, valdecoxib, Valdez, Valdixx, Valdy, Valentac, Valoxib, Valtune, Valus AT, Valz, Valzer, Vamid, Vantal, Vantelin, VAP-1 SSAO Inhibitor, vapaliximab, varespladib methyl, Varicosin, Varidase, vascular adhesion protein-1 antibody, VB110, VB120, VB201, VBY285, Vectra-P, vedolizumab, Vefren, VEGFR-1 Antibody, Veldona, veltuzumab, Vendexine, Venimmun N, Venoforte, Venoglobulin-IH, Venozel, Veral, Verax, vercirnon, vero-dexamethasone, Vero-Kladribin, Vetazone, VGX1027, VGX750, Vibex MTX, vidofludimus, Vifenac, Vimovo, Vimultisa, Vincort, Vingraf, Vioform-HC, Vioxl, Vioxx, Virobron, visilizumab, Vivaglobin, Vivalde Plus, Vivian-A, VLST002, VLST003, VLST004, VLST005, VLST007, Voalla, voclosporin, Vokam, Vokmor, Volmax, Volna-K, Voltadol, Voltagesic, Voltanase, Voltanec, Voltaren, Voltarile, Voltic, Voren, vorsetuzumab, Votan-SR, VR909, VRA002, VRP1008, VRS826, VRS826, VT111, VT214, VT224, VT310, VT346, VT362, VTX763, Vurdon, VX30 antibody, VX467, VXS, VX509, VX702, VX740, VX745, VX745, VX850, W54011, Walacort, Walix, WC3027, Wilgraf, Winflam, Winmol, Winpred, Winsolve, Wintogeno, WIP901, Woncox, WSB711 antibody, WSB712 antibody, WSB735, WSB961, X071NAB, X083NAB, Xantomicin Forte, Xedenol, Xefo, Xefocam, Xenar, Xepol, X-Flam, Xibra, Xicam, Xicotil, Xifaxan, XL499, XmAb5483, XmAb5485, XmAb5574, XmAb5871, XOMA052, Xpress, XPro1595, XtendTNF, XToll, Xtra, Xylex-H, Xynofen SR, Yang Shu-IVIG, YHB14112, YM974, Youfeline, Youfenac, Yuma, Yumerol, Yuroben, YY piroxicam, Z104657A, Zacy, Zaltokin, zaltoprofen, Zap70 Inhibitor, Zeepain, Zeloxim Fort, Zema-Pak, Zempack, Zempred, Zenapax, Zenas, Zenol, Zenos, Zenoxone, Zerax, Zerocam, Zerospasm, ZFNs, zinc oxide, Zipsor, ziralimumab, Zitis, Zix-S, Zocort, Zodixam, Zoftadex, zoledronic acid, Zolfin, Zolterol, Zopyrin, Zoralone, ZORprin, Zortress, ZP1848, zucapsaicin, Zunovate, Zwitterionic polysaccharides, ZY1400, Zybodies, Zycel, Zyrofen, Zyrogen Inhibitors, Zyser, Zytrim, and Zywin-Forte. In addition, the anti-inflammatory drugs, as listed above, may be combined with one or more agents listed above or herein or with other agents known in the art.

In one embodiment, the drug is a drug that inhibits, reduces or modulates the signaling and/or activity of PDGF-receptors (PDGFR). For example, in one embodiment, the PDGFR modulator is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFRα or PDGFRβ. In one embodiment, the PDGF antagonist is the anti-PDGF-β aptamer E10030, dasatinib, sunitinib, axitinib, sorefenib, imatinib, imatinib mesylate, nintedanib, pazopanib HCl, ponatinib, MK-2461, pazopanib, crenolanib, PP-121, telatinib, imatinib, KRN 633, CP 673451, TSU-68 (orantinib), Ki8751, amuvatinib, tivozanib, masitinib, motesanib diphosphate, dovitinib, dovitinib dilactic acid, FOVISTA, or linifanib (ABT-869). In a further embodiment, the PDGF antagonist also has VEGF antagonist activity. For example, an anti-VEGF/PDGF-B darpin, dasatinib, dovitinib, Ki8751, telatinib, TSU-68 (orantinib) or motesanib diphosphate are known inhibitors of both VEGF and PDGF, and can be used in the methods described herein.

Examples of other suitable drugs for use with the devices and methods described herein include, but are not limited to: A0003, A36 peptide, AAV2-sFLT01, ACE041, ACU02, ACU3223, ACU4429, AdPEDF, aflibercept, AG13958, aganirsen, AGN150998, AGN745, AL39324, AL78898A, AL8309B, ALN-VEG01, alprostadil, AM1101, amyloid beta antibody, anecortave acetate, Anti-VEGFR-2 Alterase, Aptocine, APX003, ARC1905, ARC1905 with Lucentis, ATG3, ATP-binding cassette, sub-family A, member 4 gene, ATXS10, Avastin with Visudyne, AVT101, AVT2, bertilimumab, bevacizumab with verteporfin, bevasiranib sodium, bevasiranib sodium; with ranibizumab, brimonidine tartrate, BVA301, canakinumab, Cand5, Cand5 with Lucentis, CERE140, ciliary neurotrophic factor, CLT009, CNT02476, collagen monoclonal antibody, complement component 5 aptamer (pegylated), complement component 5 aptamer (pegylated) with ranibizumab, complement component C3, complement factor B antibody, complement factor D antibody, copper oxide with lutein, vitamin C, vitamin E, and zinc oxide, dalantercept, DE109, bevacizumab, ranibizumab, triamcinolone, triamcinolone acetonide, triamcinolone acetonide with verteporfin, dexamethasone, dexamethasone with ranibizumab and verteporfin, disitertide, DNA damage inducible transcript 4 oligonucleotide, E10030, E10030 with Lucentis, EC400, eculizumab, EGP, EHT204, embryonic stem cells, human stem cells, endoglin monoclonal antibody, EphB4 RTK Inhibitor, EphB4 Soluble Receptor, ESBA1008, ETX6991, Evizon, Eyebar, EyePromise Five, Eyevi, Eylea, F200, FCFD4514S, fenretinide, fluocinolone acetonide, fluocinolone acetonide with ranibizumab, fms-related tyrosine kinase 1 oligonucleotide, fms-related tyrosine kinase 1 oligonucleotide with kinase insert domain receptor 169, fosbretabulin tromethamine, Gamunex, GEM220, GS101, GSK933776, HC31496, Human n-CoDeR, HYB676, IBI-20089 with ranibizumab (Lucentis®), iCo-008, Icon1, I-Gold, Ilaris, Iluvien, Iluvien with Lucentis, immunoglobulins, integrin alpha5beta1 immunoglobulin fragments, Integrin inhibitor, IRIS Lutein, I-Sense Ocushield, Isonep, isopropyl unoprostone, JPE1375, JSM6427, KH902, LentiVue, LFG316, LP590, LPO1010AM, Lucentis, Lucentis with Visudyne, Lutein ekstra, Lutein with *myrtillus* extract, Lutein with zeaxanthin, M200, M200 with Lucentis, Macugen, MC1101, MCT355, mecamylamine, Microplasmin, motexafin lutetium, MP0112, NADPH oxidase inhibitors, aeterna shark cartilage extract (Arthrovas™, Neoretna™, Psovascar™) neurotrophin 4 gene, Nova21012, Nova21013, NT501, NT503, Nutri-Stulln, ocriplasmin, OcuXan, Oftan Macula, Optrin, ORA102 with bevacizumab (Avastin®), P144, P17, Palomid 529, PAN90806, Panzem, Panzem, PARP inhibitors, pazopanib hydrochloride, pegaptanib sodium, PF4523655, PG11047, piribedil, platelet-derived growth factor beta polypeptide aptamer (pegylated), platelet-derived growth factor beta polypeptide aptamer (pegylated) with ranibizumab, PLG101, PMX20005, PMX53, POT4, PRS055, PTK787, ranibizumab, ranibizumab with triamcinolone acetonide, ranibizumab with verteporfin, ranibizumab with volociximab, RD27, Rescula, Retaane, retinal pigment epithelial cells, RetinoStat, RG7417, RN6G, RT101, RTU007, SB267268, serpin peptidase inhibitor, clade F, member 1 gene, shark cartilage extract, Shef1, SIR1046, SIR1076, Sirna027, sirolimus, SMTD004, Snelvit, SOD Mimetics, Soliris, sonepcizumab, squalamine lactate, ST602, StarGen, T2TrpRS, TA106, talaporfin sodium, Tauroursodeoxycholic acid, TG100801, TKI, TLCx99, TRC093, TRC105, Trivastal Retard, TT30, Ursa, ursodiol, Vangiolux, VAR10200, vascular endothelial growth factor antibody, vascular endothelial growth factor B, vascular endothelial growth factor kinoid, vascular endothelial growth factor oligonucleotide, VAST Compounds, vatalanib, VEGF antagonist (e.g., as described herein), verteporfin, Visudyne, Visudyne with Lucentis and dexamethasone, Visudyne with triamcinolone acetonide, Vivis, volociximab, Votrient, XV615, zeaxanthin, ZFP TF, zinc-monocysteine and Zybrestat. In one embodiment, one or more of the drugs described above is combined with one or more agents listed above or herein or with other agents known in the art.

In one embodiment, the drug is interferon gamma 1b (Actimmune®) with pirfenidone, ACUHTR028, AlphaVBeta5, aminobenzoate potassium, amyloid P, ANG1122, ANG1170, ANG3062, ANG3281, ANG3298, ANG4011, Anti-CTGF RNAi, Aplidin, *Astragalus membranaceus* extract with *salvia* and *schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, Galectin-3 inhibitors, GKT137831, GMCT01, GMCT02, GRMD01, GRMD02, GRN510, Heberon Alfa R, interferon alfa-2b, interferon gamma-1b with pirfenidone, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 Fusion Proteins, RXI109, secretin, STX100, TGF-beta Inhibitor, transforming growth factor, beta receptor 2 oligonucleotide, VA999260 or XV615. In one embodiment, one or more of the drugs for treating macular edema associated with uveitis described above is combined with one or more agents listed above or herein or with other agents known in the art.

In some embodiments, the drug is AKB9778, bevasiranib sodium, Cand5, choline fenofibrate, Cortiject, c-raf 2-methoxyethyl phosphorothioate oligonucleotide, DE109, dexamethasone, DNA damage inducible transcript 4 oligonucleotide, FOV2304, iCo007, KH902, MP0112, NCX434, Optina, Ozurdex, PF4523655, SAR1118, sirolimus, SK0503 or TriLipix.

In some embodiments, the drug is selected from VEGF modulators, PDGF modulators, anti-inflammatory drugs. Examples of drugs that can be administered via IVT include, but are not limited to: A0003, A0006, Acedolone, AdPEDF, aflibercept, AG13958, aganirsen, AGN208397, AKB9778, AL78898A, amyloid P, Angiogenesis Inhibitor Gene Therapy, ARC1905, Aurocort, bevasiranib sodium, brimonidine, Brimonidine, brimonidine tartrate, bromfenac sodium, Cand5, CERE140, Ciganclor, CLT001, CLT003, CLT004, CLT005, complement component 5 aptamer (pegylated), complement factor D antibody, Cortiject, c-raf 2-methoxyethyl phosphorothioate oligonucleotide, cyclosporine, triamcinolone, DE109, denufosol tetrasodium, dexamethasone, dexamethasone phosphate, disitertide, DNA damage inducible transcript 4 oligonucleotide, E10030, ecallantide, EG3306, Eos013, ESBA1008, ESBA105, Eylea, FCFD4514S, fluocinolone acetonide, fms-related tyrosine kinase 1 oligonucleotide, fomivirsen sodium, fosbretabulin tromethamine, FOV2301, FOV2501, ganciclovir, ganciclovir sodium, GS101, GS156, hyaluronidase, IBI20089, iCo007, Iluvien, INS37217, Isonep, JSM6427, Kalbitor, KH902, lerdelimumab, LFG316, Lucentis®, M200, Macugen, Makyueido, Microplasmin, MK0140, MP0112, NCX434, neurotrophin 4 gene, OC10X, ocriplasmin, ORA102, Ozurdex, P144, P17, Palomid 529, pazopanib hydrochloride, pegaptanib sodium, Plasma Kallikrein Inhibitors, platelet-derived growth factor beta polypeptide aptamer (pegylated), POT4, PRM167, PRS055, QPI1007, ranibizumab, resveratrol, Retilone, retinal pigment epithelium-specific protein 65 kDa gene, Retisert, rod derived cone viability factor, RPE65 Gene Therapy, RPGR Gene Therapy, RTP801, Sd-rxRNA, serpin peptidase inhibitor clade F member 1 gene, Sirna027, sirolimus, sonepcizumab, SRT501, STP601, TG100948, Trabio, triamcinolone, triamcinolone acetonide, Trivaris, tumor necrosis factor antibody, VEGF/rGel-Op, verteporfin, Visudyne, Vitrase, Vitrasert, Vitravene, Vitreals, volociximab, Votrient, XG102, Xibrom, XV615, and Zybrestat.

In some embodiments, the reference location can be identified based on a single threshold electrical impedance measurement. In some embodiments, the reference location can be identified by a sudden electrical impedance change while inserting the distal end of the hollow conduit into the eye. In some embodiments, the electrical impedance change can be a change value per μm of insertion depth into the eye.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including,"

"carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A method, comprising:

inserting a distal end portion of a hollow conduit of a medical injector into an eye of a patient until the distal end portion reaches a reference location;

confirming positioning of the distal end portion of the hollow conduit in the reference location, the confirming including:

transmitting, with an optical fiber disposed within the hollow conduit, a light beam into the eye of the patient;

detecting, with a detector, light reflected by the eye of the patient in response to the light beam transmitted; and identifying, based on the detected light, that the distal end portion of the hollow conduit is disposed in the reference location;

after the confirming, extending the distal end portion of the hollow conduit distally and from the reference location such that the distal end portion enters an injection region of the eye; and with the distal end portion of the hollow conduit disposed within the injection region of the eye, conveying a medicament into the injection region via the hollow conduit.

2. The method of claim 1, wherein the reference location is a suprachoroidal space (SCS) of the eye.

3. The method of claim 1, wherein the confirming disposal of the distal end portion of the hollow conduit in the reference location further includes measuring a pressure within the reference location, the pressure meeting a predetermined threshold pressure.

4. The method of claim 1, further comprising:

inserting a trocar into the eye, the trocar coupled to an outer sleeve.

5. The method of claim 4, further comprising:

removing the trocar while leaving the outer sleeve inserted in the eye.

6. The method of claim 1, wherein the reference location is a subretinal space (SRS) of the eye.

7. The method of claim 1, wherein the hollow conduit includes a first lumen configured to convey the medicament into the injection region, and a second lumen configured to accommodate the optical fiber.

* * * * *